US009054322B2

(12) United States Patent
Yabunouchi et al.

(10) Patent No.: US 9,054,322 B2
(45) Date of Patent: *Jun. 9, 2015

(54) AROMATIC AMINE DERIVATIVE, AND ORGANIC ELECTROLUMINESCENT ELEMENT

(75) Inventors: Nobuhiro Yabunouchi, Chiba (JP);
Masahiro Kawamura, Chiba (JP);
Tomoki Kato, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/404,360

(22) Filed: Feb. 24, 2012

(65) Prior Publication Data

US 2012/0175600 A1   Jul. 12, 2012

Related U.S. Application Data

(63) Continuation of application No. 12/998,732, filed as application No. PCT/JP2009/069808 on Nov. 24, 2009, now Pat. No. 8,614,010.

(30) Foreign Application Priority Data

Nov. 25, 2008  (JP) ................................ 2008-299983
Jan. 9, 2009   (JP) ................................ 2009-003660
Mar. 31, 2009  (JP) ................................ 2009-086441

(51) Int. Cl.
| H01L 51/54 | (2006.01) |
| C07D 307/91 | (2006.01) |
| H01L 51/00 | (2006.01) |
| C07D 405/12 | (2006.01) |
| C07D 405/14 | (2006.01) |
| C07D 407/12 | (2006.01) |
| C07D 407/14 | (2006.01) |
| C09K 11/06 | (2006.01) |
| H05B 33/14 | (2006.01) |
| H01L 51/50 | (2006.01) |

(52) U.S. Cl.
CPC .......... *H01L 51/0061* (2013.01); *H01L 51/5064* (2013.01); *C07D 307/91* (2013.01); *H01L 51/5088* (2013.01); *C07D 405/12* (2013.01); *C07D 405/14* (2013.01); *C07D 407/12* (2013.01); *C07D 407/14* (2013.01); *C09K 11/06* (2013.01); *C09K 2211/1011* (2013.01); *C09K 2211/1014* (2013.01); *H01L 51/0052* (2013.01); *H01L 51/0073* (2013.01); *H01L 51/5012* (2013.01); *H05B 33/14* (2013.01)

(58) Field of Classification Search
None
See application file for complete search history.

(56) References Cited

U.S. PATENT DOCUMENTS

| 7,998,596 | B2* | 8/2011 | Yabunouchi et al. ......... 428/690 |
| 8,044,222 | B2 | 10/2011 | Yabunouchi et al. |
| 8,106,391 | B2 | 1/2012 | Endo et al. |
| 8,129,038 | B2* | 3/2012 | Yabunouchi et al. ......... 428/690 |
| 8,518,560 | B2 | 8/2013 | Mizuki et al. |
| 2002/0076576 | A1* | 6/2002 | Li et al. .......................... 428/690 |
| 2004/0185299 | A1 | 9/2004 | Ly |
| 2004/0219387 | A1 | 11/2004 | Li et al. |
| 2005/0067951 | A1 | 3/2005 | Richter et al. |
| 2007/0247063 | A1 | 10/2007 | Murase et al. |
| 2007/0278938 | A1 | 12/2007 | Yabunouchi et al. |
| 2008/0014464 | A1 | 1/2008 | Kawamura et al. |
| 2008/0106190 | A1 | 5/2008 | Yabunouchi et al. |
| 2008/0108832 | A1 | 5/2008 | Yabunouchi et al. |
| 2008/0108839 | A1 | 5/2008 | Yabunouchi et al. |
| 2008/0124572 | A1 | 5/2008 | Mizuki et al. |
| 2008/0191614 | A1 | 8/2008 | Kim et al. |
| 2008/0303417 | A1 | 12/2008 | Yabunouchi et al. |
| 2009/0017330 | A1 | 1/2009 | Iwakuma et al. |
| 2009/0066235 | A1* | 3/2009 | Yabunouchi et al. ......... 313/504 |
| 2010/0001636 | A1* | 1/2010 | Yabunouchi .................. 313/504 |
| 2010/0219404 | A1* | 9/2010 | Endo et al. ...................... 257/40 |
| 2010/0314615 | A1 | 12/2010 | Mizuki et al. |
| 2012/0181521 | A1 | 7/2012 | Yabunouchi et al. |
| 2013/0253183 | A1 | 9/2013 | Mizuki et al. |

FOREIGN PATENT DOCUMENTS

| JP | 62 280850 | 12/1987 |
| JP | 2005 516059 | 6/2005 |

(Continued)

OTHER PUBLICATIONS

Extended European Search Report in EP Application No. 09 82 9072.9. Date of Completion: May 10, 2012. (9 pages).
Patent Abstracts of Japan, Publication No. 2006151844; Publication Date: Jun. 15, 2006; Application No. 2004-342464; Application Date: Nov. 26, 2004 Inventor: Ueno Kazunori et al.; Applicant: Canon Inc.
Konica Minolta Holdings Inc., "Organic electroluminescent device and illumination apparatus," Patent Abstract of Japan, Publication Date: Aug. 7, 2008; English Abstract of JP-2008 181937.

(Continued)

*Primary Examiner* — Marie R. Yamnitzky
(74) *Attorney, Agent, or Firm* — Millen, White, Zelano & Branigan, P.C.

(57) ABSTRACT

Provided is an organic electroluminescence device that provides high efficiency and a long lifetime. The device includes an aromatic amine including at least one substituent A having dibenzofuran and at least one substituent B selected from groups having dibenzofuran or carbazole. The substituent A and the substituent B include groups different from each other and are bonded to the same or different nitrogen atoms in the molecule. The molecules of the aromatic amine hardly crystallize, improving yield in producing the organic electroluminescence device. The device includes an organic thin film layer formed of one or more layers including at least a light emitting layer, the organic thin film layer being interposed between a cathode and an anode. The aromatic amine is contained in at least one layer, particularly a hole transport layer, in the organic thin film layer.

24 Claims, No Drawings

(56) References Cited

FOREIGN PATENT DOCUMENTS

| | | |
|---|---|---|
| JP | 2006 151844 | 6/2006 |
| JP | 2008 78362 | 4/2008 |
| JP | 2008 181937 | 8/2008 |
| JP | 2008 195841 | 8/2008 |
| JP | 2009170817 A | 7/2009 |
| JP | 2010092940 A | 4/2010 |
| WO | WO-2005 113531 | 12/2005 |
| WO | WO-2006 073054 | 7/2006 |
| WO | WO-2007 125714 | 11/2007 |
| WO | WO-2008 062636 | 5/2008 |
| WO | WO-2009 008099 | 1/2009 |
| WO | WO-2009 008100 | 1/2009 |
| WO | WO 2009/041635 A1 * | 4/2009 |

OTHER PUBLICATIONS

Toray IND Inc., "Light emitting element material and light emitting element," Patent Abstracts of Japan, Publication Date: Apr. 3, 2008; English Abstract of JP-2008 078362.

Toray IND Inc., "Material for light-emitting element and the resulting light-emitting element," Patent Abstracts of Japan, Publication Date: Aug. 28, 2008; English Abstract of JP-2008 195841.

Canon, Inc., "Electrophotgraphic sensitive body," Patent Abstracts of Japan, Publication Date: Dec. 5, 1987; English Abstract of JP-62 280850.

Office Action issued May 10, 2013 in corresponding Chinese Patent Application No. 200980147099.5. Filing Date: Nov. 24, 2009. Publication No. CN 102224150. Publication Date: Oct. 19, 2011.

* cited by examiner

AROMATIC AMINE DERIVATIVE, AND ORGANIC ELECTROLUMINESCENT ELEMENT

This application is a continuation of U.S. patent application Ser. No. 12/998,732, filed Aug. 5, 2011, now U.S. Pat. No. 8,614,010, which is a National Phase (371) filing of PCT/JP2009/069808, filed Nov. 24, 2009.

TECHNICAL FIELD

The present invention relates to an aromatic amine derivative and an organic electroluminescence (organic EL) device using the same, and more particularly, to an aromatic amine derivative capable of providing high efficiency even at high temperatures and increasing a lifetime of the organic EL device by using an aromatic amine derivative having a specific structure as a hole transporting material.

BACKGROUND ART

An organic EL device is a spontaneous light emitting device which utilizes such a principle that a fluorescent substance emits light by virtue of recombination energy of holes injected from an anode and electrons injected from a cathode by an application of an electric field. Since an organic EL device of the laminate type capable of being driven under low electric voltage has been reported by C. W. Tang et al. of Eastman Kodak Company (C. W. Tang and S. A. Vanslyke, Applied Physics Letters, Volume 51, Page 913, 1987, or the like), many studies have been conducted for an organic EL device using an organic material as a constituent material. Tang et al. used tris(8-quinolinolato) aluminum for a light emitting layer and a triphenyldiamine derivative for a hole transporting layer. Advantages of the laminate structure reside in the followings: an efficiency of the hole injection into the light emitting layer can be increased; an efficiency of forming excitons which are formed by blocking and recombining electrons injected from the cathode can be increased; and excitons formed within the light emitting layer can be enclosed. As described above, for the device structure of the organic EL device, a two-layered structure having a hole transporting (injecting) layer and an electron transporting light emitting layer and a three-layered structure having a hole transporting (injecting) layer, a light emitting layer, an electron transporting (injecting) layer, and the like are widely known. In order to increase the efficiency of recombination of injected holes and electrons in such devices of the laminate type, the device structure and the process of forming the device have been studied.

In general, when an organic EL device is driven or stored in an environment of high temperature, there occur adverse affects such as a change in luminescent color, a decrease in emission efficiency, an increase in driving voltage, and a decrease in a lifetime of light emission. In order to prevent the adverse affects, it has been necessary that the glass transition temperature (Tg) of the hole transporting material be elevated. Therefore, it is necessary that many aromatic groups be held within a molecule of the hole transporting material (for example, an aromatic diamine derivative of Patent Literature 1 and an aromatic fused ring diamine derivative of Patent Literature 2), and in general, a structure having 8 to 12 benzene rings is preferably used.

However, in the case of a highly symmetrical compound and a compound high in flatness each having a large number of aromatic groups in a molecule, crystallization is liable to occur upon production of the organic EL device through the formation of a thin film by using those hole transporting materials. As a result, there arises a problem such as clogging of an outlet of a crucible to be used in vapor deposition or a reduction in yields of the organic EL device due to generation of defects of the thin film resulting from the crystallization. In addition, a compound having a large number of aromatic groups in any one of its molecules generally has a high glass transition temperature (Tg), but has a high sublimation temperature. Accordingly, there arises a problem in that the lifetime of the compound is short probably because a phenomenon such as decomposition at the time of the vapor deposition or the formation of a nonuniform deposition film occurs.

Meanwhile, Patent Literatures 3 to 5 report amine compounds each having dibenzofuran. However, those compounds are each of a structure having dibenzofuran in the central skeleton of a diamine compound. Patent Literatures 6 to 9 report compounds each having dibenzofuran bonded to a monoamine through an aryl group. However, none of the compounds provides sufficient performance when used in an organic EL device.

In addition, a large number of reports have been made on amine compounds in each of which N-carbazole is bonded to an amine through an aryl group. Examples of the reports include Patent Literatures 10 to 12. However, none of the compounds provides sufficient performance when used in an organic EL device.

Further, Patent Literatures 13 and 14 report amine compounds in each of which 3-carbazole is directly bonded to an amine. However, none of the compounds provides sufficient performance when used in an organic EL device. In addition, Patent Literatures 15 and 16 report amine compounds in each of which 3-carbazole is bonded to an amine through an aryl group. However, none of the compounds provides sufficient performance when used in an organic EL device.

As described above, high-efficiency, long-lifetime organic EL devices have been reported, but none of them provides sufficient performance, and hence the development of an organic EL device having additionally excellent performance has been strongly desired.

CITATION LIST

Patent Literature

[PTL 1] U.S. Pat. No. 4,720,432 A
[PTL 2] U.S. Pat. No. 5,061,569 A
[PTL 3] JP 2005-112765 A
[PTL 4] JP 11-111460 A
[PTL 5] WO 2006/122630 A1
[PTL 6] WO 2006/128800 A1
[PTL 7] JP 2006-151844 A
[PTL 8] JP 2008-021687 A
[PTL 9] WO 2007/125714 A1
[PTL 10] U.S. Pat. No. 6,242,115 A
[PTL 11] JP 2007-284431 A
[PTL 12] JP 2003-031371 A
[PTL 13] JP 2007-318101 A
[PTL 14] JP 2006-151979 A
[PTL 15] JP 2005-290000 A
[PTL 16] WO 2008/062636 A1

SUMMARY OF INVENTION

Technical Problem

The present invention has been made to solve the problems, and an object of the present invention is to provide an organic electroluminescence device that not only provides high efficiency even at high temperatures but also has a long lifetime, and an aromatic amine derivative that realizes the device.

Solution to Problem

The inventors of the present invention have made extensive studies to achieve the object. As a result, the inventors have found that the use of a novel aromatic amine derivative having two kinds of specific substituents as a material for an organic EL device, in particular, a hole injecting material or a hole transporting material can solve the problems.

The following facts have been found. The specific substituents are suitably a group having a dibenzofuran structure and a group having a dibenzofuran structure or a carbazole structure. The molecular symmetry of an amine derivative having at least one group having a dibenzofuran structure and at least one group having a dibenzofuran structure and/or a carbazole structure, the groups being different from each other, can be reduced. Accordingly, the derivative shows a small intermolecular interaction, crystallizes to a reduced extent, and can improve the yield in the production of an organic EL device. In addition, the above-mentioned amine derivative improves efficiency because the derivative has so large an Eg as to be capable of effectively blocking electrons from a light emitting layer. In addition, the derivative has a lifetime-lengthening effect because the derivative suppresses the injection of electrons into a hole transporting layer. In particular, a combination of the derivative and a blue light emitting device exerts a significant lifetime-lengthening effect. The inventors of the present invention have completed the present invention on the basis of those findings.

That is, the present invention provides the following.

1. An aromatic amine derivative, including at least one substituent A represented by the following general formula (1) and at least one substituent B represented by the following general formula (2) or (3) in a molecule thereof, in which: the substituent A and the substituent B include groups different from each other; and the substituent A and the substituent B are bonded to the same nitrogen atom, or different nitrogen atoms, in the molecule:

[Chem. 1]

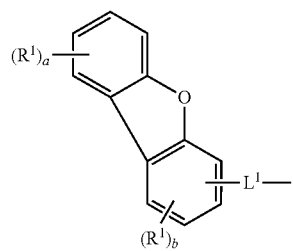

(1)

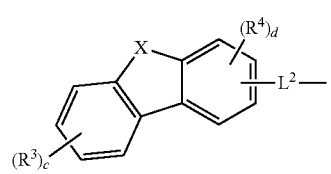

(2)

-continued

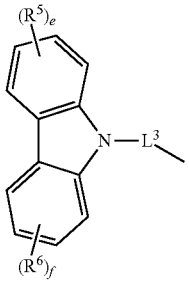

(3)

[in the formula
$L^1$ and $L^2$ each independently represent a single bond, or a substituted or unsubstituted arylene group having 6 to 50 ring carbon atoms, and $L^3$ represents a substituted or unsubstituted arylene group having 6 to 50 ring carbon atoms, provided that a substituent which any one of $L^1$ to $L^3$ may have includes a linear or branched alkyl group having 1 to 10 carbon atoms, a cycloalkyl group having 3 to 10 ring carbon atoms, a trialkylsilyl group having 3 to 10 carbon atoms, a triarylsilyl group having 18 to 30 ring carbon atoms, an alkylarylsilyl group having 8 to 15 carbon atoms whose aryl portion has 6 to 14 ring carbon atoms, an aryl group having 6 to 14 ring carbon atoms, a halogen atom, or a cyano group;

X represents an oxygen atom or a $—N(Ar^1)—$ group;

$Ar^1$ represents a substituted or unsubstituted aryl group having 6 to 14 ring carbon atoms, and a substituent which $Ar^1$ may have includes a linear or branched alkyl group having 1 to 10 carbon atoms, a cycloalkyl group having 3 to 10 ring carbon atoms, a trialkylsilyl group having 3 to 10 carbon atoms, a triarylsilyl group having 18 to 30 ring carbon atoms, an alkylarylsilyl group having 8 to 15 carbon atoms whose aryl portion has 6 to 14 ring carbon atoms, an aryl group having 6 to 14 ring carbon atoms, a halogen atom, or a cyano group;

a, c, e, and f each independently represent an integer of 0 to 4;

b and d each independently represent an integer of 0 to 3; and $R^1$ to $R^6$ each independently represent a linear or branched alkyl group having 1 to 10 carbon atoms, a cycloalkyl group having 3 to 10 ring carbon atoms, a trialkylsilyl group having 3 to 10 carbon atoms, a triarylsilyl group having 18 to 30 ring carbon atoms, an alkylarylsilyl group having 8 to 15 carbon atoms whose aryl portion has 6 to 14 ring carbon atoms, an aryl group having 6 to 14 ring carbon atoms, a halogen atom, or a cyano group, and a plurality of $R^1$'s to $R^6$'s adjacent to each other may be bonded to each other to form a saturated or unsaturated, divalent group that forms a ring, provided that hydrogen atoms in the aromatic amine derivative include deuterium atoms].

2. The aromatic amine derivative according to the above-mentioned item 1, in which when the X in the general formula (2) represents a $—N(Ar^1)—$ group, the $L^2$ is represented by the following general formula (4):

[Chem. 2]

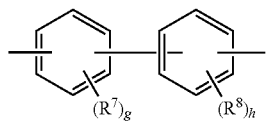

(4)

[in the formula:

R⁷ and R⁸ each independently represent a linear or branched alkyl group having 1 to 10 carbon atoms, a cycloalkyl group having 3 to 10 ring carbon atoms, a trialkylsilyl group having 3 to 10 carbon atoms, a triarylsilyl group having 18 to 30 ring carbon atoms, an alkylarylsilyl group having 8 to 15 carbon atoms whose aryl portion has 6 to 14 ring carbon atoms, an aryl group having 6 to 16 ring carbon atoms, a halogen atom, or a cyano group, and a plurality of R⁷'s and R⁸'s adjacent to each other may be bonded to each other to form a saturated or unsaturated ring; and g and h each independently represent an integer of 0 to 4].

3. The aromatic amine derivative according to the above-mentioned item 1, in which the substituent B is represented by the general formula (3).

4. The aromatic amine derivative according to the above-mentioned item 1, in which when the L³ in the general formula (3) is represented by the following general formula (4):

[Chem. 3]

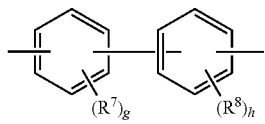

(4)

[in the formula:

R⁷ and R⁸ each independently represent a linear or branched alkyl group having 1 to 10 carbon atoms, a cycloalkyl group having 3 to 10 ring carbon atoms, a trialkylsilyl group having 3 to 10 carbon atoms, a triarylsilyl group having 18 to 30 ring carbon atoms, an alkylarylsilyl group having 8 to 15 carbon atoms whose aryl portion has 6 to 14 ring carbon atoms, an aryl group having 6 to 16 ring carbon atoms, a halogen atom, or a cyano group, and a plurality of R⁷'s and R⁸'s adjacent to each other may be bonded to each other to form a saturated or unsaturated ring; and g and h each independently represent an integer of 0 to 4].

5. The aromatic amine derivative according to the above-mentioned item 1, in which the substituent A is represented by the following general formula (1) and the substituent B is represented by the following general formula (2-1) or (3):

[Chem. 4]

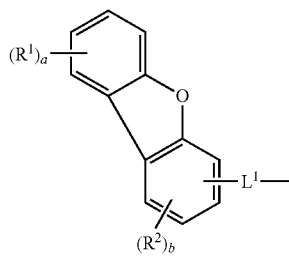

(1)

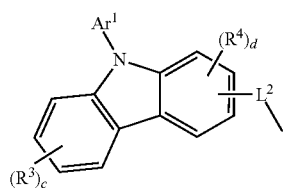

(2-1)

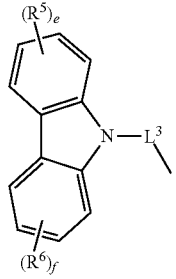

(3)

[in the formula:

L¹ and L² each independently represent a single bond, or a substituted or unsubstituted arylene group having 6 to 50 ring carbon atoms, and L³ represents a substituted or unsubstituted arylene group having 6 to 50 ring carbon atoms, provided that a substituent which any one of L¹ to L³ may have includes a linear or branched alkyl group having 1 to 10 carbon atoms, a cycloalkyl group having 3 to 10 ring carbon atoms, a trialkylsilyl group having 3 to 10 carbon atoms, a triarylsilyl group having 18 to 30 ring carbon atoms, an alkylarylsilyl group having 8 to 15 carbon atoms whose aryl portion has 6 to 14 ring carbon atoms, an aryl group having 6 to 14 ring carbon atoms, a halogen atom, or a cyano group;

Ar¹ represents a substituted or unsubstituted aryl group having 6 to 14 ring carbon atoms, and a substituent which Ar¹ may have includes a linear or branched alkyl group having 1 to 10 carbon atoms, a cycloalkyl group having 3 to 10 ring carbon atoms, a trialkylsilyl group having 3 to 10 carbon atoms, a triarylsilyl group having 18 to 30 ring carbon atoms, an alkylarylsilyl group having 8 to 15 carbon atoms whose aryl portion has 6 to 14 ring carbon atoms, an aryl group having 6 to 14 ring carbon atoms, a halogen atom, or a cyano group;

a, c, e, and f each independently represent an integer of 0 to 4;

b and d each independently represent an integer of 0 to 3; and

R¹ to R⁶ each independently represent a linear or branched alkyl group having 1 to 10 carbon atoms, a cycloalkyl group having 3 to 10 ring carbon atoms, a trialkylsilyl group having 3 to 10 carbon atoms, a triarylsilyl group having 18 to 30 ring carbon atoms, an alkylarylsilyl group having 8 to 15 carbon atoms whose aryl portion has 6 to 14 ring carbon atoms, an aryl group having 6 to 14 ring carbon atoms, a halogen atom, or a cyano group, and a plurality of R¹'s to R⁶'s adjacent to each other may be bonded to each other to form a saturated or unsaturated, divalent group that forms a ring].

6. The aromatic amine derivative according to the above-mentioned item 5, in which the substituent A is represented by the following general formula (1-1) or (1-2).

[Chem. 5]

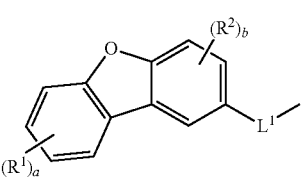

(1-1)

-continued

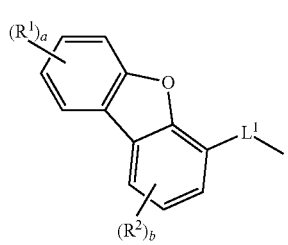
(1-2)

7. The aromatic amine derivative according to the above-mentioned item 1, in which the substituent A and the substituent B are each independently represented by the following general formula (1):

[Chem. 6]

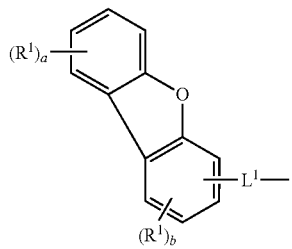
(1)

[in the formula:

$L^1$ represents a single bond, or a substituted or unsubstituted arylene group having 6 to 50 ring carbon atoms, and a substituent which $L^1$ may have includes a linear or branched alkyl group having 1 to 10 carbon atoms, a cycloalkyl group having 3 to 10 ring carbon atoms, a trialkylsilyl group having 3 to 10 carbon atoms, a triarylsilyl group having 18 to 30 ring carbon atoms, an alkylarylsilyl group having 8 to 15 carbon atoms whose aryl portion has 6 to 14 ring carbon atoms, an aryl group having 6 to 14 ring carbon atoms, a halogen atom, or a cyano group;

a represents an integer of 0 to 4;

b represents an integer of 0 to 3; and $R^1$ and $R^2$ each independently represent a linear or branched alkyl group having 1 to 10 carbon atoms, a cycloalkyl group having 3 to 10 ring carbon atoms, a trialkylsilyl group having 3 to 10 carbon atoms, a triarylsilyl group having 18 to 30 ring carbon atoms, an alkylarylsilyl group having 8 to 15 carbon atoms whose aryl portion has 6 to 14 ring carbon atoms, an aryl group having 6 to 14 ring carbon atoms, a halogen atom, or a cyano group, and a plurality of $R^1$'s and $R^2$'s adjacent to each other may be bonded to each other to form a saturated or unsaturated, divalent group that forms a ring].

8. The aromatic amine derivative according to the above-mentioned item 7, in which the substituent A and the substituent B are each independently represented by any one of the following general formulae (1-1) to (1-3).

[Chem. 7]

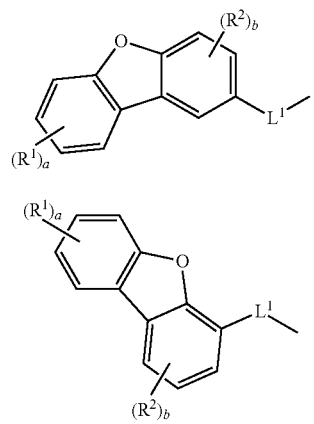

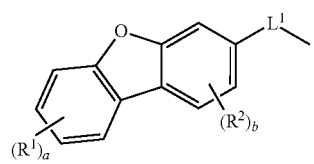

9. The aromatic amine derivative according to the above-mentioned item 8, in which the substituent A is represented by the general formula (1-1) and the substituent B is represented by the general formula (1-2).

10. The aromatic amine derivative according to the above-mentioned item 1, further including at least one terphenyl group.

11. The aromatic amine derivative according to the above-mentioned item 1, in which the aromatic amine derivative is represented by any one of the following general formulae (5) to (9):

[Chem. 8]

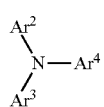
(5)

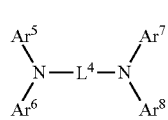
(6)

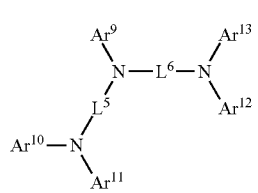
(7)

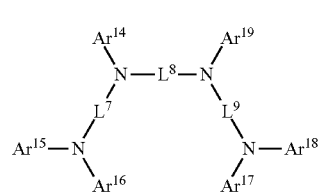
(8)

-continued

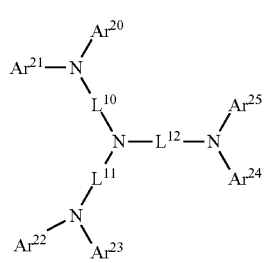

(9)

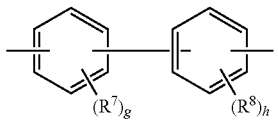

(4)

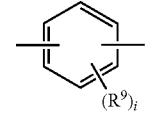

(10)

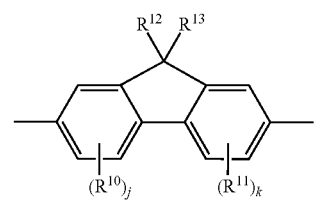

(11)

{in the formulae:
at least one of $Ar^2$ to $Ar^4$ represents the substituent A represented by the general formula (1), at least one of $Ar^2$ to $Ar^4$ represents the substituent B represented by the general formula (2) or (3), and the substituent A and the substituent B include groups different from each other;

at least one of $Ar^5$ to $Ar^8$ represents the substituent A represented by the general formula (1), at least one of $Ar^5$ to $Ar^8$ represents the substituent B represented by the general formula (2) or (3), and the substituent A and the substituent B include groups different from each other;

at least one of $Ar^9$ to $Ar^{13}$ represents the substituent A represented by the general formula (1), at least one of $Ar^9$ to $Ar^{13}$ represents the substituent B represented by the general formula (2) or (3), and the substituent A and the substituent B include groups different from each other;

at least one of $Ar^{14}$ to $Ar^{19}$ represents the substituent A represented by the general formula (1), at least one of $Ar^{14}$ to $Ar^{19}$ represents the substituent B represented by the general formula (2) or (3), and the substituent A and the substituent B include groups different from each other;

at least one of $Ar^{20}$ to $Ar^{25}$ represents the substituent A represented by the general formula (1), at least one of $Ar^{20}$ to $Ar^{25}$ represents the substituent B represented by the general formula (2) or (3), and the substituent A and the substituent B include groups different from each other;

groups out of $Ar^2$ to $Ar^{25}$ except the substituent A and the substituent B each independently include a substituted or unsubstituted aryl group having 6 to 50 ring carbon atoms;

$L^4$ to $L^{12}$ each independently represent a substituted or unsubstituted arylene group having 6 to 50 ring carbon atoms; and substituents which $Ar^2$ to $Ar^{25}$ and $L^4$ to $L^{12}$ may have each independently include a linear or branched alkyl group having 1 to 10 carbon atoms, a cycloalkyl group having 3 to 10 ring carbon atoms, a trialkylsilyl group having 3 to 10 carbon atoms, a triaryl silyl group having 18 to 30 ring carbon atoms, an alkylarylsilyl group having 8 to 15 carbon atoms whose aryl portion has 6 to 14 ring carbon atoms, an aryl group having 6 to 14 ring carbon atoms, a halogen atom, or a cyano group.

12. The aromatic amine derivative according to the above-mentioned item 11, in which the aromatic amine derivative is represented by the general formula (5).

13. The aromatic amine derivative according to the above-mentioned item 11, in which the $L^1$ to $L^{12}$ each independently represent a phenylene group, a naphthylene group, a biphenylene group, a terphenylene group, a fluorenylene group, or a 9,9-dimethylfluorenylene group.

14. The aromatic amine derivative according to the above-mentioned item 11, in which the $L^1$ to $L^{12}$ are each independently represented by any one of the following general formulae (4), (10), and (11):

[in the formulae:
$R^7$ to $R^{11}$ each independently represent a linear or branched alkyl group having 1 to 10 carbon atoms, a cycloalkyl group having 3 to 10 ring carbon atoms, a trialkylsilyl group having 3 to 10 carbon atoms, a triarylsilyl group having 18 to 30 ring carbon atoms, an alkylarylsilyl group having 8 to 15 carbon atoms whose aryl portion has 6 to 14 ring carbon atoms, an aryl group having 6 to 16 ring carbon atoms, a halogen atom, or a cyano group, and a plurality of $R^7$'s to $R^{11}$'s adjacent to each other may be bonded to each other to form a saturated or unsaturated ring;

$R^{12}$ and $R^{13}$ each independently represent a linear or branched alkyl group having 1 to 10 carbon atoms, or a cycloalkyl group having 3 to 10 ring carbon atoms;

g, h, and i each independently represent an integer of 0 to 4; and j and k each independently represent an integer of 0 to 3].

15. The aromatic amine derivative according to the above-mentioned item 11, in which the aromatic amine derivative includes an aromatic amine derivative represented by the general formula (5) in which the $Ar^2$ is represented by the general formula (1), and the $Ar^3$ and the $Ar^4$ are each independently represented by the general formula (3) or (2-1).

16. The aromatic amine derivative according to the above-mentioned item 11, in which the aromatic amine derivative includes an aromatic amine derivative represented by the general formula (5) in which the $Ar^2$ and the $Ar^3$ are each represented by the general formula (1), and the $Ar^4$ is represented by the general formula (3) or (2-1).

17. The aromatic amine derivative according to the above-mentioned item 11, in which the aromatic amine derivative includes an aromatic amine derivative represented by the general formula (5) in which the $Ar^2$ is represented by the general formula (1), the $Ar^3$ is represented by the general formula (3) or (2-1), and the $Ar^4$ represents a substituted or unsubstituted aryl group having 6 to 50 ring carbon atoms [provided that substituents of the $Ar^4$ each independently include any one of an aryl group having 6 to 50 ring carbon atoms, a branched or linear alkyl group having 1 to 50 carbon atoms, a halogen atom, and a cyano group].

18. The aromatic amine derivative according to the above-mentioned item 11, in which the aromatic amine derivative includes an aromatic amine derivative represented by the general formula (6) in which the $Ar^5$ and the $Ar^6$ are each represented by the general formula (1), and the $Ar^7$ and the $Ar^8$ are each independently represented by the general formula (3) or (2-1).

19. The aromatic amine derivative according to the abovementioned item 11, in which the aromatic amine derivative includes an aromatic amine derivative represented by the general formula (6) in which the $Ar^5$ and the $Ar^7$ are each represented by the general formula (1), and the $Ar^6$ and the $Ar^8$ are each independently represented by the general formula (3) or (2-1).

20. The aromatic amine derivative according to the abovementioned item 11, in which the aromatic amine derivative includes an aromatic amine derivative represented by the general formula (7) in which the $Ar^9$ is represented by the general formula (1), and the $Ar^{11}$ and the $Ar^{12}$ are each independently represented by the general formula (3) or (2-1).

21. The aromatic amine derivative according to the abovementioned item 11, in which the aromatic amine derivative includes an aromatic amine derivative represented by the general formula (7) in which the $Ar^{11}$ and the $Ar^{12}$ are each represented by the general formula (1), and the $Ar^9$ is represented by the general formula (3) or (2-1).

22. The aromatic amine derivative according to the abovementioned item 11, in which the aromatic amine derivative includes an aromatic amine derivative represented by the general formula (8) in which the $Ar^{14}$ and the $Ar^{19}$ are each represented by the general formula (1), and the $Ar^{16}$ and the $Ar^{17}$ are each independently represented by the general formula (3) or (1).

23. The aromatic amine derivative according to the abovementioned item 11, in which the aromatic amine derivative includes an aromatic amine derivative represented by the general formula (8) in which the $Ar^{16}$ and the $Ar^{17}$ are each represented by the general formula (1), and the $Ar^{14}$ and the $Ar^{19}$ are each independently represented by the general formula (3) or (2-1).

24. The aromatic amine derivative according to the abovementioned item 11, in which the aromatic amine derivative includes an aromatic amine derivative represented by the general formula (9) in which the $Ar^{20}$, the $Ar^{22}$, and the $Ar^{24}$ are each represented by the general formula (1), and the $Ar^{21}$, the $Ar^{23}$, and the $Ar^{25}$ are each independently represented by the general formula (3) or (2-1).

25. The aromatic amine derivative according to the abovementioned item 11, in which the aromatic amine derivative includes an aromatic amine derivative represented by the general formula (5) in which the $Ar^2$ to $Ar^4$ are each represented by the general formula (1-2).

26. The aromatic amine derivative according to the abovementioned item 11, in which the aromatic amine derivative includes an aromatic amine derivative represented by the general formula (5) in which the $Ar^2$ to $Ar^4$ are each represented by the general formula (1-1).

27. The aromatic amine derivative according to the abovementioned item 11, in which the aromatic amine derivative includes an aromatic amine derivative represented by the general formula (5) in which two of the $Ar^2$ to $Ar^4$ are each represented by the general formula (1-2), and one of the $Ar^2$ to $Ar^4$ represents a substituted or unsubstituted aryl group having 6 to 16 ring carbon atoms.

28. The aromatic amine derivative according to the abovementioned item 11, in which the aromatic amine derivative includes an aromatic amine derivative represented by the general formula (5) in which two of the $Ar^2$ to $Ar^4$ are each represented by the general formula (1-1), and one of the $Ar^2$ to $Ar^4$ represents a substituted or unsubstituted aryl group having 6 to 16 ring carbon atoms.

29. The aromatic amine derivative according to the abovementioned item 11, in which the aromatic amine derivative includes an aromatic amine derivative represented by the general formula (5) in which at least one of the $Ar^2$ to $Ar^4$ is represented by the general formula (1-2), and at least one of the $Ar^2$ to $Ar^4$ is represented by the general formula (1-1).

30. The aromatic amine derivative according to the abovementioned item 11, in which the aromatic amine derivative includes an aromatic amine derivative represented by the general formula (5) in which the $Ar^2$ is represented by the general formula (1-2), and the $Ar^3$ and the $Ar^4$ are each independently represented by the general formula (1).

31. The aromatic amine derivative according to the abovementioned item 11, in which the aromatic amine derivative includes an aromatic amine derivative represented by the general formula (5) in which the $Ar^2$ and the $Ar^3$ are each represented by the general formula (1-2), and the $Ar^4$ is represented by the general formula (1-1).

32. The aromatic amine derivative according to the abovementioned item 11, in which at least two of the $Ar^5$ to $Ar^8$ are each, at least two of the $Ar^9$ to $Ar^{13}$ are each, at least one of the $Ar^{14}$ to $Ar^{19}$ is, or at least one of the $Ar^{20}$ to $Ar^{25}$ is represented by the general formula (1-2) or (1-1).

33. The aromatic amine derivative according to the abovementioned item 11, in which the aromatic amine derivative includes any one of an aromatic amine derivative represented by the general formula (6) in which at least one of the $Ar^5$ to $Ar^8$ is represented by the general formula (1-2) and at least one of the $Ar^5$ to $Ar^8$ except the at least one represented by the general formula (1-2) is represented by the general formula (1-1), an aromatic amine derivative represented by the general formula (7) in which at least one of the $Ar^9$ to $Ar^{13}$ is represented by the general formula (1-2) and at least one of the $Ar^9$ to $Ar^{13}$ except the at least one represented by the general formula (1-2) is represented by the general formula (1-1), an aromatic amine derivative represented by the general formula (8) in which at least one of the $Ar^{14}$ to $Ar^{19}$ is represented by the general formula (1-2) and at least one of the $Ar^{14}$ to $Ar^{19}$ except the at least one represented by the general formula (1-2) is represented by the general formula (1-1), and an aromatic amine derivative, represented by the general formula (9) in which at least one of the $Ar^{20}$ to $Ar^{25}$ is represented by the general formula (1-2) and at least one of the $Ar^{20}$ to $Ar^{25}$ except the at least one represented by the general formula (1-2) is represented by the general formula (1-1).

34. The aromatic amine derivative according to the abovementioned item 11, in which the aromatic amine derivative includes an aromatic amine derivative represented by the general formula (5) in which the $Ar^5$ is represented by the general formula (1-2) and the $Ar^6$ is represented by the general formula (1-1).

35. The aromatic amine derivative according to the abovementioned item 11, in which the aromatic amine derivative includes an aromatic amine derivative represented by the general formula (5) in which the $Ar^5$ and the $Ar^7$ are each represented by the general formula (1-2) and the $Ar^6$ and the $Ar^8$ are each represented by the general formula (1-1).

36. The aromatic amine derivative according to the abovementioned item 11, in which the aromatic amine derivative includes an aromatic amine derivative represented by the general formula (6) in which the $Ar^9$ is represented by the general formula (1-2) and the $Ar^{11}$ and the $Ar^{12}$ are each represented by the general formula (1-1).

37. The aromatic amine derivative according to the abovementioned item 11, in which the aromatic amine derivative includes an aromatic amine derivative represented by the general formula (6) in which the $Ar^{10}$ and the $Ar^{13}$ are each represented by the general formula (1-2) and the $Ar^{11}$ and the $Ar^{12}$ are each represented by the general formula (1-1).

38. The aromatic amine derivative according to the above-mentioned item 11, in which the aromatic amine derivative includes an aromatic amine derivative represented by the general formula (8) in which the $Ar^{14}$ and the $Ar^{19}$ are each represented by the general formula (1-2) and the $Ar^{16}$ and the $Ar^{17}$ are each represented by the general formula (1-1).

39. The aromatic amine derivative according to the above-mentioned item 11, in which the aromatic amine derivative includes an aromatic amine derivative represented by the general formula (8) in which the $Ar^{15}$ and the $Ar^{18}$ are each represented by the general formula (1-2) and the $Ar^{16}$ and the $Ar^{17}$ are each represented by the general formula (1-1).

40. The aromatic amine derivative according to the above-mentioned item 11, in which the aromatic amine derivative includes an aromatic amine derivative represented by the general formula (9) in which the $Ar^{20}$, the $Ar^{22}$, and the $Ar^{24}$ are each represented by the general formula (1-2) and the $Ar^{21}$, the $Ar^{23}$, and the $Ar^{25}$ are each represented by the general formula (1-1).

41. The aromatic amine derivative according to the above-mentioned item 11, in which groups out of the $Ar^2$ to $Ar^{25}$ except the substituent A and the substituent B each independently include a phenyl group, a naphthyl group, a biphenyl group, a terphenyl group, or a fluorenyl group.

42. The aromatic amine derivative according to the above-mentioned item 1, in which the aromatic amine derivative is used as a material for an organic electroluminescence device.

43. The aromatic amine derivative according to the above-mentioned item 1, in which the aromatic amine derivative is used as a hole transporting material for an organic electroluminescence device.

44. An organic electroluminescence device, including an organic thin film layer formed of one or more layers including at least a light emitting layer, the organic thin film layer being interposed between a cathode and an anode, in which at least one layer of the organic thin film layer contains the aromatic amine derivative according to the above-mentioned item 1.

45. The organic electroluminescence device according to the above-mentioned item 1, in which: the organic thin film layer has a hole transporting layer and/or a hole injecting layer; and the aromatic amine derivative according to the above-mentioned item 44 is incorporated into the hole transporting layer and/or the hole injecting layer.

46. The organic electroluminescence device according to the above-mentioned item 44, in which: the organic thin film layer has a hole transporting zone including at least a hole transporting layer and a hole injecting layer; and the aromatic amine derivative according to the above-mentioned item 1 is incorporated into a layer out of direct contact with the light emitting layer in the hole transporting zone.

47. The organic electroluminescence device according to the above-mentioned item 44, in which the aromatic amine derivative according to any one of the above-mentioned items 1 to 41 is incorporated as a main component into the hole transporting layer and/or the hole injecting layer.

48. The organic electroluminescence device according to the above-mentioned item 44, in which the light emitting layer contains a styrylamine compound and/or an arylamine compound.

49. The organic electroluminescence device according to the above-mentioned item 44, in which a layer in contact with the anode out of layers for forming the hole injecting layer and/or the hole transporting layer includes a layer containing an acceptor material.

50. The organic electroluminescence device according to the above-mentioned item 44, in which the organic electroluminescence device emits blue light.

Advantageous Effects of Invention

The aromatic amine derivative of the present invention hardly crystallizes, and the use of the derivative as a material for an organic EL device provides a device that not only provides high efficiency even at high temperatures but also has a long lifetime.

DESCRIPTION OF EMBODIMENTS

The aromatic amine derivative of the present invention is a compound having at least one substituent A represented by the general formula (1) and at least one substituent B represented by the general formula (2) or (3) in any one of its molecules, in which: the substituent A and the substituent B are groups different from each other; and the substituent A and the substituent B are bonded to the same nitrogen atom, or different nitrogen atoms, in the molecule.

The "aromatic amine derivative" in the present invention is preferably an amine compound having a molecular weight of 300 to 2,000 and having a substituent formed of an aromatic compound. The molecular weight is more preferably 400 to 1,500, particularly preferably 500 to 1,200. When the molecular weight is 300 to 2,000, the compound can be purified by sublimation, and as a result, the purity of the compound can be improved. The use of the compound improves the performance of a device to be obtained. In addition, the case where the molecular weight is 300 to 2,000 is preferred because the device can be produced by a deposition method.

The "aromatic amine derivative", which is not particularly limited, is represented by preferably any one of the general formulae (5) to (9), more preferably the general formula (5) or (6), particularly preferably the general formula (5). A monoamine derivative represented by the general formula (5) and a diamine derivative represented by the general formula (6) can be expected to be produced at low costs because the derivatives can each be synthesized with relative ease. In addition, the monoamine derivative and the diamine derivative each have a large ionization potential (which may hereinafter be abbreviated as "IP"). Accordingly, when any such derivative is used as a hole transporting material, the property by which holes are injected into a light emitting layer is improved, and hence a reduction in the voltage at which the device is driven can be expected. In particular, an improvement in the luminous efficiency, and the lengthening of the lifetime, of the device can be expected from the monoamine derivative because the derivative has so large an energy gap as to be capable of suppressing the injection of electrons into a hole transporting layer.

In the general formulae (1) to (3), (1-1) to (1-3), and (2-1), $R^1$ to $R^6$ each independently represent a linear or branched alkyl group having 1 to 10, preferably 1 to 6, carbon atoms, a cycloalkyl group having 3 to 10, preferably 5 to 7, ring carbon atoms, a trialkylsilyl group having 3 to 10, preferably 3 to 6, carbon atoms, a triarylsilyl group having 18 to 30, preferably 18 to 24, ring carbon atoms, an alkylarylsilyl group having 8 to 15, preferably 8 to 12, carbon atoms (its aryl portion has 6 to 14, preferably 6 to 10, ring carbon atoms), an aryl group having 6 to 16, preferably 6 to 10, ring carbon atoms, a halogen atom (a fluorine atom is preferred), or a cyano group, and a plurality of $R^1$'s to $R^6$'s adjacent to each other may be bonded to themselves, or $R^1$ and $R^2$, $R^3$ and $R^4$, or $R^5$ and $R^6$ may be bonded to each other, to form a saturated or unsaturated ring.

Specific examples of the alkyl group include a methyl group, an ethyl group, a propyl group, an isopropyl group, an n-butyl group, an isobutyl group, a sec-butyl group, a tert-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, and a 1,2,3-trihydroxypropyl group. Preferred are a methyl group, an ethyl group, a propyl group, an isopropyl group, an n-butyl group, an isobutyl group, a sec-butyl group, and a tert-butyl group.

Specific examples of the cycloalkyl group include a cyclopropyl group, a cyclobutyl group, a cyclopentyl group, a cyclohexyl group, a cyclopentylmethyl group, a cyclohexylmethyl group, a cyclohexylethyl group, a 4-fluorocyclohexyl group, a 1-adamantyl group, a 2-adamantyl group, a 1-norbornyl group, and a 2-norbornyl group. Preferred are a cyclopentyl group and a cyclohexyl group.

Specific examples of the trialkylsilyl group include a trimethylsilyl group, a vinyldimethylsilyl group, a triethylsilyl group, a tripropylsilyl group, a propyldimethylsilyl group, a tributylsilyl group, a t-butyldimethylsilyl group, a tripentylsilyl group, a triheptylsilyl group, and a trihexylsilyl group. Preferred are a trimethylsilyl group and a triethylsilyl group. A silyl group may be substituted with alkyl groups identical to or different from each other.

Specific examples of the triarylsilyl group include a triphenylsilyl group, a trinaphthylsilyl group, and a trianthrylsilyl group. Preferred is a triphenylsilyl group. A silyl group may be substituted with aryl groups identical to or different from each other.

Specific examples of the alkylarylsilyl group include a dimethylphenylsilyl group, a diethylphenylsilyl group, a dipropylphenylsilyl group, a dibutylphenylsilyl group, a dipentylphenylsilyl group, a diheptylphenylsilyl group, a dihexylphenylsilyl group, a dimethylnaphthylsilyl group, a dipropylnaphthylsilyl group, a dibutylnaphthylsilyl group, a dipentylnaphthylsilyl group, a diheptylnaphthylsilyl group, a dihexylnaphthylsilyl group, a dimethylanthrylsilyl group, a diethylanthrylsilyl group, a dipropylanthrylsilyl group, a dibutylanthrylsilyl group, a dipentylanthrylsilyl group, a diheptylanthrylsilyl group, a dihexylanthrylsilyl group, and a diphenylmethyl group. Preferred are a dimethylphenylsilyl group, a diethylphenylsilyl group, and a diphenylmethyl group.

Specific examples of the aryl group include a phenyl group, a 2-methylphenyl group, a 3-methylphenyl group, a 4-methylphenyl group, a 4-ethylphenyl group, a biphenylyl group, a 4-methylbiphenylyl group, a 4-ethylbiphenylyl group, a 4-cyclohexylbiphenylyl group, an anthracenyl group, a naphthacenyl group, a terphenyl group, a triphenylyl group, a 3,5-dichlorophenylyl group, a naphthyl group, a 5-methylnaphthyl group, a phenanthryl group, a chrysenyl group, a benzophenanthryl group, a terphenyl group, a benzanthranyl group, a benzochrysenyl group, a pentacenyl group, a picenyl group, a pentaphenyl group, a pyrenyl group, a chrysenyl group, a fluorenyl group, an indenyl group, an acenaphthylenyl group, a fluoranthenyl group, and a perylenyl group. Preferred are a phenyl group, a biphenylyl group, and a naphthyl group. Specific examples of the halogen atom include fluorine, chlorine, and bromine.

Specific examples of the saturated or unsaturated ring which the plurality of $R^1$'s to $R^6$'s are bonded to themselves, or $R^1$ and $R^2$, $R^3$ and $R^4$, or $R^5$ and $R^6$ are bonded to each other, to form include the aryl groups and cycloalkyl groups, and heteroaryl groups to be described later.

The skeletal structure of the substituent A represented by the general formula (1) from which $L^1$, $R^1$, and $R^2$ are removed, and the skeletal structure of the substituent B represented by the general formula (2) from which $L^2$, $R^3$, and $R^4$ are removed and in which X represents an oxygen atom are specifically, for example, the following skeletal structures.

[Chem. 10]

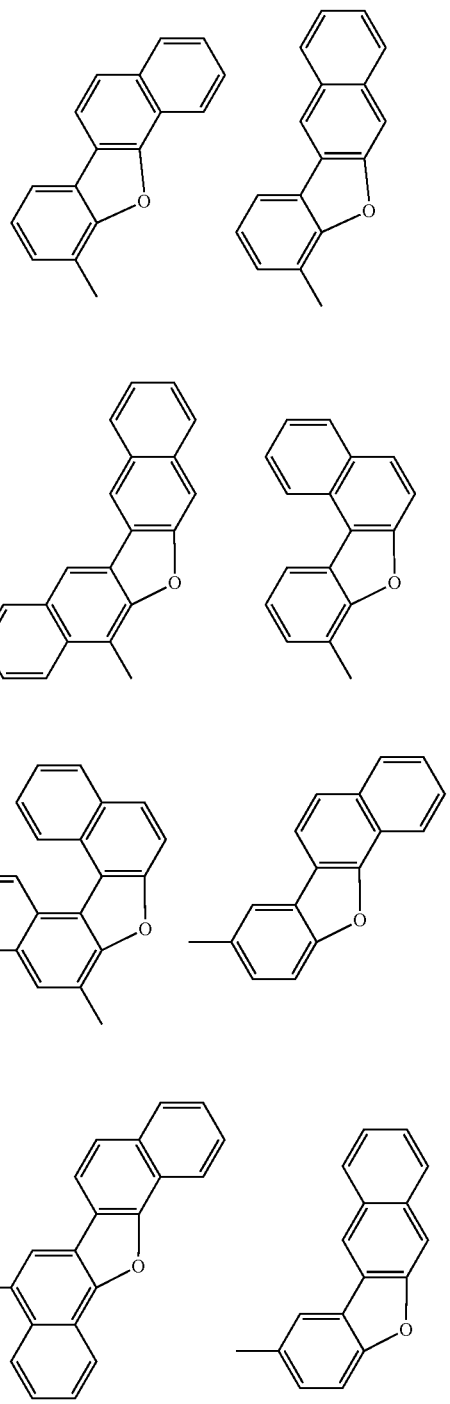

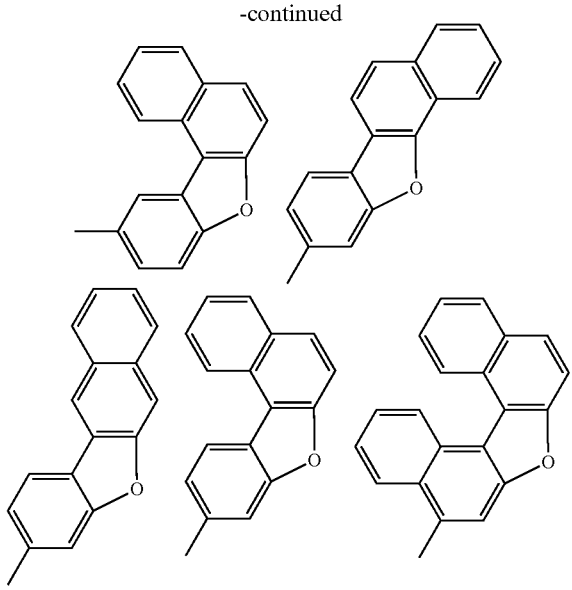

In the general formulae (1) to (3), (1-1) to (1-3), and (2-1):

a, c, e, and f each independently represent an integer of 0 to 3, and b and d each independently represent an integer of 0 to 4; and $L^1$ and $L^2$ each independently represent a single bond, or a substituted or unsubstituted arylene group having 6 to 50, preferably 6 to 21, more preferably 6 to 15, ring carbon atoms, and $L^3$ represents a substituted or unsubstituted arylene group having 6 to 50, preferably 6 to 21, more preferably 6 to 15, ring carbon atoms, provided that a substituent which any one of $L^1$ to $L^3$ may have is a linear or branched alkyl group having 1 to 10, preferably 1 to 6, carbon atoms, a cycloalkyl group having 3 to 10, preferably 5 to 7, ring carbon atoms, a trialkylsilyl group having 3 to 10, preferably 3 to 6, carbon atoms, a triarylsilyl group having 18 to 30, preferably 18 to 24, ring carbon atoms, an alkylarylsilyl group having 8 to 15, preferably 8 to 12, carbon atoms (its aryl portion has 6 to 14, preferably 6 to 12, ring carbon atoms), an aryl group having 6 to 16, preferably 6 to 10, ring carbon atoms, a halogen atom (a fluorine atom is preferred), or a cyano group.

When the linking groups $L^1$ and $L^2$ are single bonds, and a dibenzofuran structure or a carbazole structure is directly bonded to a nitrogen atom, the electron density of the amine compound increases and the IP of the compound can be reduced. On the other hand, when any such structure is bonded to a nitrogen atom through the linking group $L^1$ or $L^2$ serving as a substituted or unsubstituted arylene group, an increase in the electron density of the amine compound is suppressed and the IP can be increased.

When the aromatic amine derivative is represented by the general formula (5) to be described later, $L^1$ and $L^2$ each preferably represent a substituted or unsubstituted arylene group.

That is, the IP of the amine compound can be adjusted by selecting the linking groups $L^1$ and $L^2$. When the IP is set to a value suitable as a hole injecting material or hole transporting material, the property by which holes are injected into the light emitting layer is improved, and hence a reduction in the voltage at which the device is driven can be expected.

Specific examples of the arylene group represented by any one of $L^1$ to $L^3$ include arylene groups such as a phenylene group, a biphenylene group, a terphenylene group, a tetrafluorophenylene group, a dimethylphenylene group, a naphthylene group, an anthranylene group, a phenanthrylene group, a pyrenylene group, a naphthacenylene group, a quarterphenylene group, a pentacenylene group, a perylenylene group, a pyrenylene group, a coronylene group, a fluorenylene group, an acenaphthofluorenylene group, and a 9,9-dimethylfluorenylene group.

In the general formulae (1) to (3), (1-1) to (1-3), and (2-1), an arylene group represented by any one of $L^1$ to $L^3$ is preferably represented by any one of the following general formulae (4), (10), and (11).

In each of the general formulae (2) and (2-1) in the case where X represents a —N(Ar¹)— group, when an arylene group represented by $L^2$ is represented by the general formula (4), an increase in the electron density of the amine compound is suppressed, and as a result, the IP increases. When the compound is used as a hole transporting material, the property by which holes are injected into the light emitting layer is improved, and hence a reduction in the voltage at which the device is driven can be expected. In particular, when the aromatic amine derivative of the present invention has a dibenzofuran structure-containing group and a carbazole structure-containing group, specifically, when the derivative has the substituent A represented by the general formula (1) and the substituent B represented by the general formula (2-1) or (3), an arylene group represented by $L_2$ or $L_3$ in the substituent B is preferably represented by the general formula (4).

When the substituent B is represented by the general formula (3), an improvement in the luminous efficiency, and the lengthening of the lifetime, of the device can be expected because the aromatic amine derivative has so large an energy gap as to be capable of suppressing the injection of electrons into a hole transporting layer. In particular, when the aromatic amine derivative is an amine having the substituent A having a dibenzofuran structure and the substituent B having a carbazole structure, the substituent B is preferably represented by the general formula (3).

When the aromatic amine derivative of the present invention has the plurality of substituents A, the plurality of substituents A are preferably groups different from each other. In addition, when the aromatic amine derivative of the present invention has the plurality of substituents B, the plurality of substituents B are preferably groups different from each other. When the substituents A and/or the substituents B are groups different from each other, the molecular symmetry can be further reduced, and hence additional suppression of the crystallization can be expected.

In addition, the substituent having a dibenzofuran structure is preferably represented by the formula (1-1) or (1-2) out of the formulae (1-1), (1-2), and (1-3) from the viewpoints of the ease of synthesis and the ease of purification.

[Chem. 11]

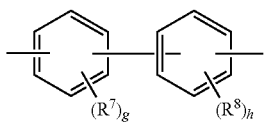

(4)

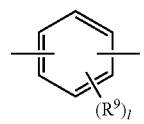

(10)

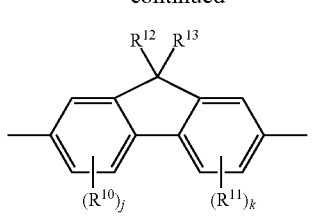

(11)

In the general formulae (4), (10), and (11), $R^7$ to $R^{11}$ each independently represent a linear or branched alkyl group having 1 to 10, preferably 1 to 6, carbon atoms, a cycloalkyl group having 3 to 10, preferably 5 to 7, ring carbon atoms, a trialkylsilyl group having 3 to 10, preferably 3 to 6, carbon atoms, a triarylsilyl group having 18 to 30, preferably 18 to 24, ring carbon atoms, an alkylarylsilyl group having 8 to 15, preferably 8 to 12, carbon atoms (its aryl portion has 6 to 14, preferably 6 to 10, ring carbon atoms), an aryl group having 6 to 14, preferably 6 to 10, ring carbon atoms, a halogen atom (a fluorine atom is preferred), or a cyano group, and a plurality of $R^7$'s to $R^{11}$'s adjacent to each other may be bonded to each other to form a saturated or unsaturated ring.

Specific examples and preferred examples of the alkyl group, cycloalkyl group, trialkylsilyl group, triarylsilyl group, alkylarylsilyl group, aryl group, and halogen atom each represented by any one of $R^7$ to $R^{11}$ in the general formulae (4), (10), and (11) are the same as those listed in the description of the $R^1$ to $R^{16}$. $R^7$ To $R^{11}$ each preferably represent a methyl group, an ethyl group, a propyl group, an isopropyl group, an n-butyl group, an isobutyl group, an sec-butyl group, or a tert-butyl group.

In the general formula (11), $R^{12}$ and $R^{13}$ each independently represent a linear or branched alkyl group having 1 to 10, preferably 1 to 6, carbon atoms, or a cycloalkyl group having 3 to 10, preferably 5 to 7, ring carbon atoms. Specific examples and preferred examples of the alkyl group and cycloalkyl group are the same as those listed in the description of the $R^1$ to $R^6$.

In the general formulae (4), (10), and (11), g, h, and i each independently represent an integer of 0 to 4, preferably an integer of 0 or 1, and j and k each independently represent an integer of 0 to 3, preferably an integer of 0 or 1.

The substituents of $L^1$ to $L^6$ in the general formulae (1) to (3), (1-1) to (1-3), and (2-1) are each a linear or branched alkyl group having 1 to 10, preferably 1 to 6, carbon atoms, a cycloalkyl group having 3 to 10, preferably 5 to 7, ring carbon atoms, a trialkylsilyl group having 3 to 10, preferably 3 to 6, ring carbon atoms, a triarylsilyl group having 18 to 30, preferably 18 to 24, ring carbon atoms, an alkylarylsilyl group having 8 to 15, preferably 8 to 12, carbon atoms (its aryl portion has 6 to 14, preferably 6 to 10, ring carbon atoms), an aryl group having 6 to 14, preferably 6 to 10, ring carbon atoms, a halogen atom, or a cyano group.

Specific examples and preferred examples of the alkyl group, cycloalkyl group, trialkylsilyl group, triarylsilyl group, alkylarylsilyl group, aryl group, and halogen atom are the same as those listed in the description of the $R^1$ to $R^6$.

Preferred specific examples of the general formulae (8) to (10) include a substituted or unsubstituted phenylene group, a substituted or unsubstituted biphenylene group, and a substituted or unsubstituted 9,9-dimethylfluorenylene group.

In the general formula (2), $Ar^1$ represents a substituted or unsubstituted aryl group having 6 to 14, preferably 6 to 10, ring carbon atoms. Specific examples and preferred examples of the aryl group are the same as those listed in the description of the $R^1$ to $R^6$.

The substituents of the aryl group are each independently a linear or branched alkyl group having 1 to 10, preferably 1 to 6, carbon atoms, a cycloalkyl group having 3 to 10, preferably 5 to 7, ring carbon atoms, a trialkylsilyl group having 3 to 10, preferably 3 to 6, carbon atoms, a triarylsilyl group having 18 to 30, preferably 18 to 24, ring carbon atoms, an alkylarylsilyl group having 8 to 15, preferably 8 to 12, carbon atoms (its aryl portion has 6 to 14 ring carbon atoms), an aryl group having 6 to 16, preferably 6 to 10, ring carbon atoms, a halogen atom (a fluorine atom is preferred), or a cyano group.

Specific examples and preferred examples of the alkyl group, cycloalkyl group, trialkylsilyl group, triarylsilyl group, alkylarylsilyl group, and aryl group are the same as those listed in the description of the $R^1$ to $R^6$.

Next, the compounds represented by the general formulae (5) to (9) are described.

In the general formula (5), at least one of $Ar^2$ to $Ar^4$ represents the substituent A represented by the general formula (1), at least one of $Ar^2$ to $Ar^4$ represents the substituent B represented by the general formula (2) or (3), and the substituent A and the substituent B are groups different from each other.

In the general formula (6), at least one of $Ar^5$ to $Ar^8$ represents the substituent A represented by the general formula (1), at least one of $Ar^5$ to $Ar^8$ represents the substituent B represented by the general formula (2) or (3), and the substituent A and the substituent B are groups different from each other.

In the general formula (7), at least one of $Ar^9$ to $Ar^{13}$ represents the substituent A represented by the general formula (1), at least one of $Ar^9$ to $Ar^{13}$ represents the substituent B represented by the general formula (2) or (3), and the substituent A and the substituent B are groups different from each other.

In the general formula (8), at least one of $Ar^{14}$ to $Ar^{19}$ represents the substituent A represented by the general formula (1), at least one of $Ar^{14}$ to $Ar^{19}$ represents the substituent B represented by the general formula (2) or (3), and the substituent A and the substituent B are groups different from each other.

In the general formula (9), at least one of $Ar^{20}$ to $Ar^{25}$ represents the substituent A represented by the general formula (1), at least one of $Ar^{20}$ to $Ar^{25}$ represents the substituent B represented by the general formula (2) or (3), and the substituent A and the substituent B are groups different from each other.

In the general formulae (3) to (7), groups out of $Ar^2$ to $Ar^{25}$ except the substituent A and the substituent B are each independently a substituted or unsubstituted aryl group having 6 to 50, preferably 6 to 21, more preferably 6 to 14, ring carbon atoms, and specific examples and preferred examples of the aryl group are the same as those listed in the description of the $R^1$ to $R^6$. The aryl group is particularly preferably a terphenyl group. When the aromatic amine derivative has a terphenyl group excellent in reduction stability, the reduction stability of any one of its molecules is improved, and a lengthening effect on the lifetime of an organic EL device to be obtained is exerted. In particular, a combination of the derivative and a blue light emitting device exerts a significant lifetime-lengthening effect.

Specific examples and preferred examples of the substituents of $Ar^2$ to $Ar^{25}$ are the same as those listed in the description of the $R^1$ to $R^6$.

In the general formulae (5) to (9), $L^4$ to $L^{12}$ each independently represent a substituted or unsubstituted arylene group having 6 to 50, preferably 6 to 21, more preferably 6 to 15, ring carbon atoms. Specific examples and preferred examples of the arylene group represented by any one of $L^4$ to $L^{12}$ are the same as those listed in $L^1$ to $L^3$ described for the general formulae (1) to (3), (1-1) to (1-3), and (2-1).

When $Ar^2$ to $Ar^{25}$ in the general formulae (5) to (9) are each the substituent A or the substituent B, $R^1$ to $R^6$, $L^1$ to $L^3$, and a to f in the general formulae (1) to (3), (1-1) to (1-3), and (2-1) are as described for the aromatic amine derivative represented by the general formula (1).

The aromatic amine derivative represented by any one of the general formulae (5) to (9) is preferably a compound having any such combination as described below.

(I) The aromatic amine derivative, in which the aromatic amine derivative includes an aromatic amine derivative represented by the general formula (5) in which the $Ar^2$ is represented by the general formula (1), and the $Ar^3$ and the $Ar^4$ are each independently represented by the general formula (3) or (2-1).

(II) The aromatic amine derivative, in which the aromatic amine derivative includes an aromatic amine derivative represented by the general formula (5) in which the $Ar^2$ and the $Ar^3$ are each represented by the general formula (1), and the $Ar^4$ is represented by the general formula (3) or (2-1).

(III) The aromatic amine derivative, in which the aromatic amine derivative includes an aromatic amine derivative represented by the general formula (5) in which the $Ar^2$ is represented by the general formula (1), the $Ar^3$ is represented by the general formula (3) or (2-1), and the $Ar^4$ represents a substituted or unsubstituted aryl group having 6 to 50 ring carbon atoms, provided that substituents of the $Ar^4$ each independently include any one of an aryl group having 6 to 50 ring carbon atoms, a branched or linear alkyl group having 1 to 50 carbon atoms, a halogen atom, and a cyano group.

(IV) The aromatic amine derivative, in which the aromatic amine derivative includes an aromatic amine derivative represented by the general formula (6) in which the $Ar^5$ and the $Ar^6$ are each represented by the general formula (1), and the $Ar^7$ and the $Ar^8$ are each independently represented by the general formula (3) or (2-1).

(V) The aromatic amine derivative, in which the aromatic amine derivative includes an aromatic amine derivative represented by the general formula (6) in which the $Ar^5$ and the $Ar^7$ are each represented by the general formula (1), and the $Ar^6$ and the $Ar^8$ are each independently represented by the general formula (3) or (2-1).

(VI) The aromatic amine derivative, in which the aromatic amine derivative includes an aromatic amine derivative represented by the general formula (7) in which the $Ar^9$ is represented by the general formula (1), and the $Ar^{11}$ and the $Ar^{12}$ are each independently represented by the general formula (3) or (2-1).

(VII) The aromatic amine derivative, in which the aromatic amine derivative includes an aromatic amine derivative represented by the general formula (7) in which the $Ar^{11}$ and the $Ar^{12}$ are each represented by the general formula (1), and the $Ar^9$ is represented by the general formula (3) or (2-1).

(VIII) The aromatic amine derivative, in which the aromatic amine derivative includes an aromatic amine derivative represented by the general formula (8) in which the $Ar^{14}$ and the $Ar^{19}$ are each represented by the general formula (1), and the $Ar^{16}$ and the $Ar^{17}$ are each independently represented by the general formula (3) or (1).

(IX) The aromatic amine derivative, in which the aromatic amine derivative includes an aromatic amine derivative represented by the general formula (8) in which the $Ar^{16}$ and the $Ar^{17}$ are each represented by the general formula (1-1), and the $Ar^{14}$ and the $Ar^{19}$ are each independently represented by the general formula (3) or (2-1).

(X) The aromatic amine derivative, in which the aromatic amine derivative includes an aromatic amine derivative represented by the general formula (9) in which the $Ar^{20}$, the $Ar^{22}$, and the $Ar^{24}$ are each represented by the general formula (1), and the $Ar^{21}$, the $Ar^{23}$, and the $Ar^{25}$ are each independently represented by the general formula (3) or (2-1).

(XI) The aromatic amine derivative, in which the aromatic amine derivative includes an aromatic amine derivative represented by the general formula (5) in which the $Ar^2$ to $Ar^4$ are each represented by the general formula (1-3).

(XII) The aromatic amine derivative, in which the aromatic amine derivative includes an aromatic amine derivative represented by the general formula (5) in which the $Ar^2$ to $Ar^4$ are each represented by the general formula (1-1).

(XIII) The aromatic amine derivative, in which the aromatic amine derivative includes an aromatic amine derivative represented by the general formula (5) in which two of the $Ar^2$ to $Ar^4$ are each represented by the general formula (1-3), and one of the $Ar^2$ to $Ar^4$ represents a substituted or unsubstituted aryl group having 6 to 16 ring carbon atoms.

(XIV) The aromatic amine derivative, in which the aromatic amine derivative includes an aromatic amine derivative represented by the general formula (5) in which two of the $Ar^2$ to $Ar^4$ are each represented by the general formula (1-1), and one of the $Ar^2$ to $Ar^4$ represents a substituted or unsubstituted aryl group having 6 to 16 ring carbon atoms.

(XV) The aromatic amine derivative, in which the aromatic amine derivative includes an aromatic amine derivative represented by the general formula (5) in which at least one of the $Ar^2$ to $Ar^4$ is represented by the general formula (1-3), and at least one of the $Ar^2$ to $Ar^4$ is represented by the general formula (1-1).

(XVI) The aromatic amine derivative, in which the aromatic amine derivative includes an aromatic amine derivative represented by the general formula (5) in which the $Ar^2$ is represented by the general formula (1-3), and the $Ar^3$ and the $Ar^4$ are each independently represented by the general formula (1-1).

(XVII) The aromatic amine derivative, in which the aromatic amine derivative includes an aromatic amine derivative represented by the general formula (5) in which the $Ar^2$ and the $Ar^3$ are each represented by the general formula (1-3), and the $Ar^4$ is represented by the general formula (1-1).

(XVIII) The aromatic amine derivative, in which at least two of the $Ar^5$ to $Ar^8$ are each, at least two of the $Ar^9$ to $Ar^{13}$ are each, at least one of the $Ar^{14}$ to $Ar^{19}$ is, or at least one of the $Ar^{20}$ to $Ar^{25}$ is represented by the general formula (1-3) or the general formula (1-1).

(XIX) The aromatic amine derivative, in which the aromatic amine derivative includes any one of an aromatic amine derivative represented by the general formula (6) in which at least one of the $Ar^5$ to $Ar^8$ is represented by the general formula (1-3) and at least one of the $Ar^5$ to $Ar^8$ except the at least one represented by the general formula (1-3) is represented by the general formula (1-1), an aromatic amine derivative represented by the general formula (7) in which at least one of the $Ar^9$ to $Ar^{13}$ is represented by the general formula (1-3) and at least one of the $Ar^9$ to $Ar^{13}$ except the at least one represented by the general formula (1-3) is represented by the general formula (1-1), an aromatic amine derivative represented by the general formula (8) in which at least one of the $Ar^{14}$ to $Ar^{19}$ is represented by the general formula (1-3) and at least one of the $Ar^{14}$ to $Ar^{19}$ except the at least one represented by the general formula (1-3) is represented by the general formula (1-1), and an aromatic amine derivative represented by the general formula (9) in which at least one of the $Ar^{20}$ to $Ar^{25}$ is represented by the following general formula (1-3) and at least one of the $Ar^{20}$ to $Ar^{25}$ except the at least one represented by the general formula (1-3) is represented by the following general formula (1-1).

(XX) The aromatic amine derivative, in which the aromatic amine derivative includes an aromatic amine derivative represented by the general formula (5) in which the $Ar^5$ is represented by the general formula (1-3) and the $Ar^6$ is represented by the general formula (1-1).

(XXI) The aromatic amine derivative, in which the aromatic amine derivative includes an aromatic amine derivative represented by the general formula (5) in which the $Ar^5$ and the $Ar^7$ are each represented by the general formula (1-3) and the $Ar^6$ and the $Ar^8$ are each represented by the general formula (1-1).

(XXII) The aromatic amine derivative, in which the aromatic amine derivative includes an aromatic amine derivative represented by the general formula (6) in which the $Ar^9$ is represented by the general formula (1-3) and the $Ar^{11}$ and the $Ar^{12}$ are each represented by the general formula (1-1).

(XXIII) The aromatic amine derivative, in which the aromatic amine derivative includes an aromatic amine derivative represented by the general formula (6) in which the $Ar^{10}$ and the $Ar^{13}$ are each represented by the general formula (1-3) and the $Ar^{11}$ and the $Ar^{12}$ are each represented by the general formula (1-1).

(XXIV) The aromatic amine derivative, in which the aromatic amine derivative includes an aromatic amine derivative represented by the general formula (8) in which the $Ar^{14}$ and the $Ar^{19}$ are each represented by the general formula (1-3) and the $Ar^{16}$ and the $Ar^{17}$ are each represented by the general formula (1-1).

(XXV) The aromatic amine derivative, in which the aromatic amine derivative includes an aromatic amine derivative represented by the general formula (8) in which the $Ar^{15}$ and the $Ar^{18}$ are each represented by the general formula (1-3) and the $Ar^{16}$ and the $Ar^{17}$ are each represented by the general formula (1-1).

(XXVI) The aromatic amine derivative, in which the aromatic amine derivative includes an aromatic amine derivative represented by the general formula (9) in which the $Ar^{20}$, the $Ar^{22}$, and the $Ar^{24}$ are each represented by the general formula (1-3) and the $Ar^{21}$, the $Ar^{23}$, and the $Ar^{25}$ are each represented by the general formula (1-1).

(XXVII) The aromatic amine derivative, in which groups out of the $Ar^2$ to $Ar^{25}$ except the substituent A and the substituent B each independently represent a phenyl group, a naphthyl group, a biphenyl group, a terphenyl group, or a fluorenyl group.

Specific examples of the aromatic amine derivative represented by any one of the general formulae (5) to (9) include the following compounds.

[Chem. 12]

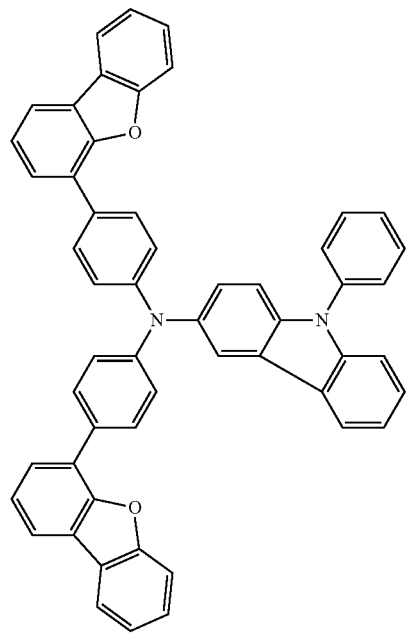

AD-1

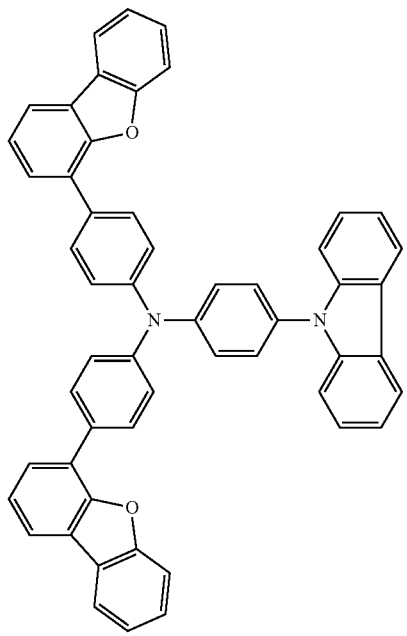

AD-2

-continued
AD-3
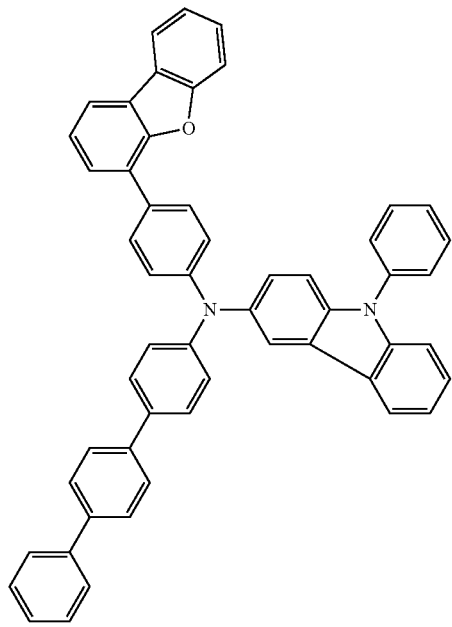
AD-4
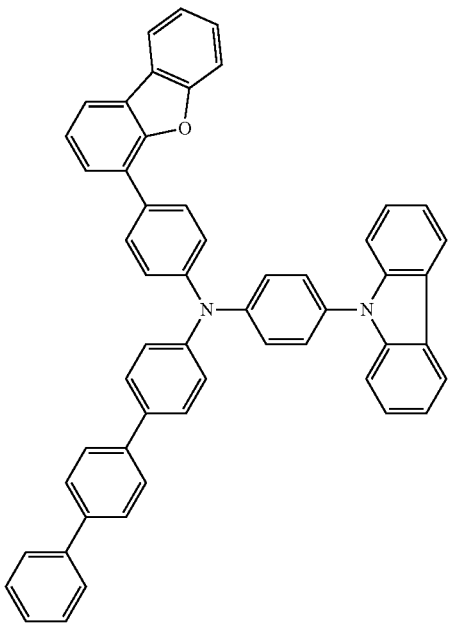
AD-5
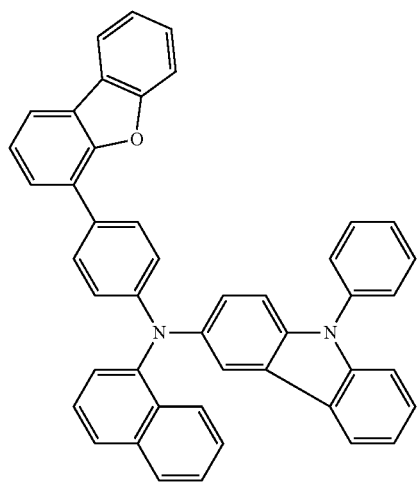
AD-6
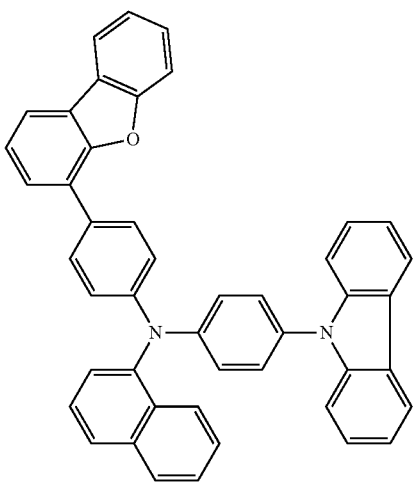
AD-7
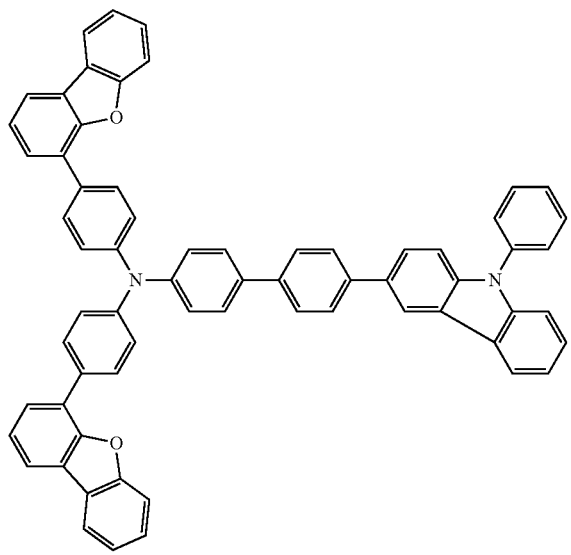
AD-8
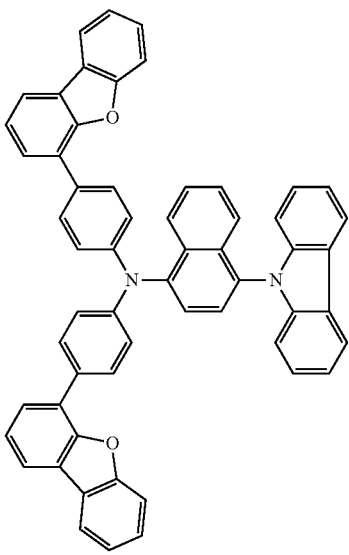

-continued
AD-9
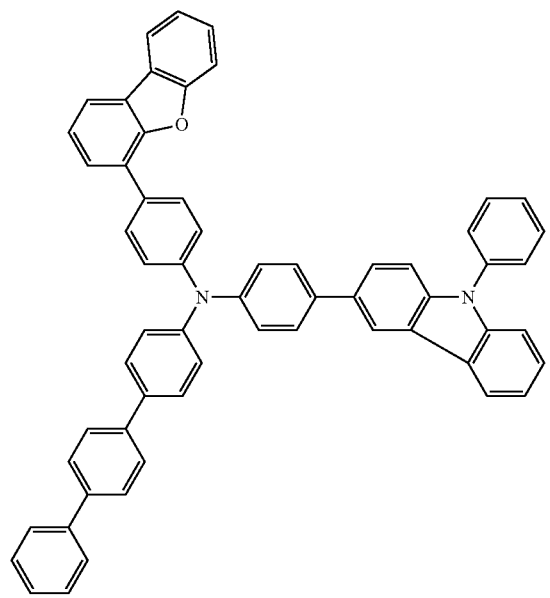
AD-10
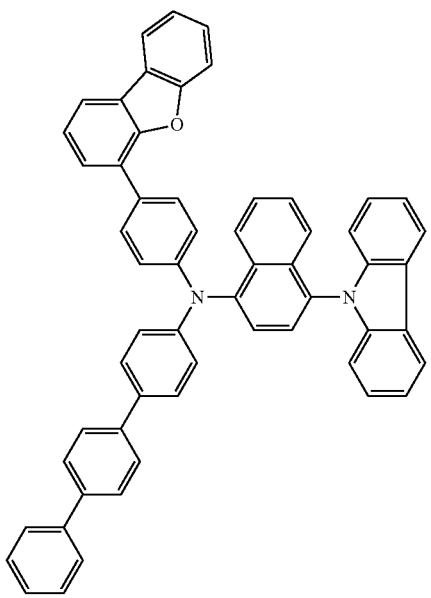
AD-11
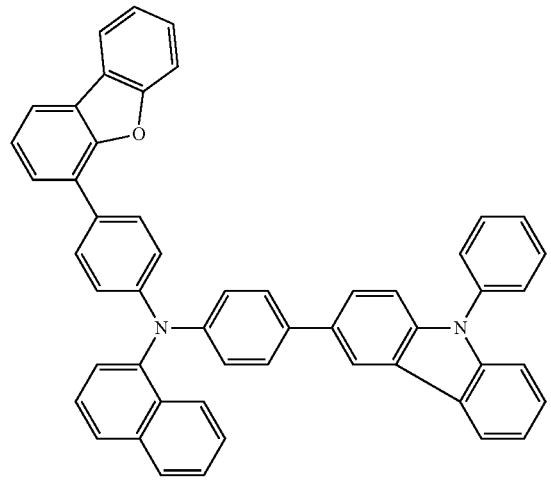
AD-12
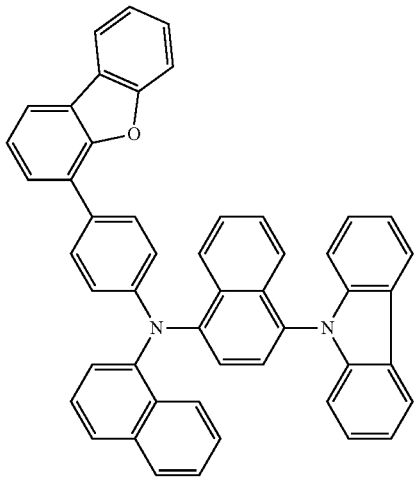

-continued
AD-13
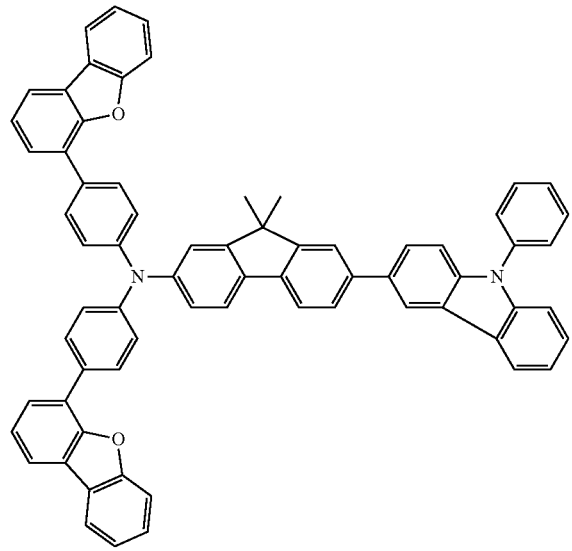
AD-14
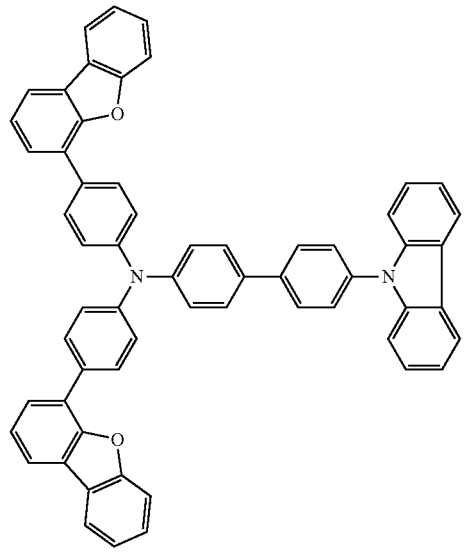
AD-15
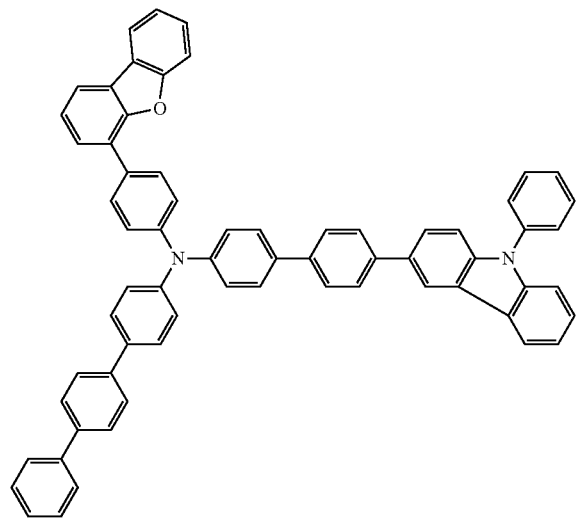
AD-16
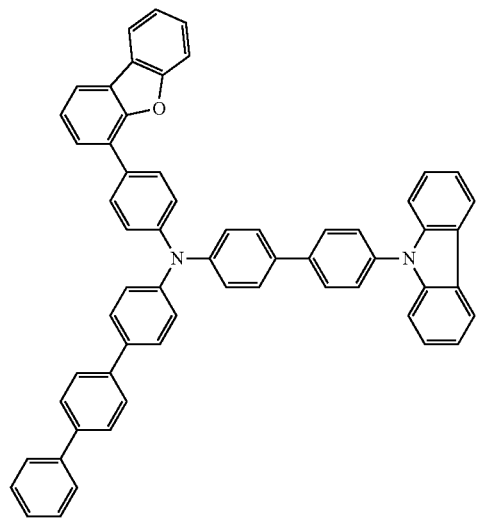
AD-17
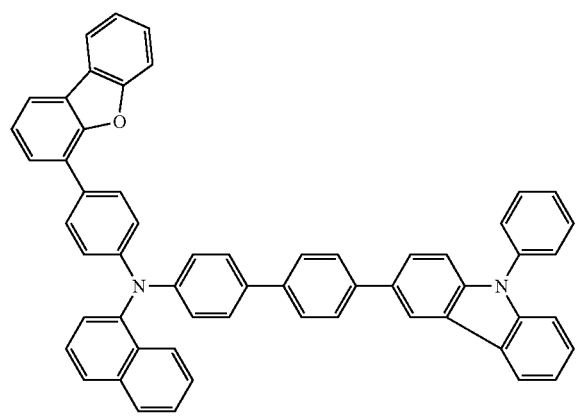
AD-18
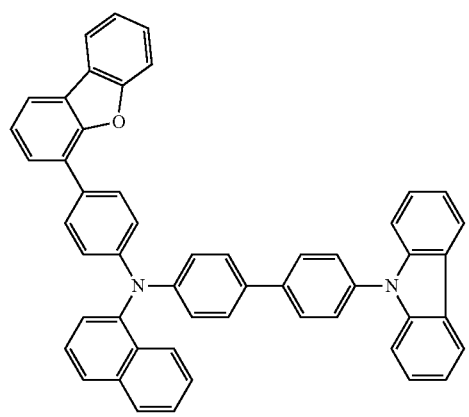

-continued
AD-19
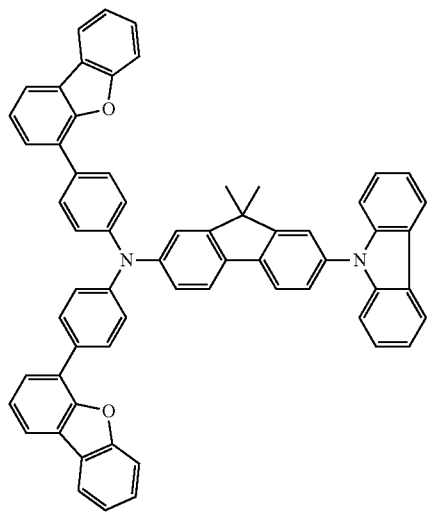
AD-20
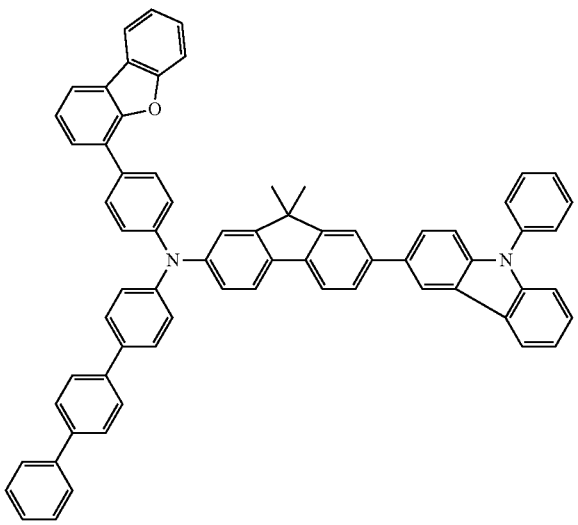
AD-21
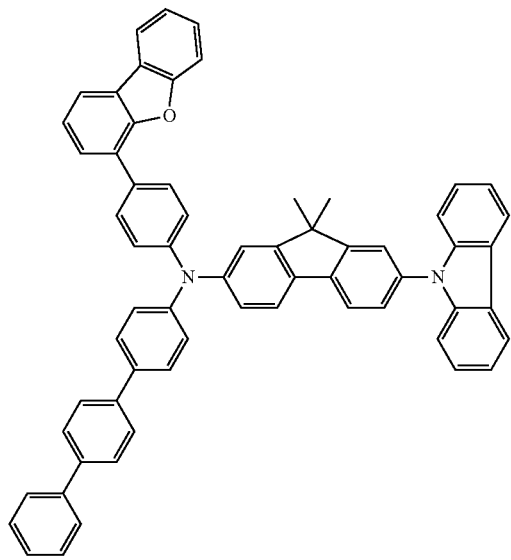
AD-22
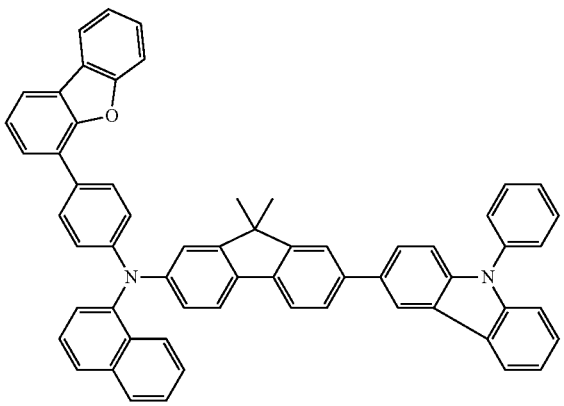
AD-23
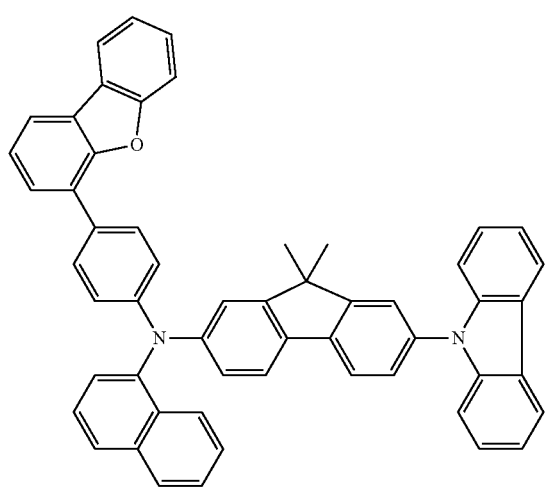

[Chem. 13]
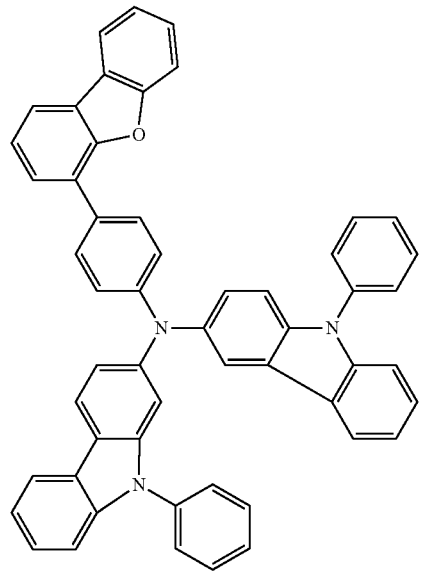
AD-24
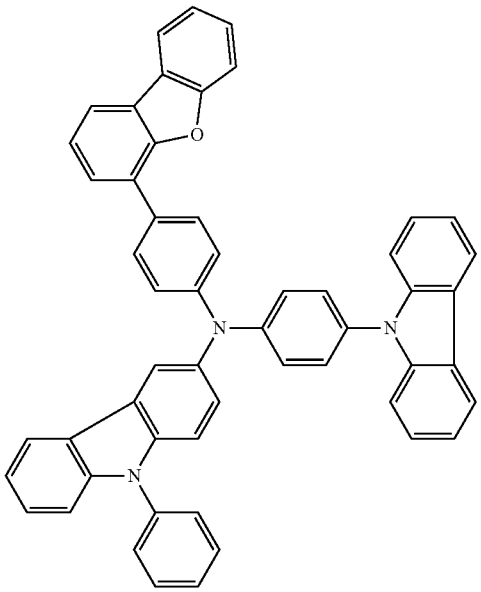
AD-25
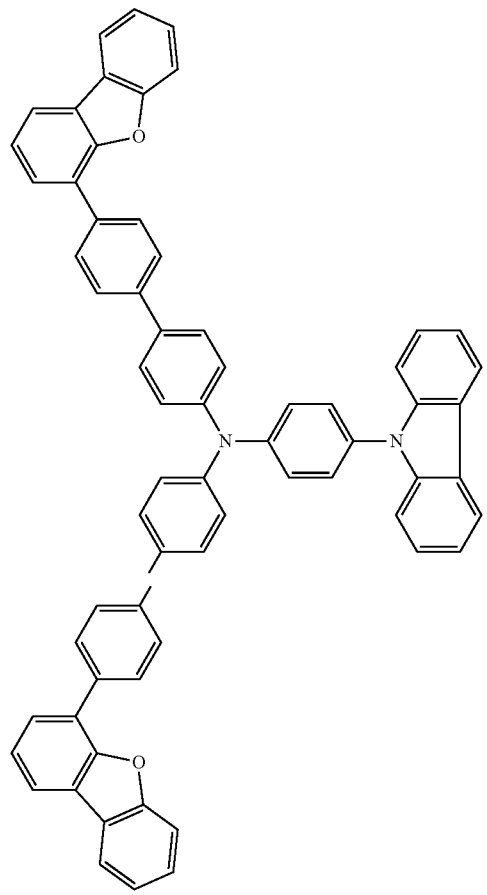
AD-26

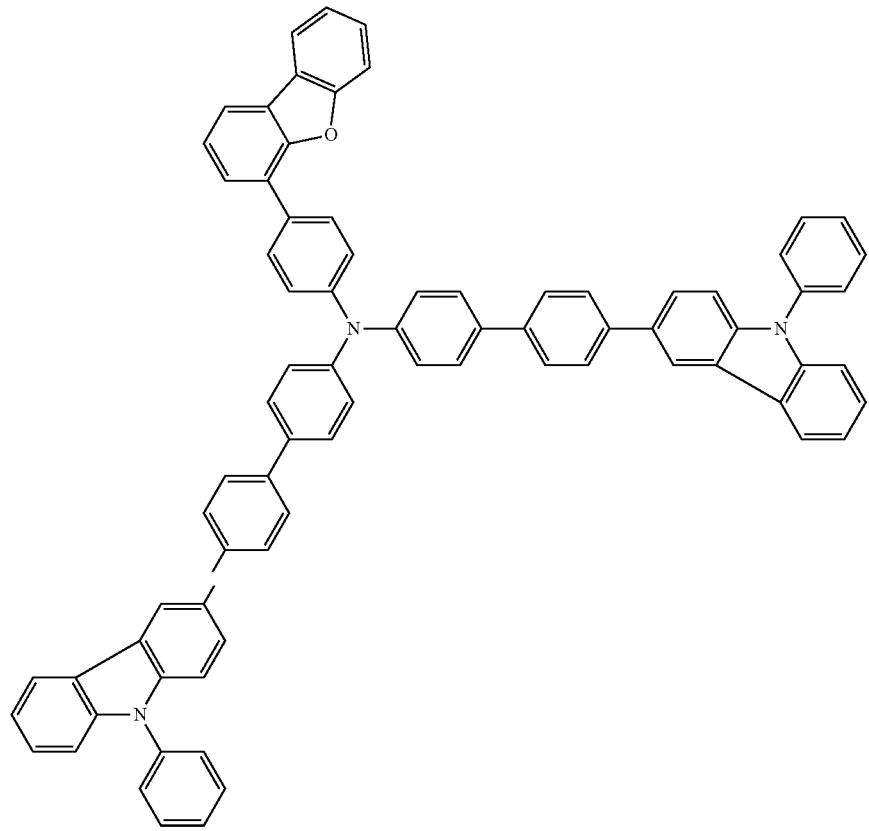
AD-27
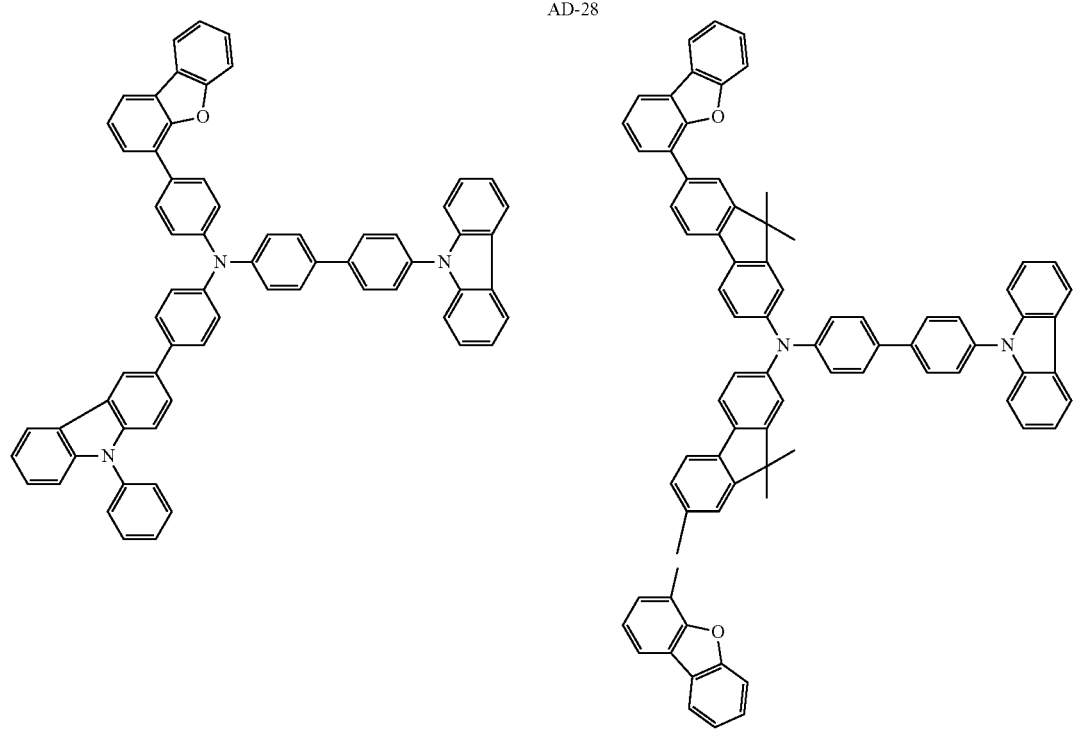
AD-28
AD-29

AD-30
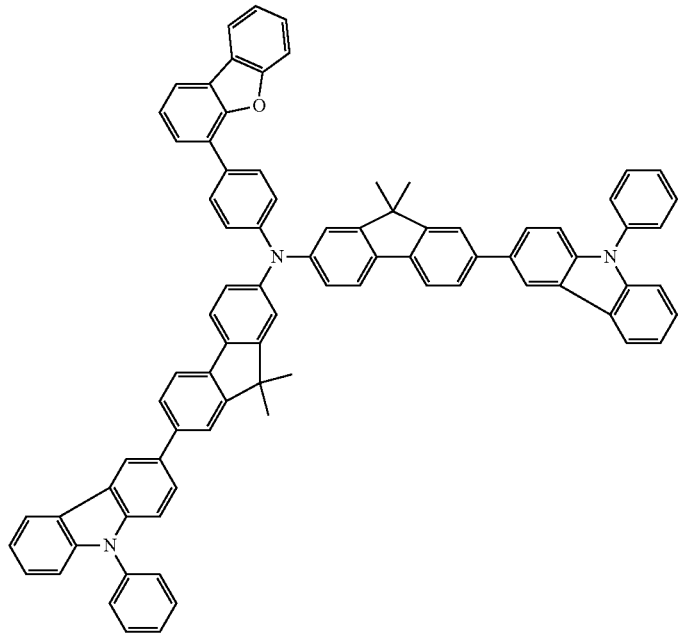
AD-31 AD-32
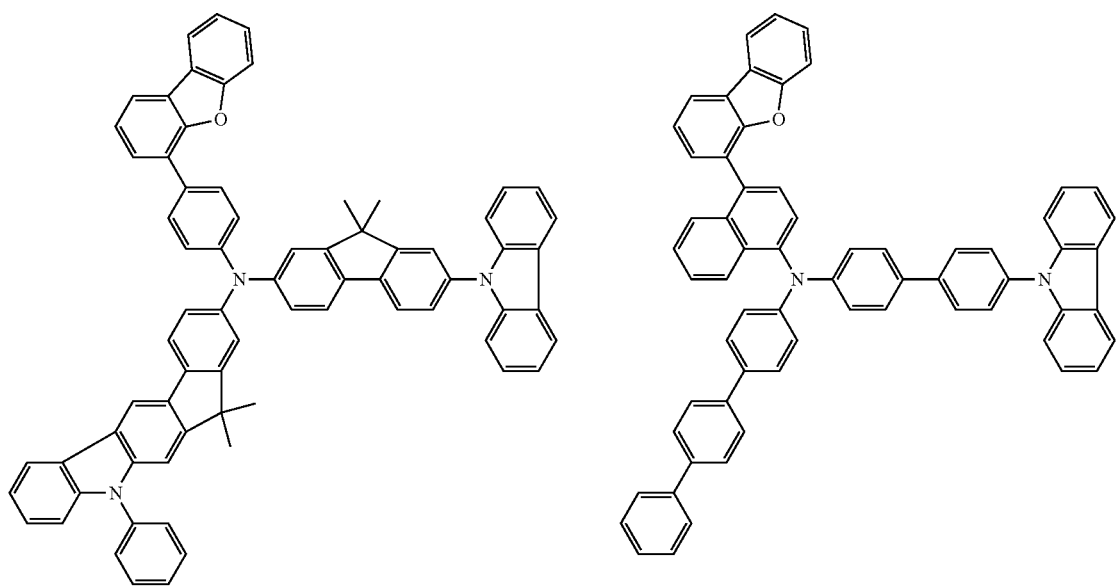

[Chem. 14]
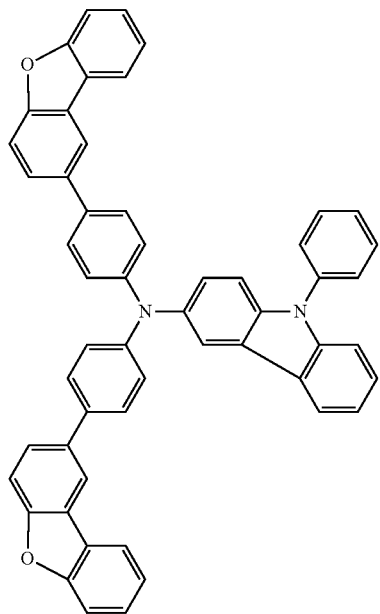
AD-33
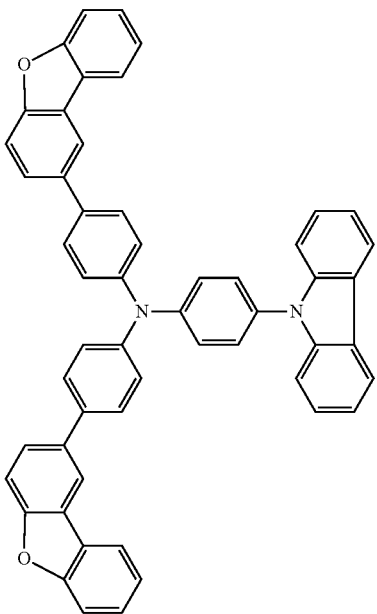
AD-34
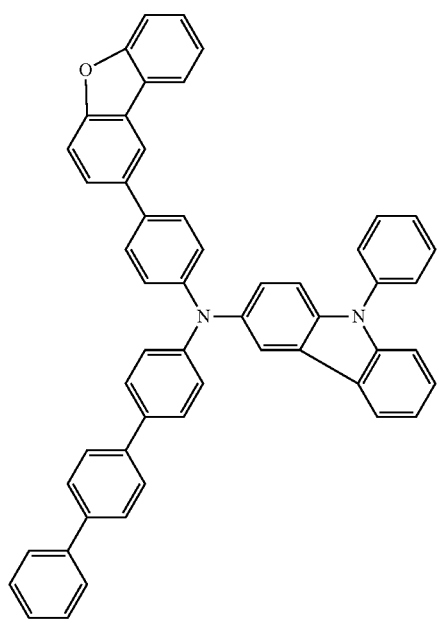
AD-35
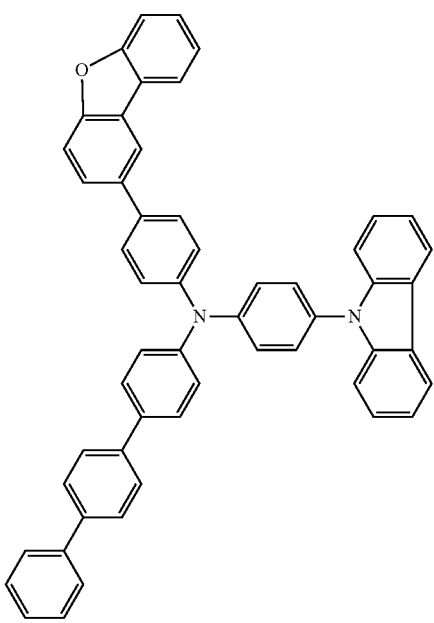
AD-36

AD-37
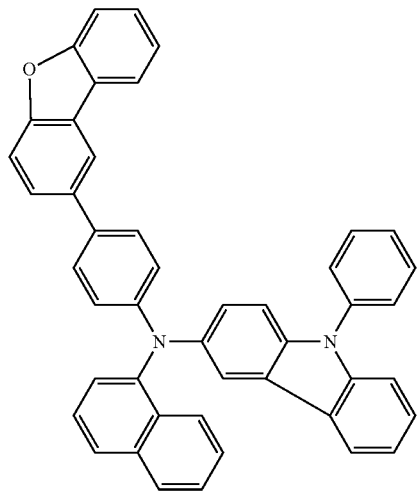
AD-38
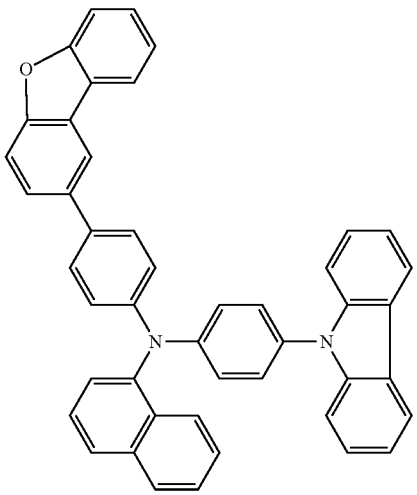
AD-39
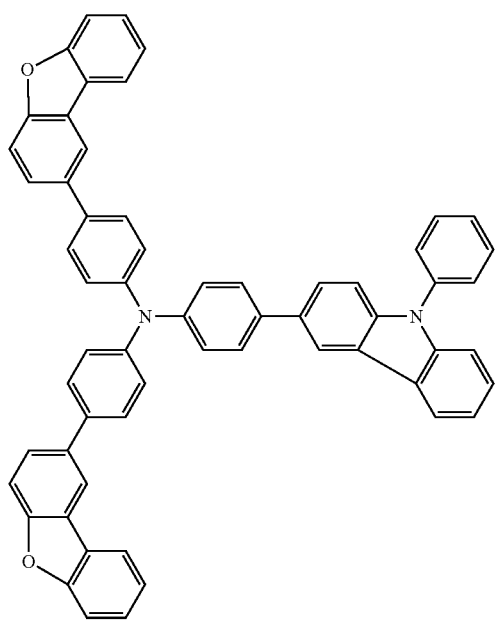
AD-40
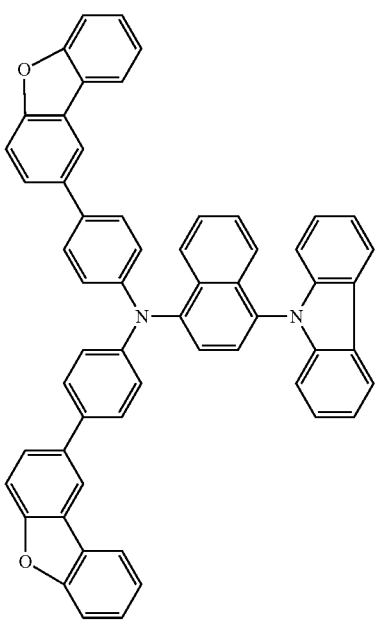

AD-41
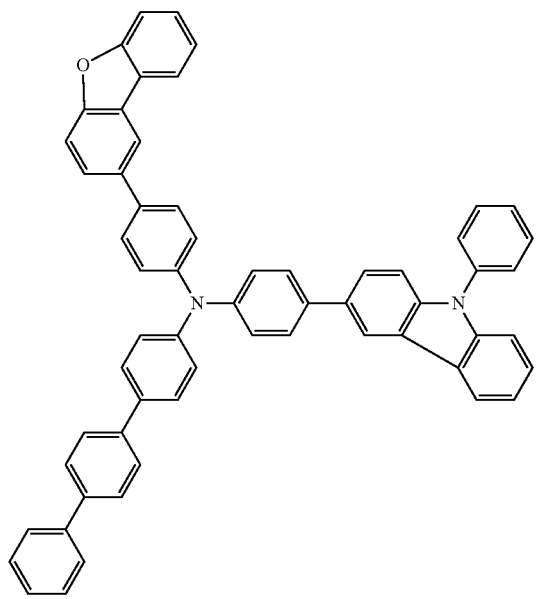
AD-42
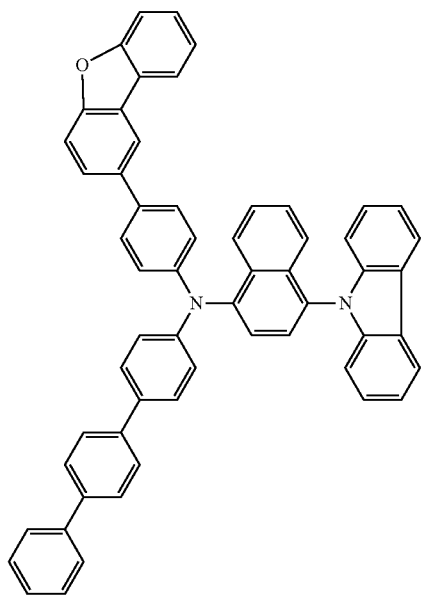
AD-43
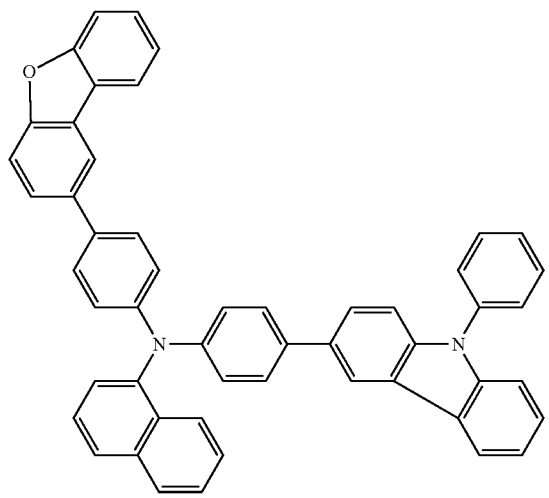
AD-44
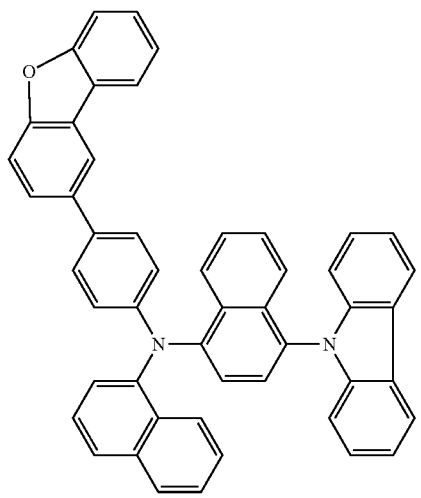

-continued

AD-45

AD-46

AD-47

AD-48

AD-49

AD-50

-continued
AD-51
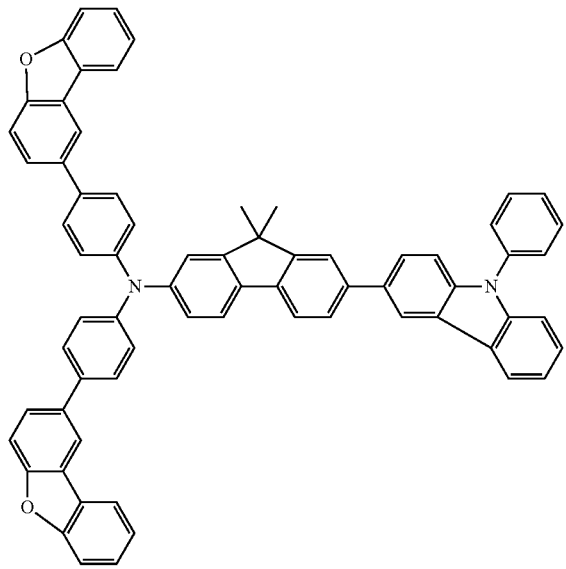
AD-52
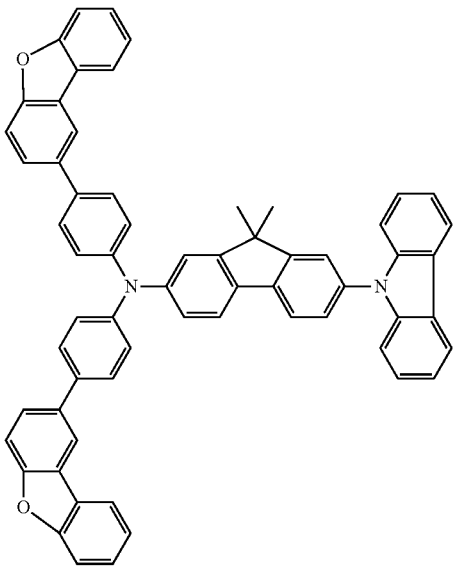
AD-53
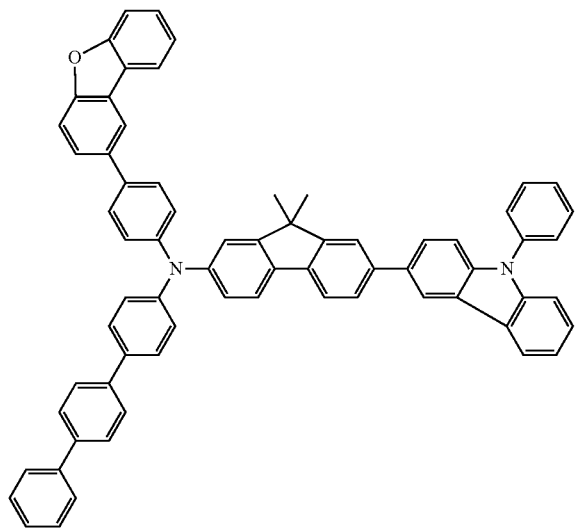
AD-54
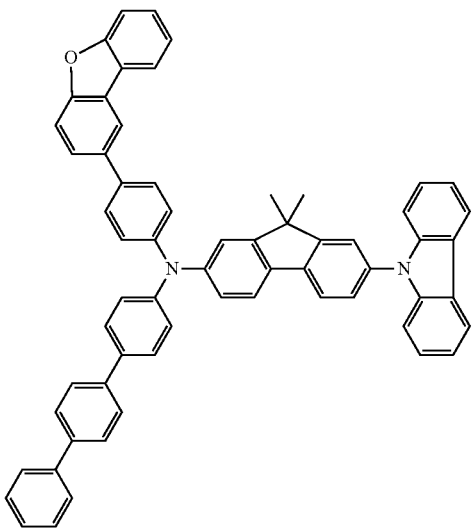
AD-55
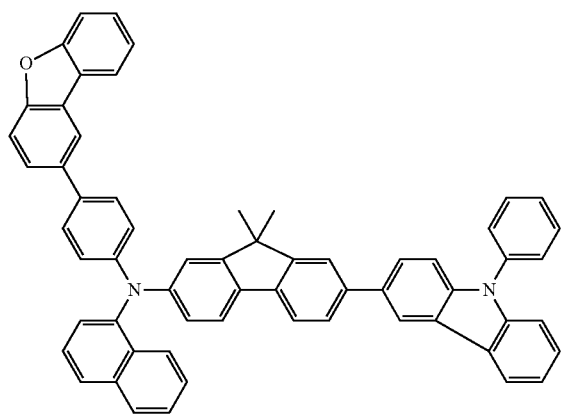
AD-56
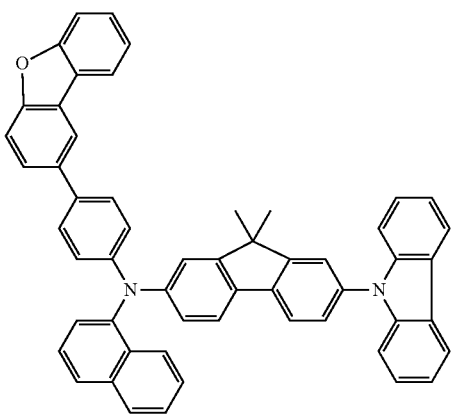

[Chem. 15]
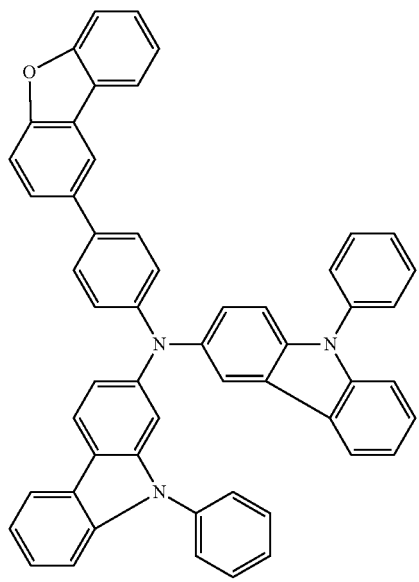
AD-57
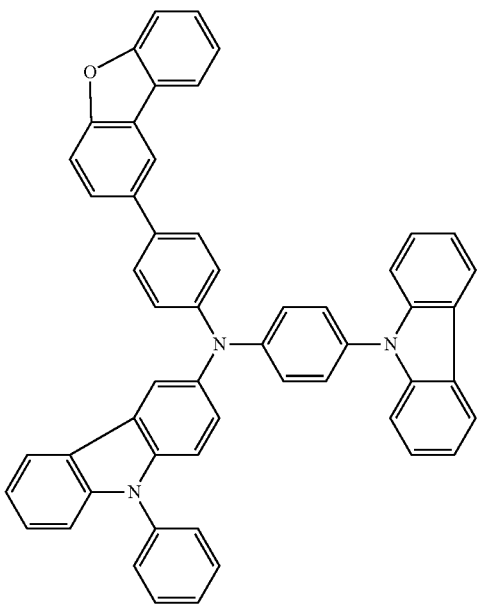
AD-58
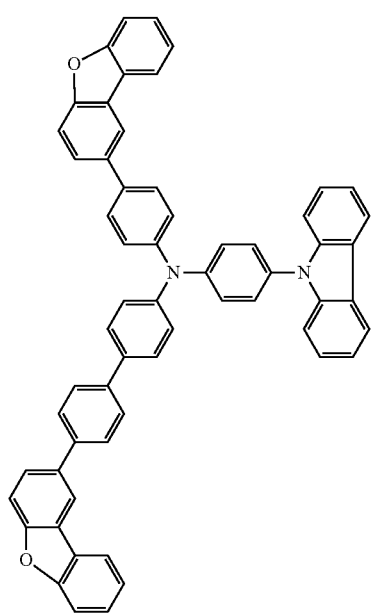
AD-59

AD-60
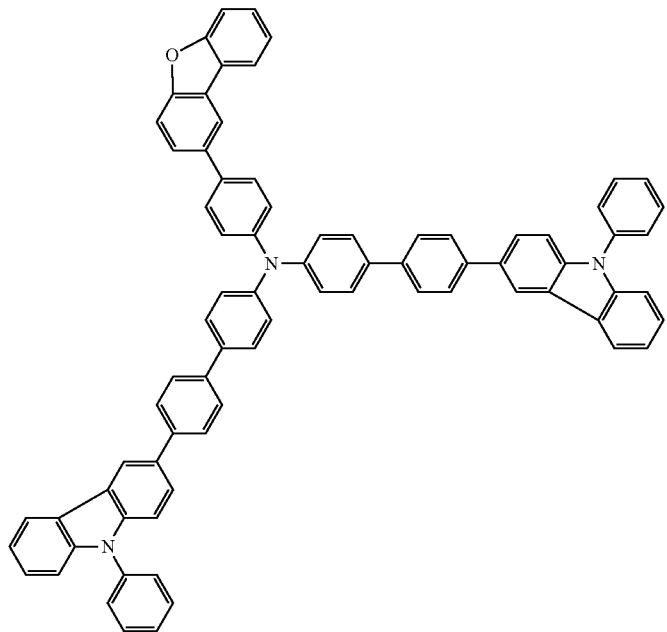
AD-61
AD-62
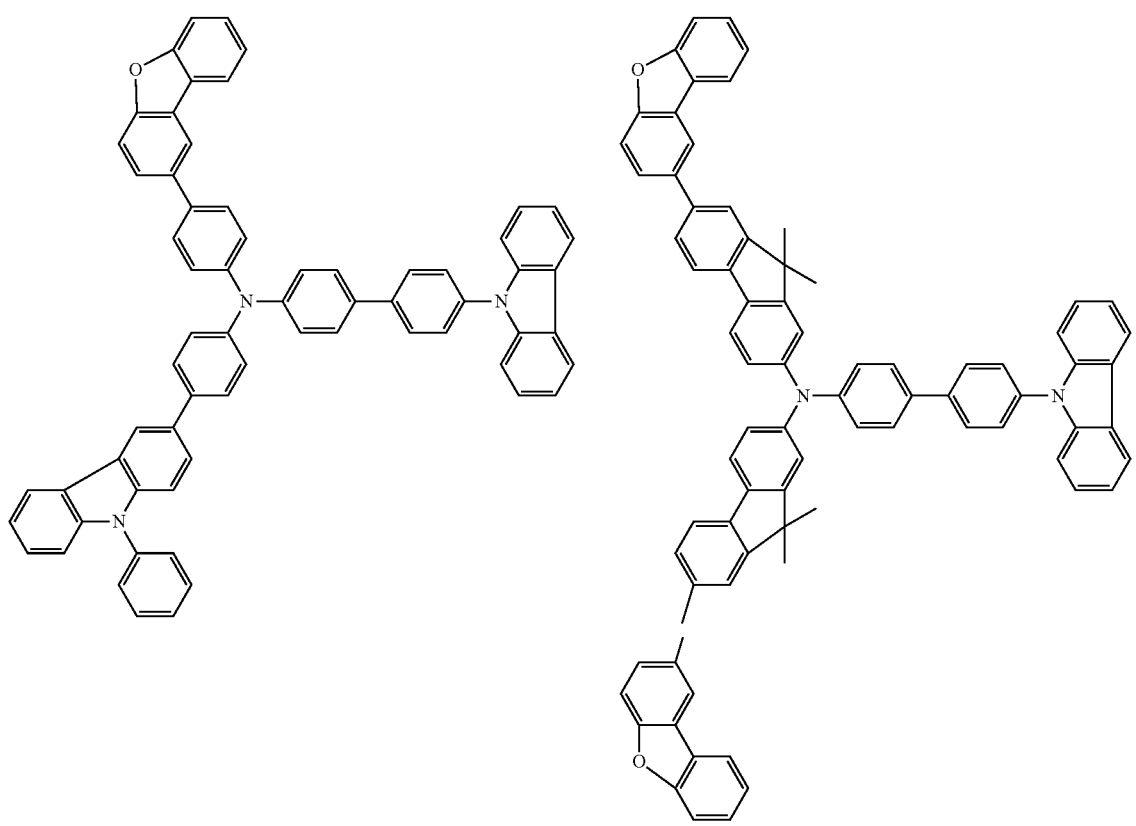

AD-63
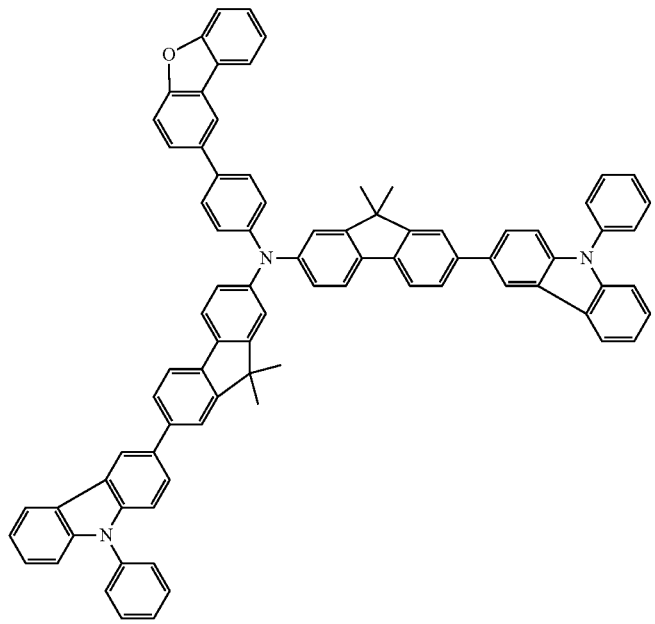
AD-64
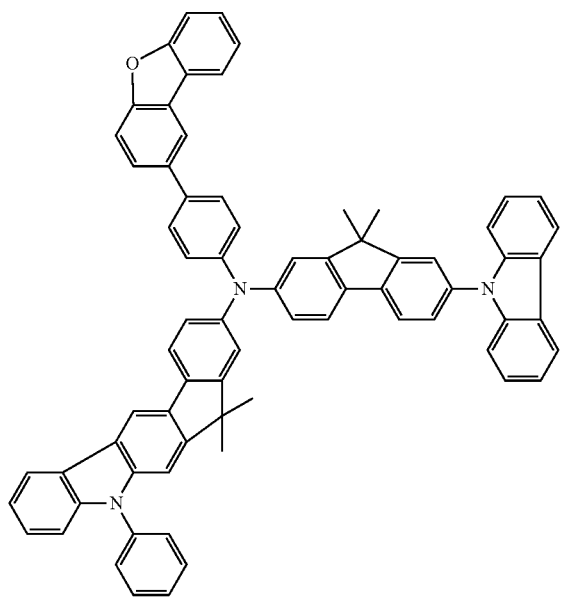
AD-65
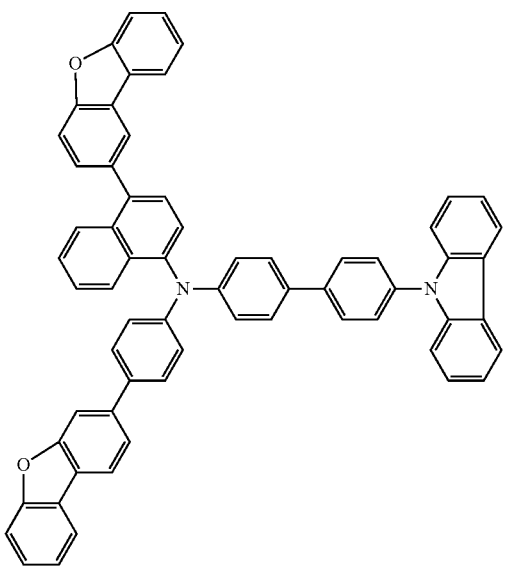

[Chem. 16]
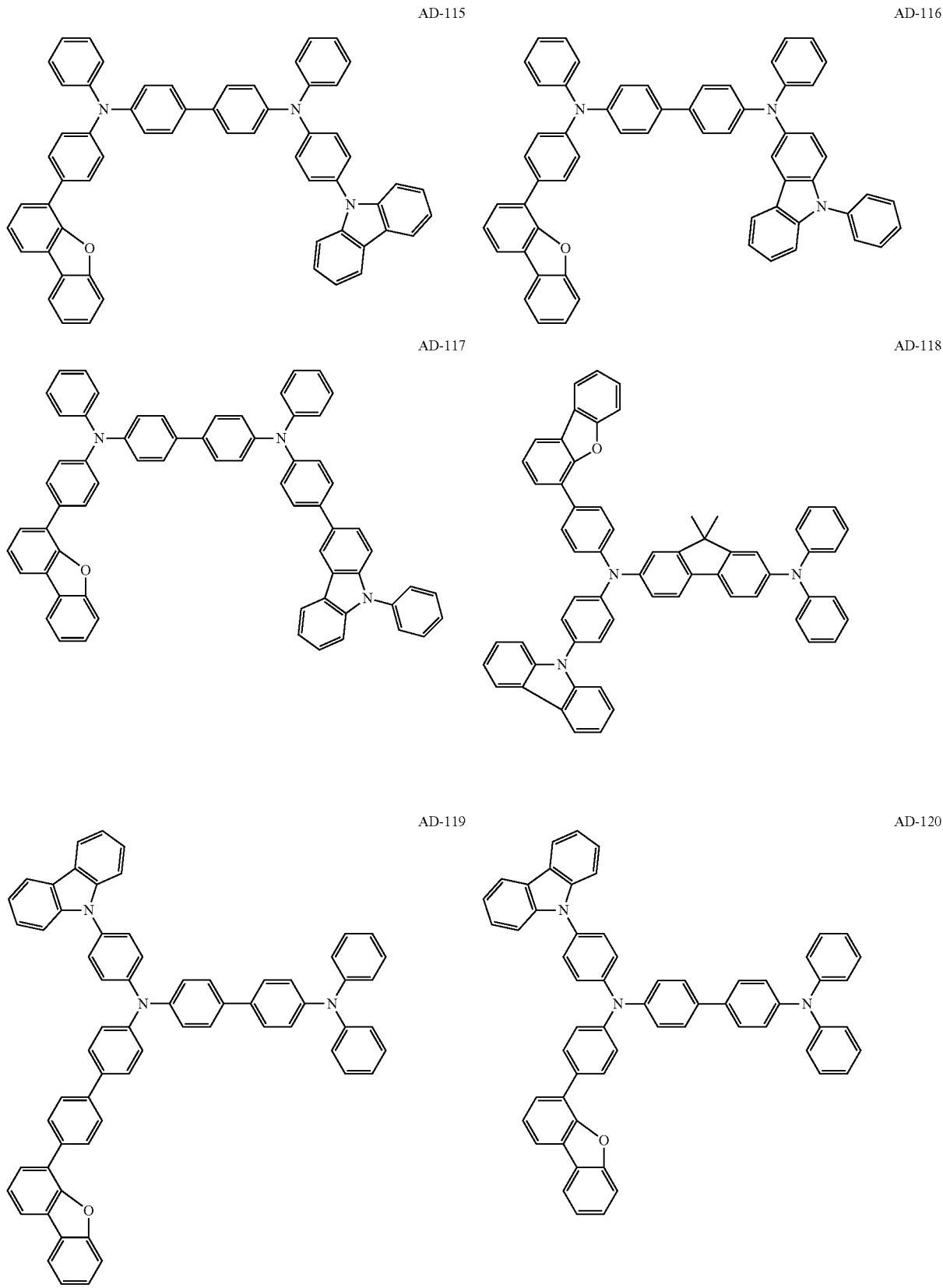

-continued
AD-121
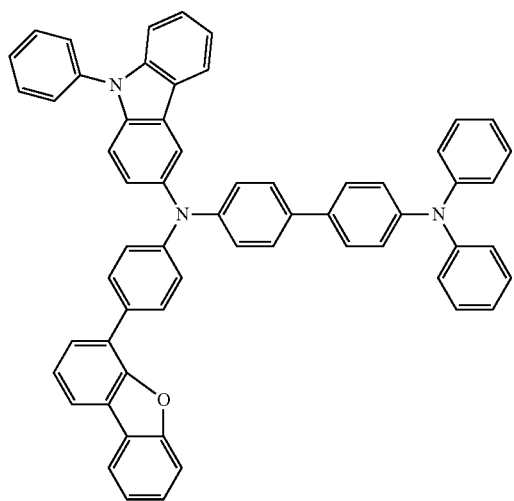
AD-122
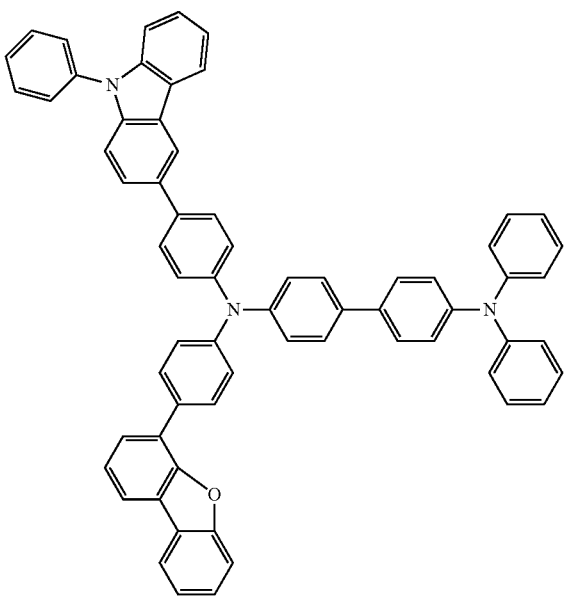
AD-123
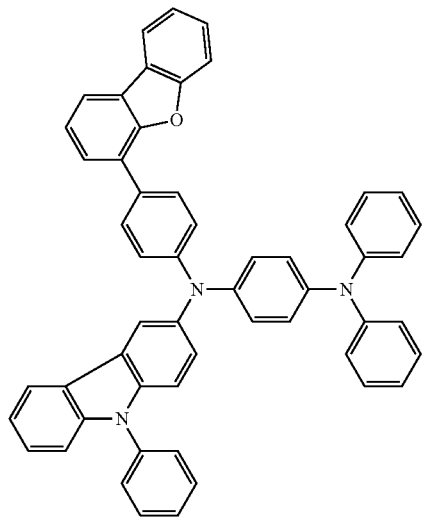
AD-124
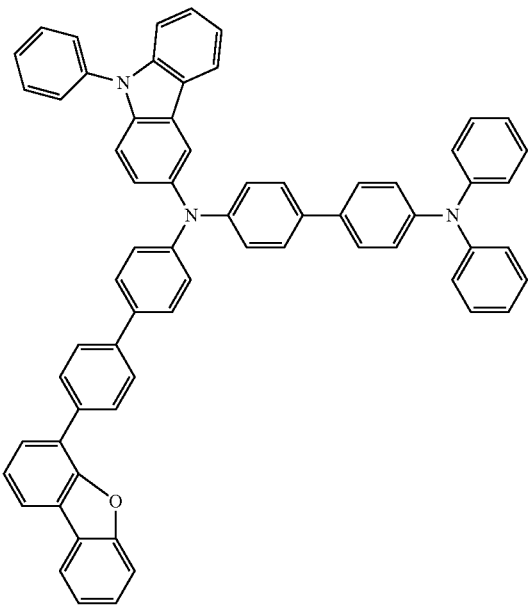

-continued
AD-125
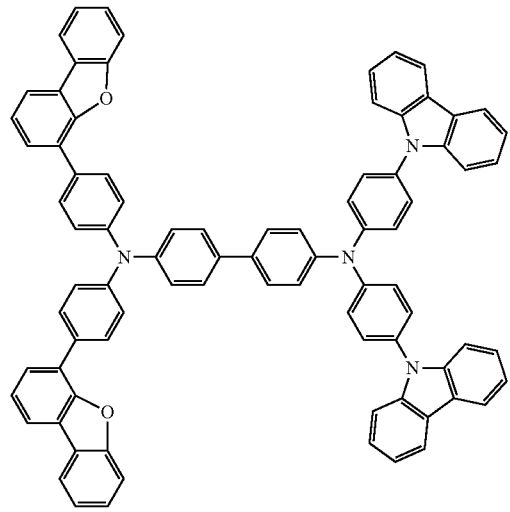
AD-126
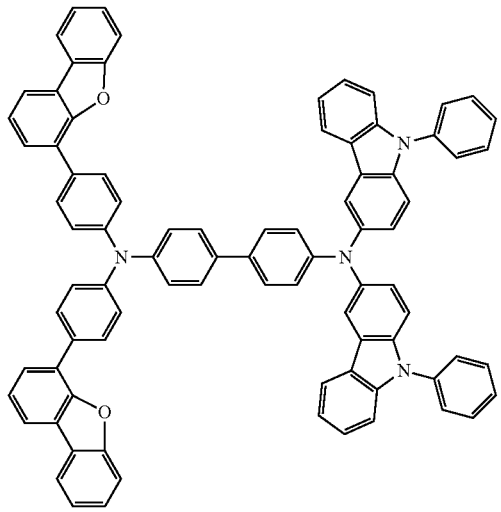
AD-127
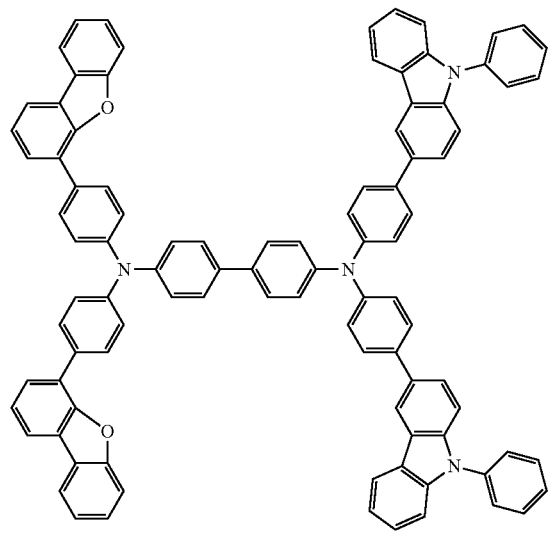
AD-128
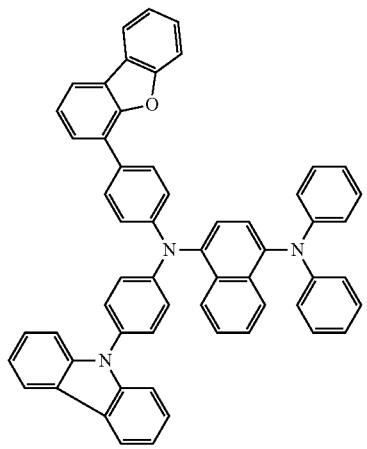
AD-129
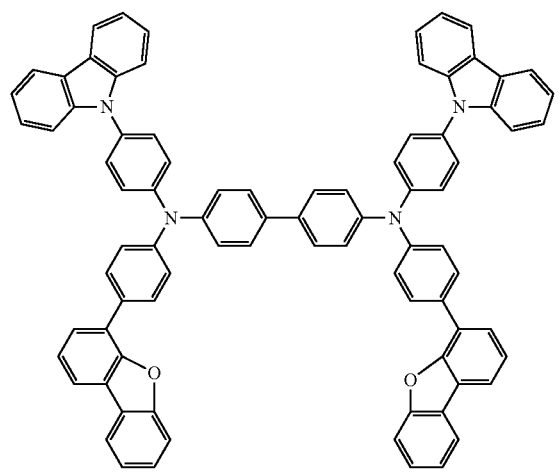
AD-130
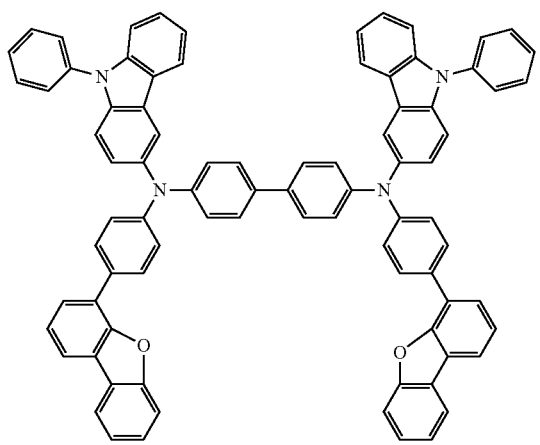

-continued
AD-131
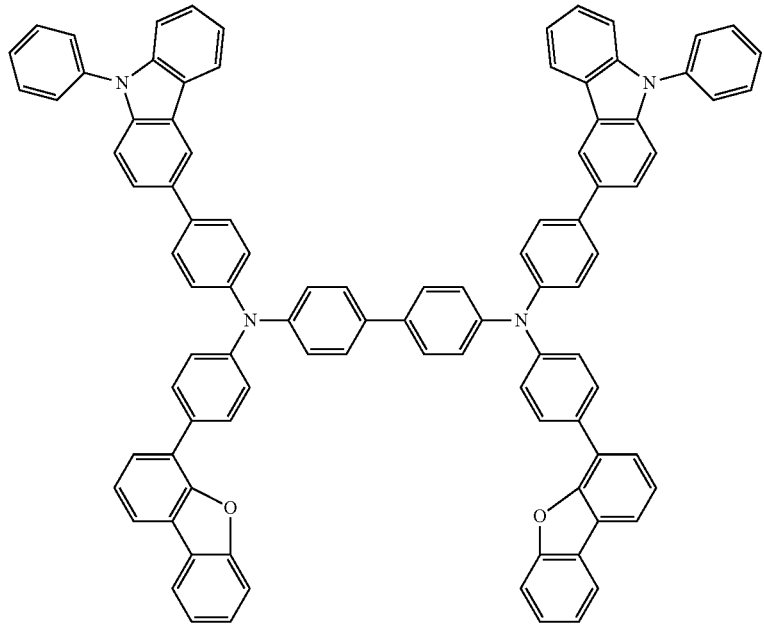
AD-132
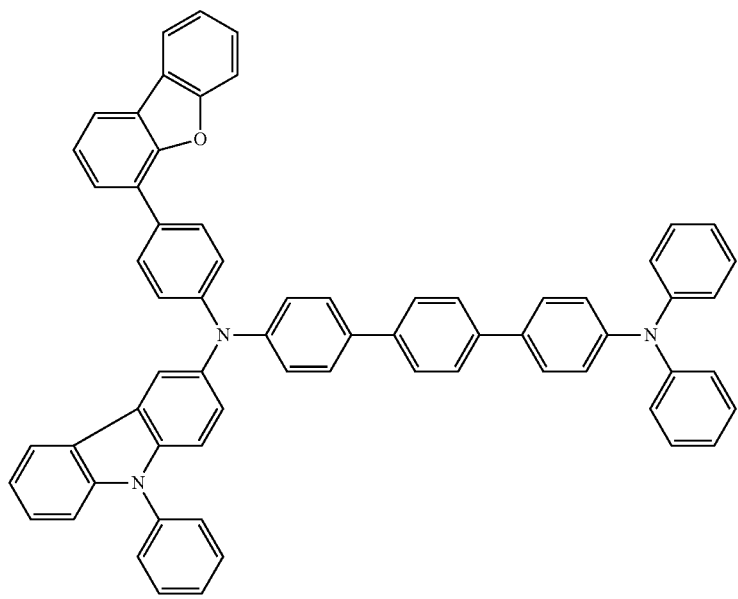
[Chem. 17]
AD-133
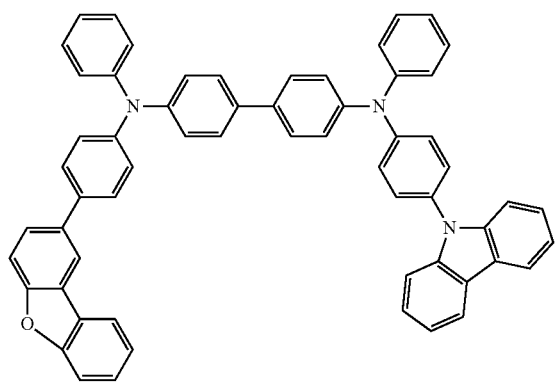
AD-134
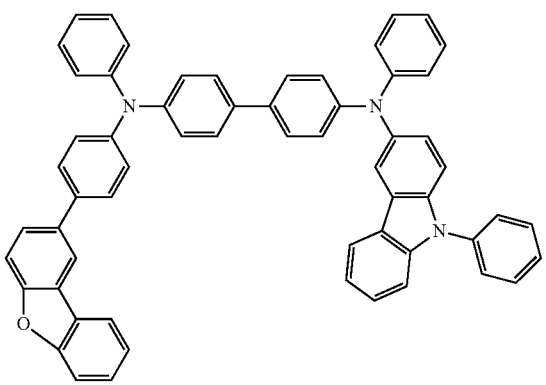

AD-135
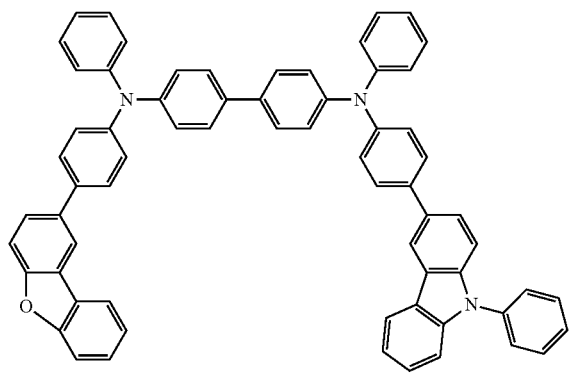
AD-136
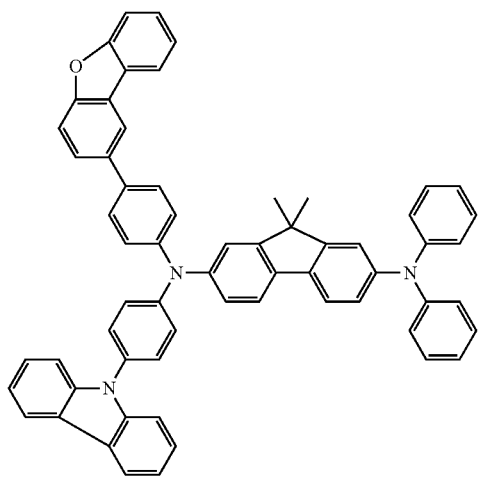
AD-137
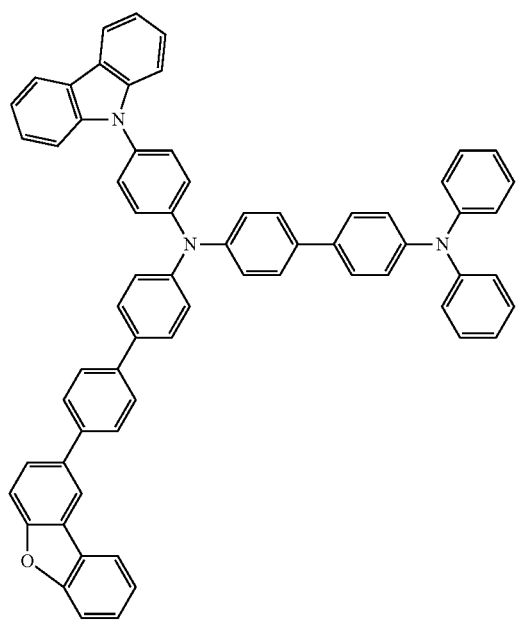
AD-138
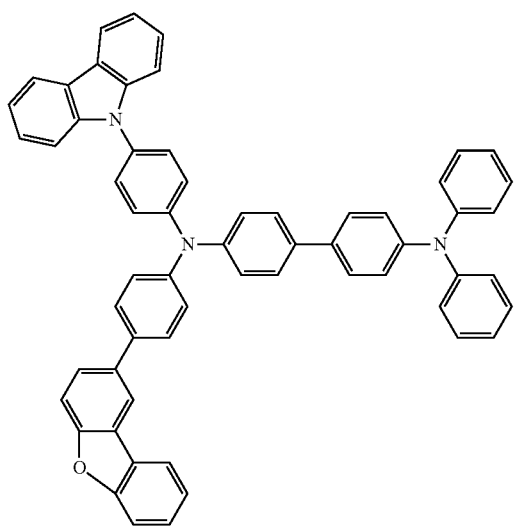

AD-139
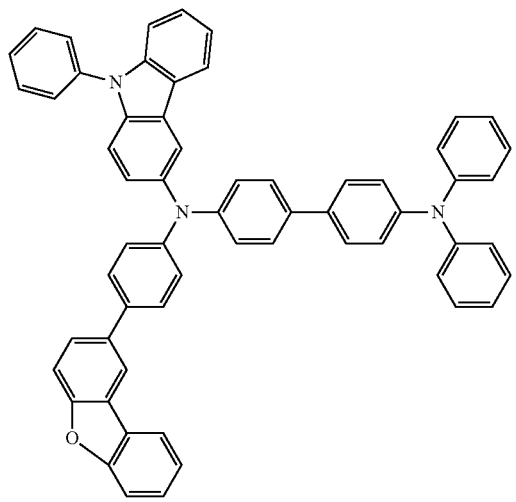
AD-140
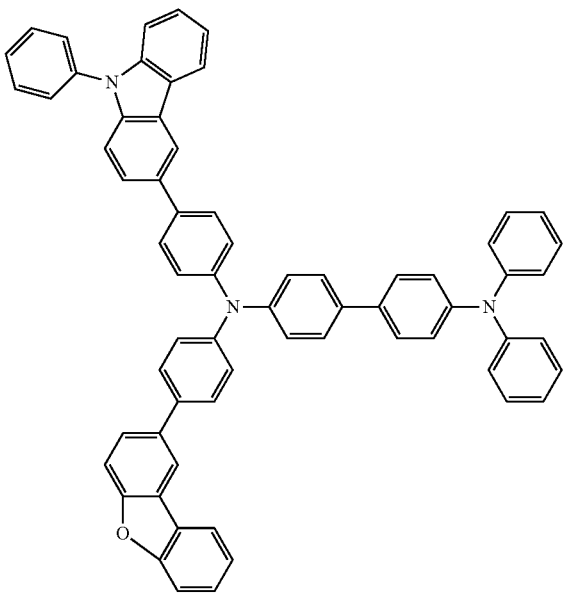
AD-141
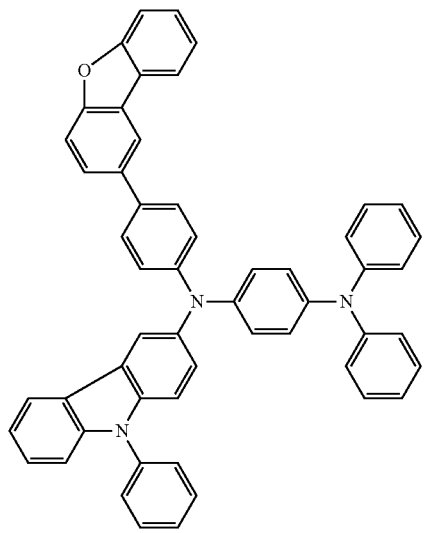
AD-142
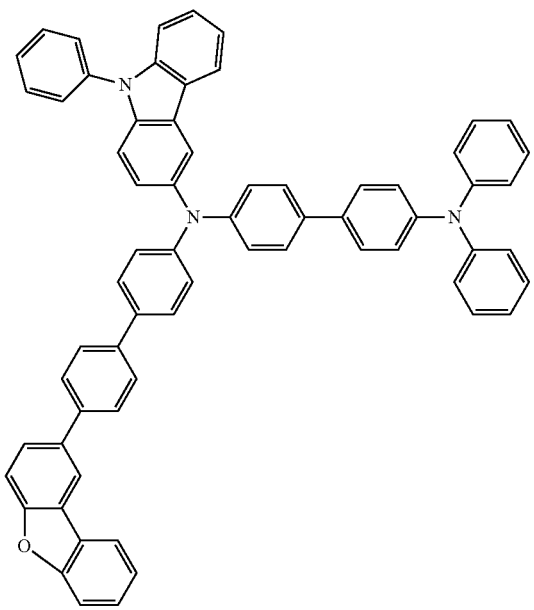

-continued
AD-143
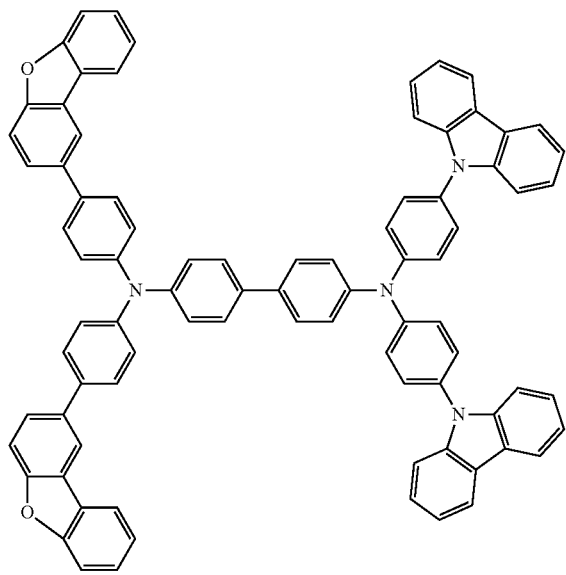
AD-144
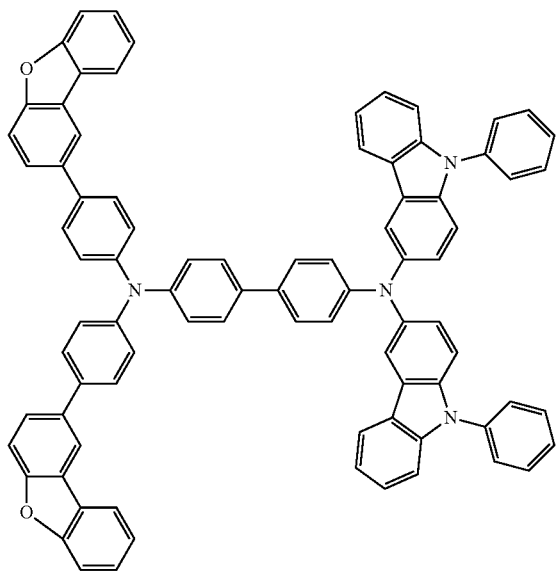
AD-145
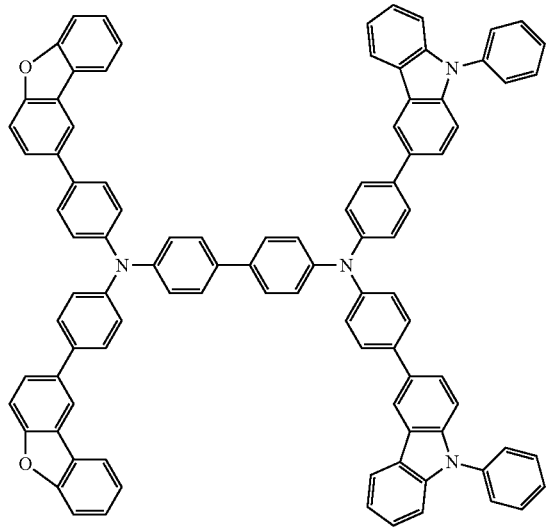
AD-146
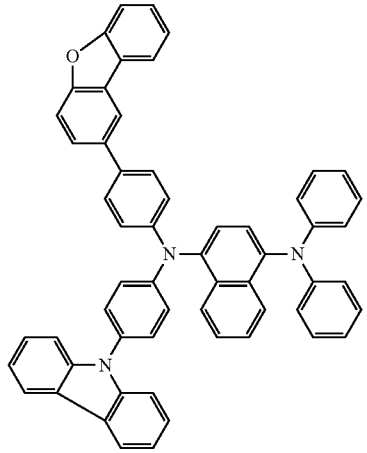
AD-147
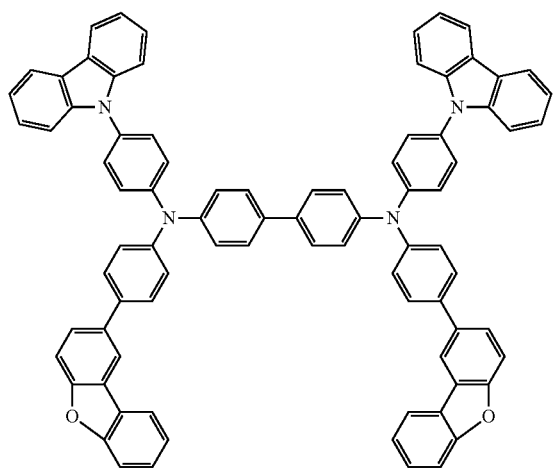
AD-148
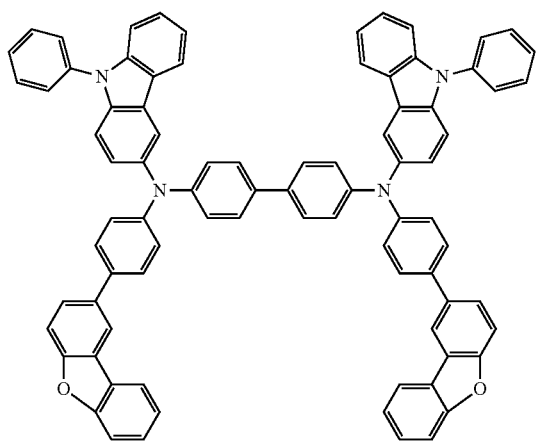

AD-149
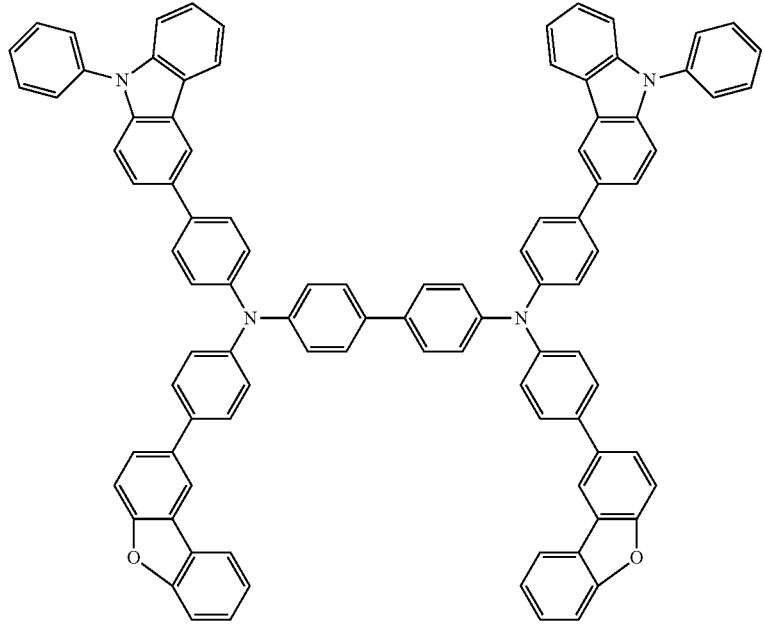
AD-150
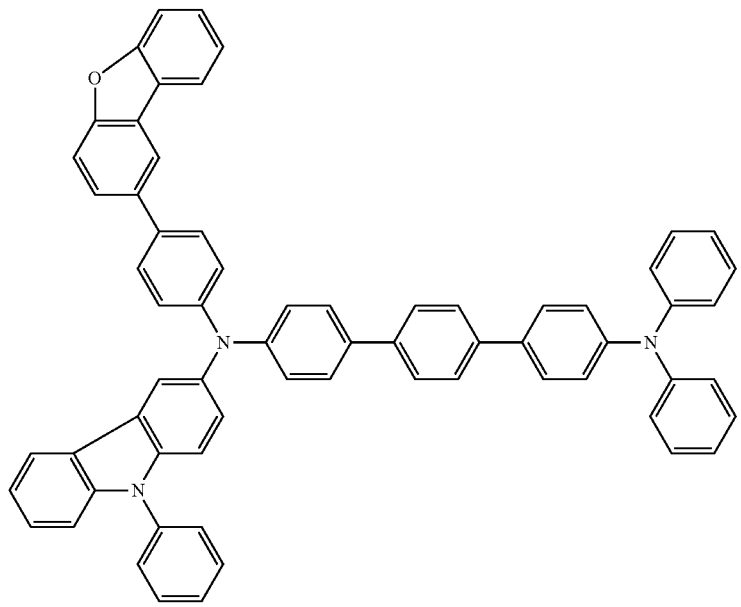

[Chem. 18]
AD-151
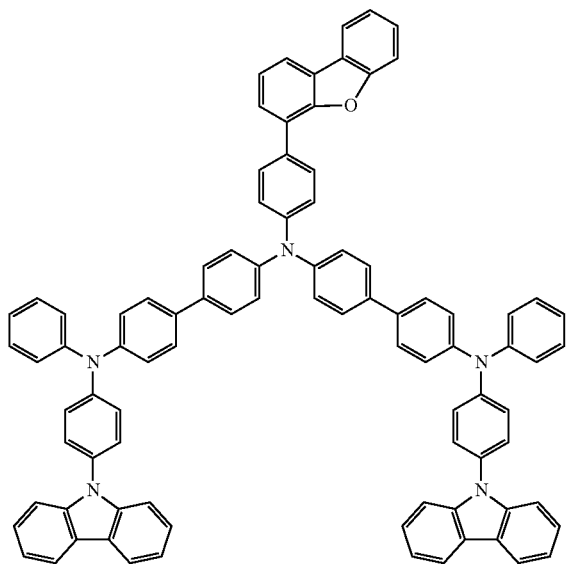
AD-152
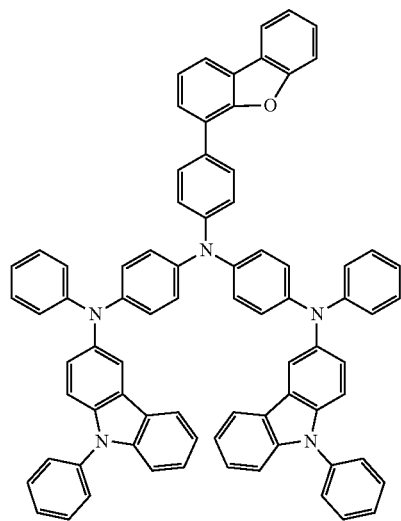
AD-153
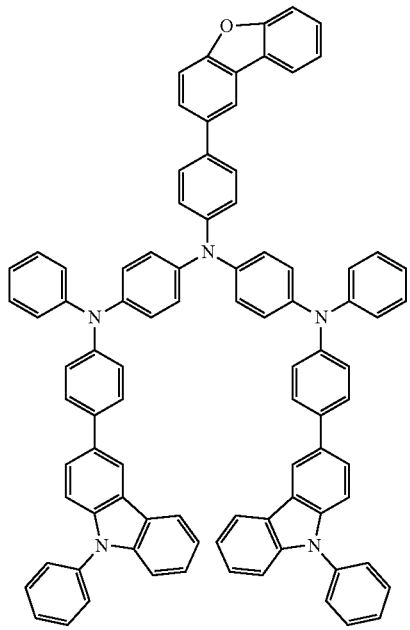
AD-154
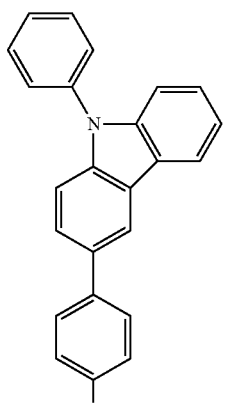

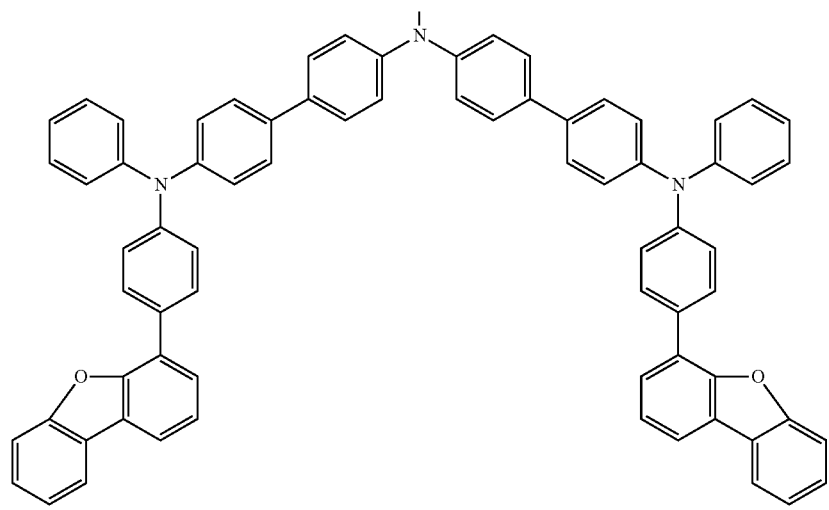
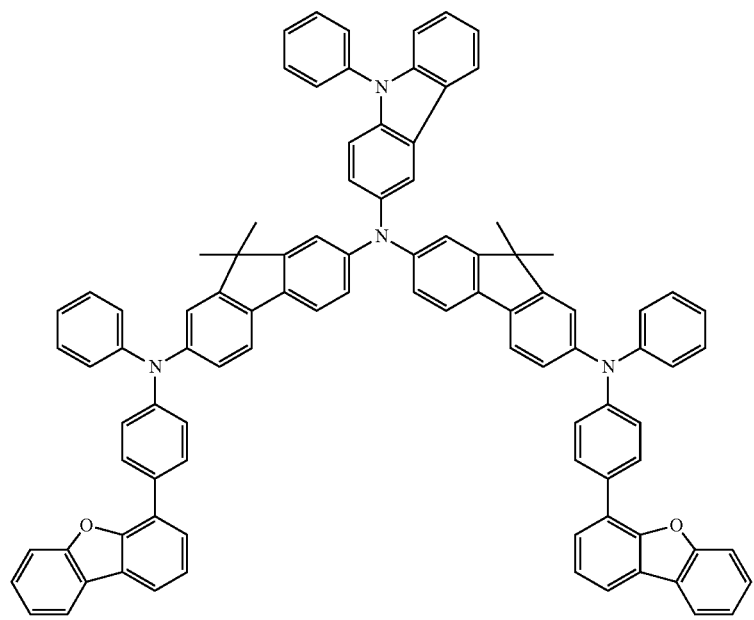
AD-155

AD-156
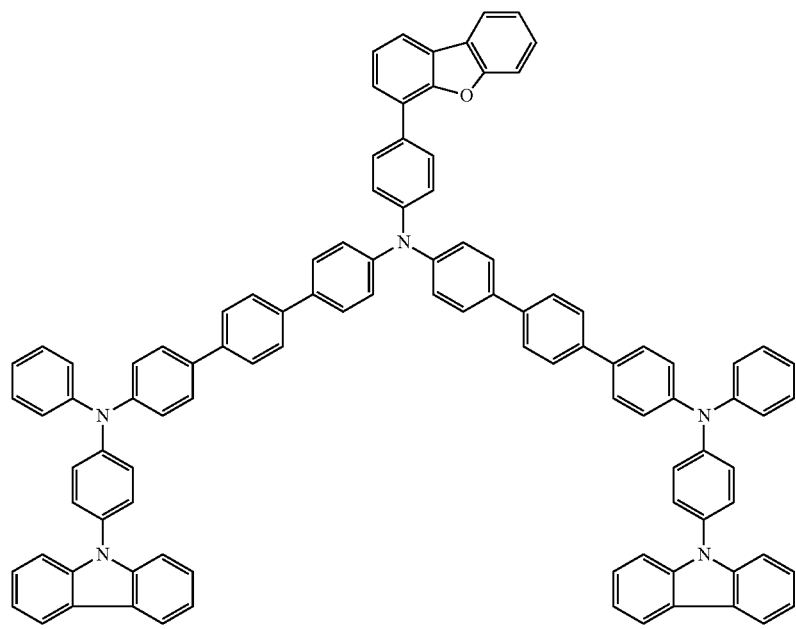
AD-157
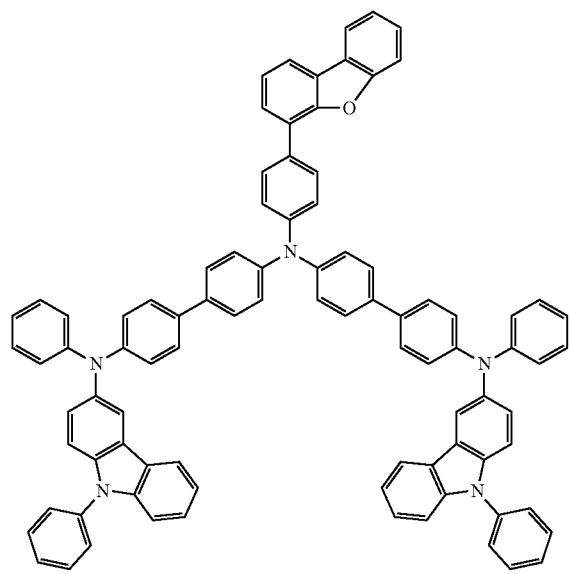
AD-158
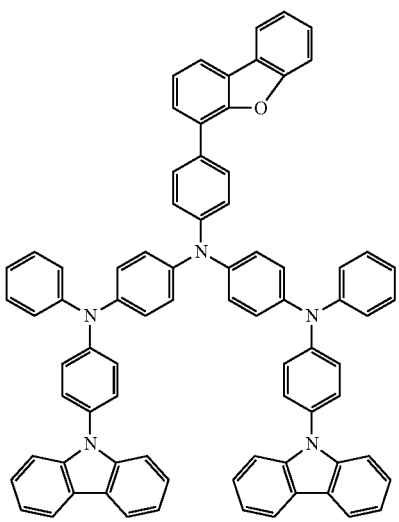

AD-159
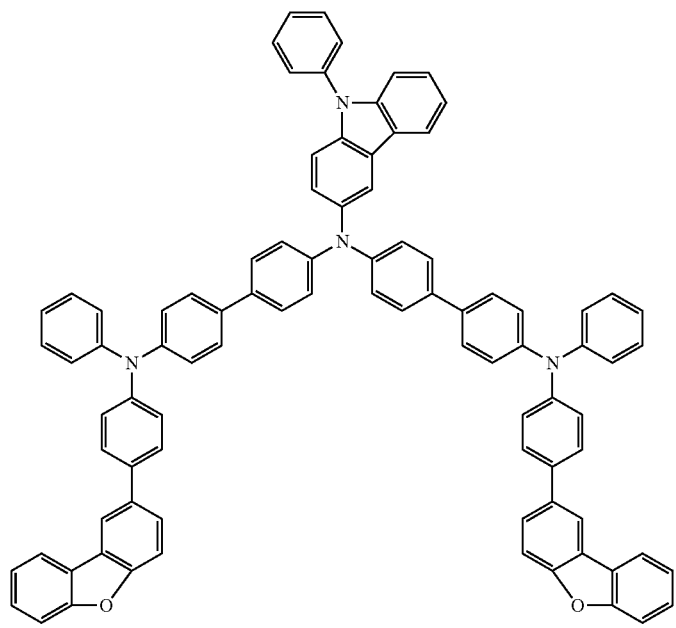
AD-160
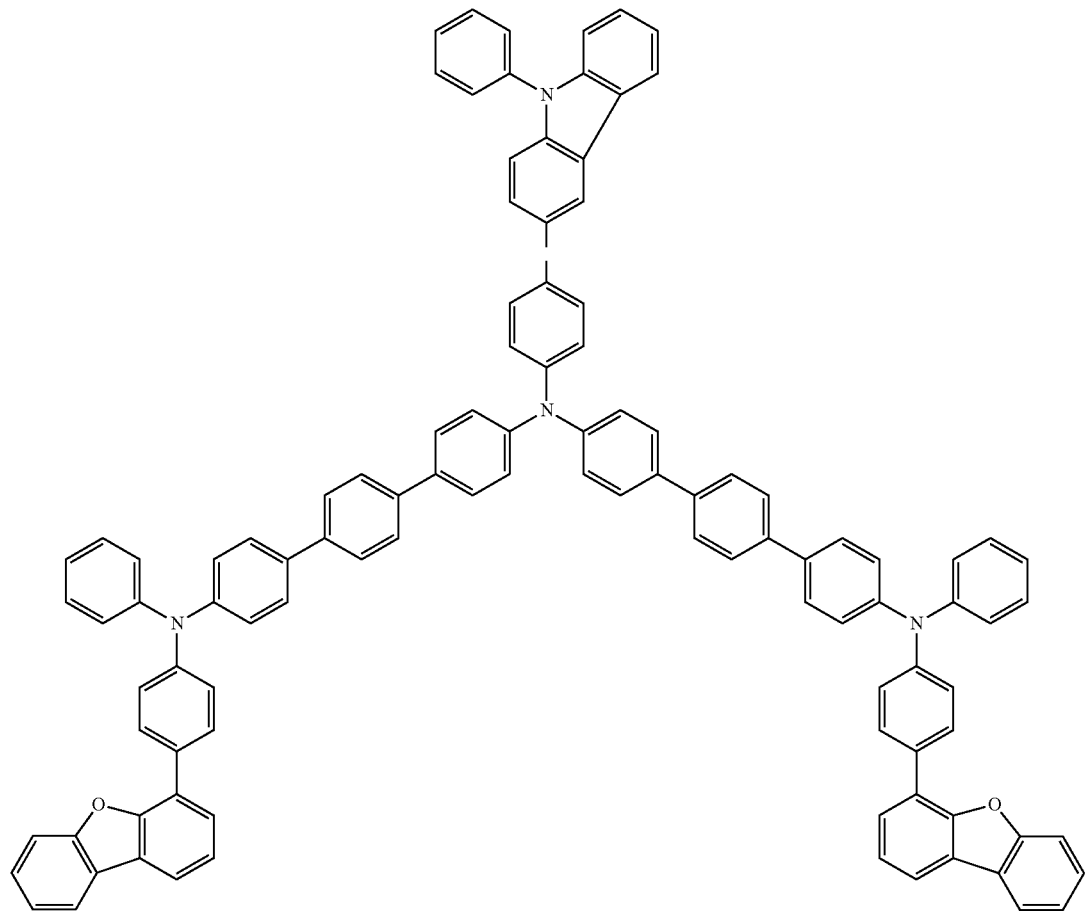

-continued
AD-161
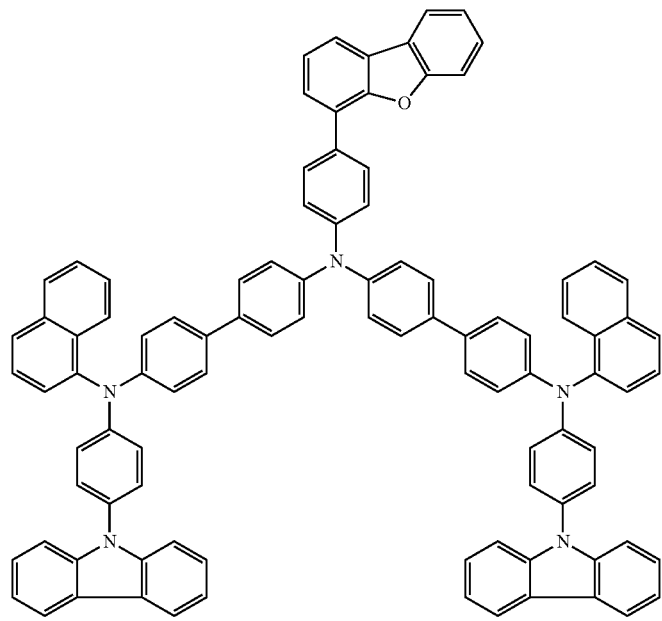
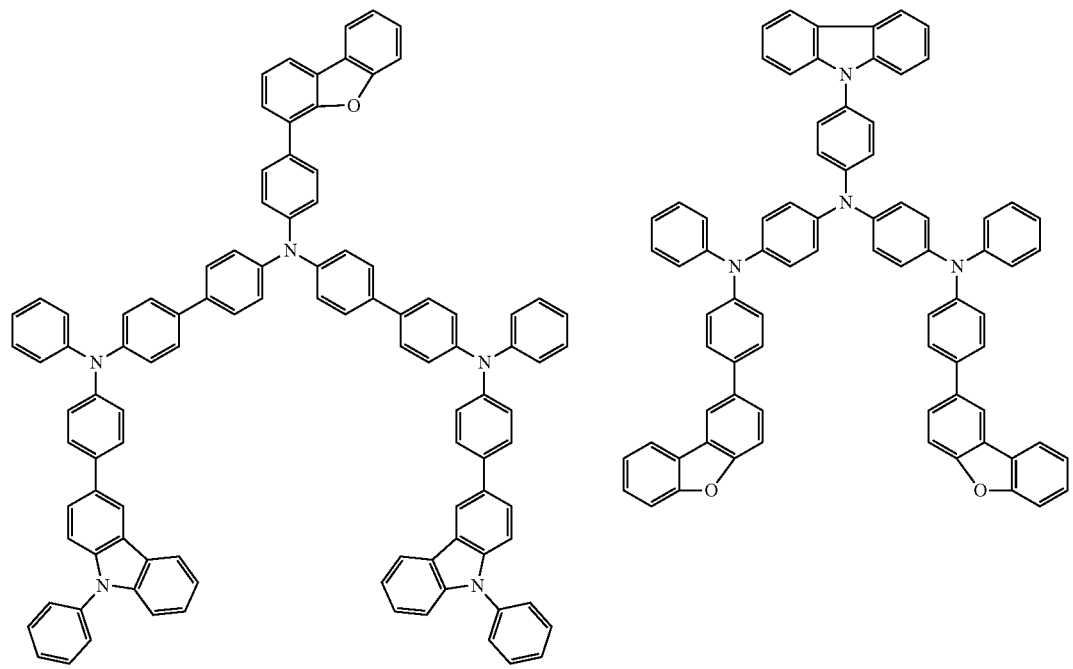
AD-162
AD-163

AD-164
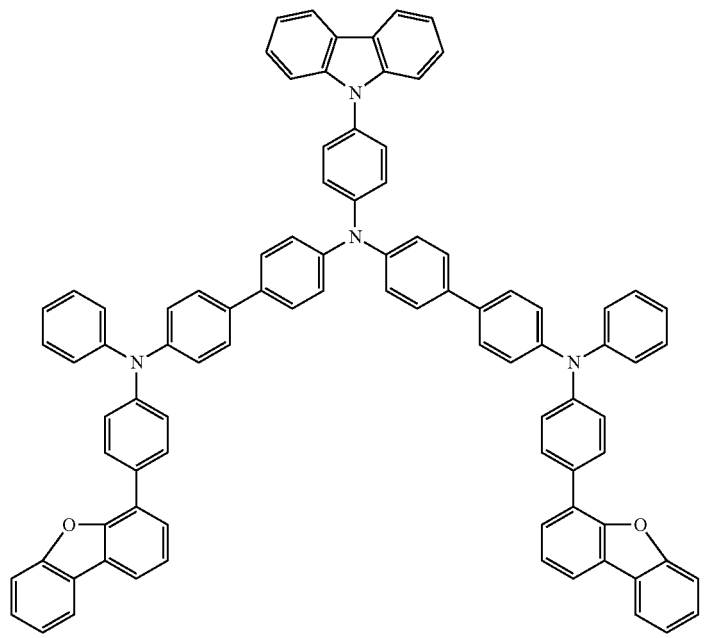
AD-165
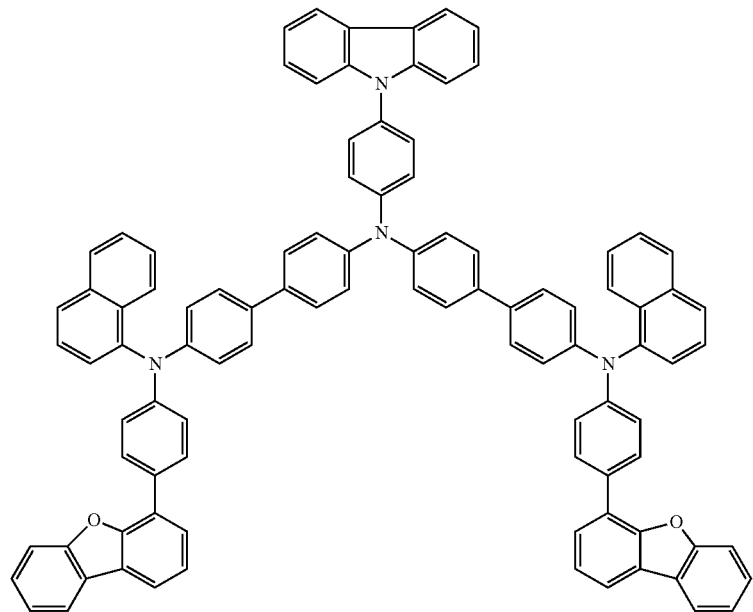

[Chem. 19]
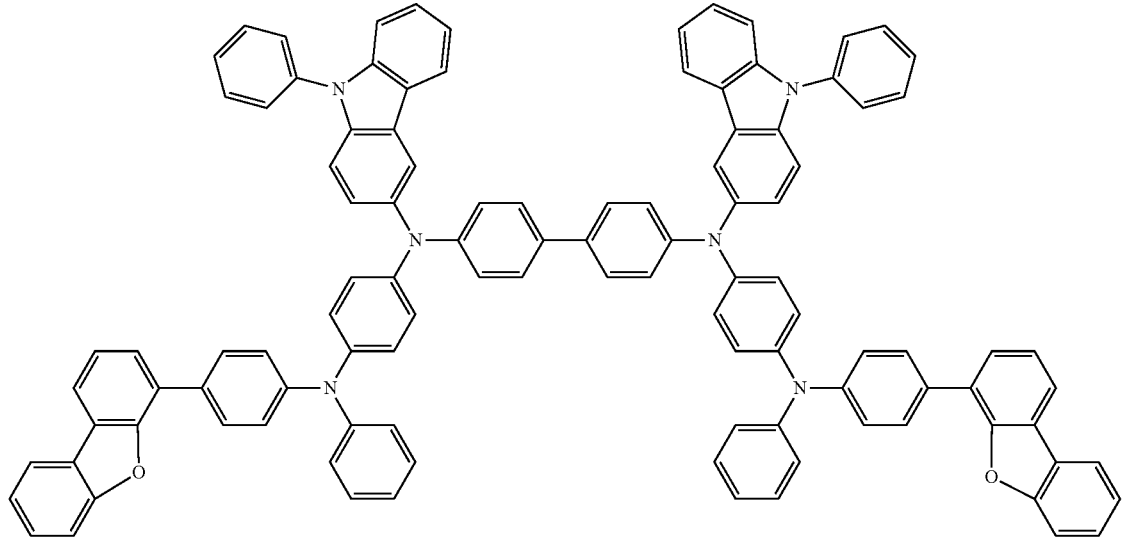
AD-166
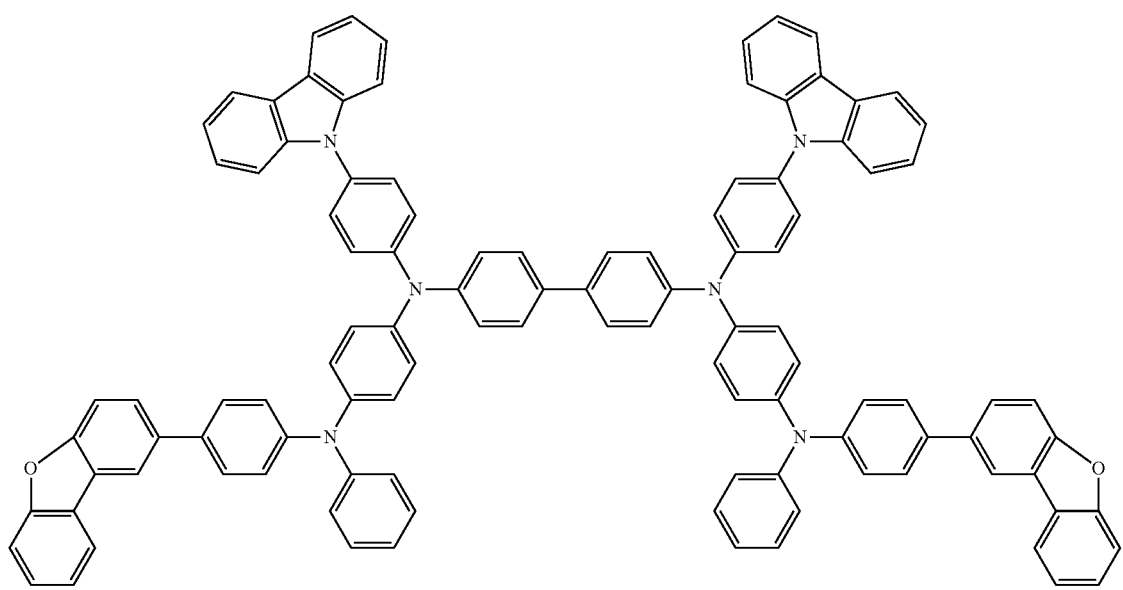
AD-167

AD-168
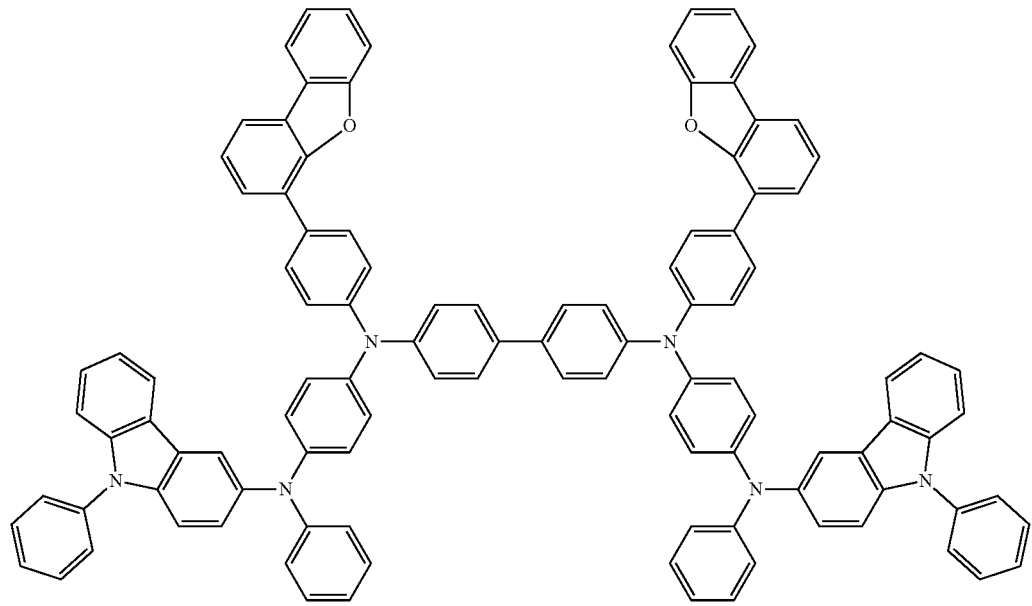
AD-169
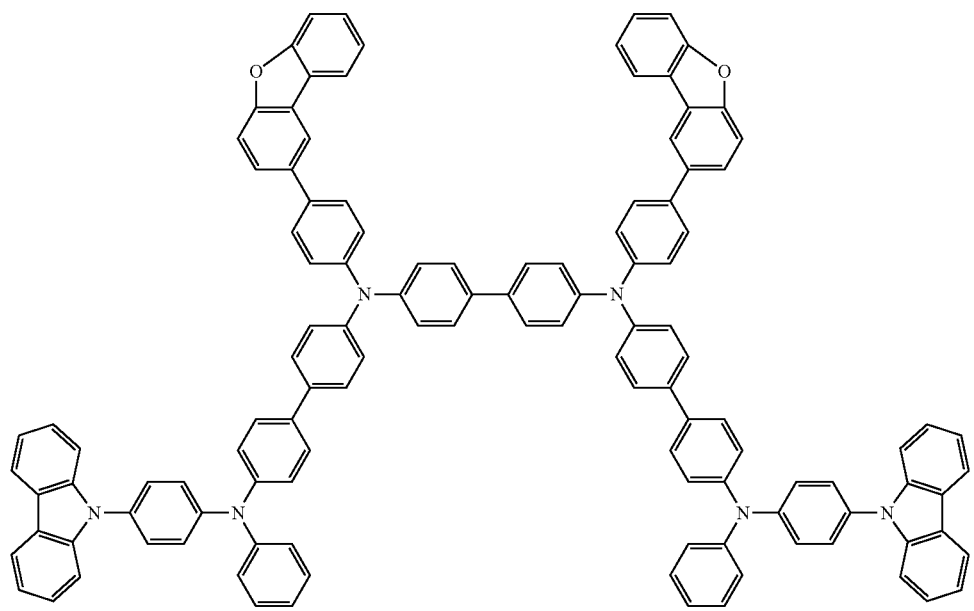

-continued
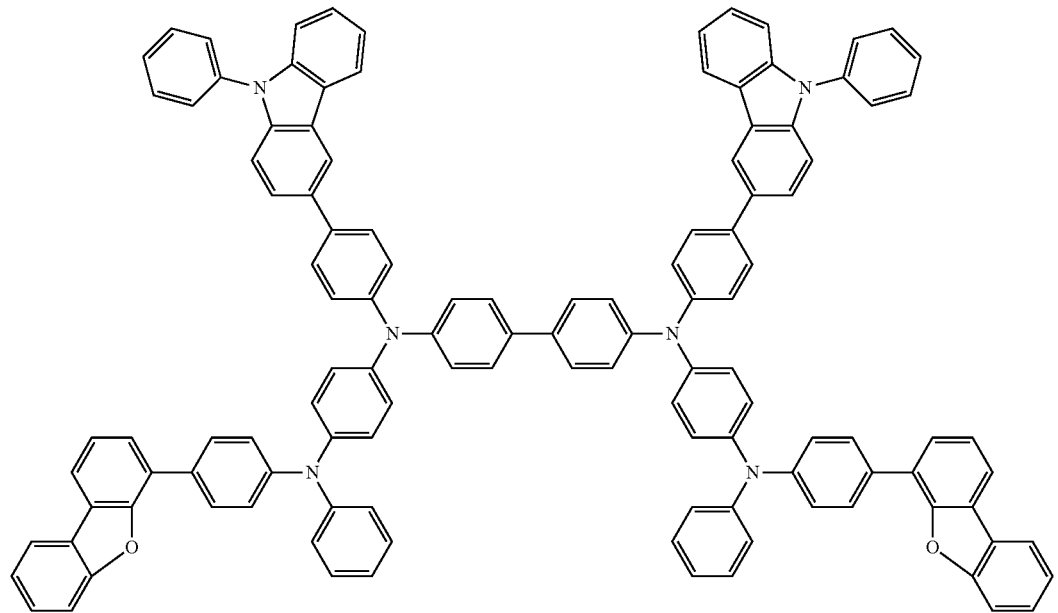
AD-170
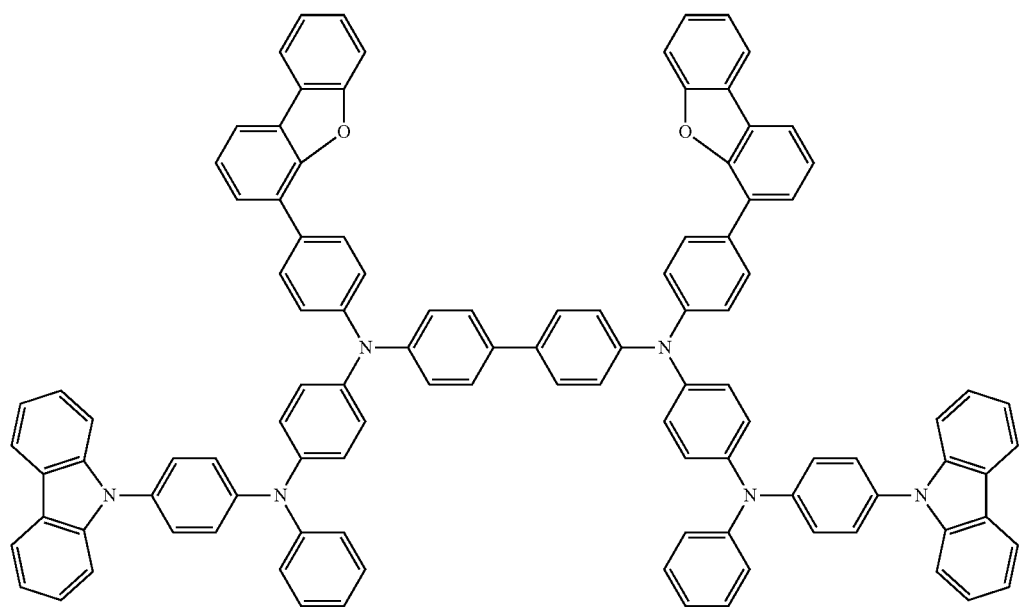
AD-171

-continued
AD-172
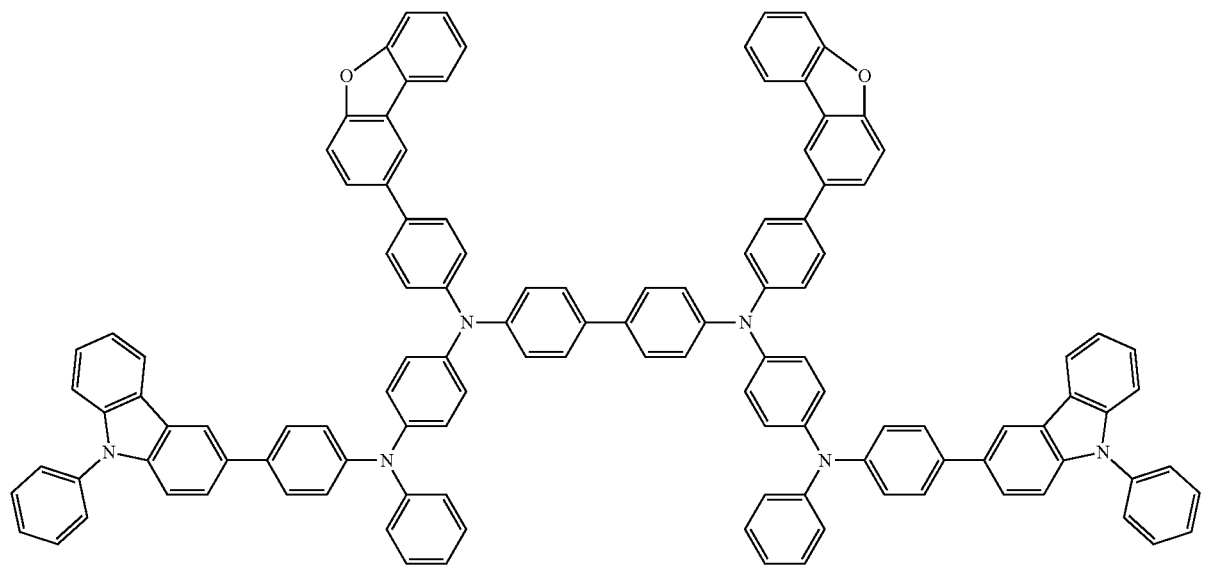
AD-173
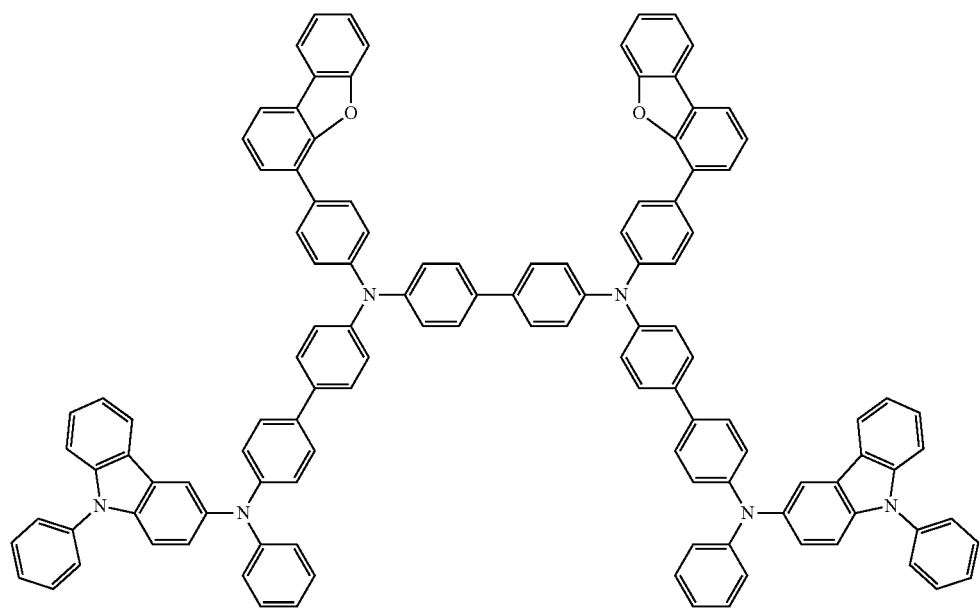

[Chem. 20]
AD-174
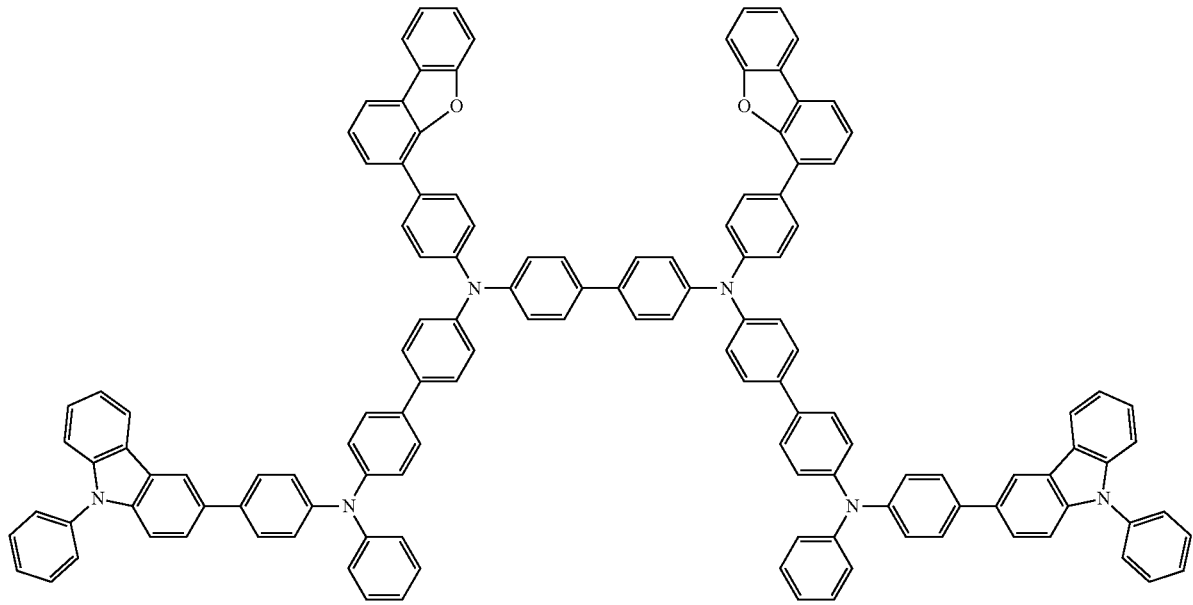
AD-175
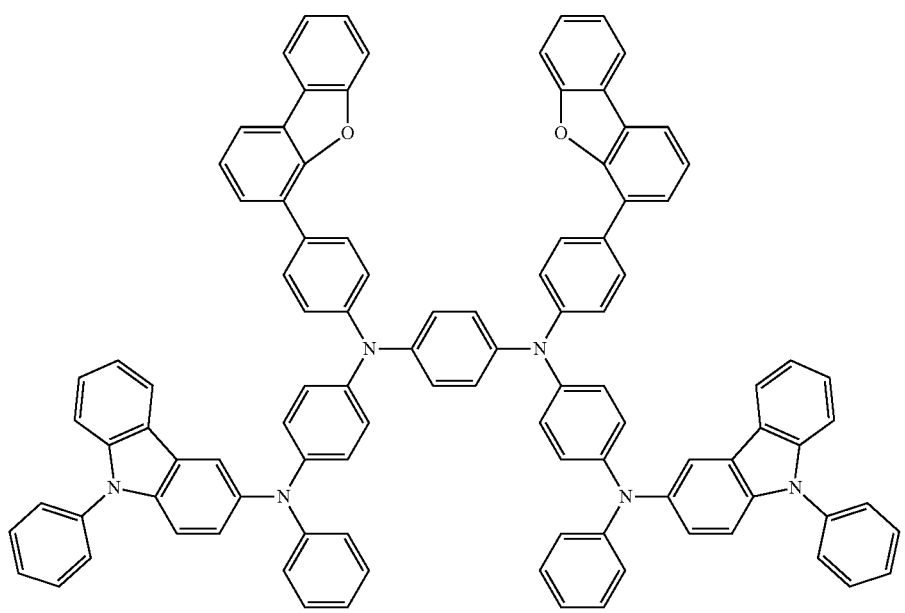

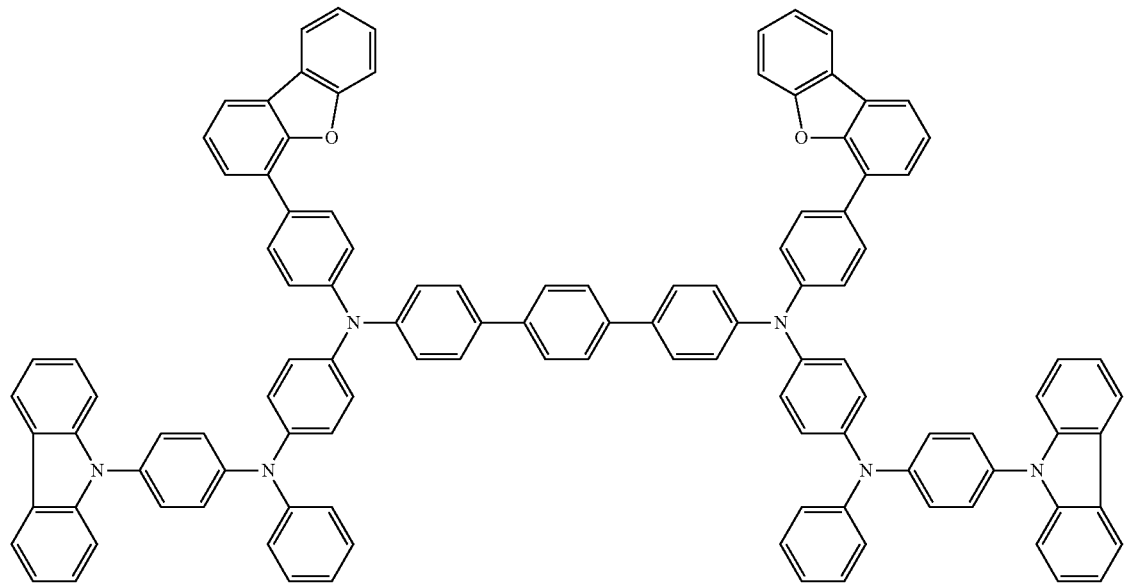
AD-176
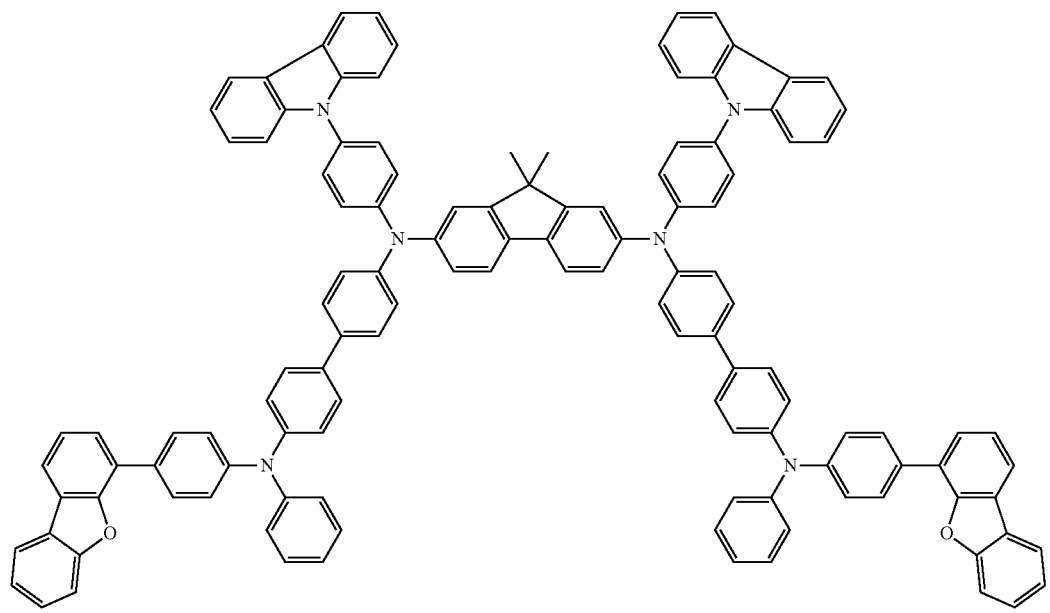
AD-177

AD-178
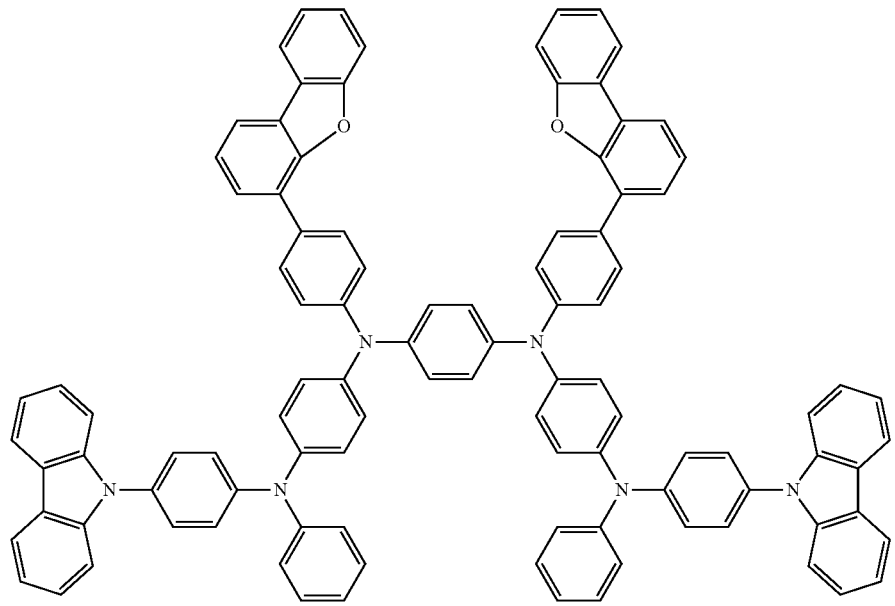
AD-179
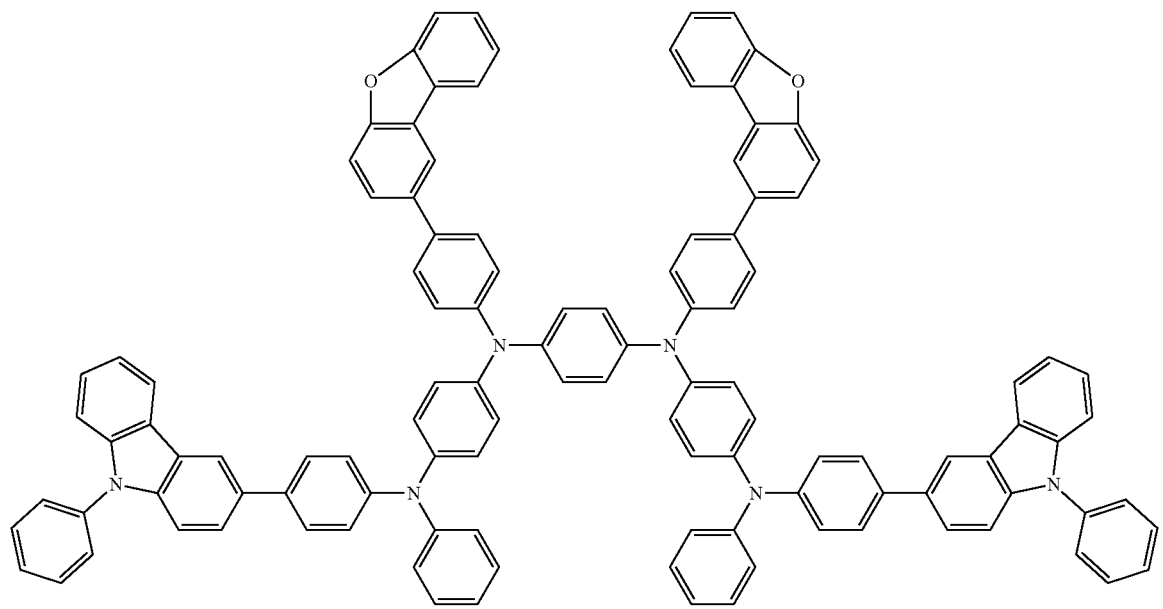

AD-180
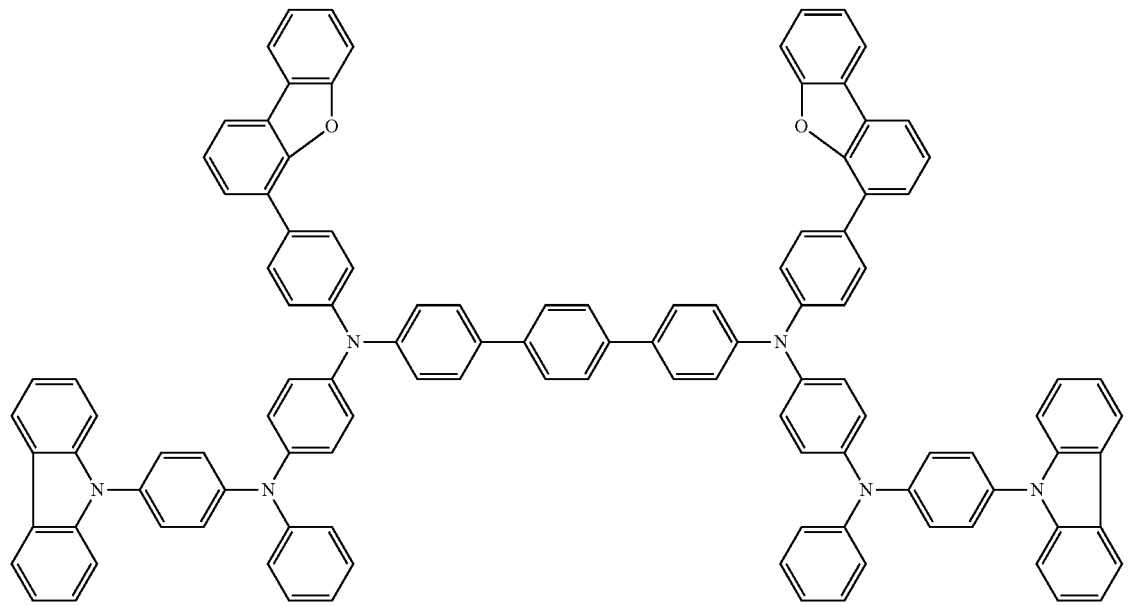
AD-181
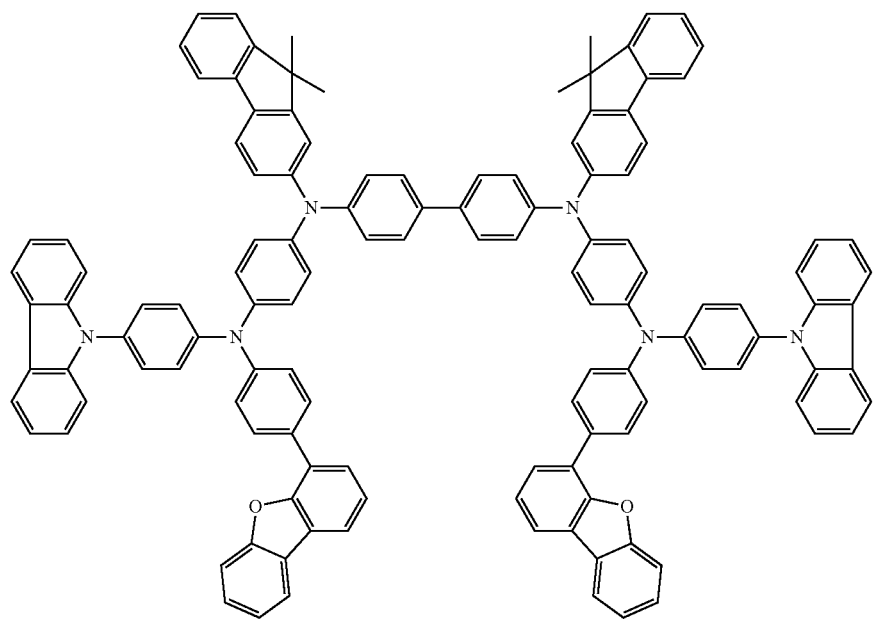
[Chem. 21]
AD-182
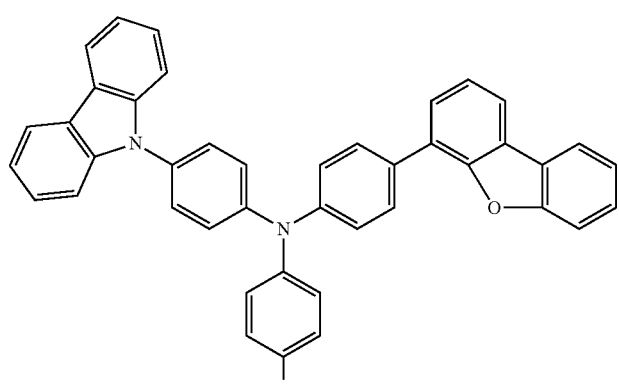

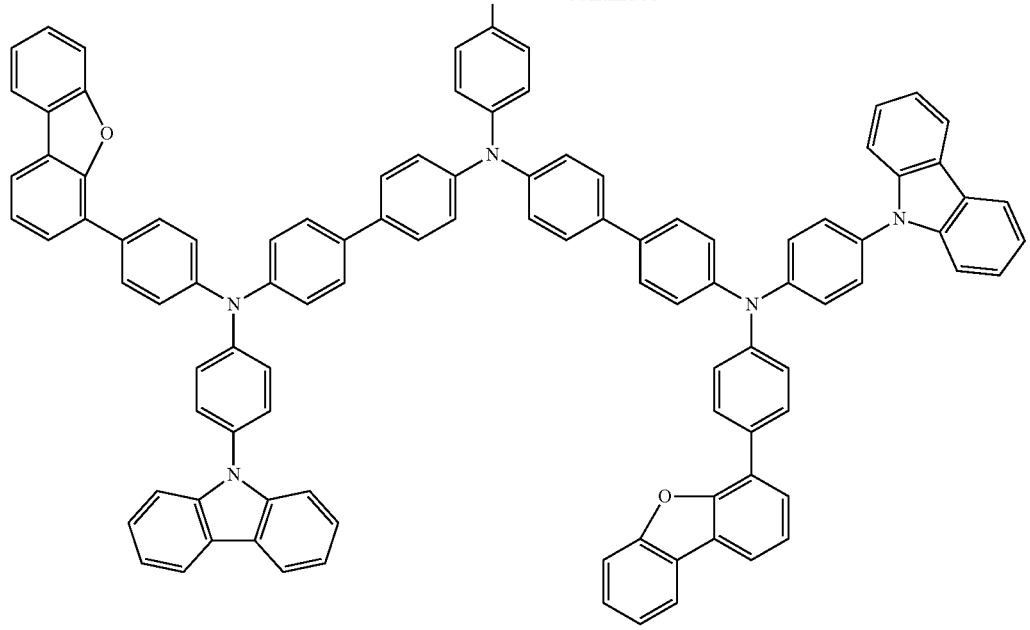
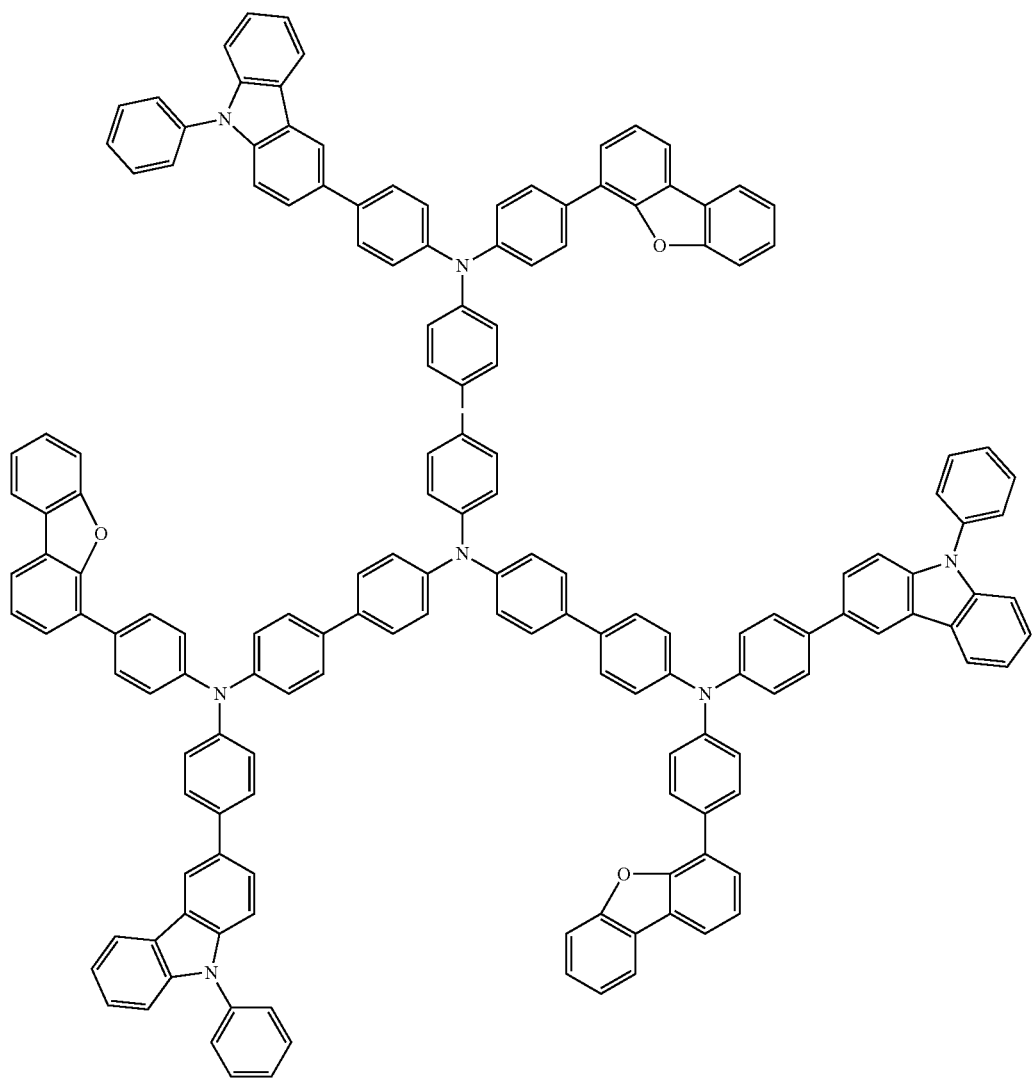
AD-183

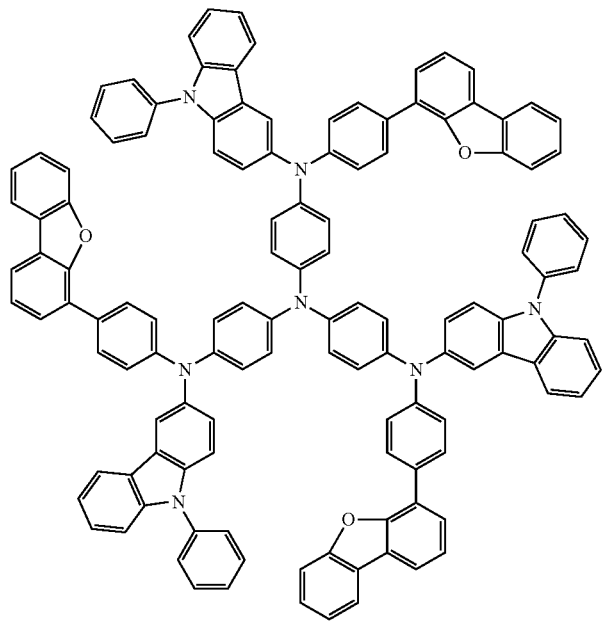
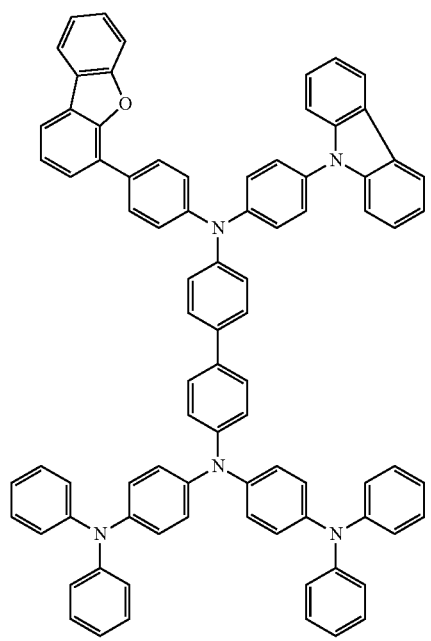
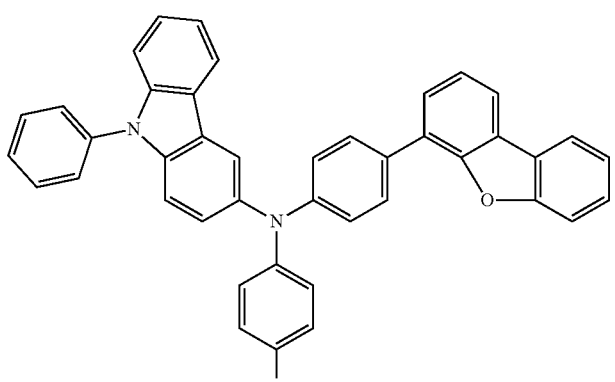
AD-184
AD-185
AD-186

-continued
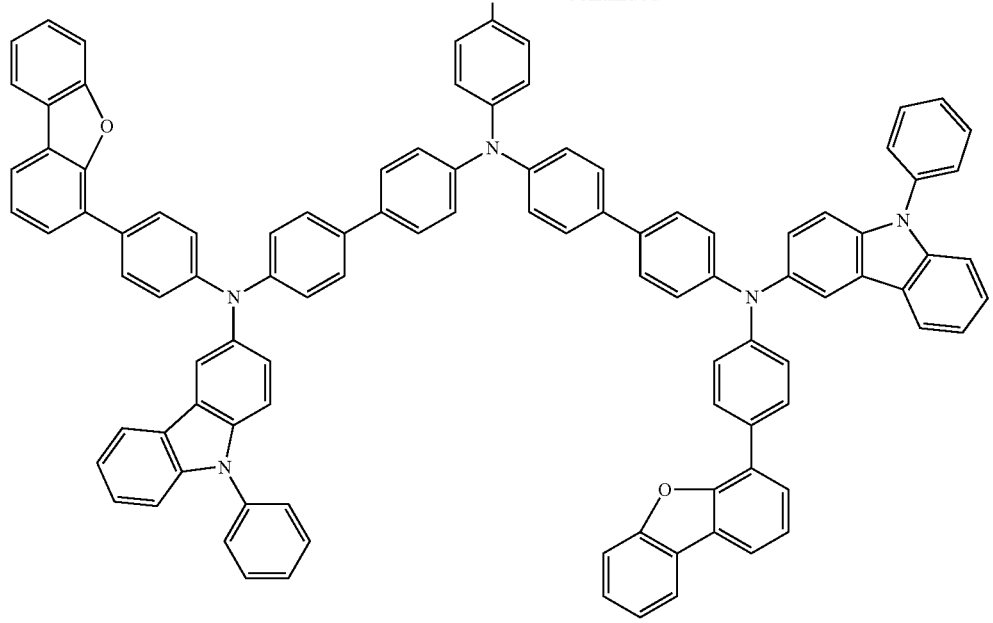
AD-187
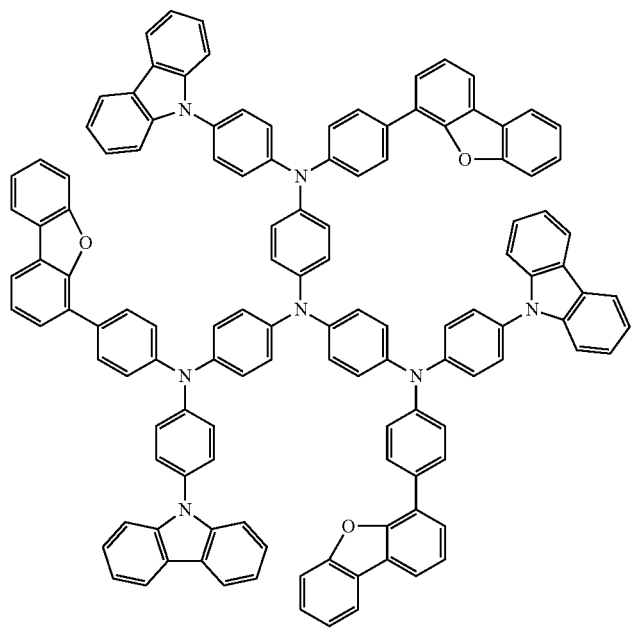
AD-188
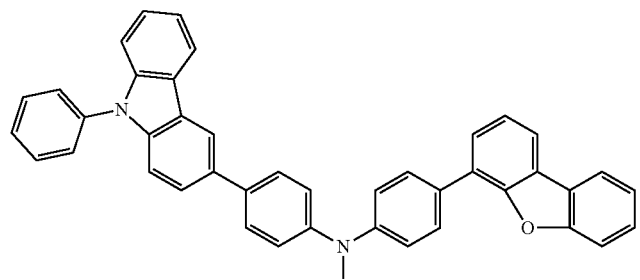

105
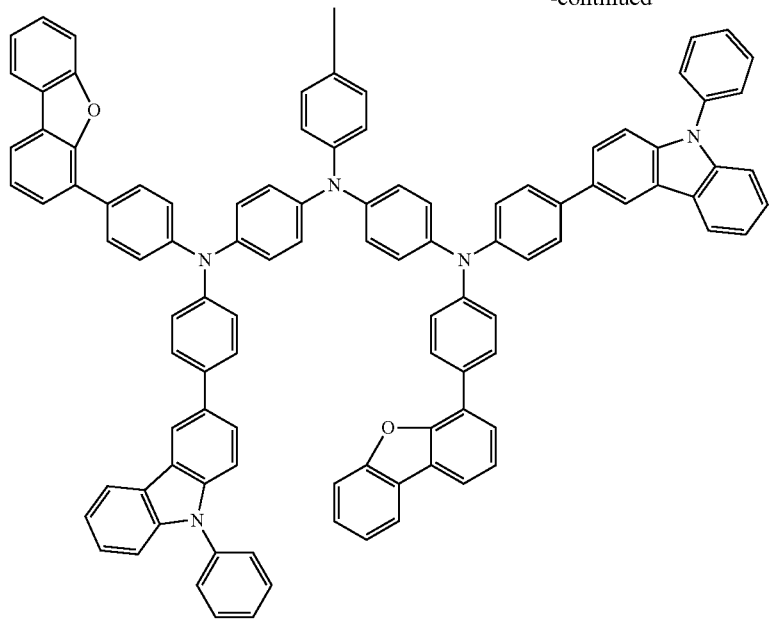
106
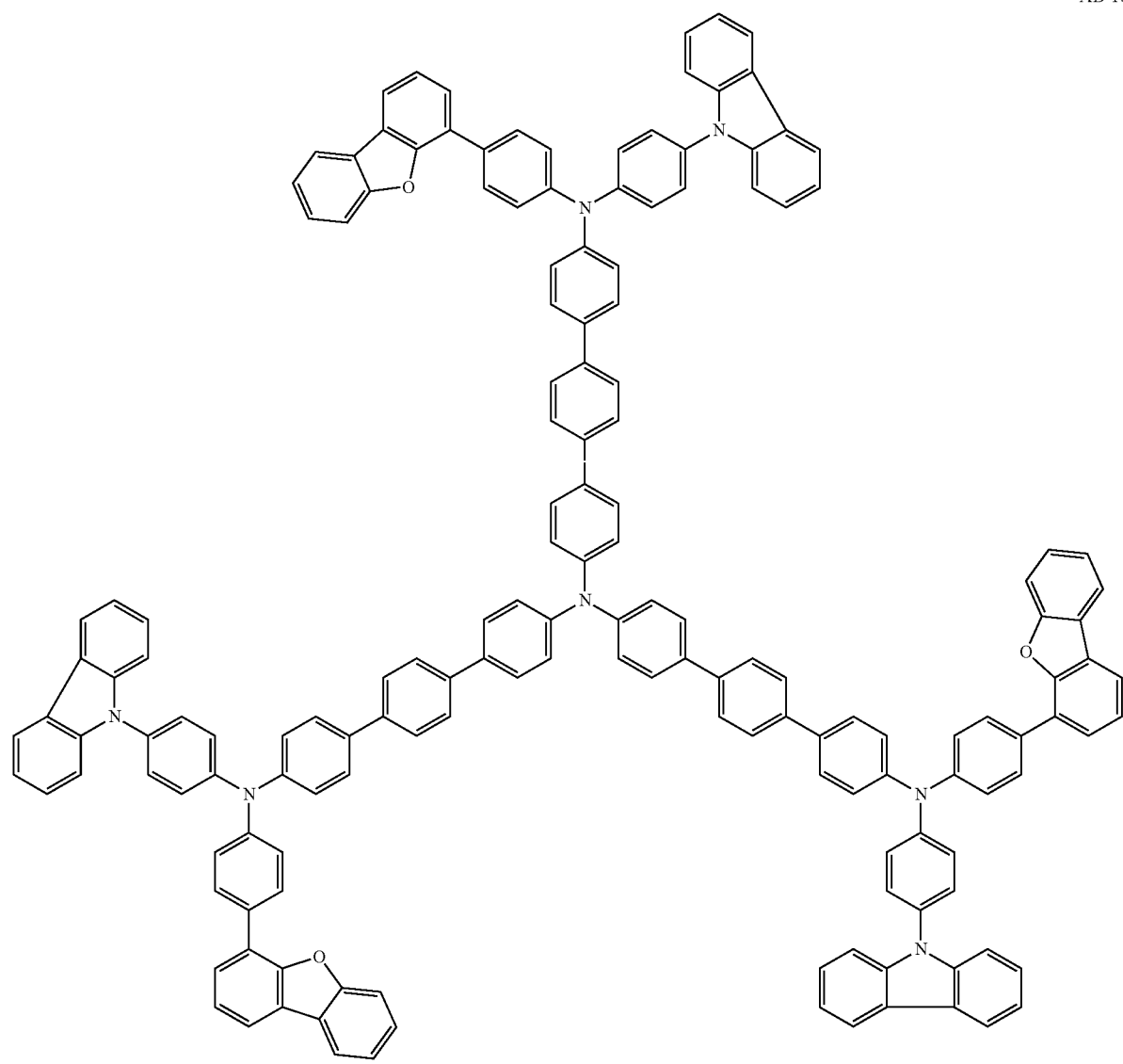
AD-189

[Chem. 22]
AD-190
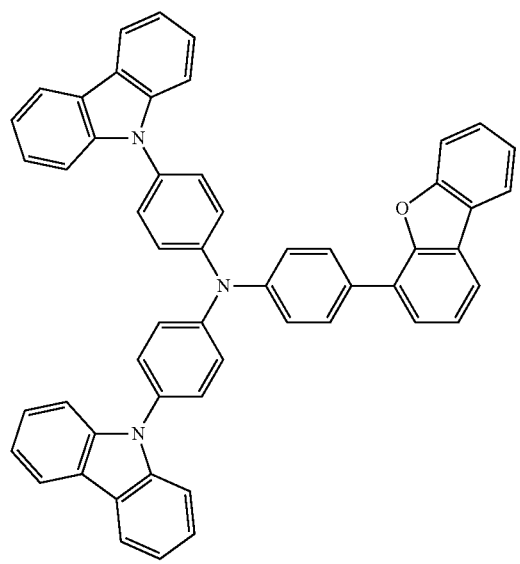
AD-191
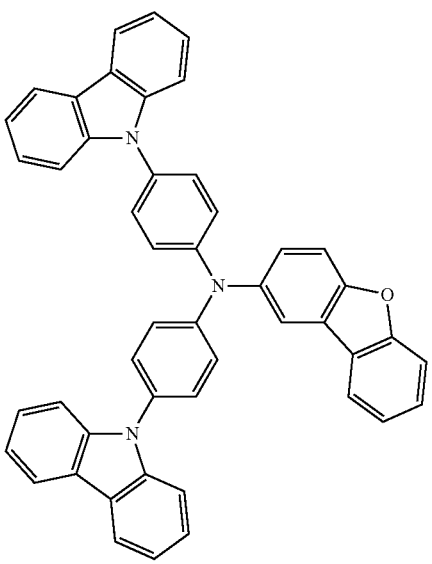
AD-192
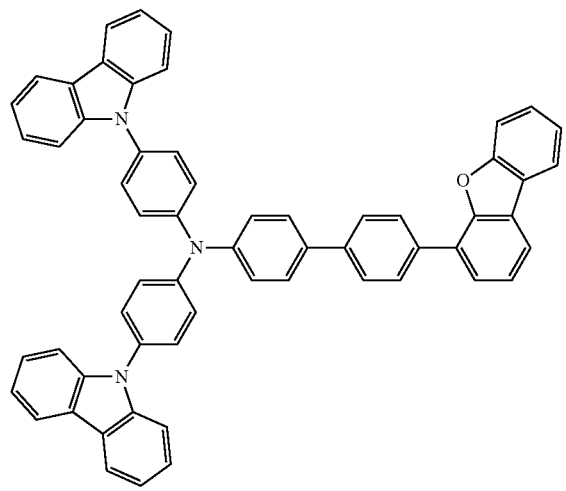
AD-193
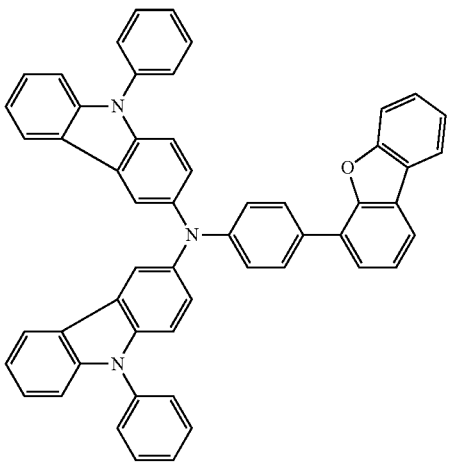
AD-194
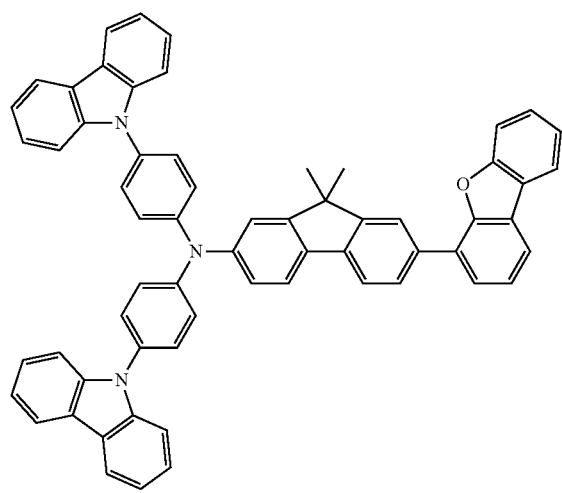
AD-195
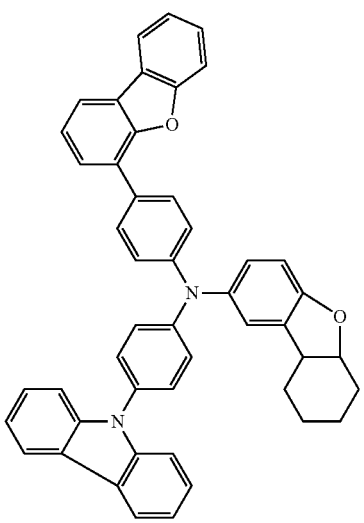

[Chem. 23]
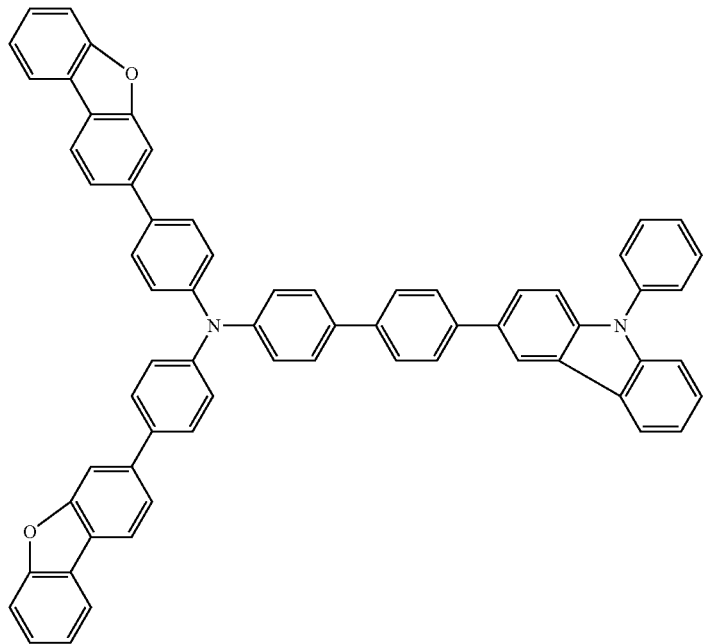
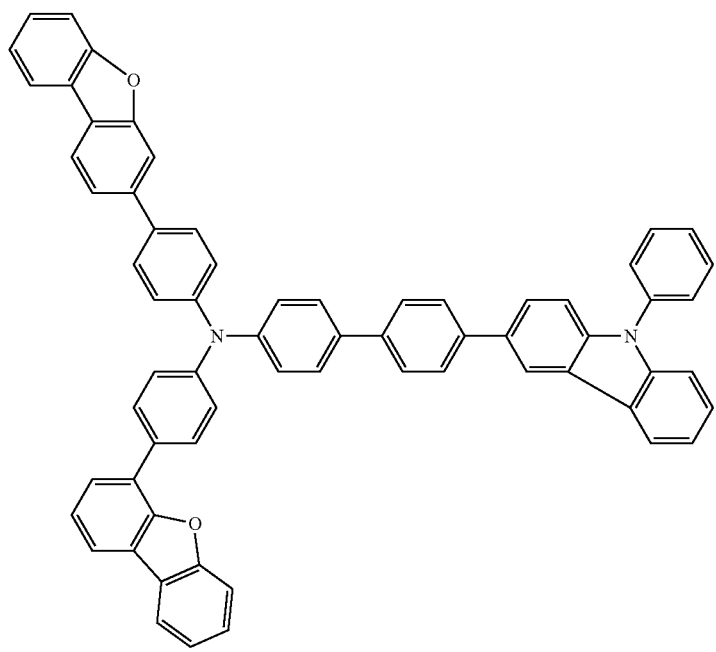

111
112
-continued
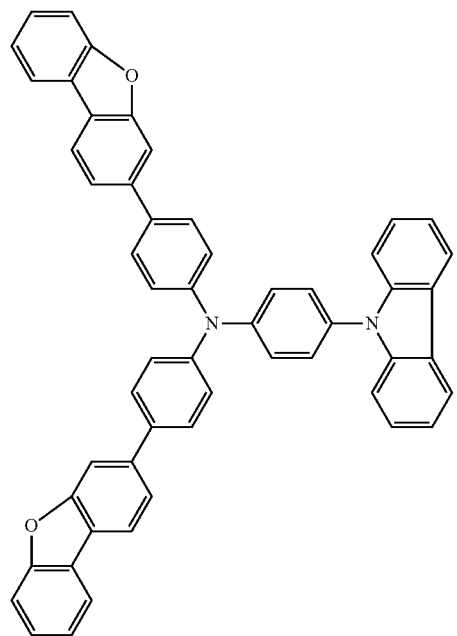
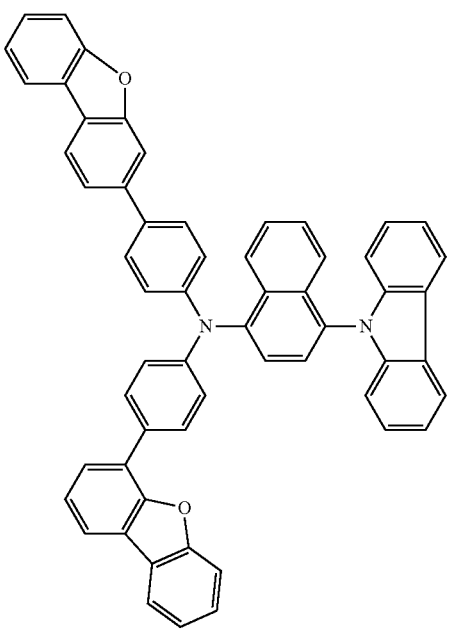
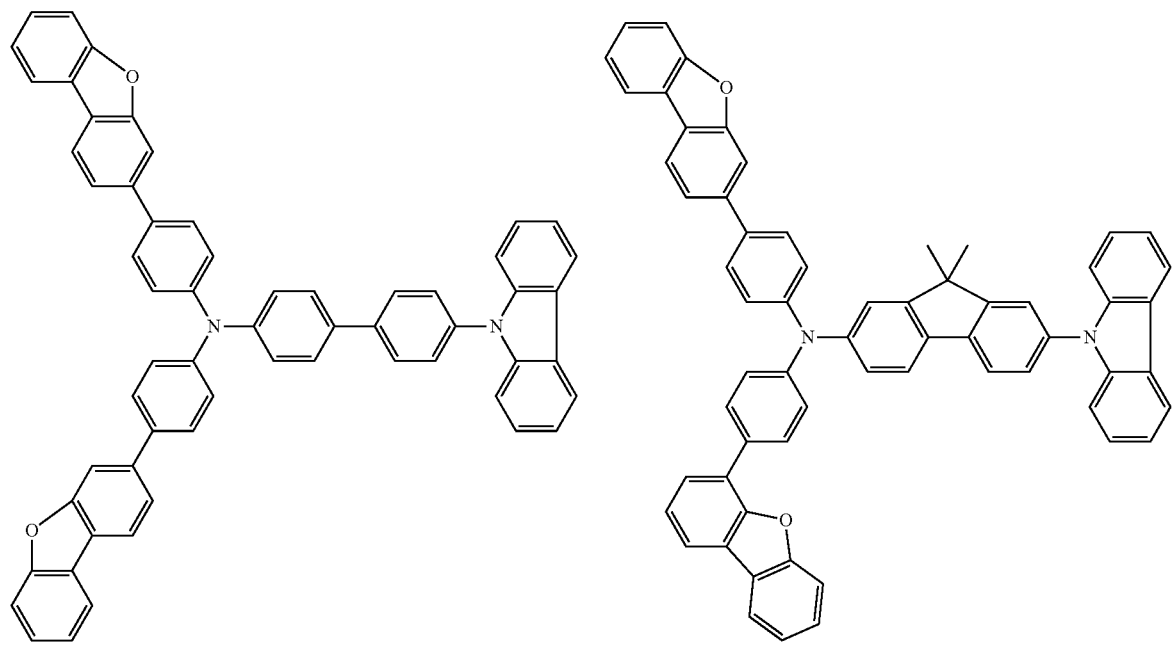

-continued
113
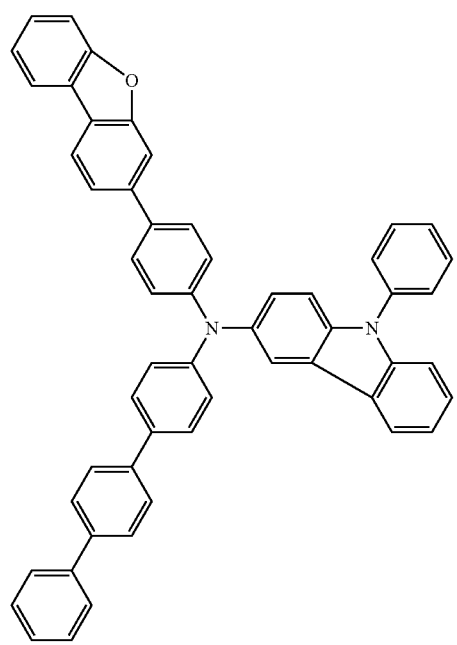
114
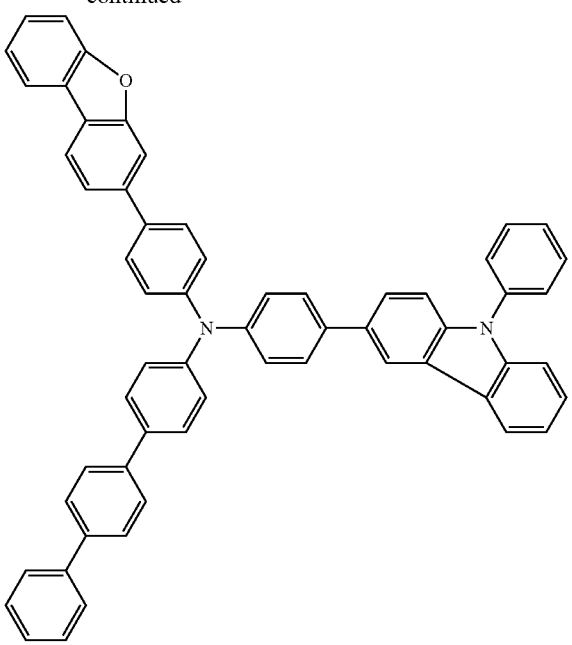
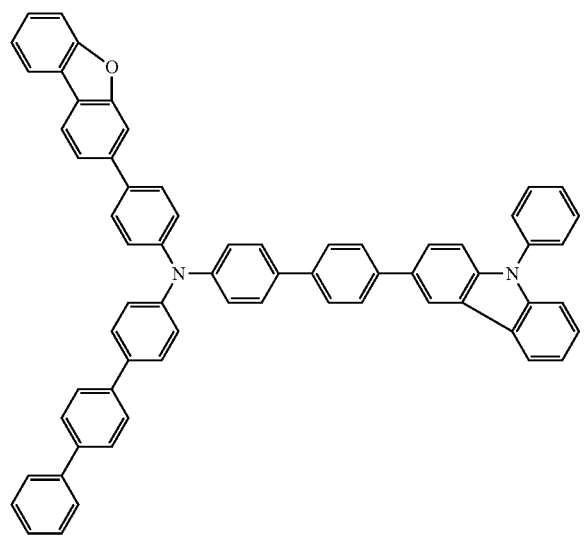
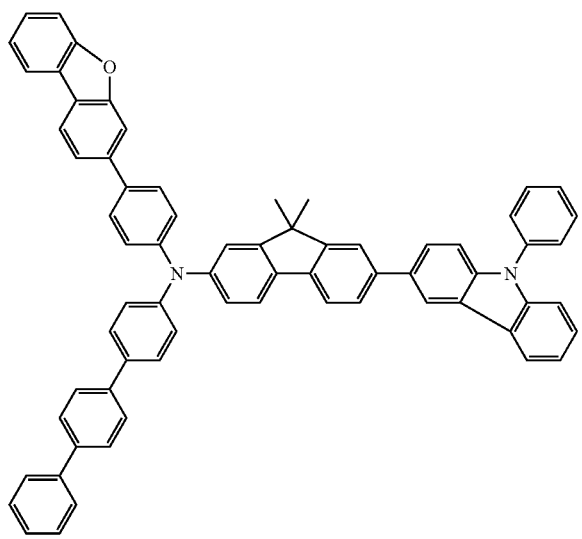

115 116
-continued
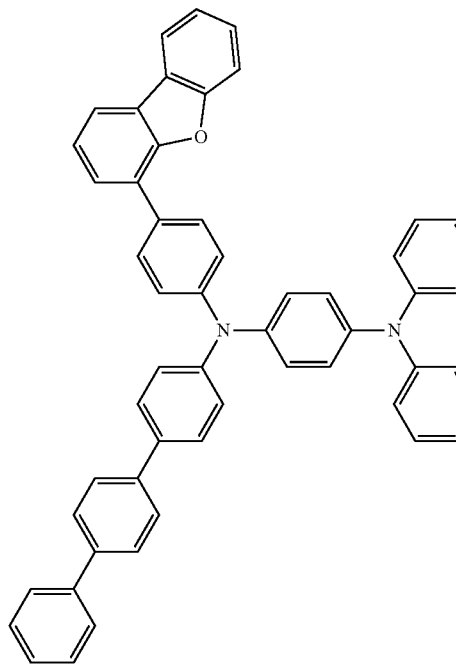
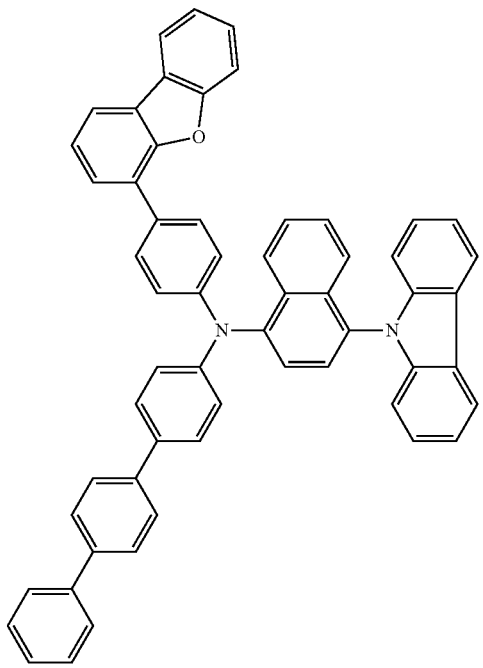
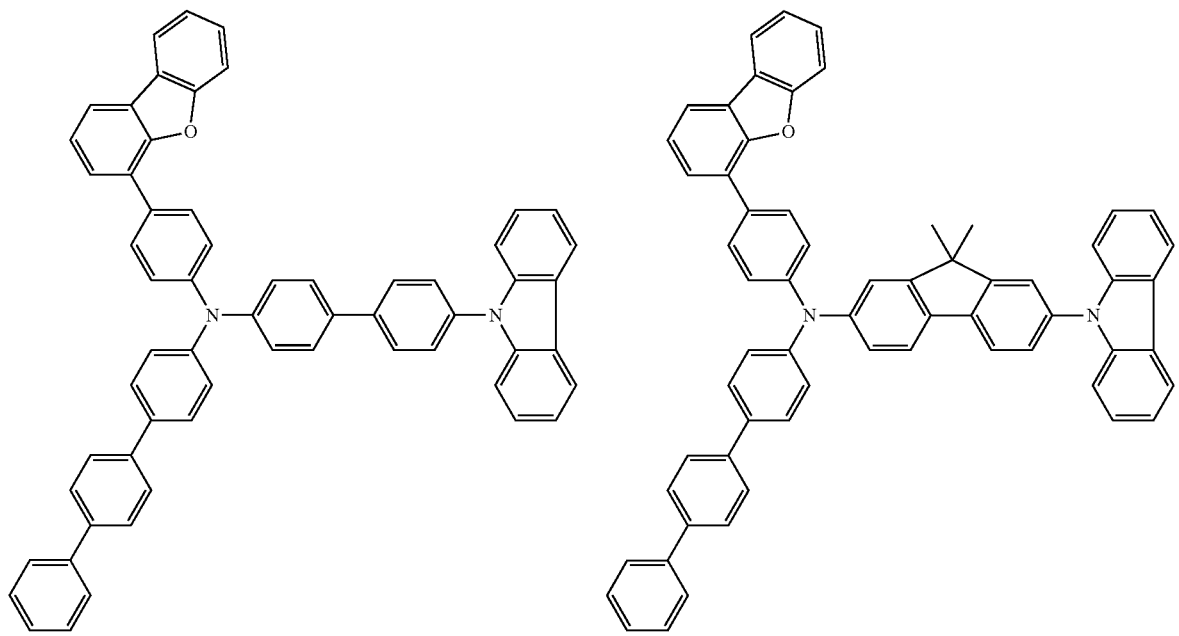

-continued
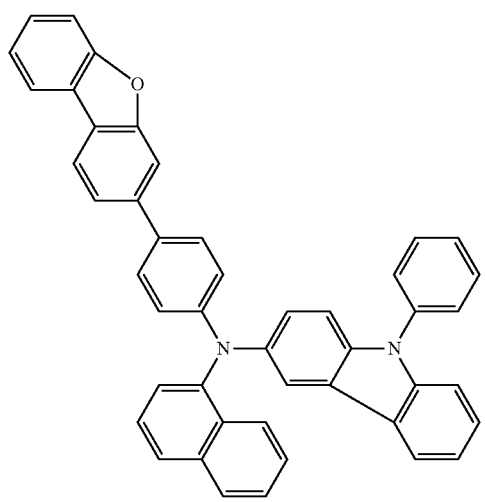
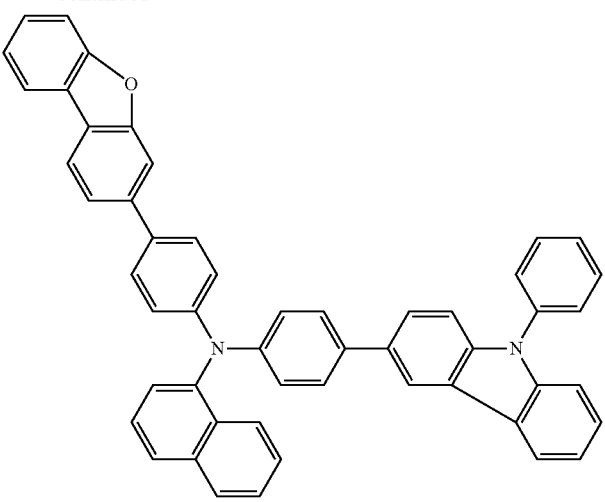
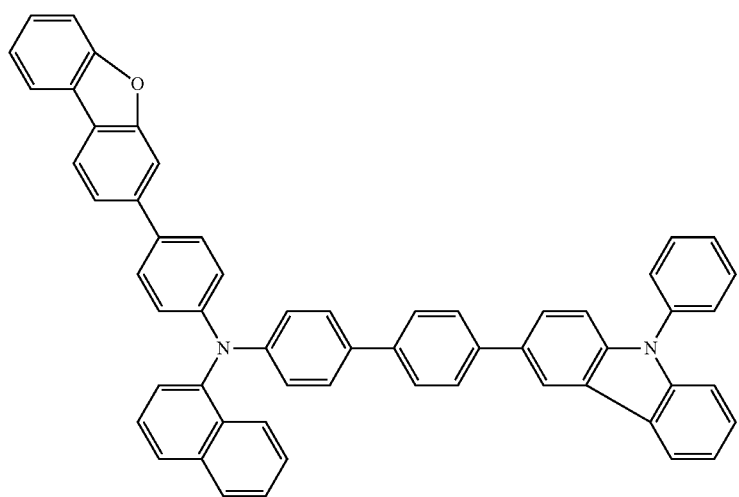

-continued
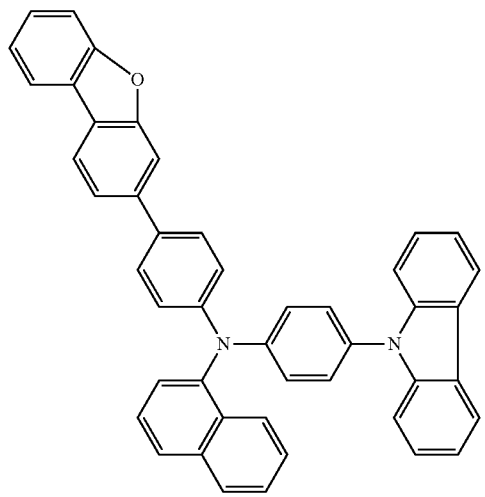
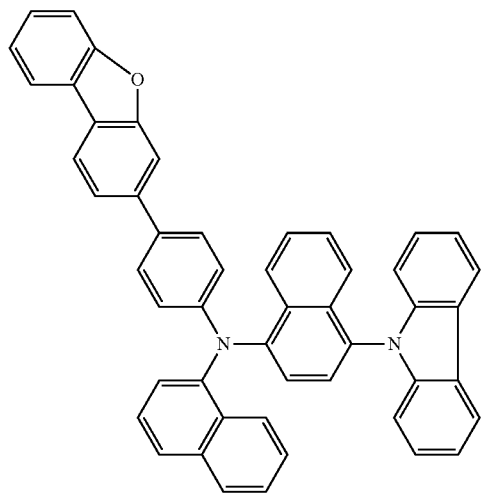
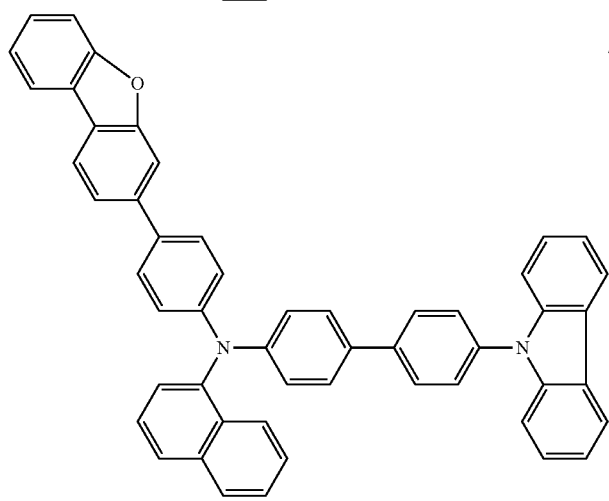
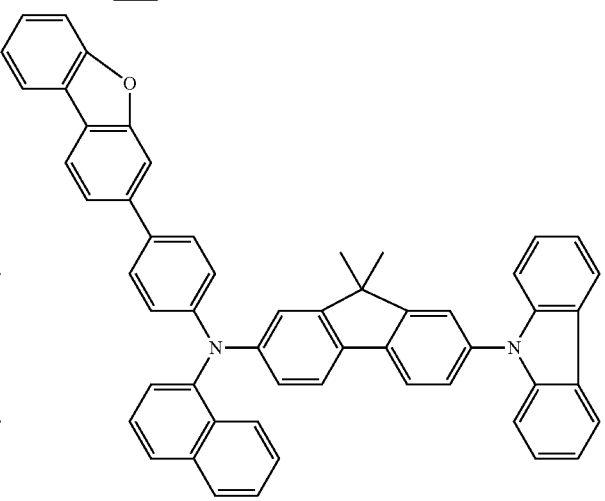
[Chem. 24]
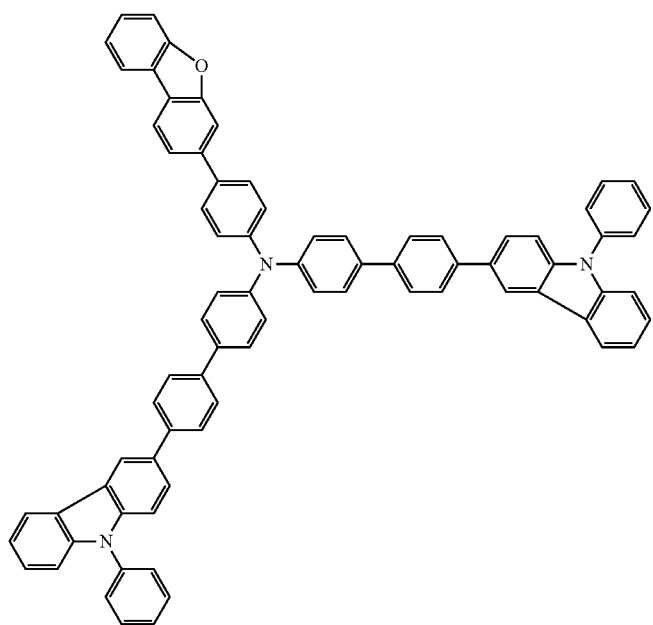

121
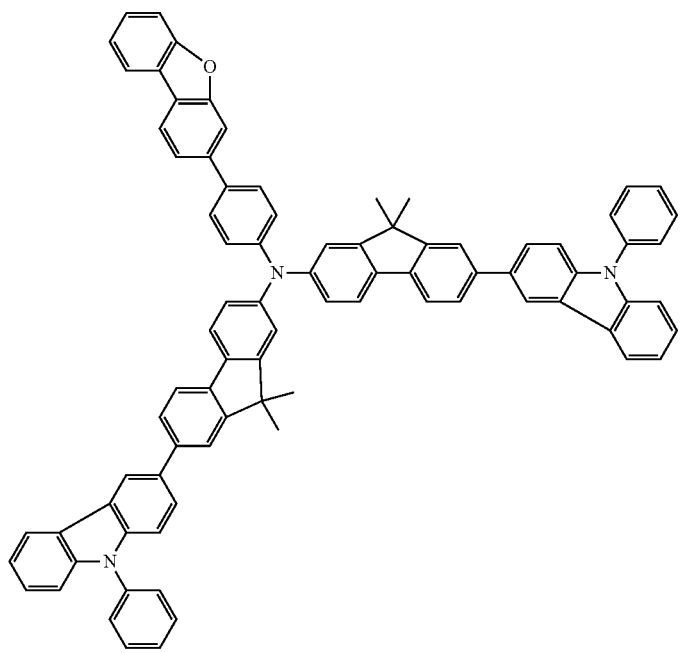
122
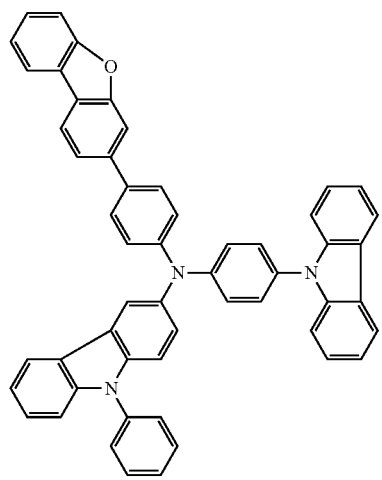
-continued
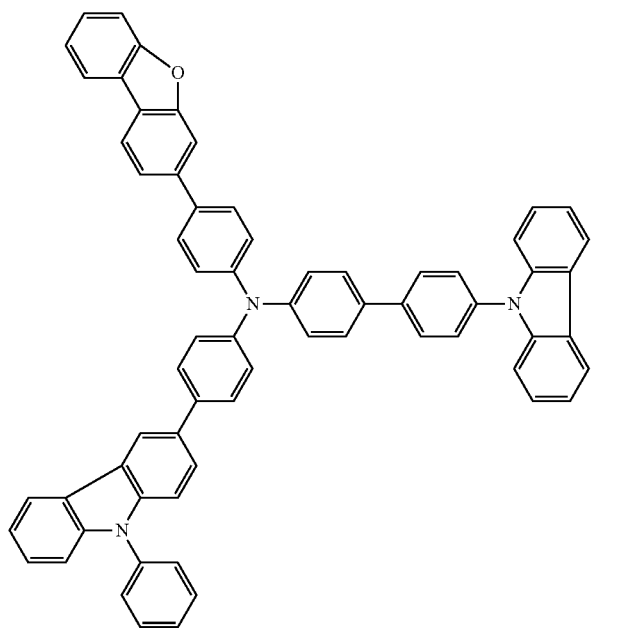
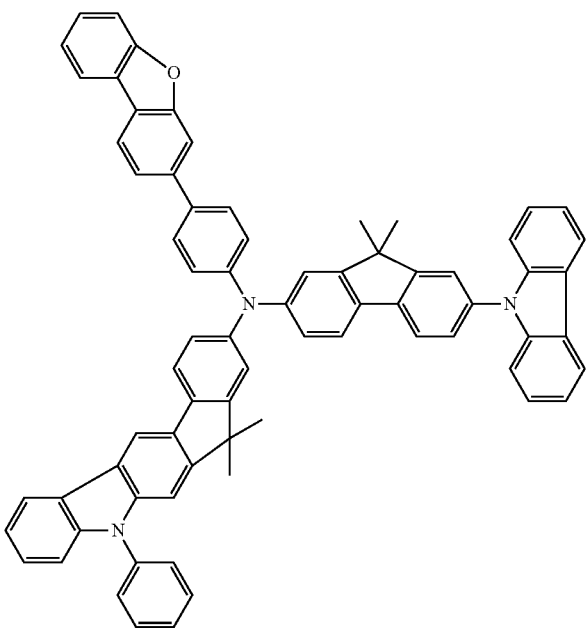

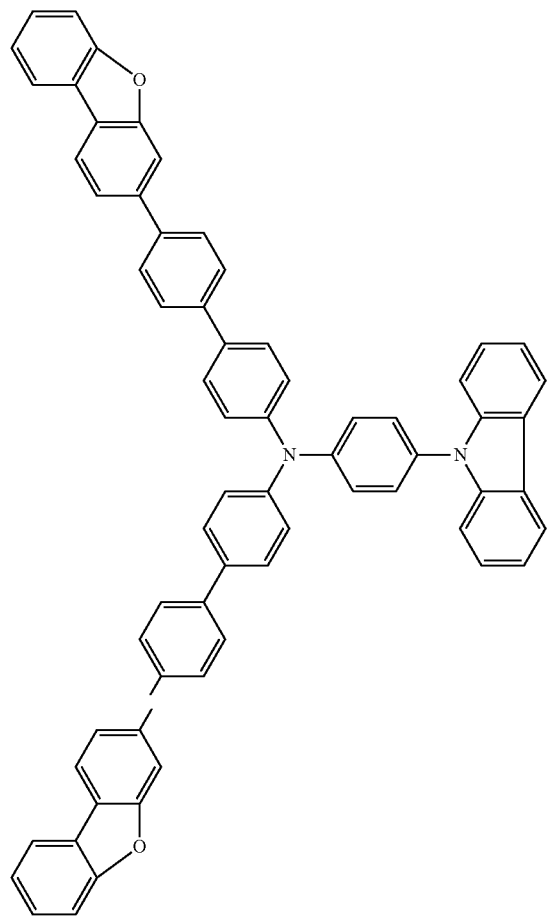
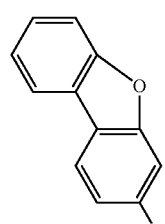

-continued
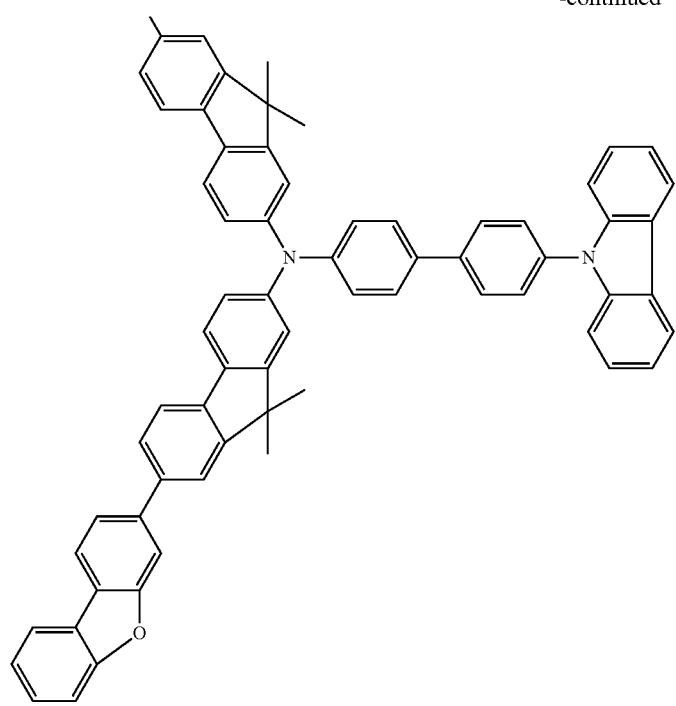
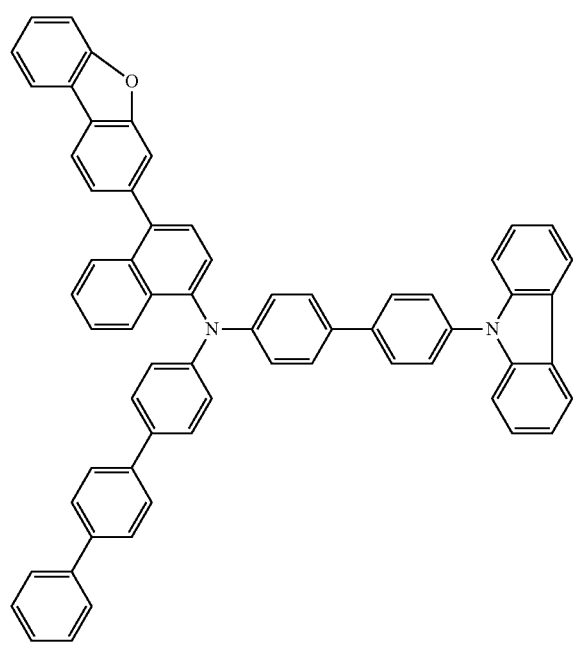

[Chem. 25]
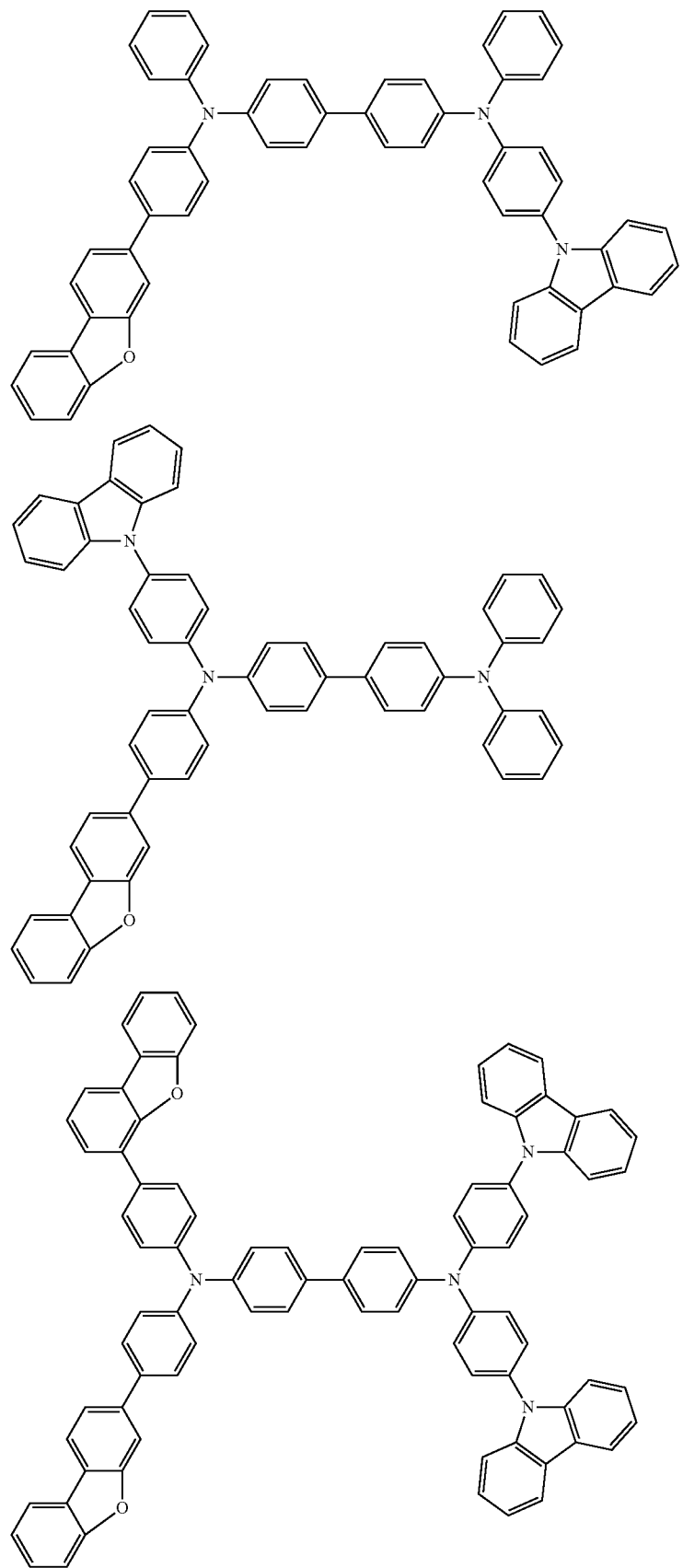
-continued

-continued
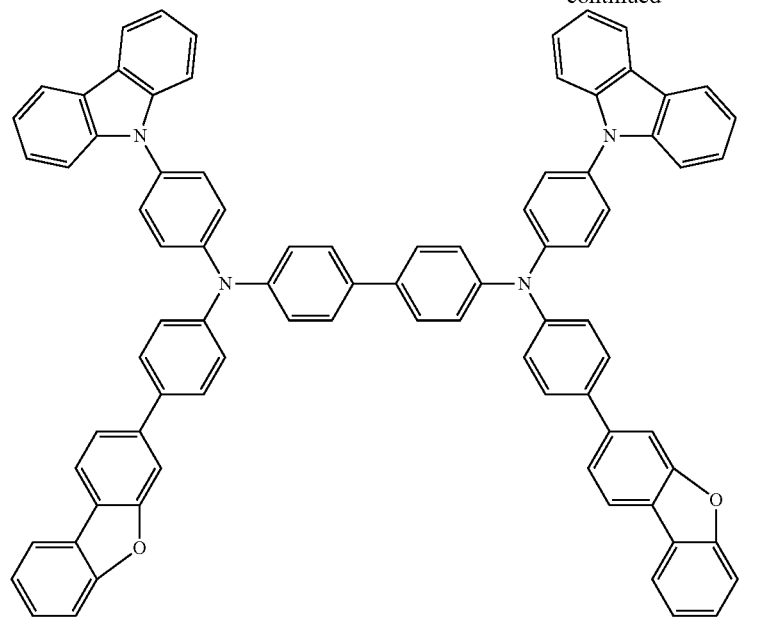
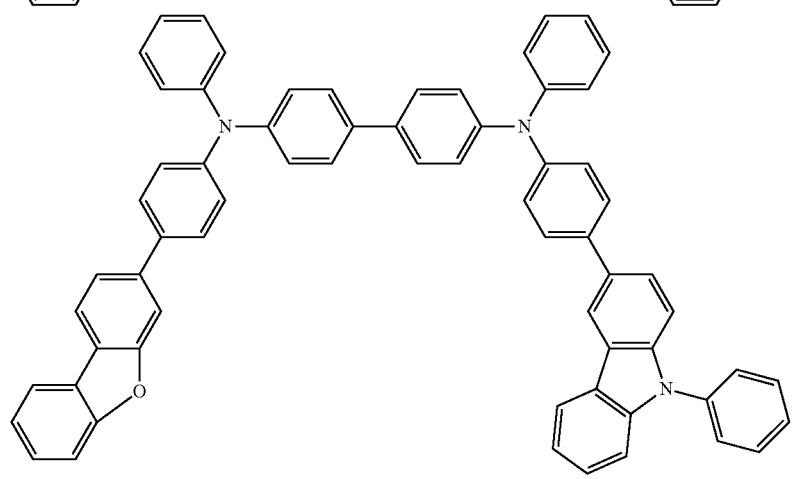
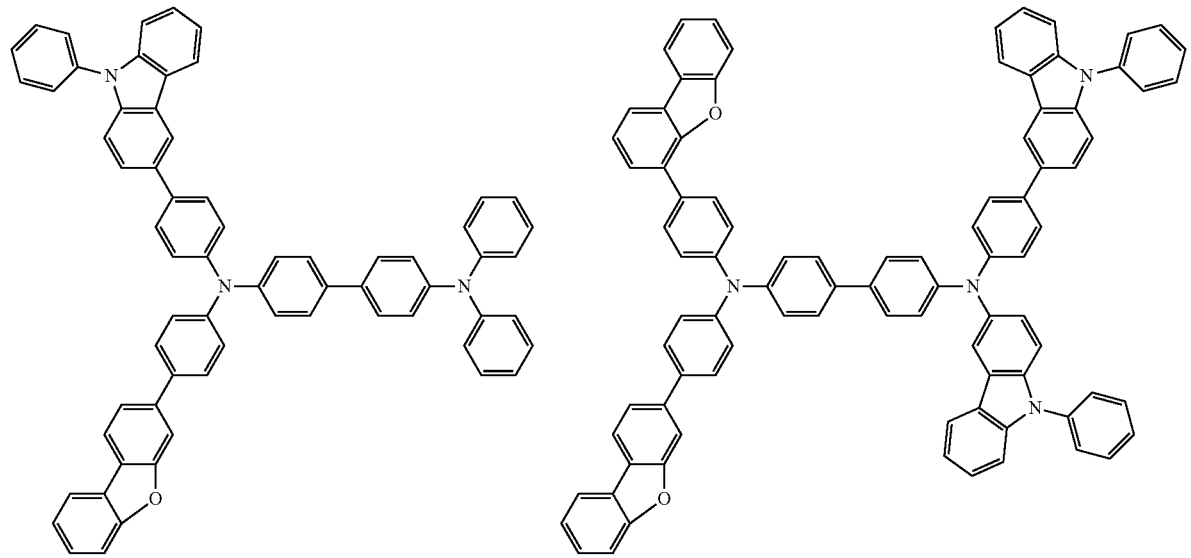

131 132
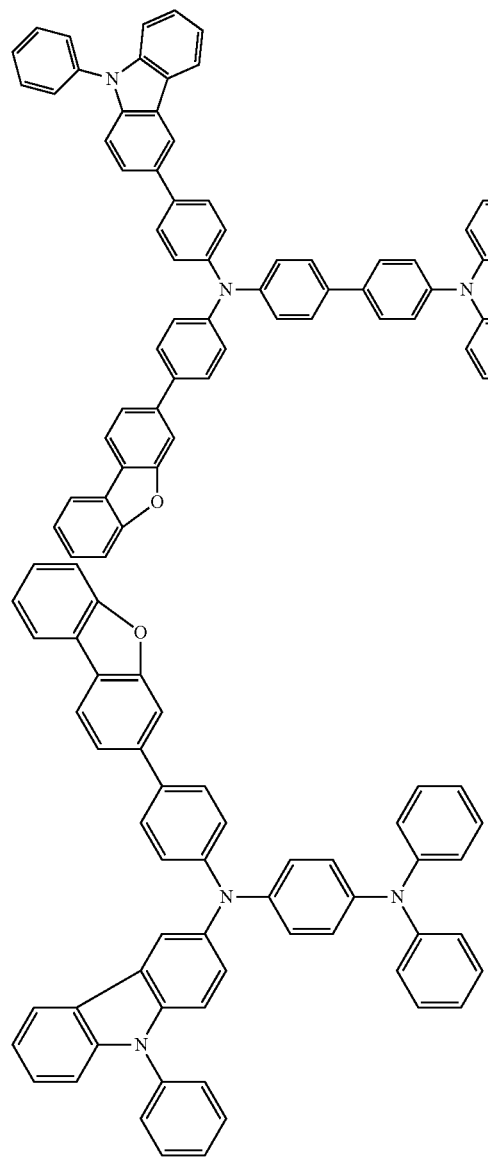
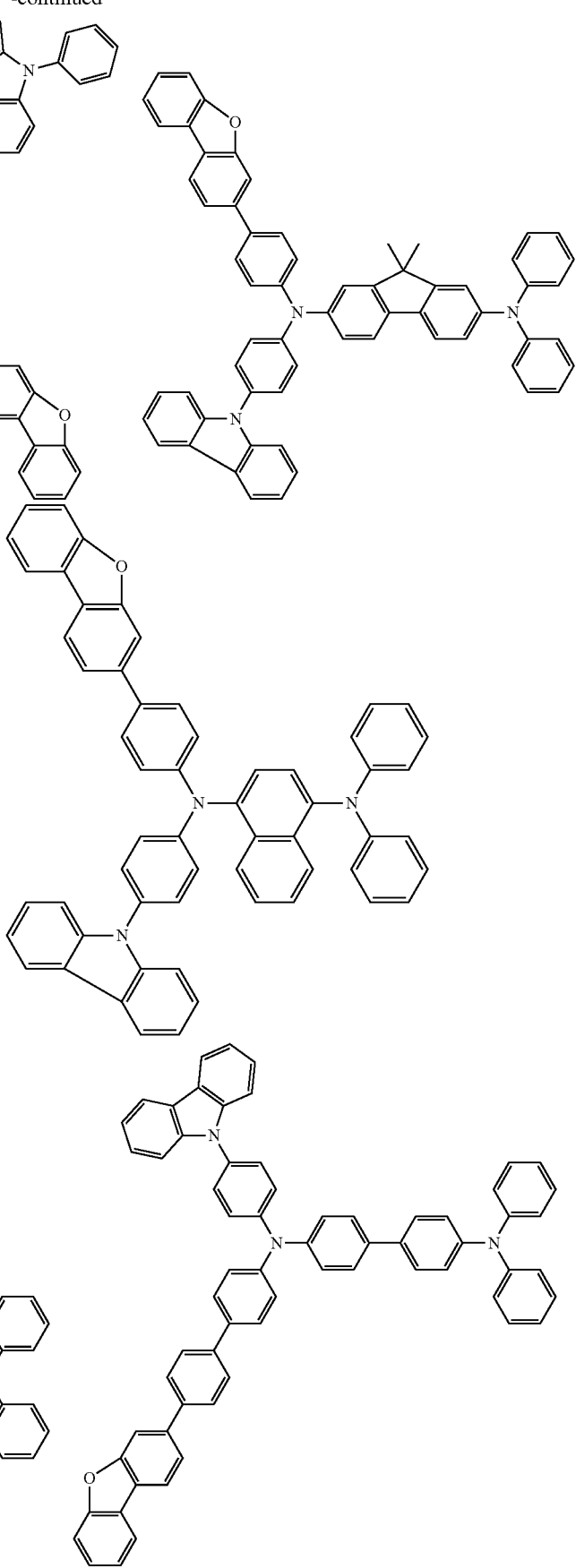

[Chem. 26]
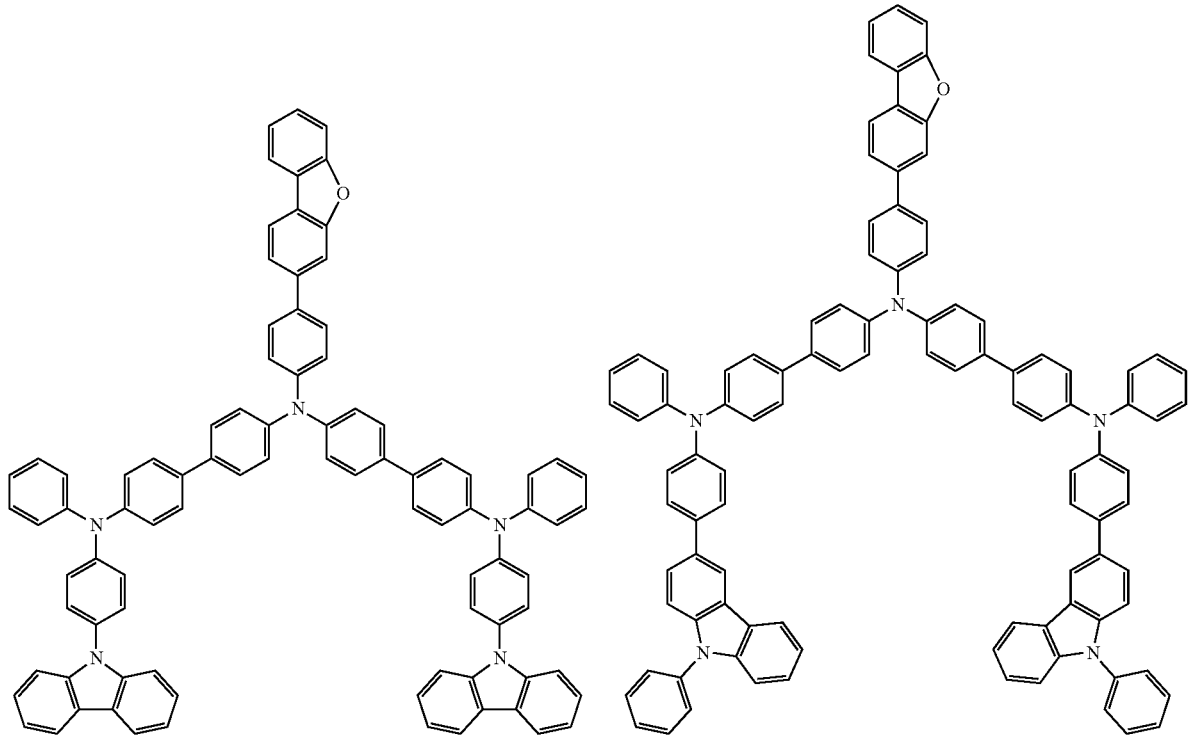
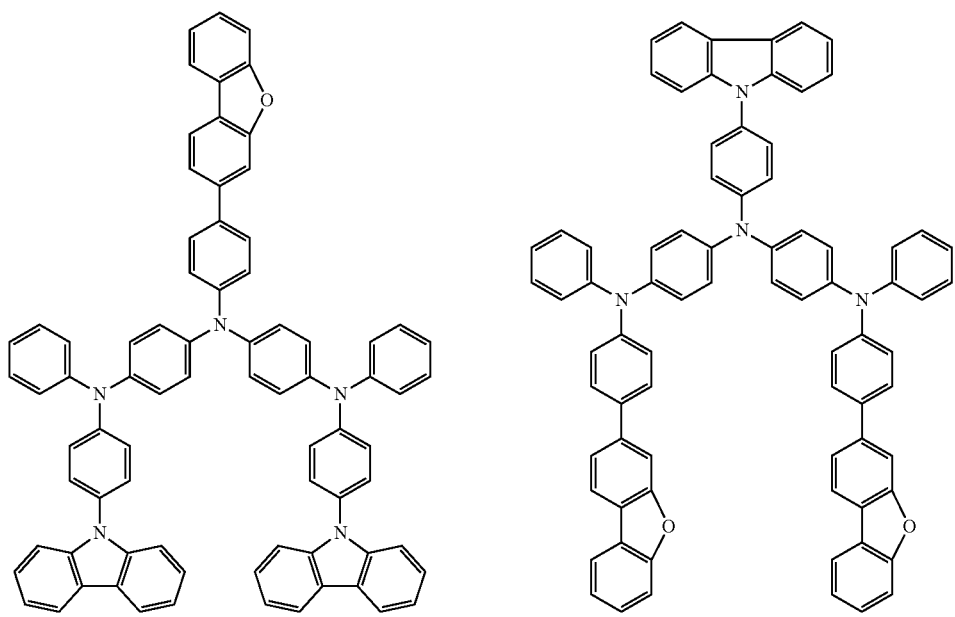

-continued
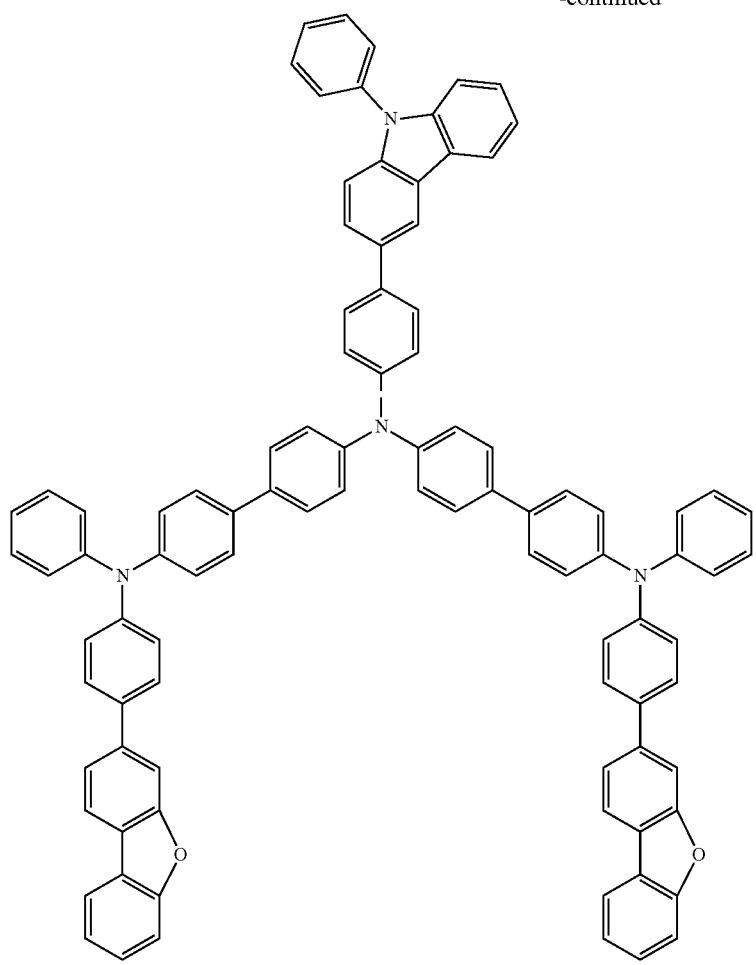
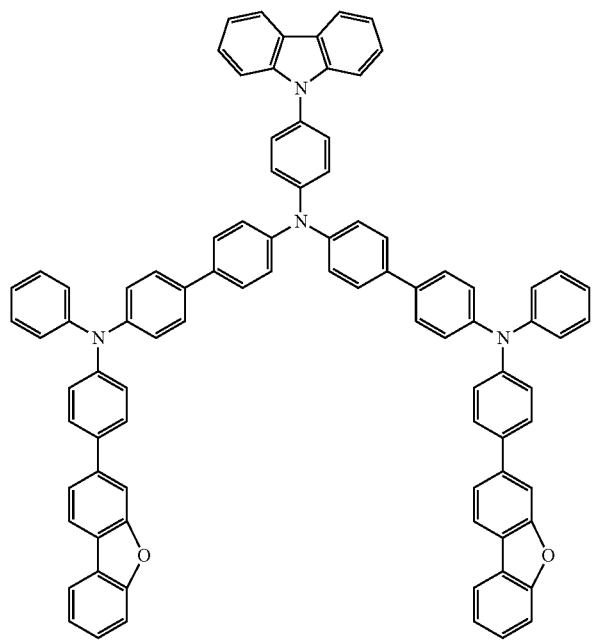 [SMILES: c1ccc(N(c2ccc(-c3ccc(N(c4ccc(-c5ccc(N(c6ccccc6)c6ccc(-c7ccc8c(c7)oc7ccccc78)cc6)cc5)cc4)c4ccc(-n5c6ccccc6c6ccccc65)cc4)cc3)cc2)c2ccc(-c3ccc4c(c3)oc3ccccc34)cc2)cc1]

-continued
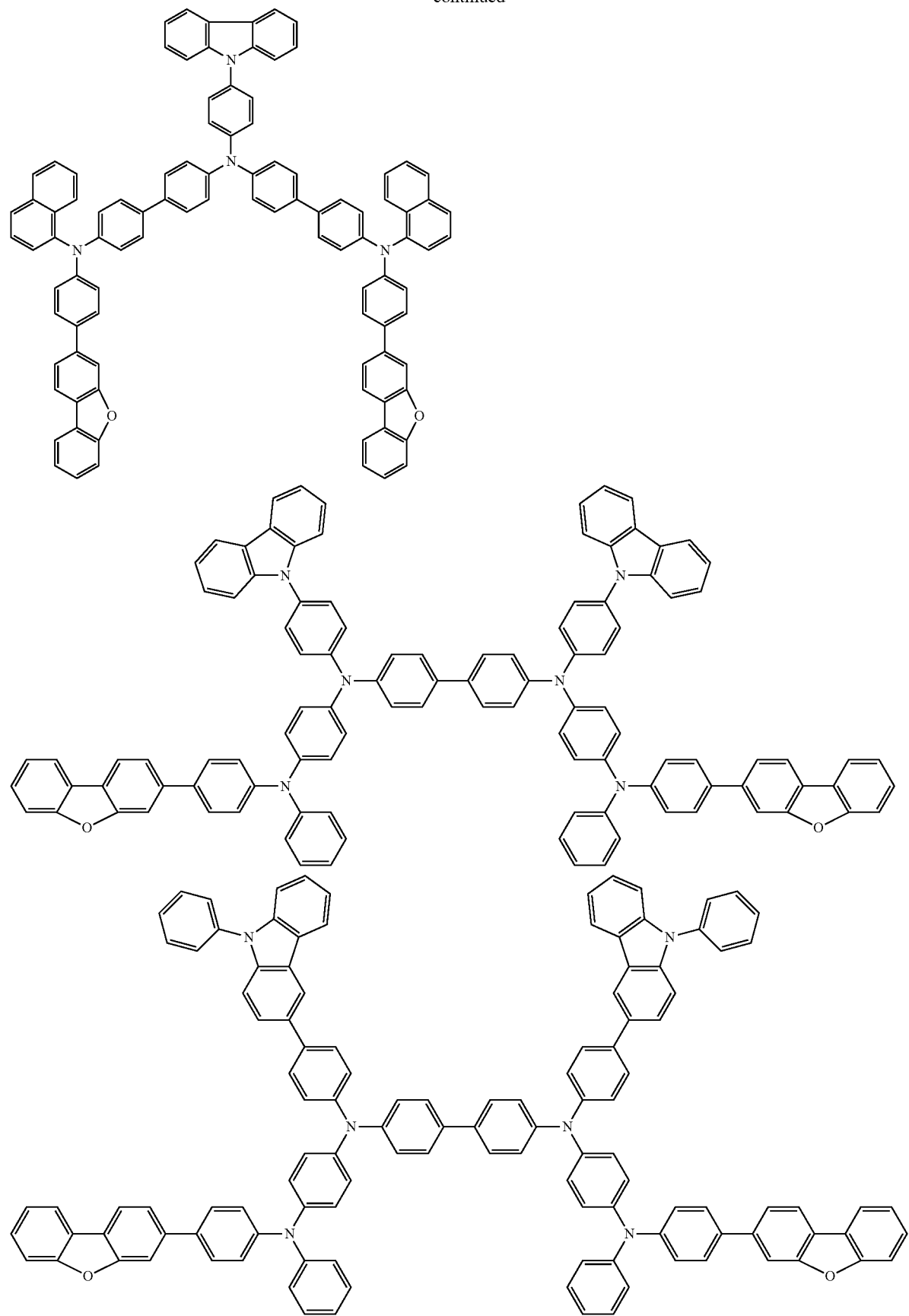

-continued
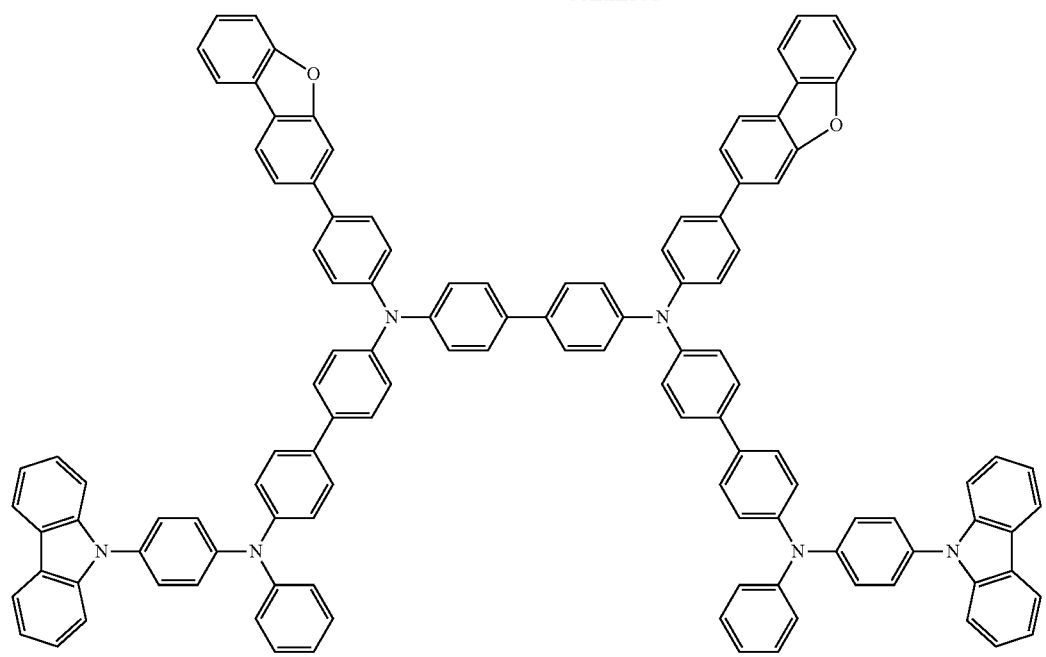
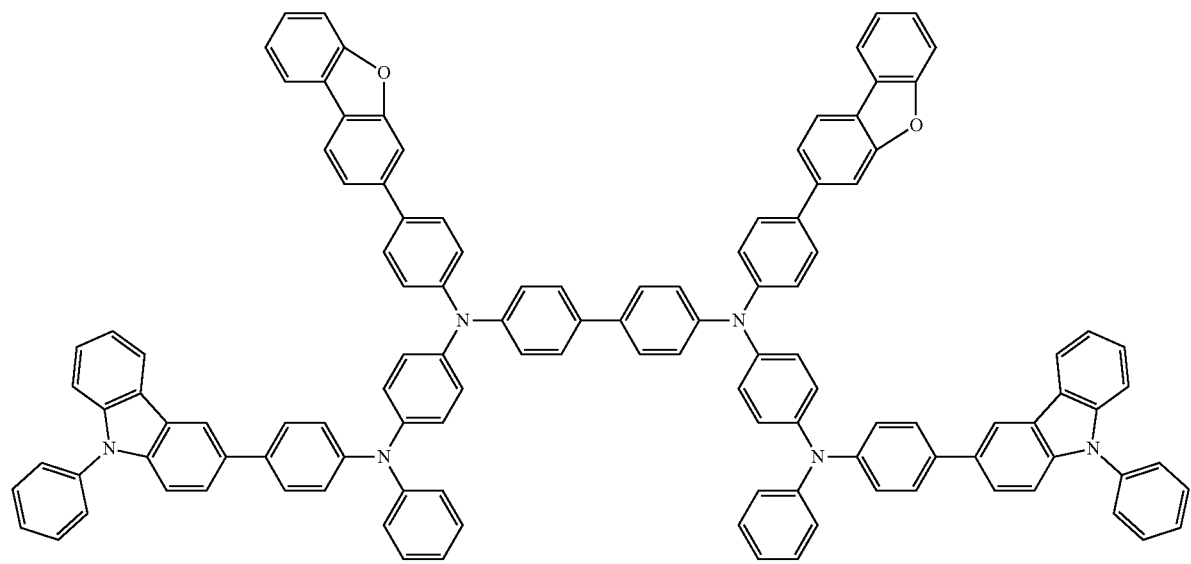

[Chem. 27]
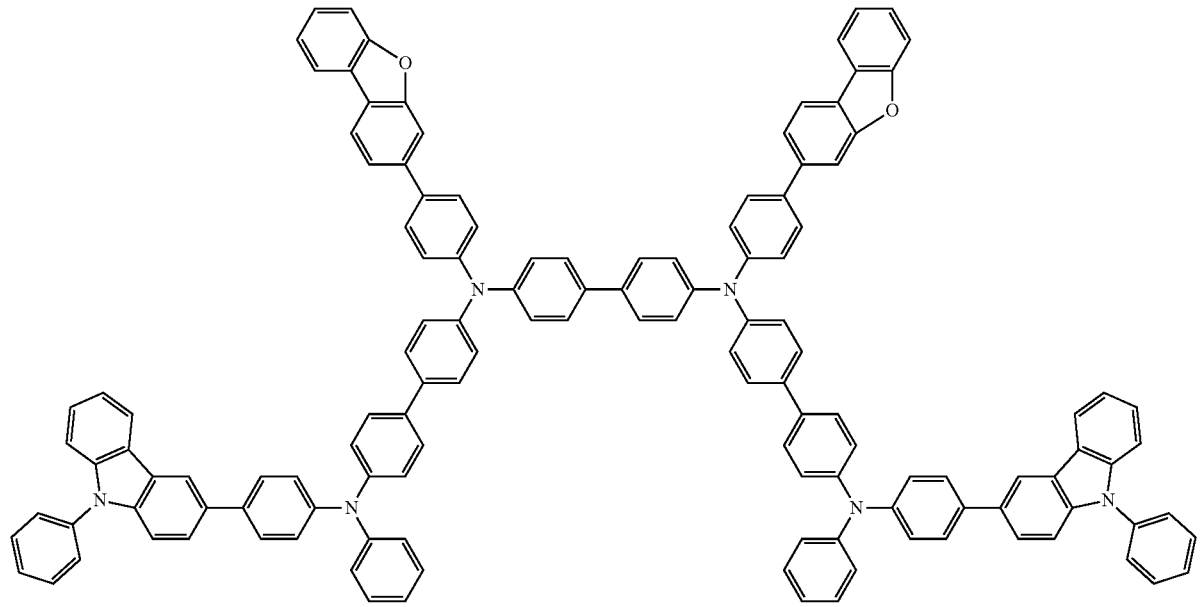
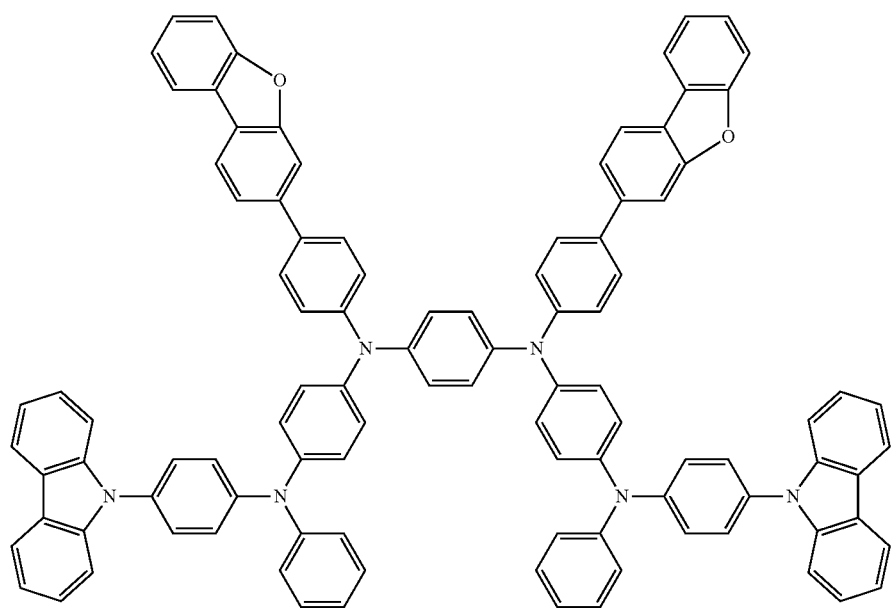

143
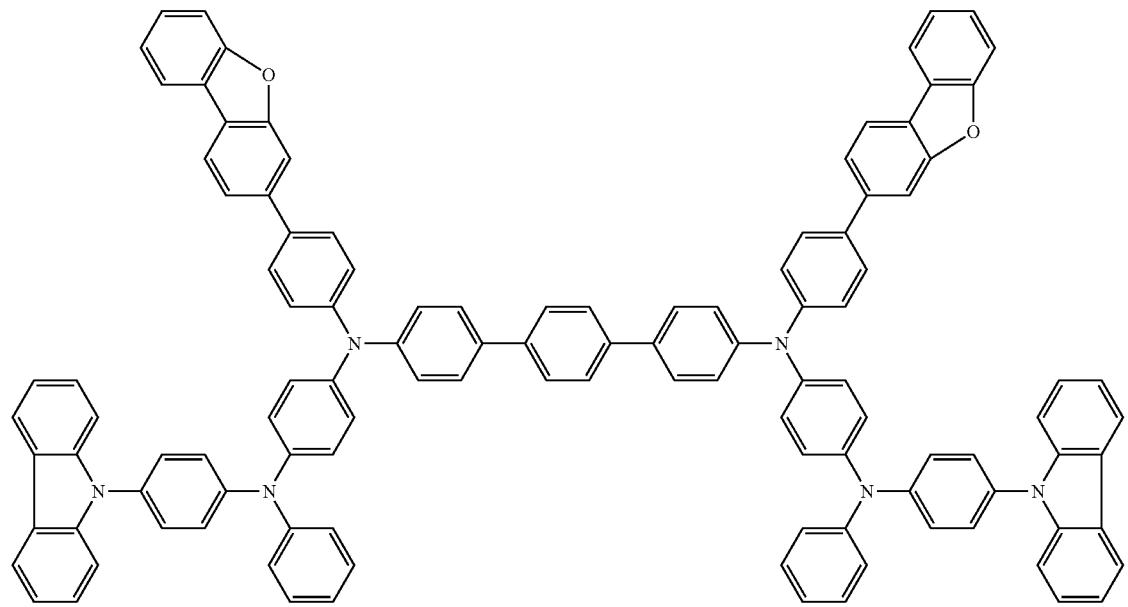
144
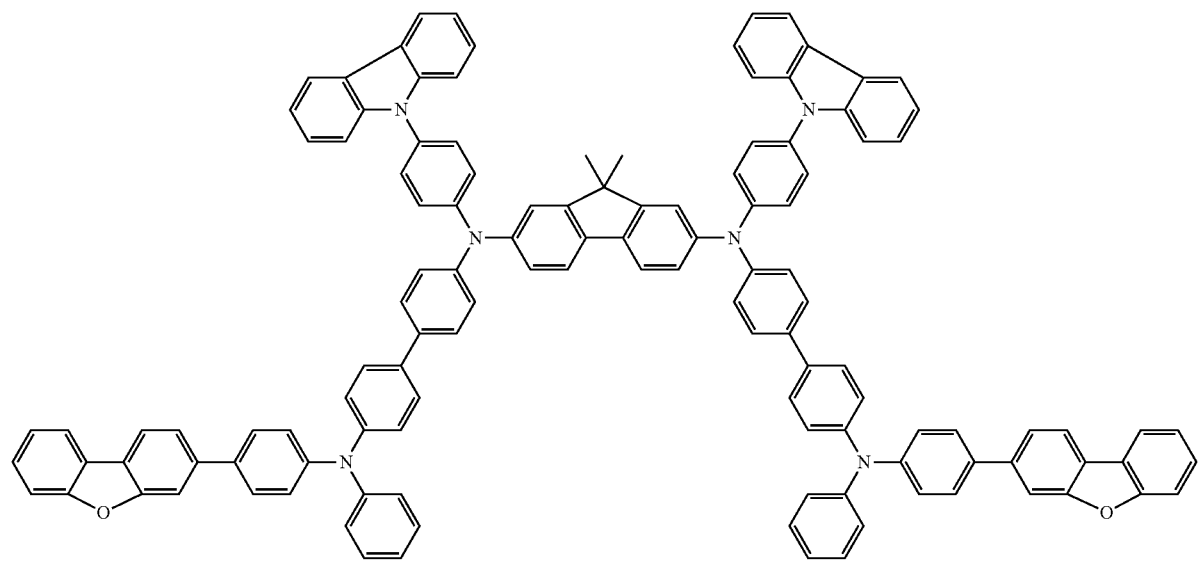
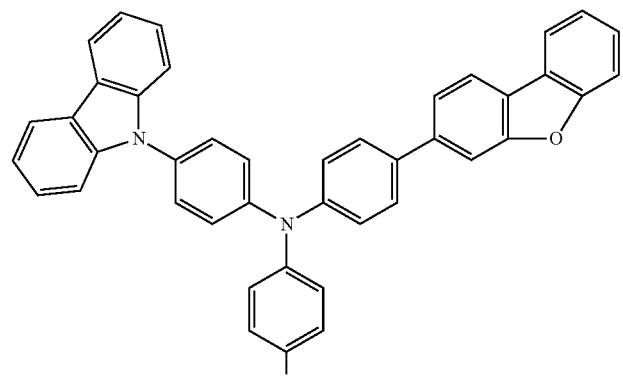

-continued
145
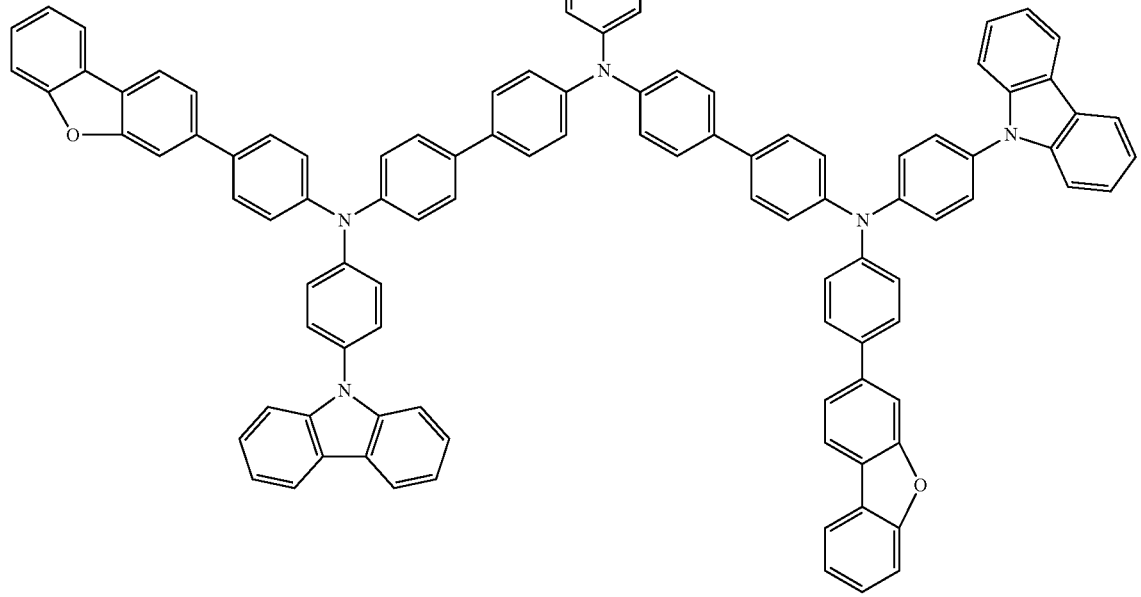
146
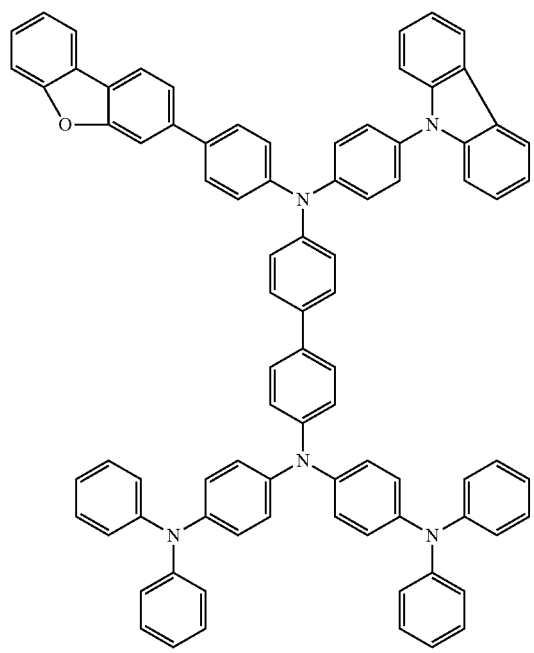

-continued
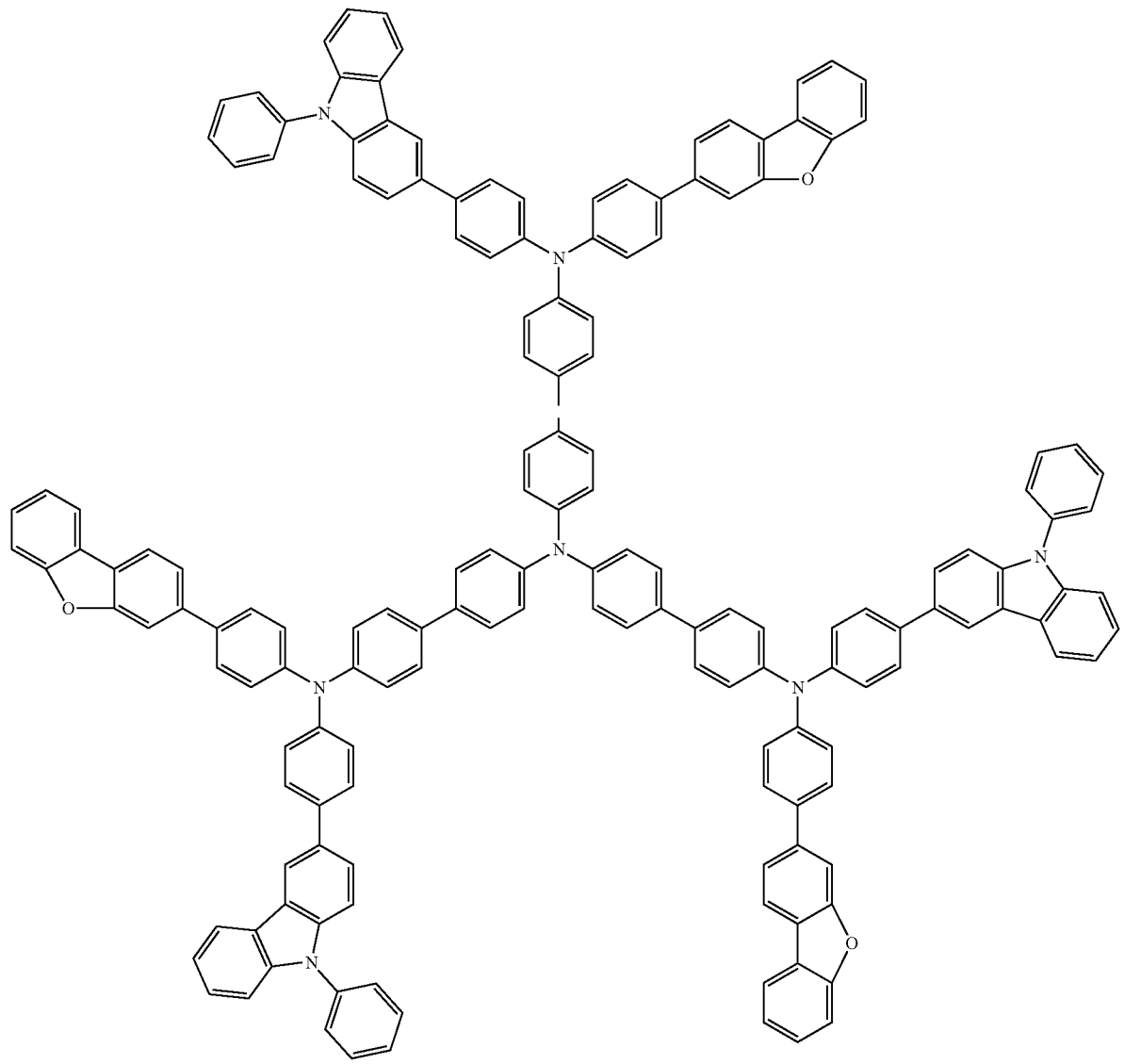 [SMILES: c1ccc(-n2c3ccccc3c3cc(-c4ccc(N(c5ccc(-c6ccc(N(c7ccc(-c8ccc(N(c9ccc(-c%10ccc%11c(c%10)oc%10ccccc%10%11)cc9)c9ccc(-c%10ccc%11c(c%10)c%10ccccc%10n%11-c%10ccccc%10)cc9)cc8)cc7)c7ccc(-c8ccc(N(c9ccc(-c%10ccc%11c(c%10)oc%10ccccc%10%11)cc9)c9ccc(-c%10ccc%11c(c%10)c%10ccccc%10n%11-c%10ccccc%10)cc9)cc8)cc7)cc6)cc5)c5ccc(-c6ccc7c(c6)oc6ccccc67)cc5)cc4)ccc32)cc1]

-continued
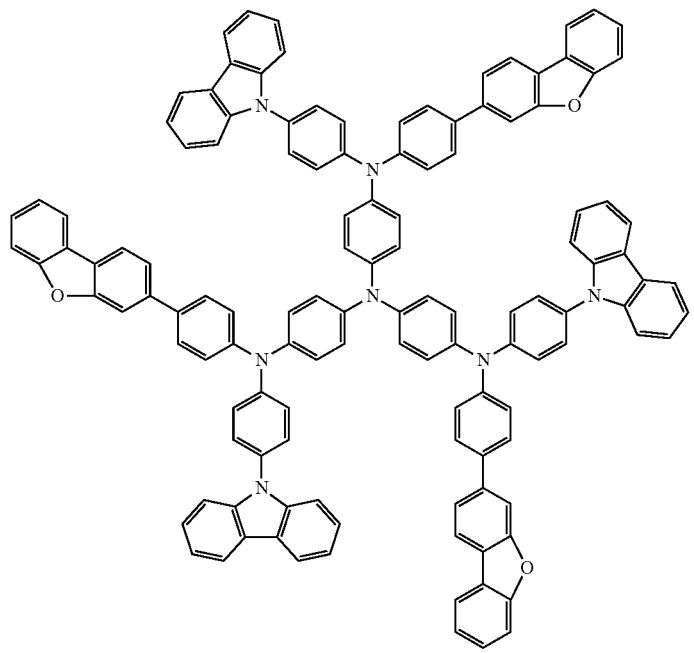
[Chem. 28]
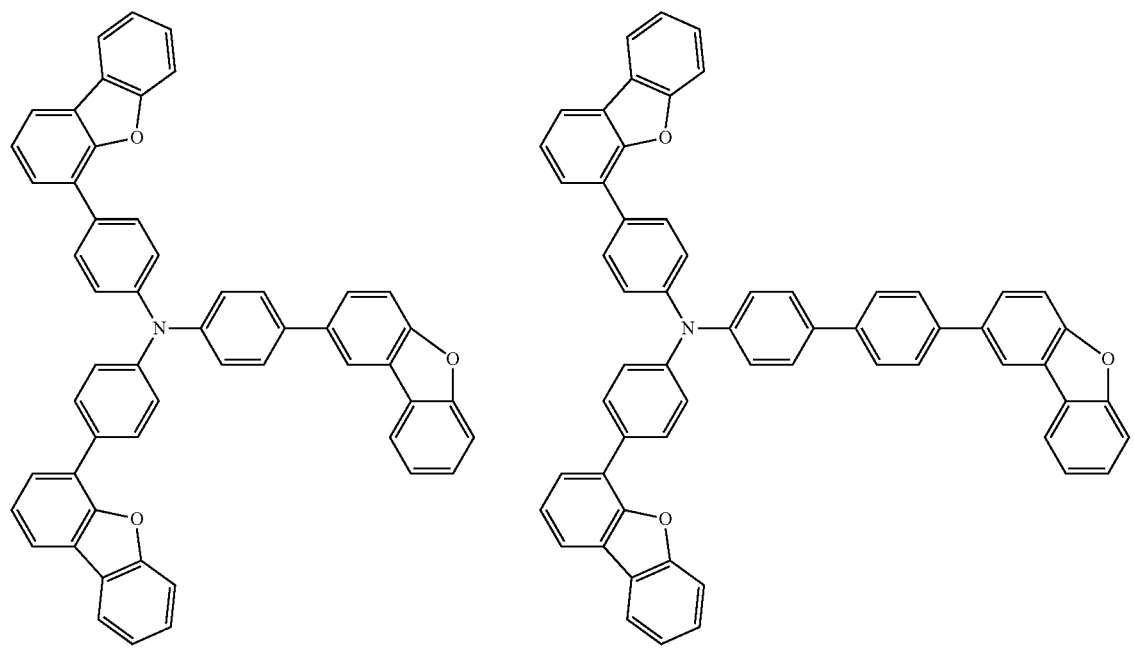

151
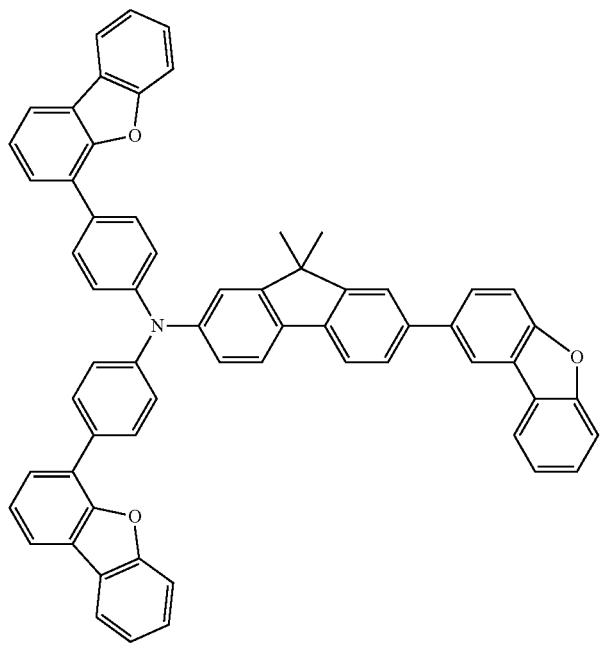
152
-continued
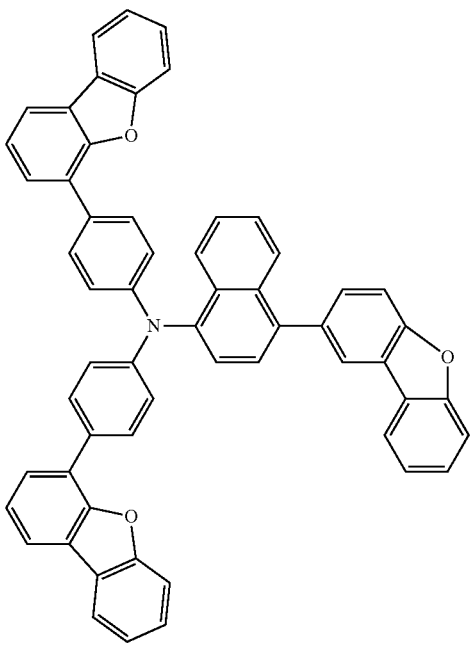
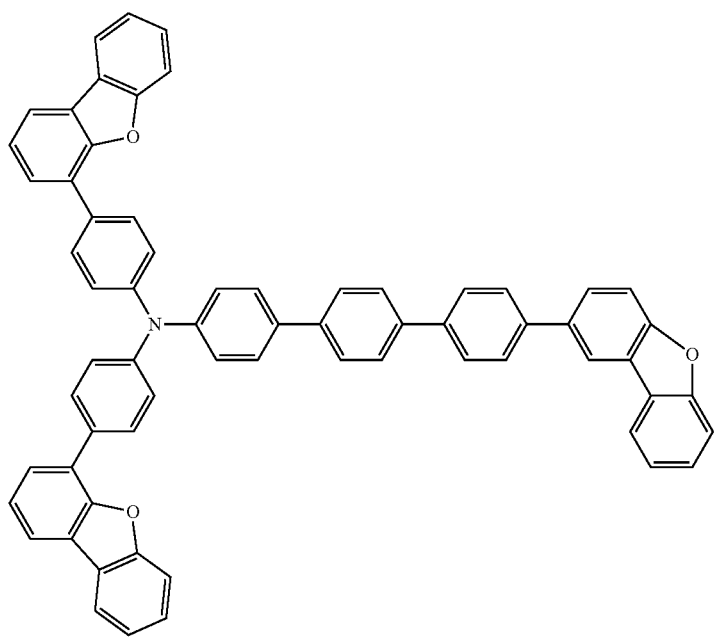

153
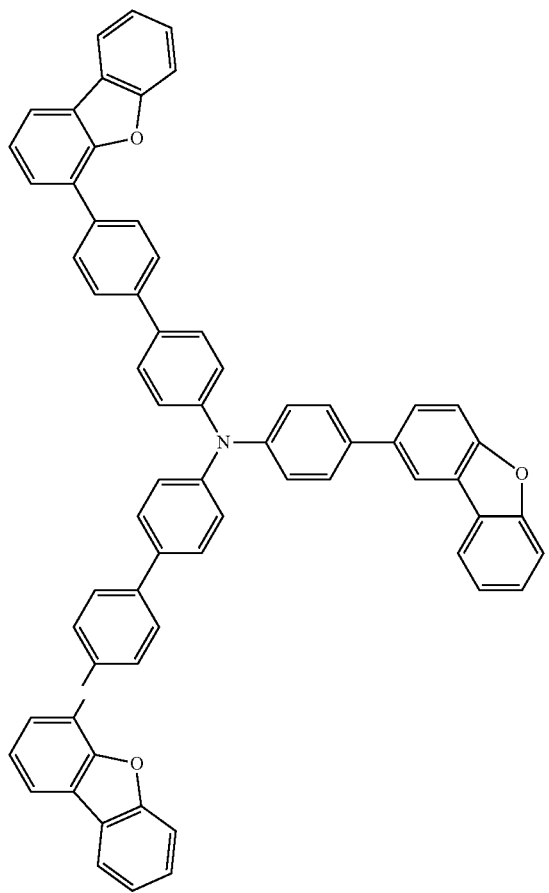
154
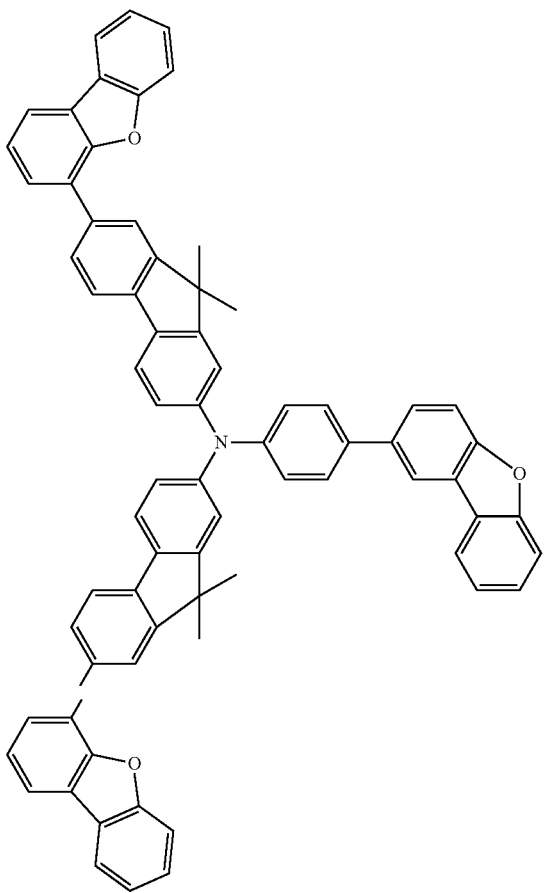
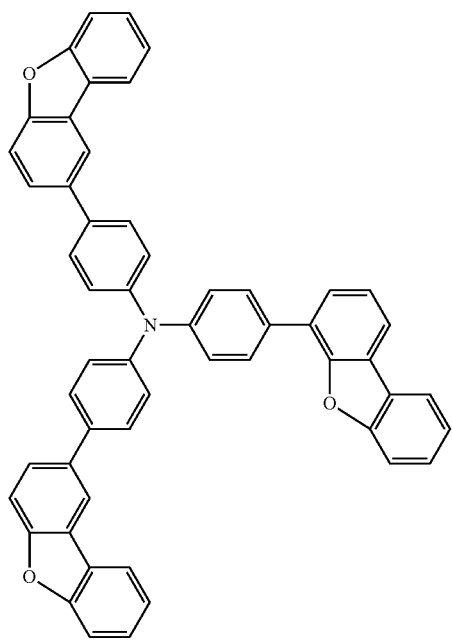
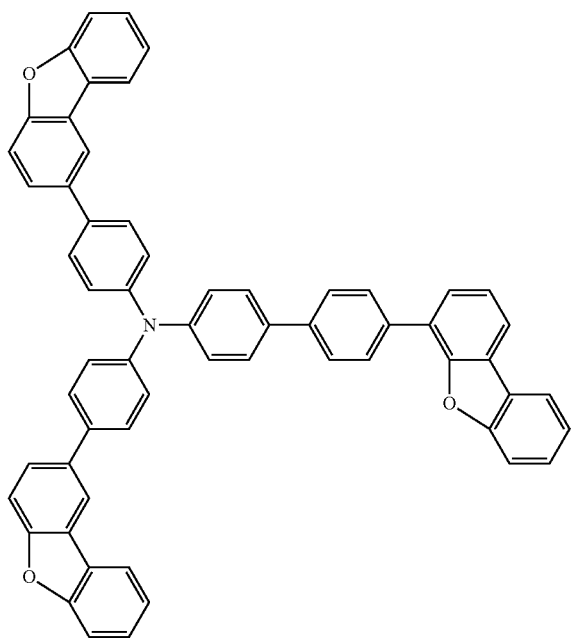

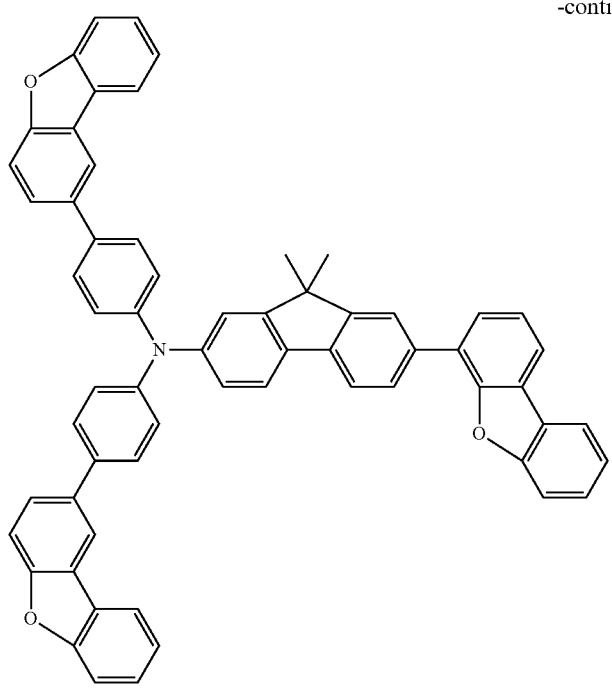
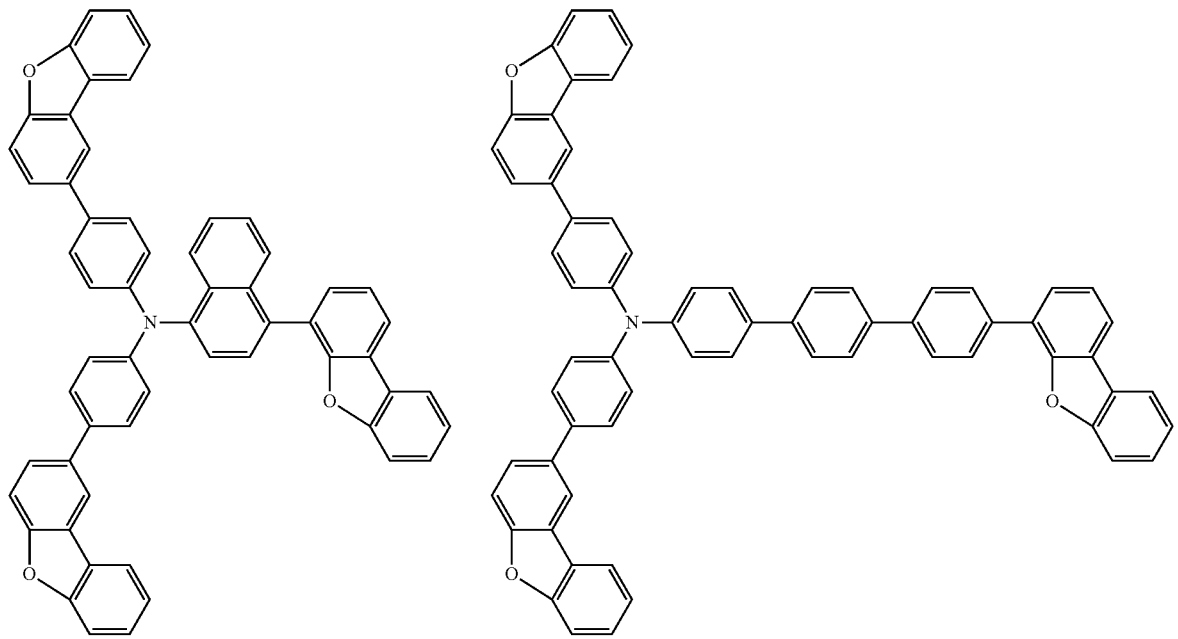
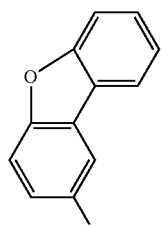
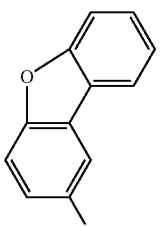

157
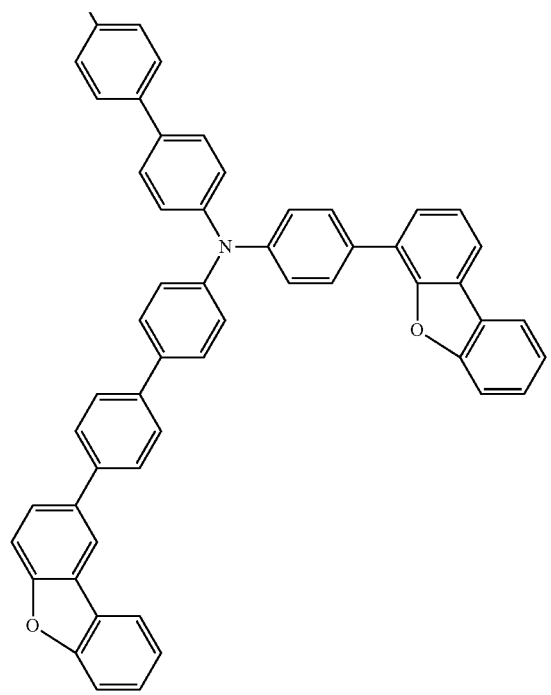
158
-continued
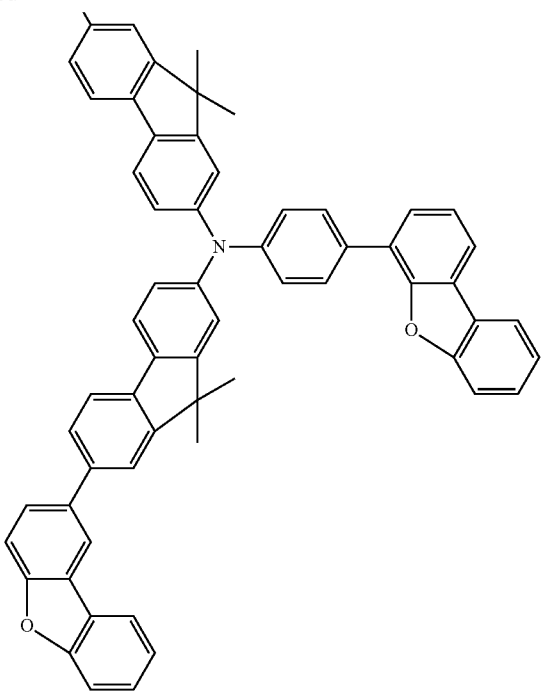
[Chem. 29]
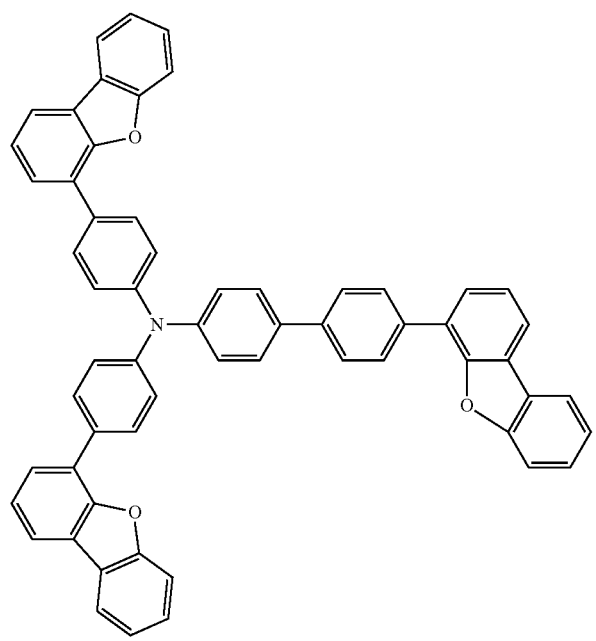
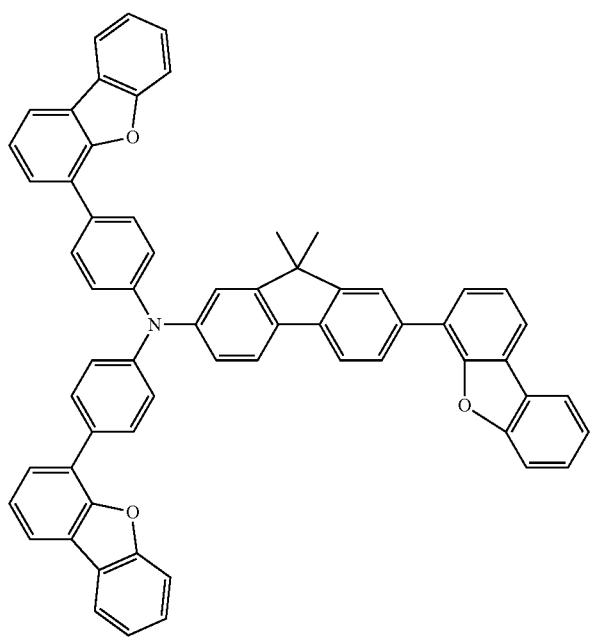

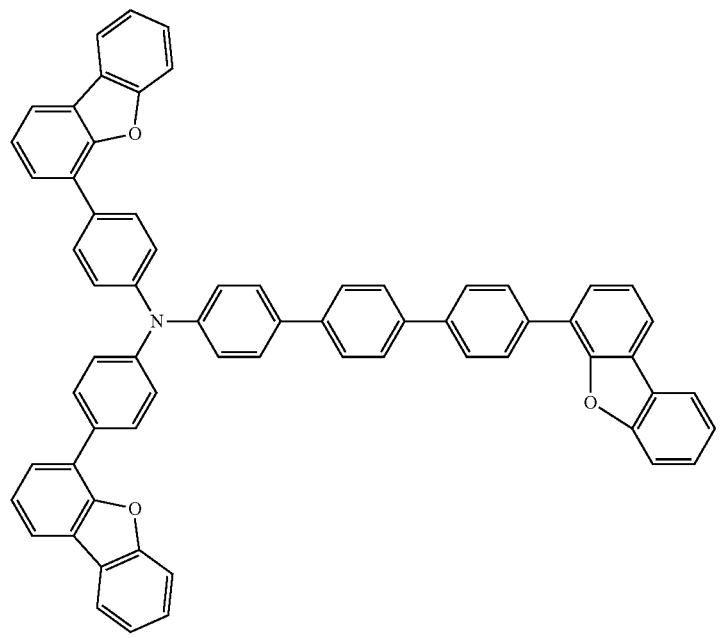
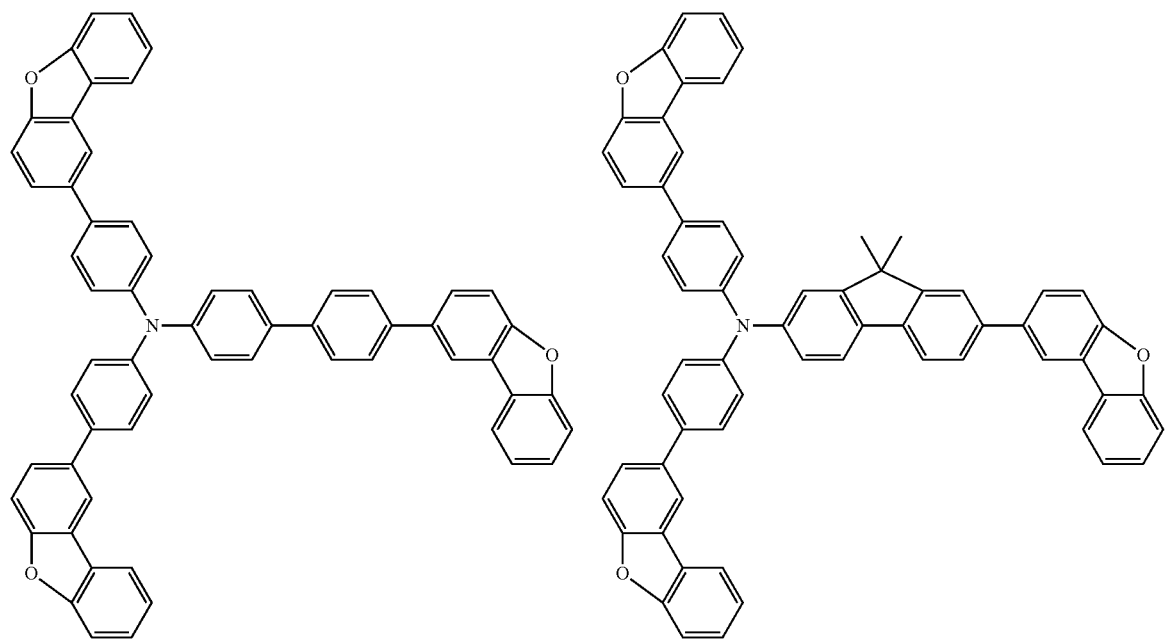

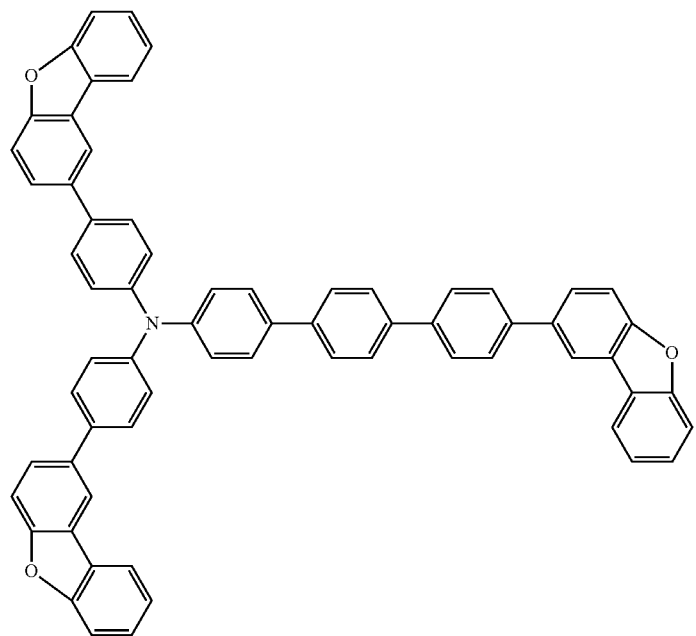
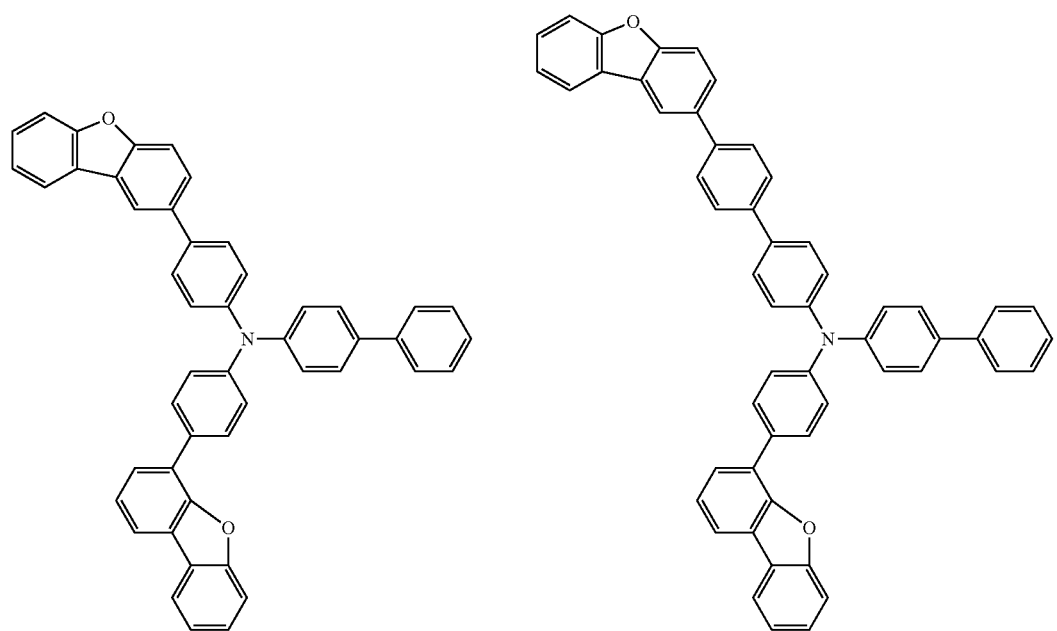

-continued
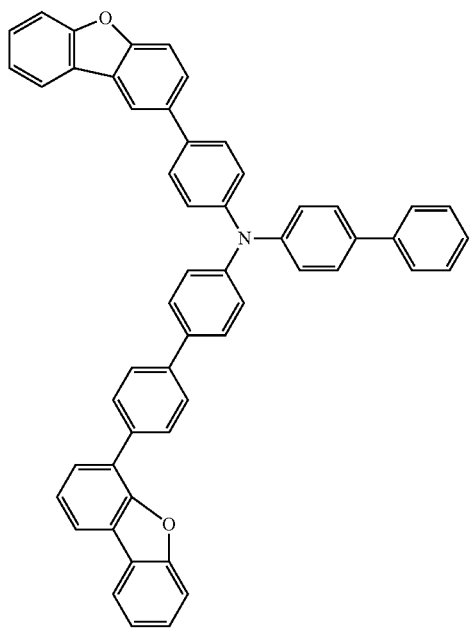
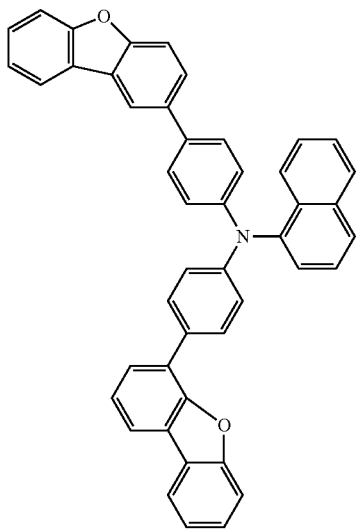
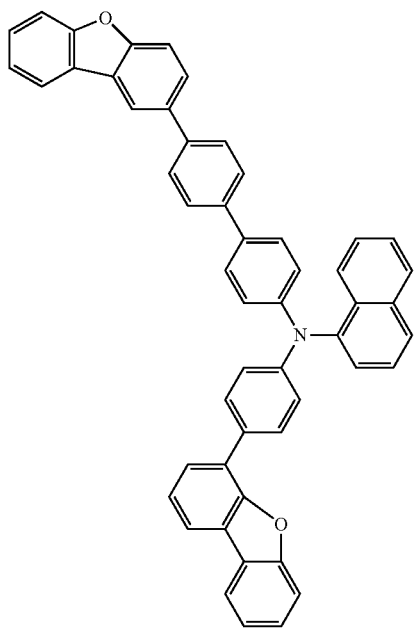
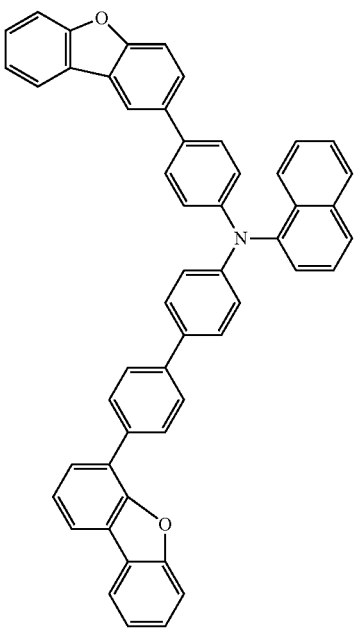

[Chem. 30]
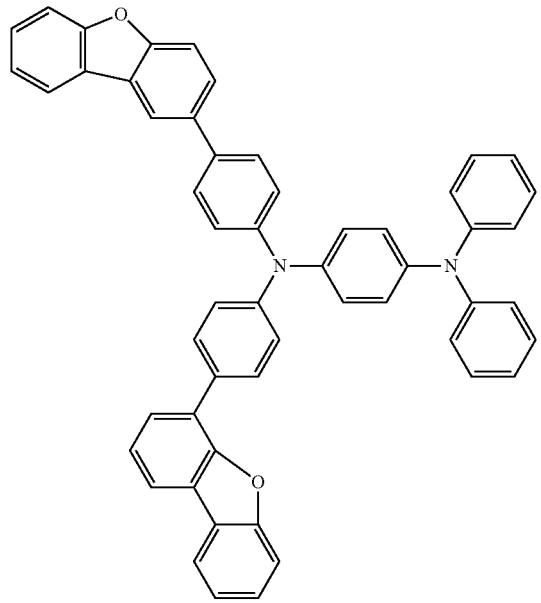
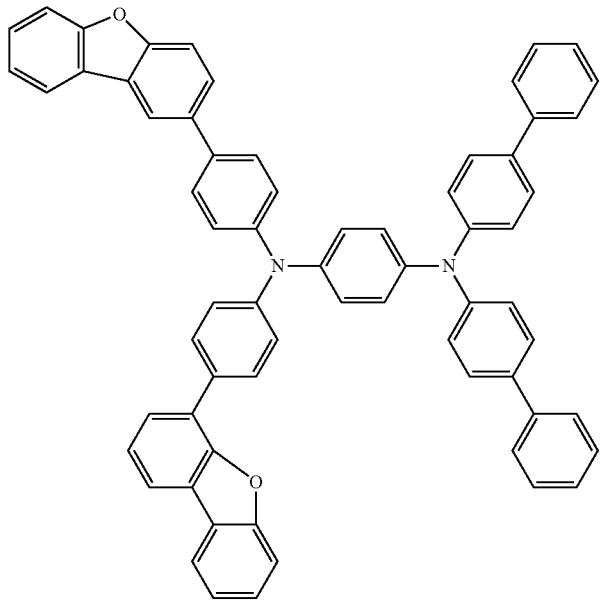
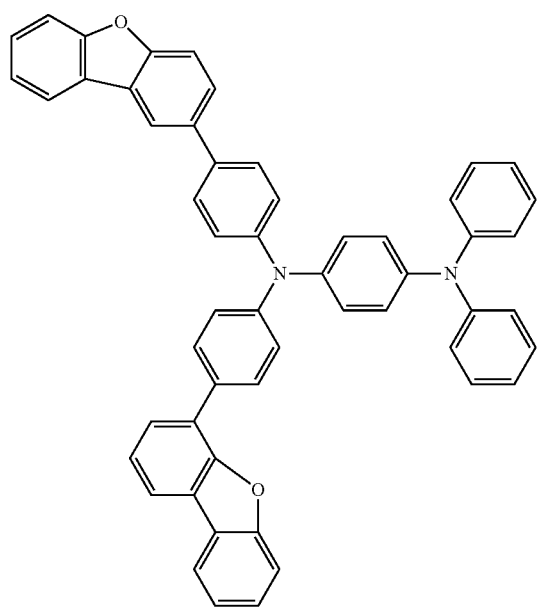
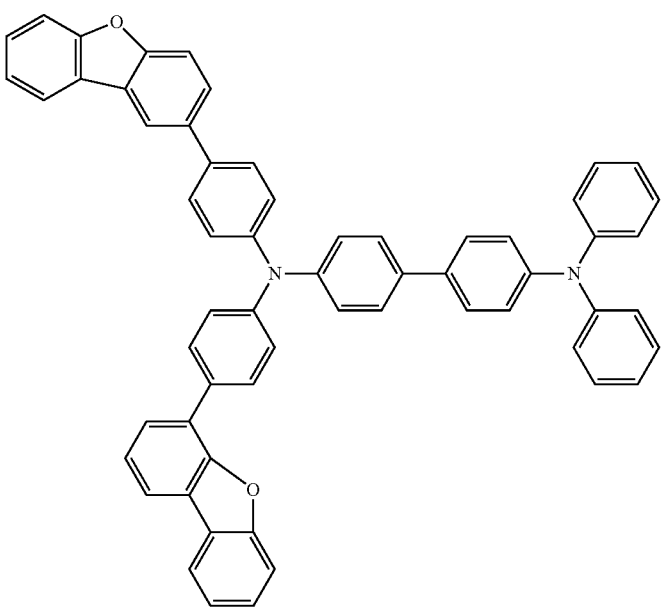

-continued
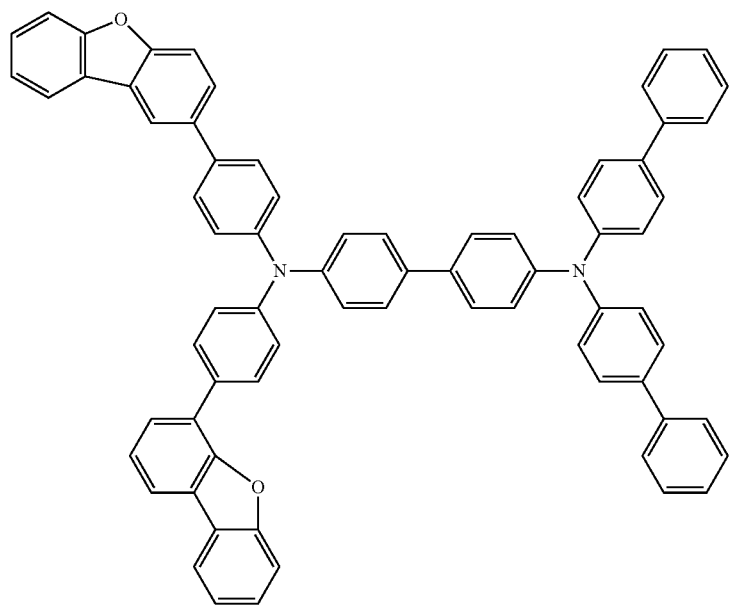
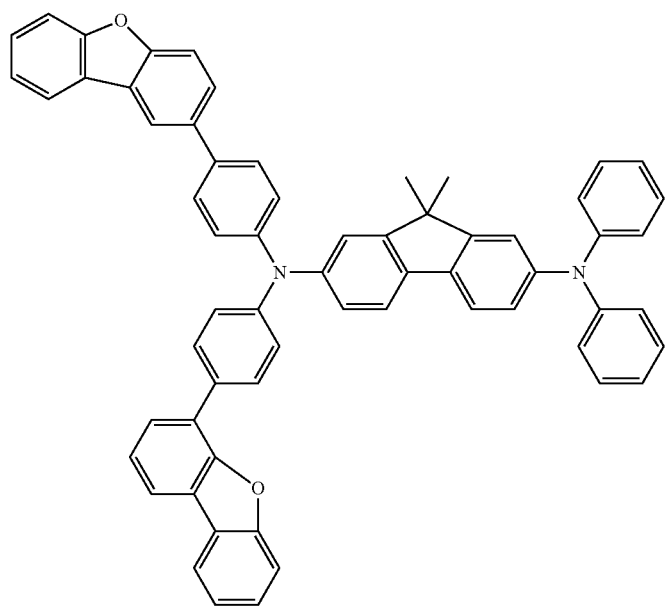

-continued
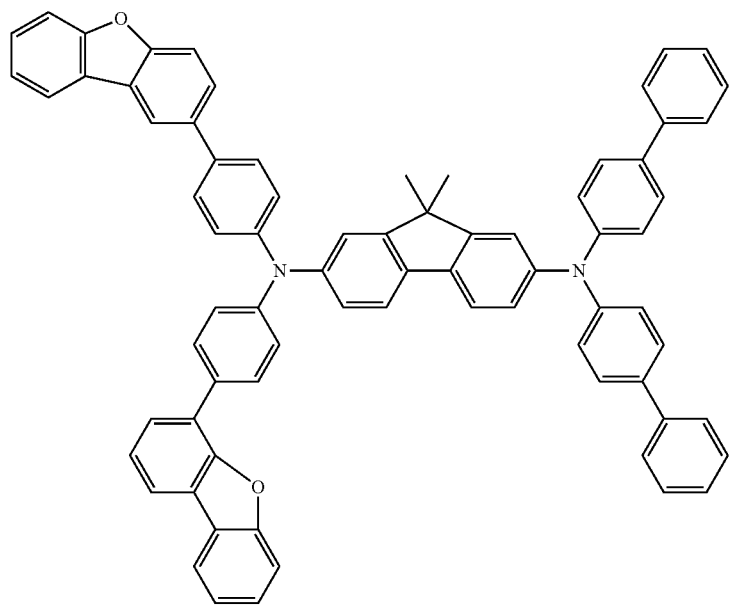
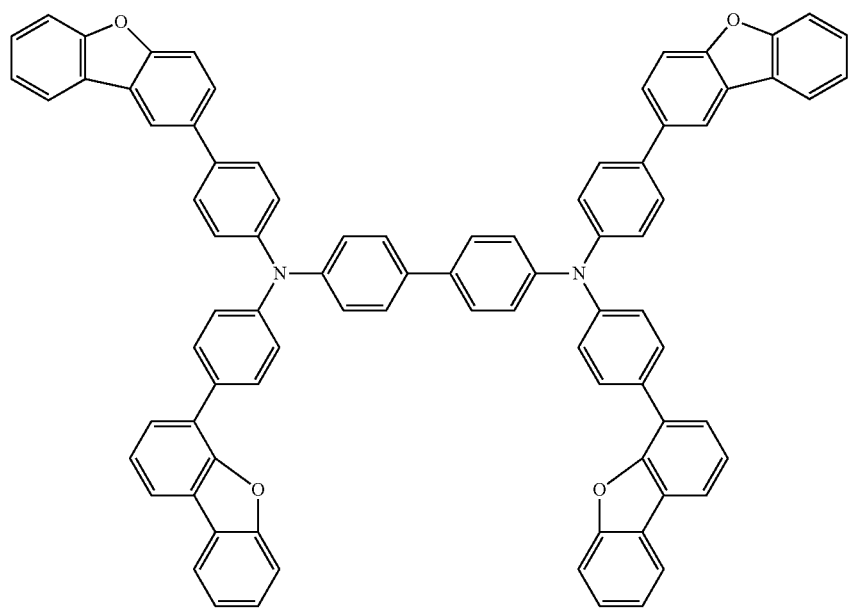

-continued
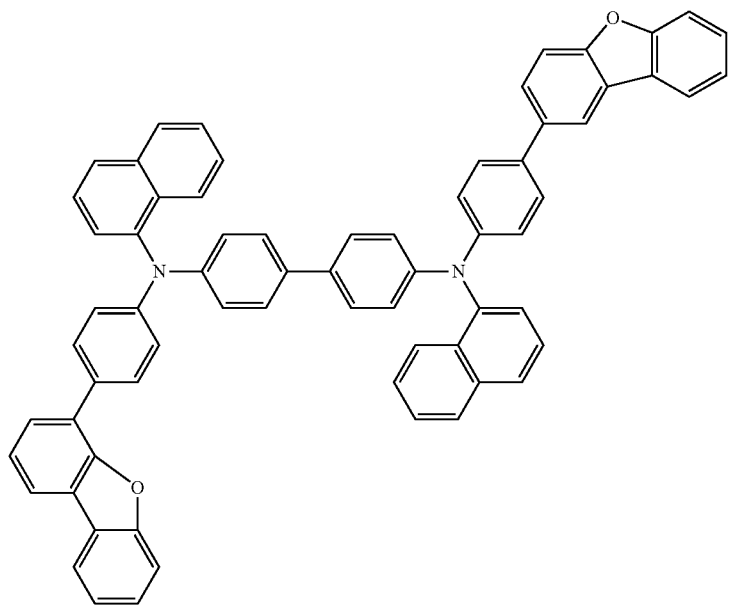
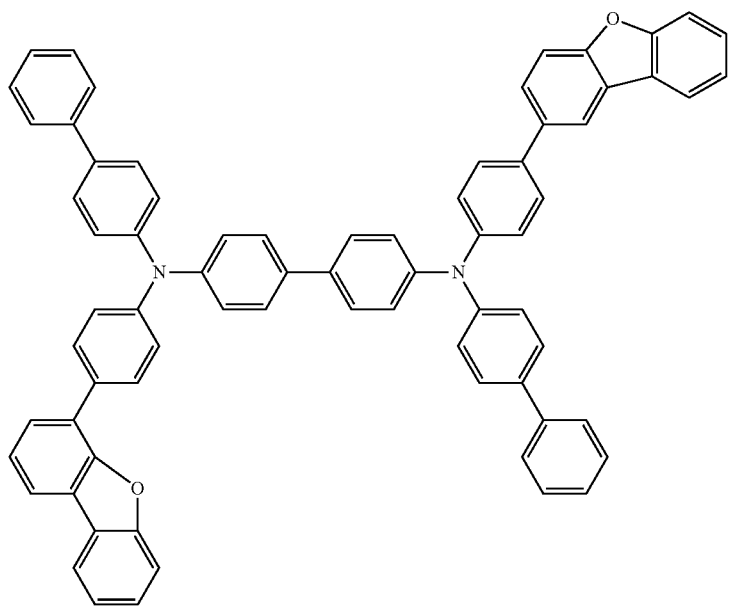

173 174
-continued
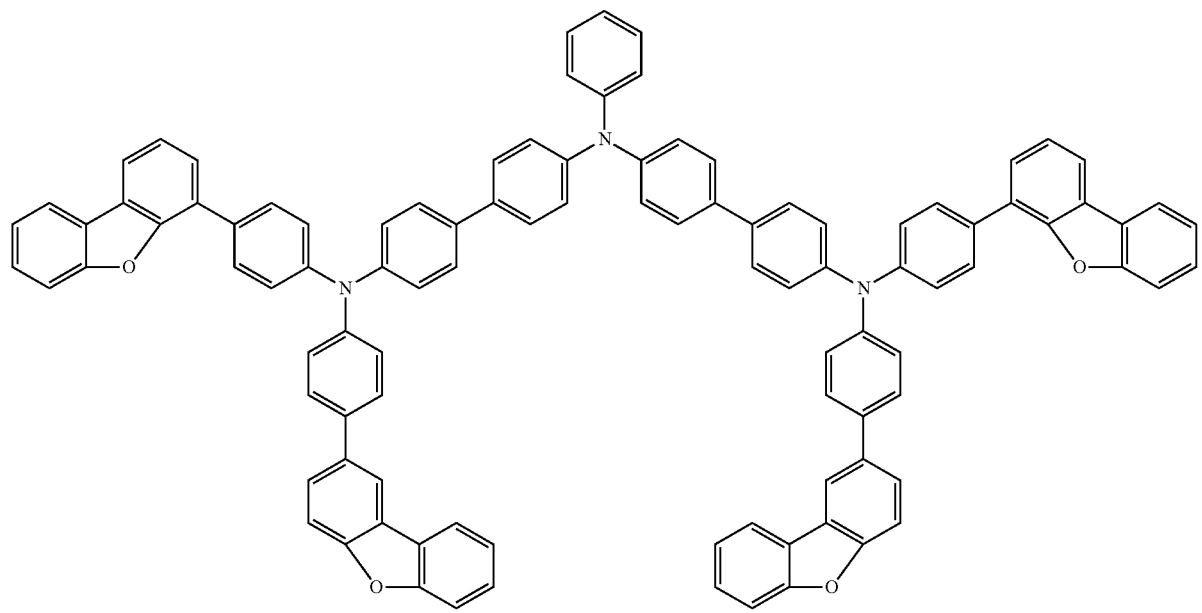
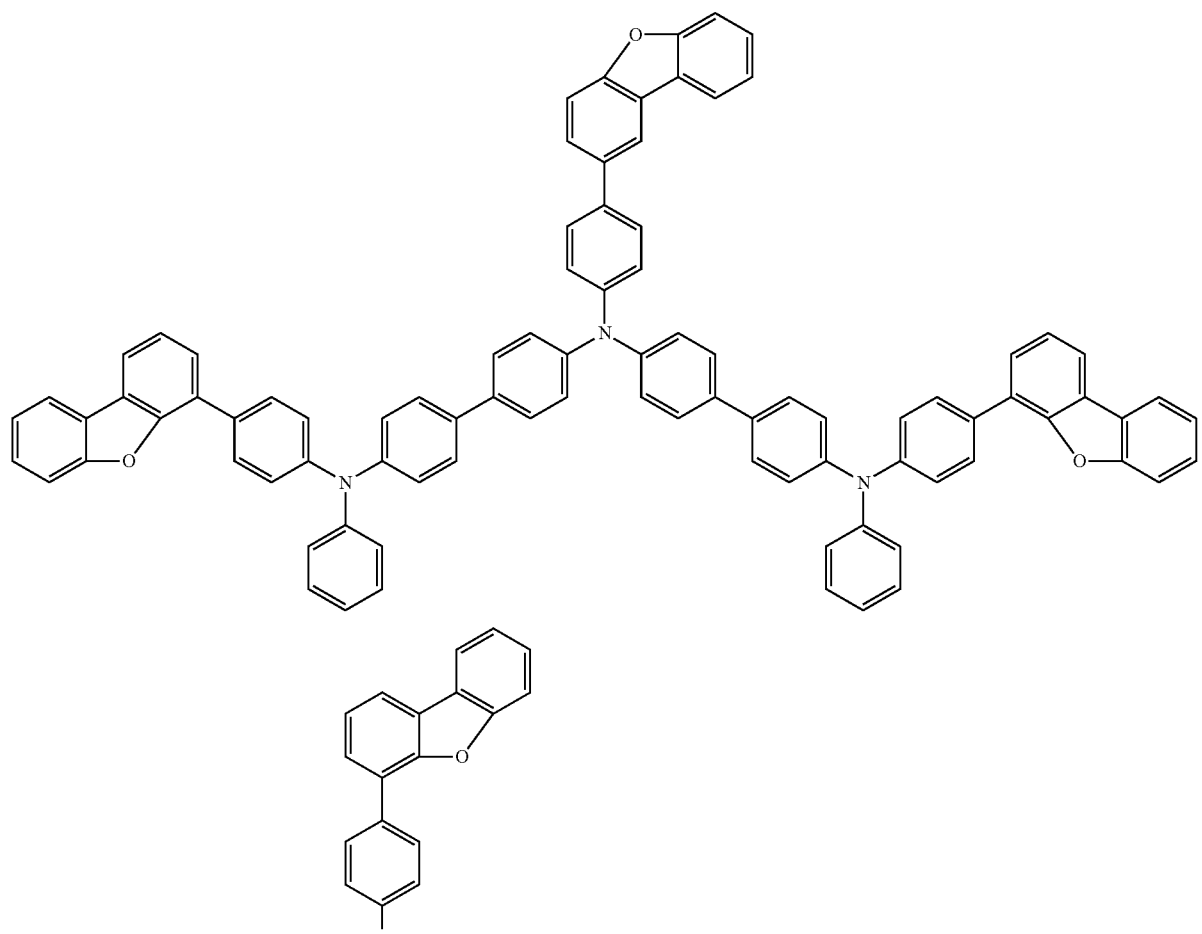

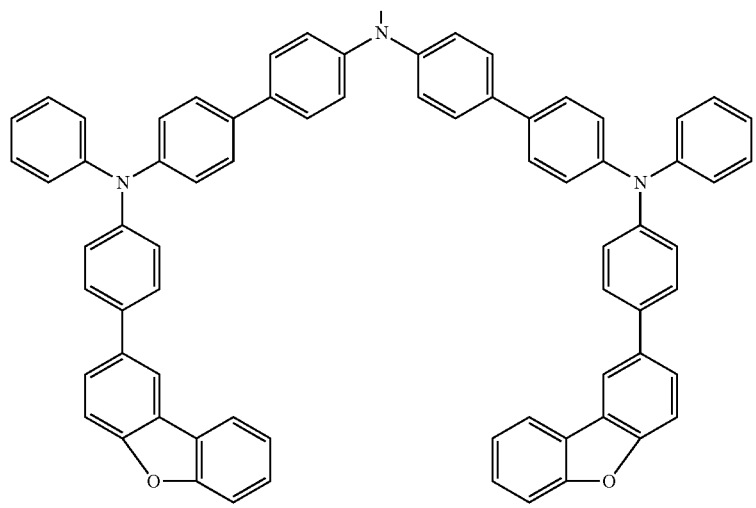
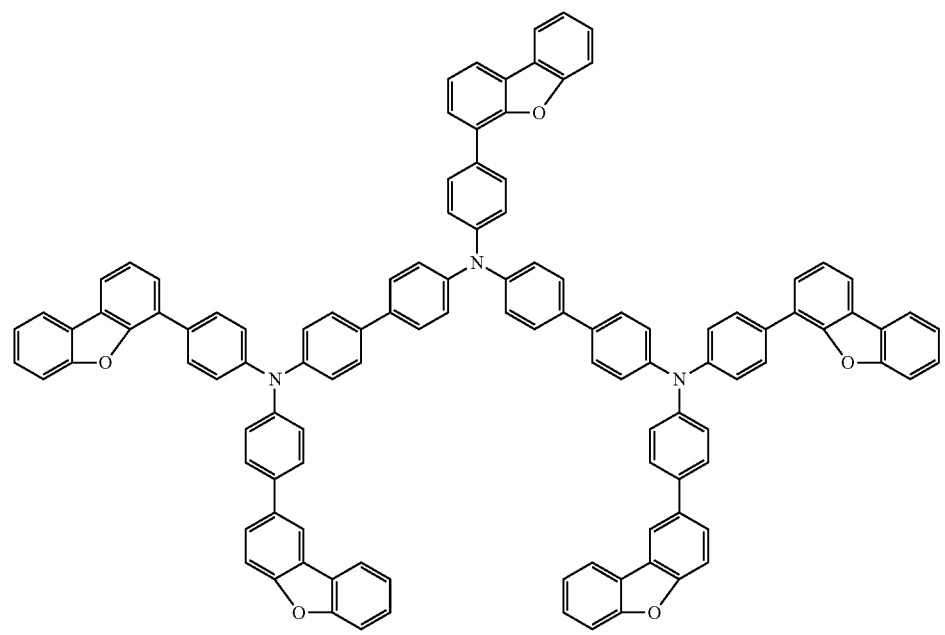

-continued
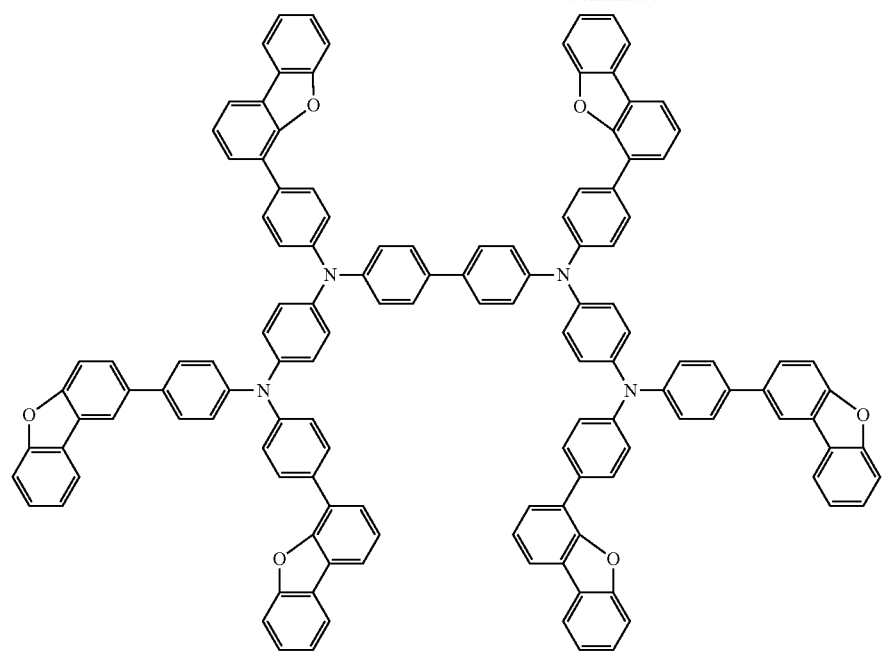
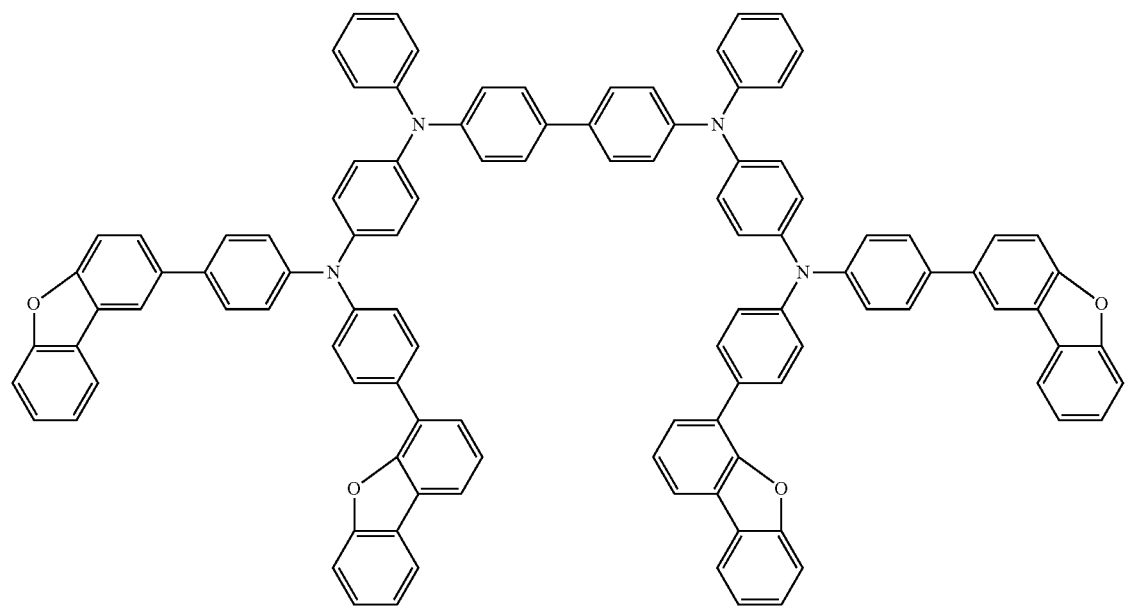

-continued
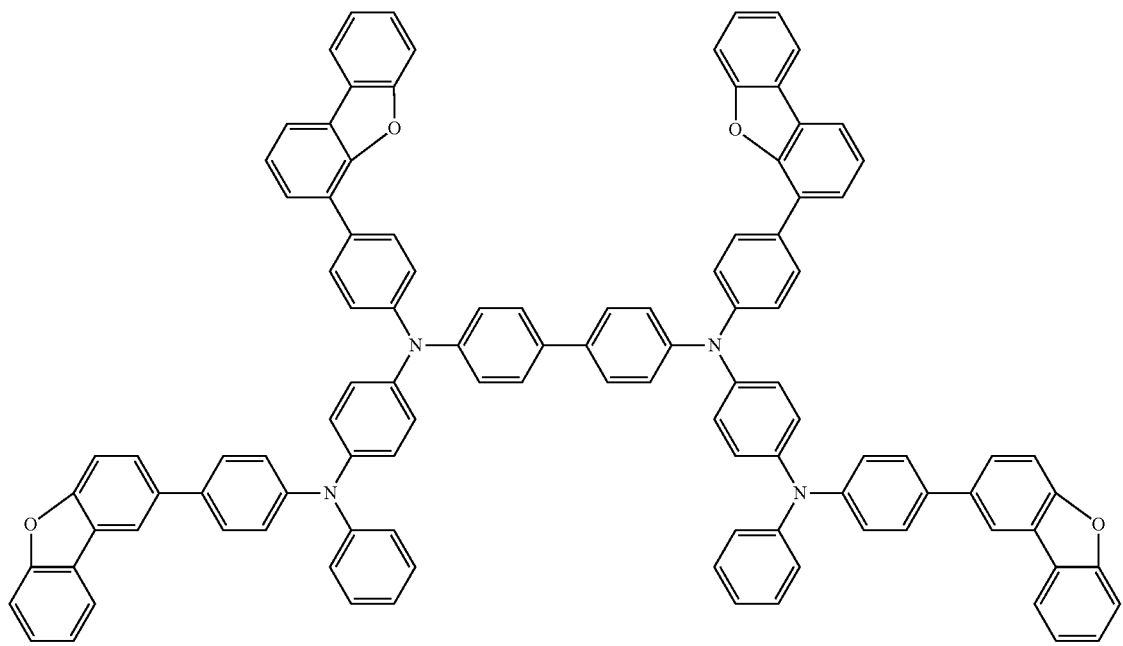
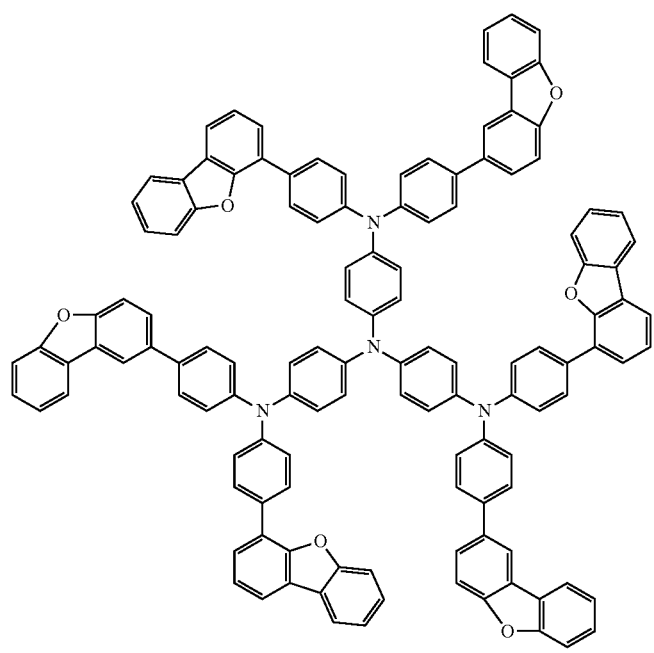

[Chem. 31]
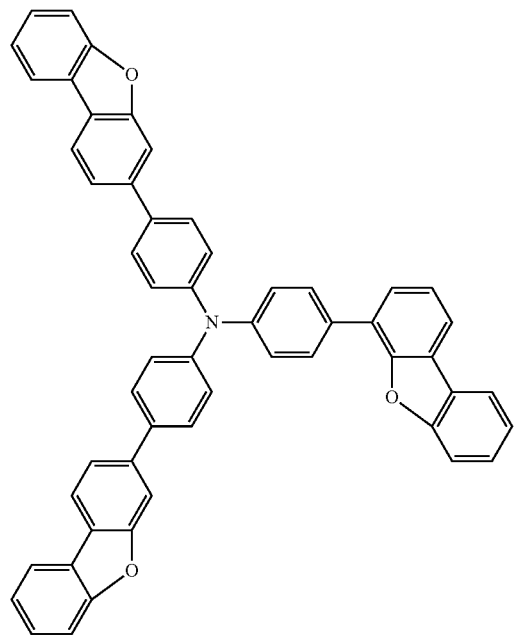
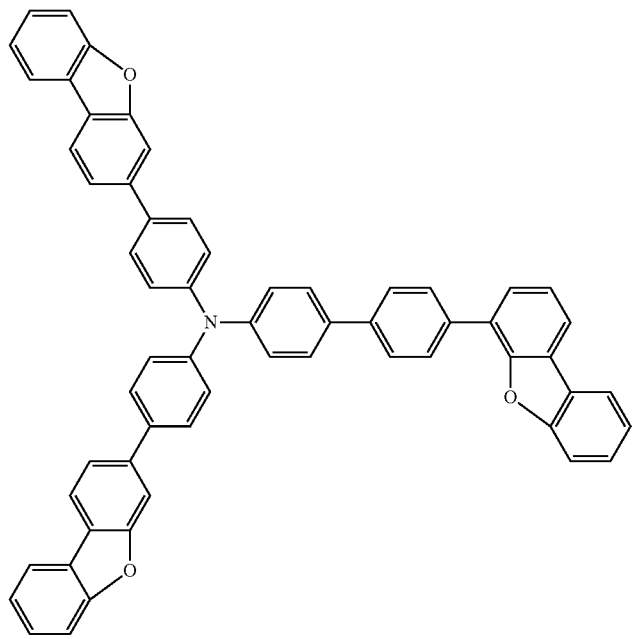
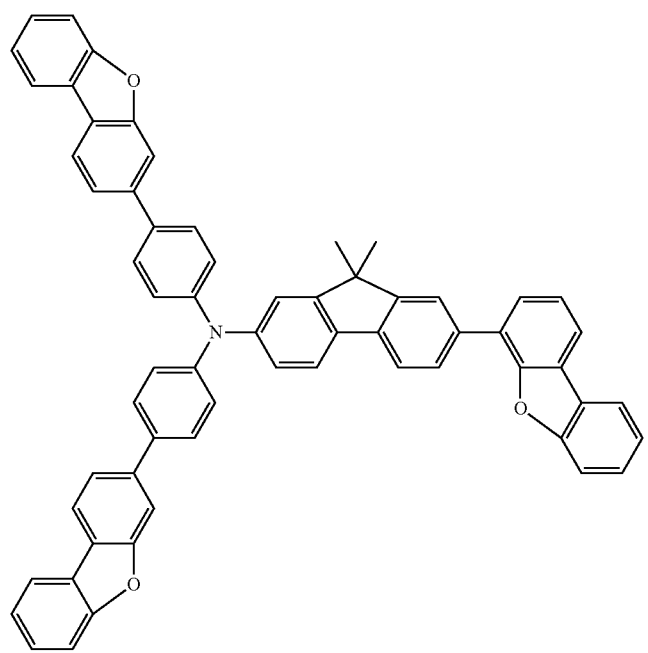
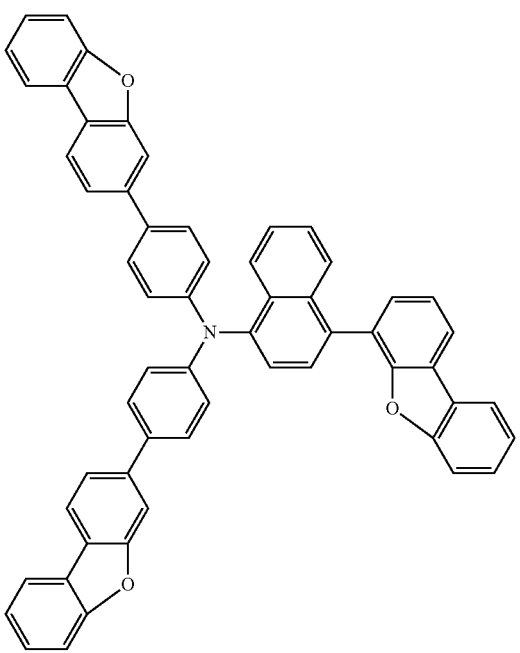

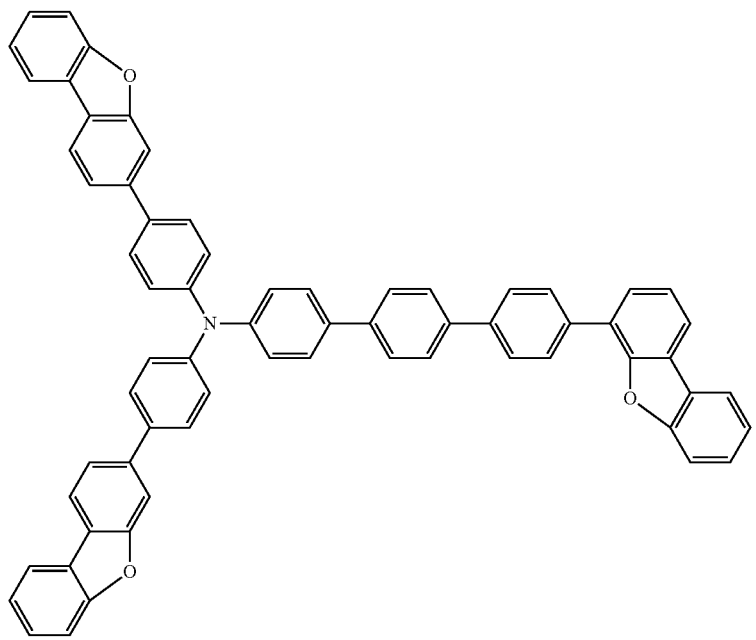
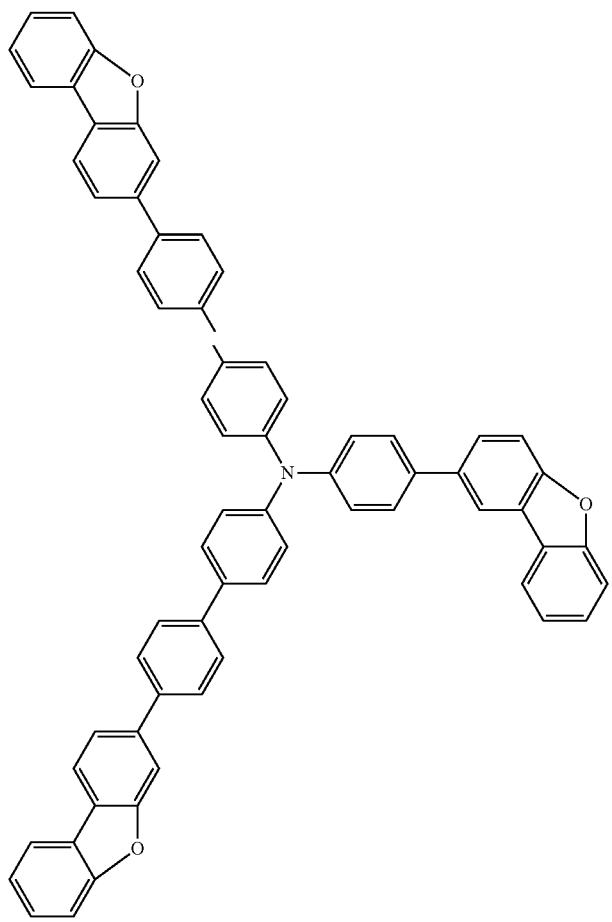

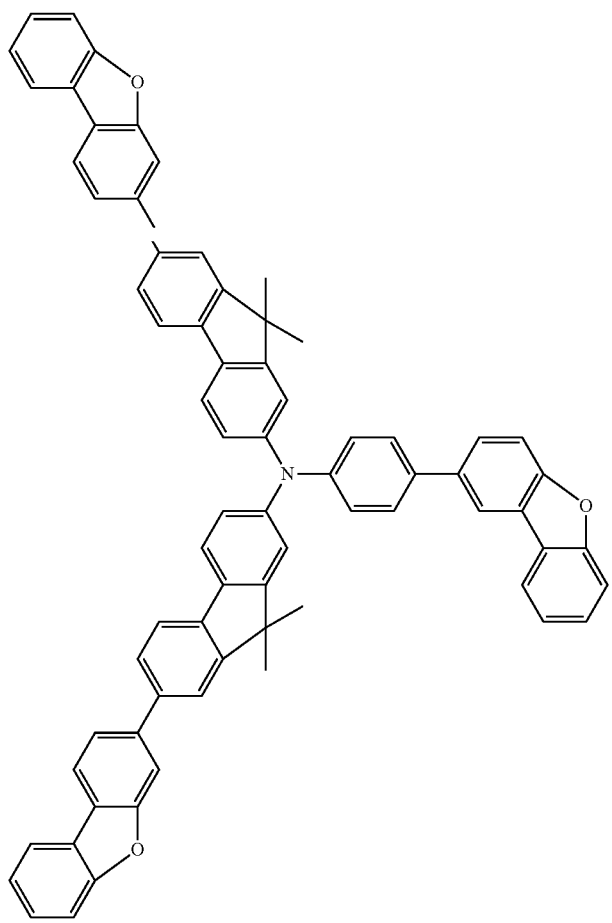
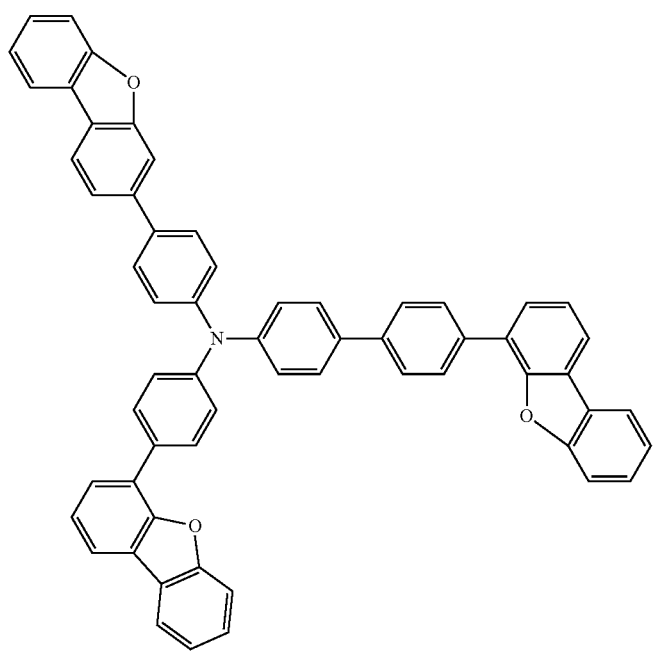

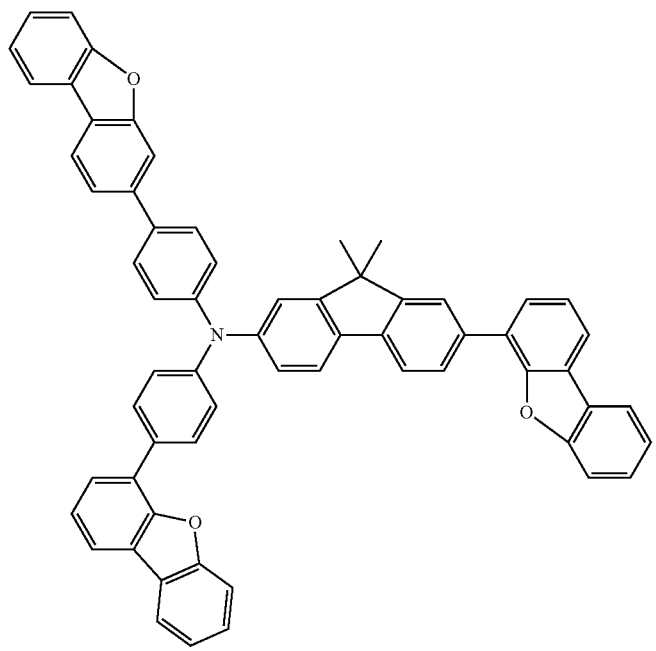
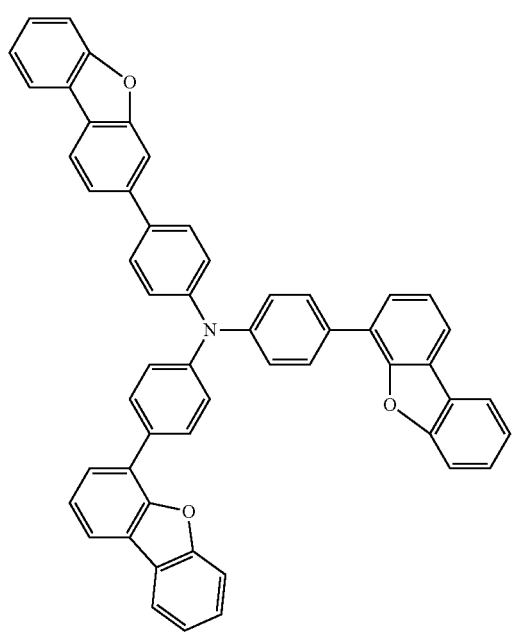

-continued
189
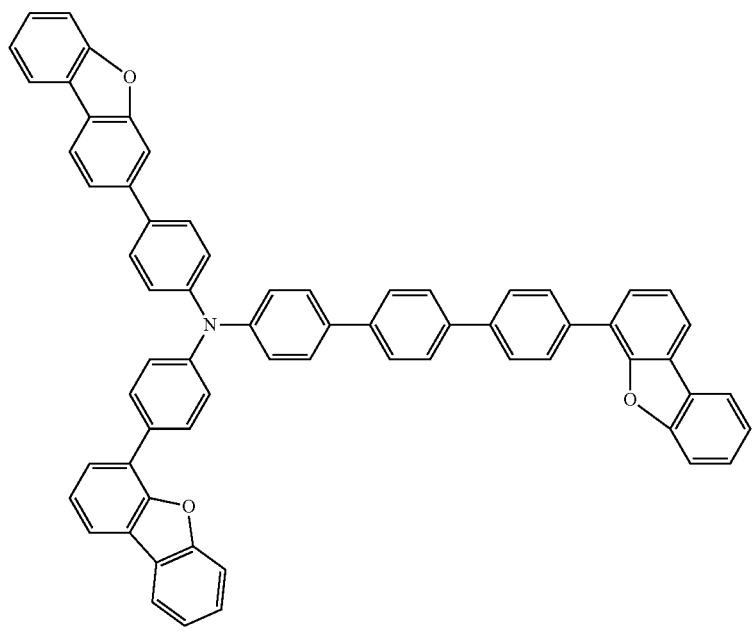
190
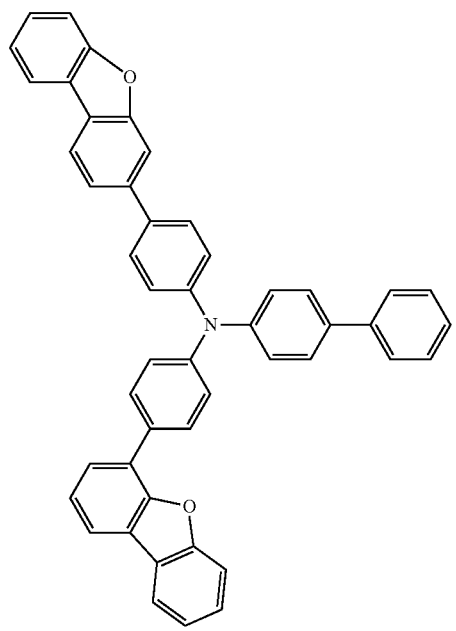
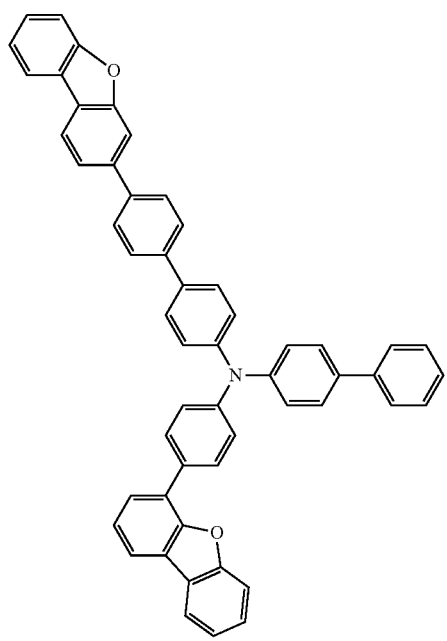
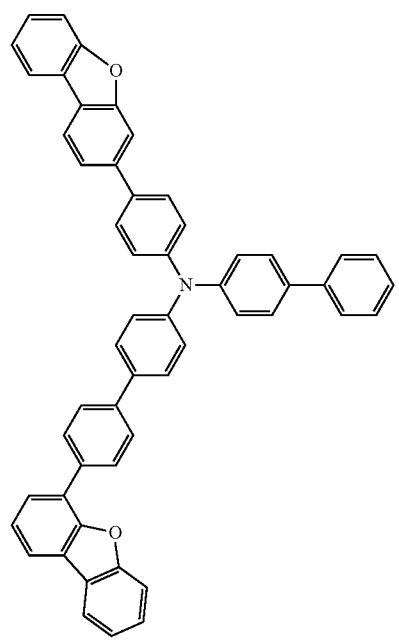

-continued
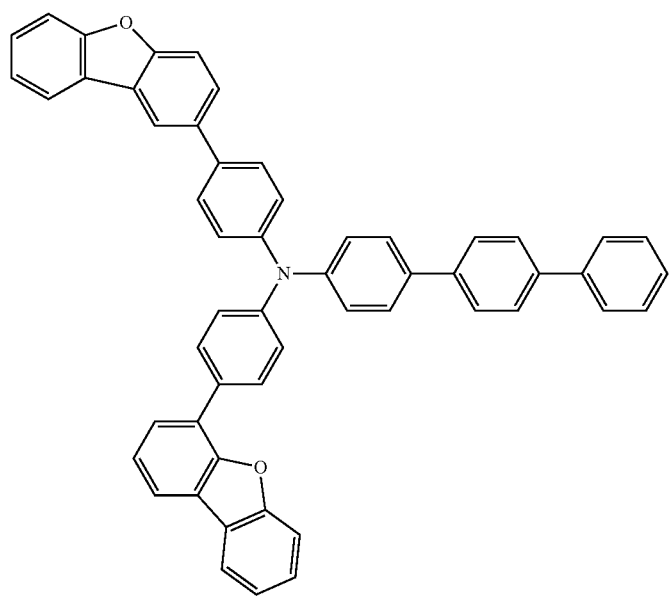
[Chem. 32]
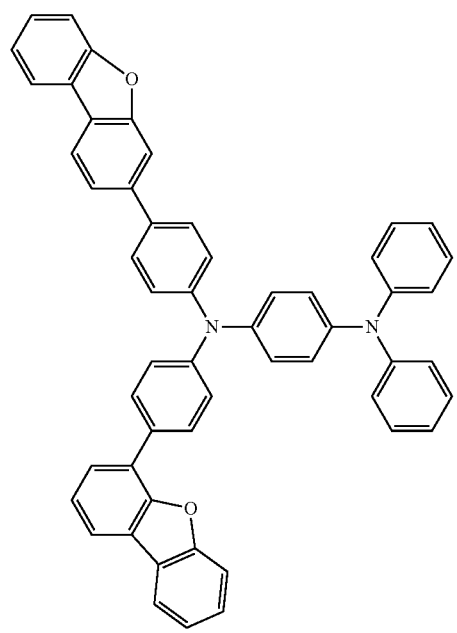 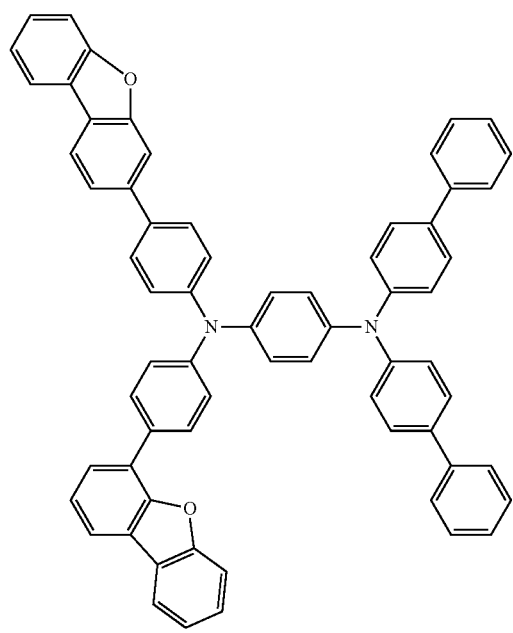

-continued
| 193 | 194 |
|---|---|
| 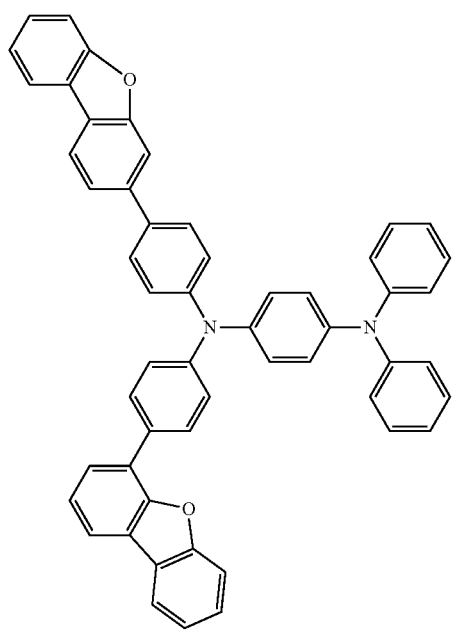 | 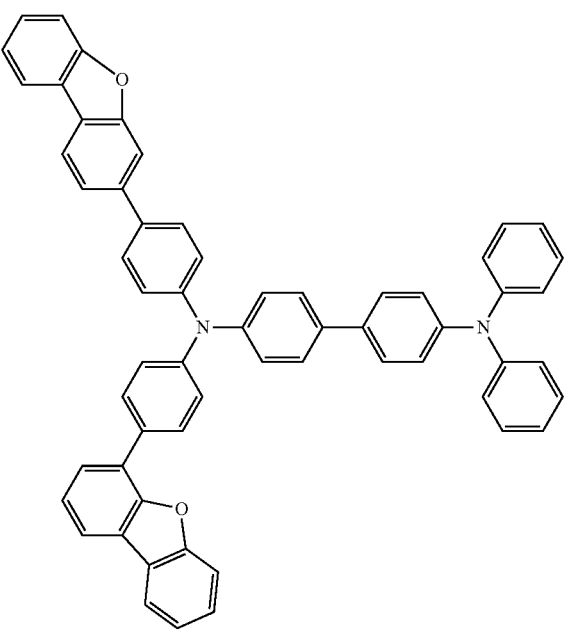 |
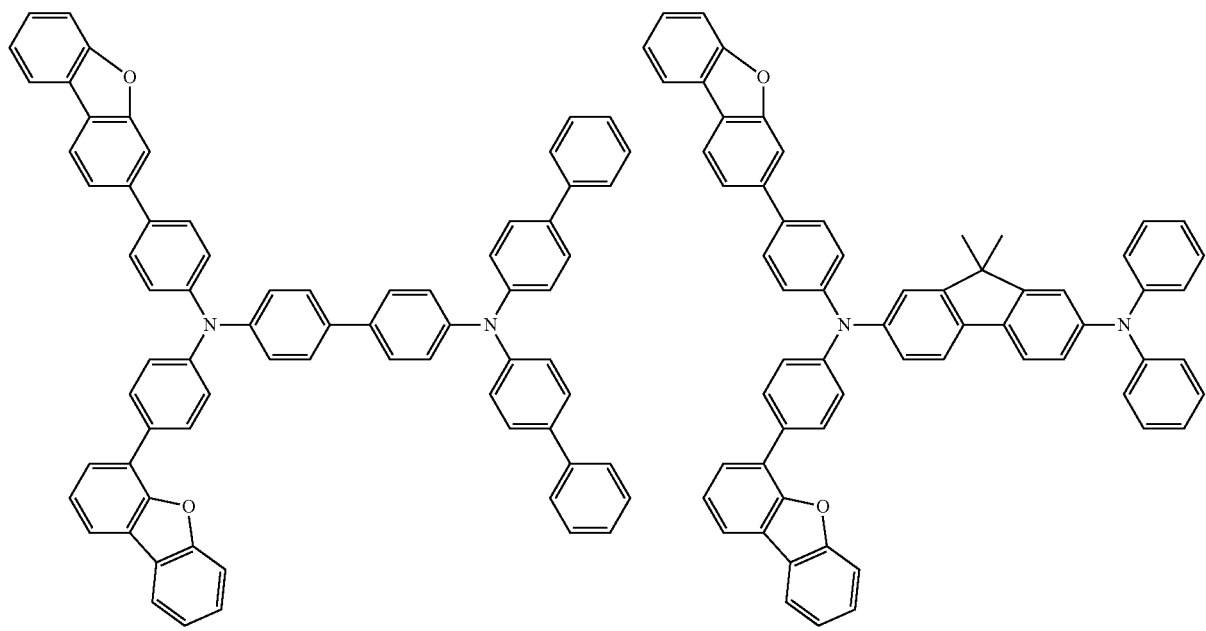

195 196
-continued
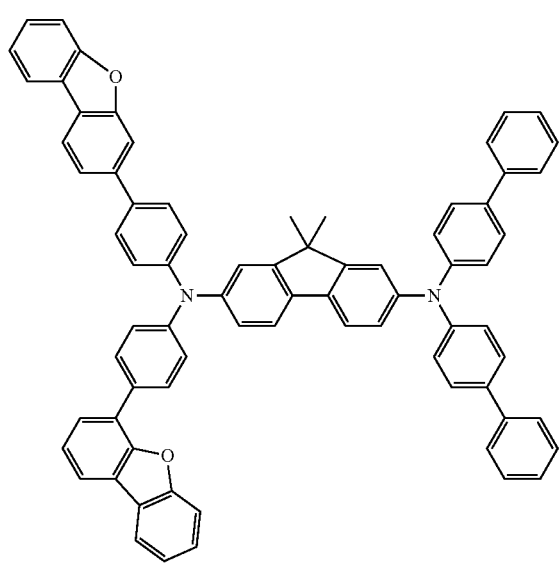
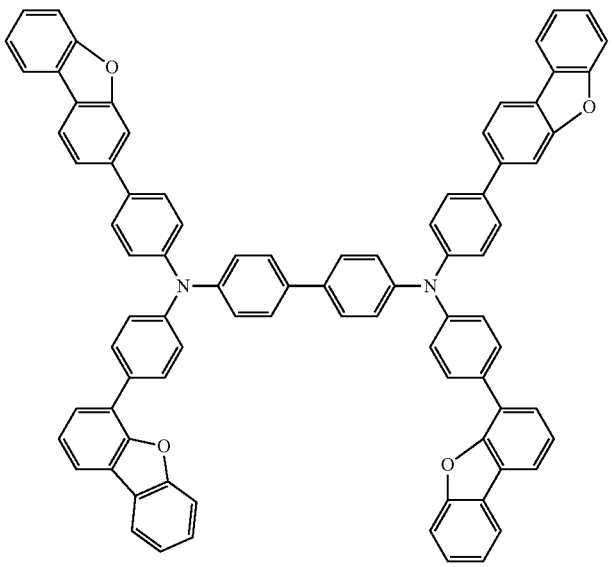
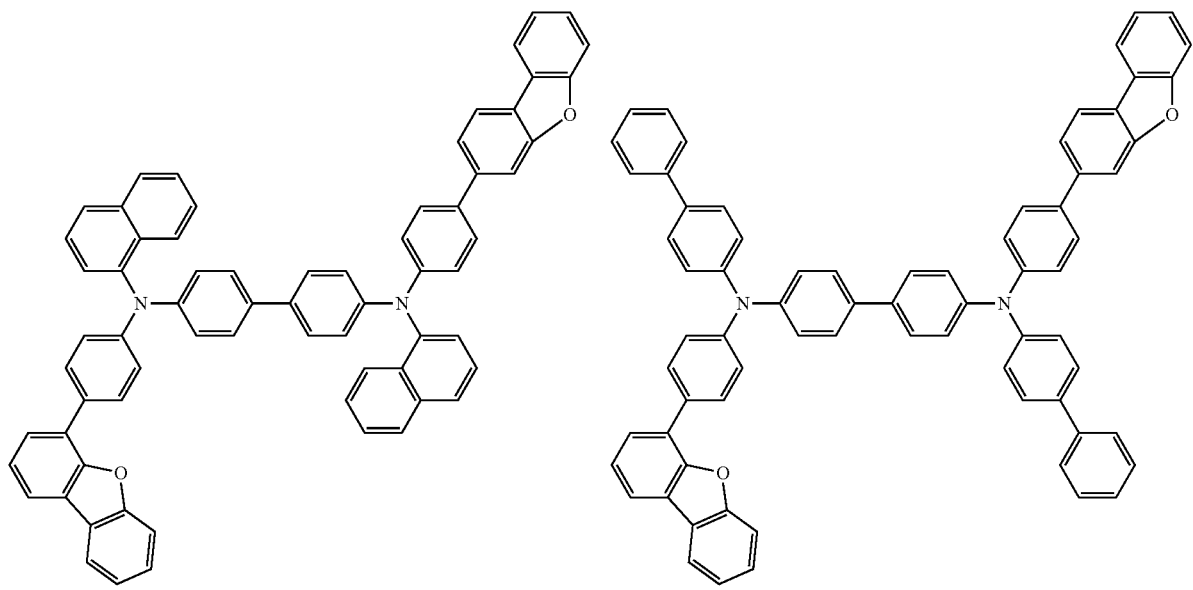

197
198
-continued
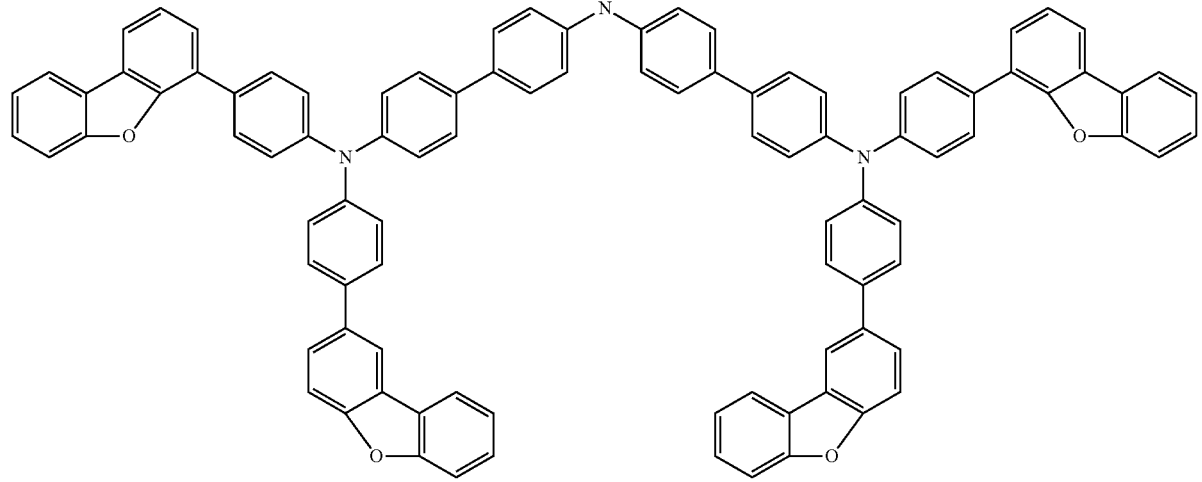
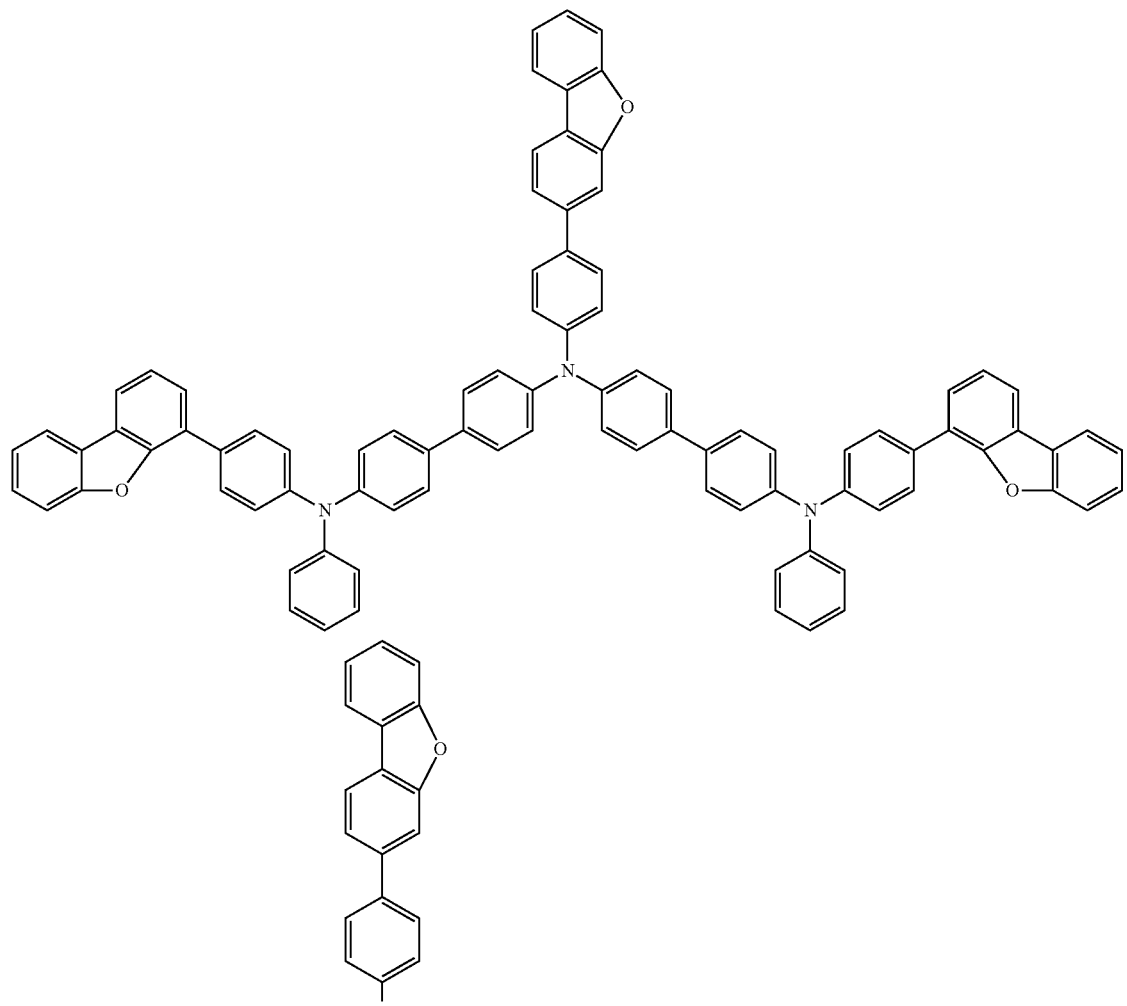

199
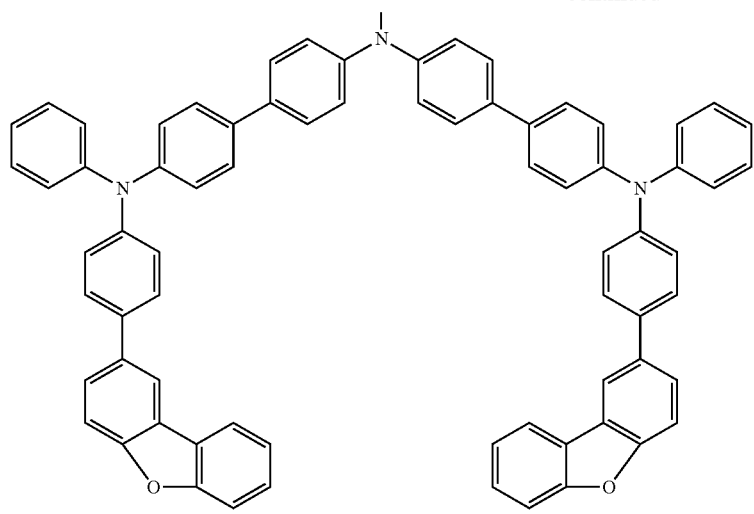
200
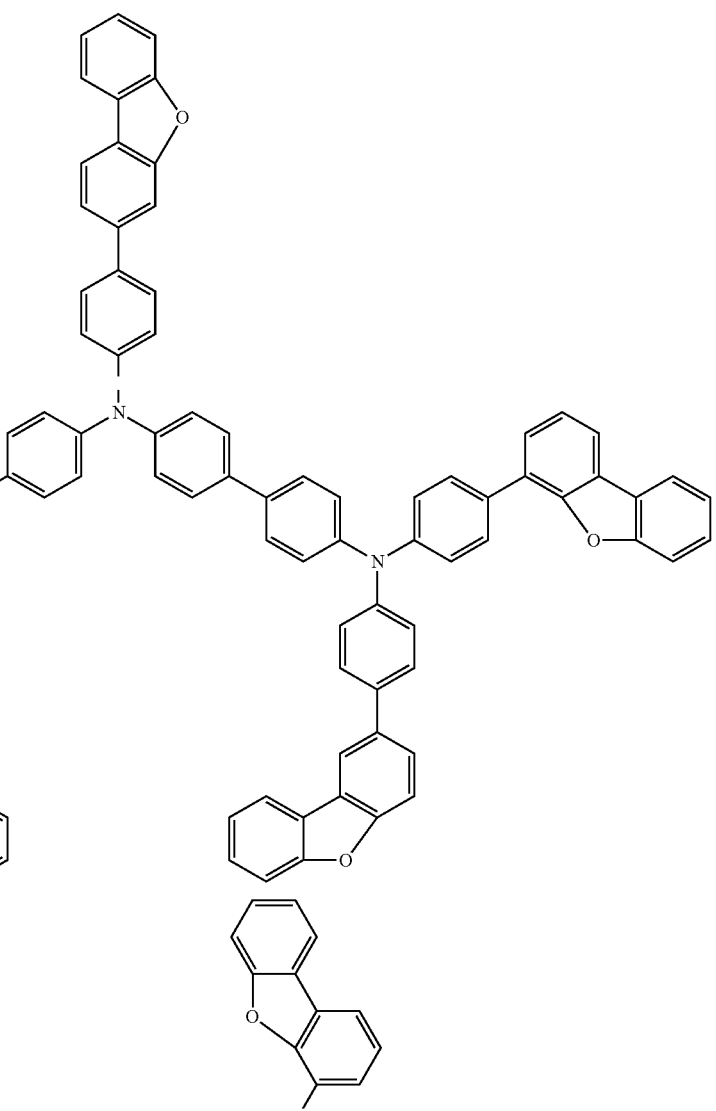

-continued
201
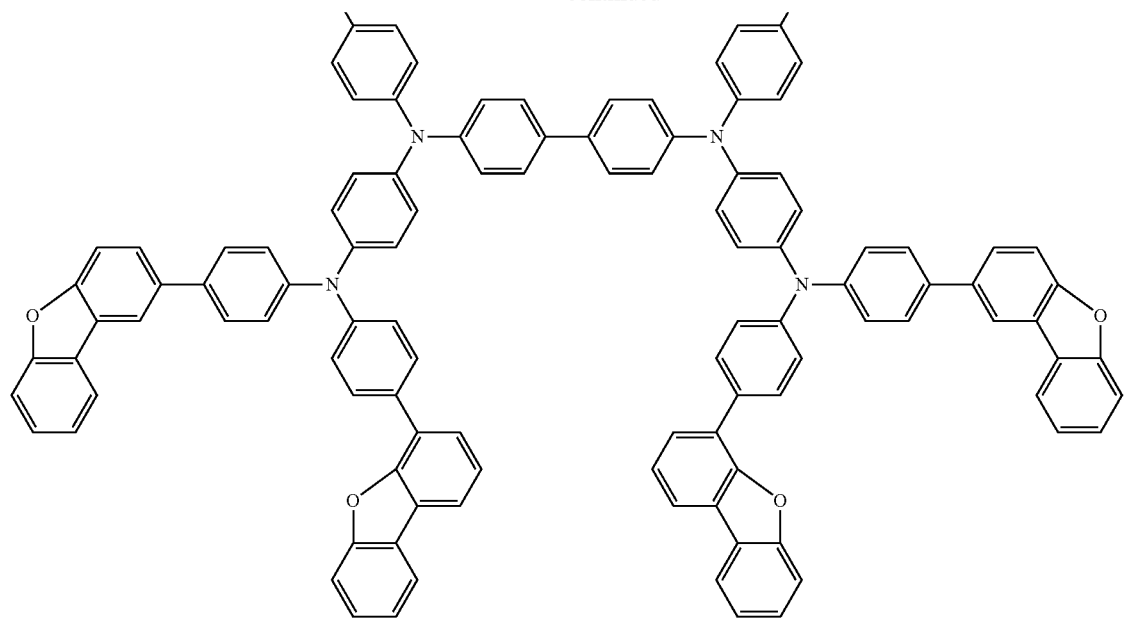
202
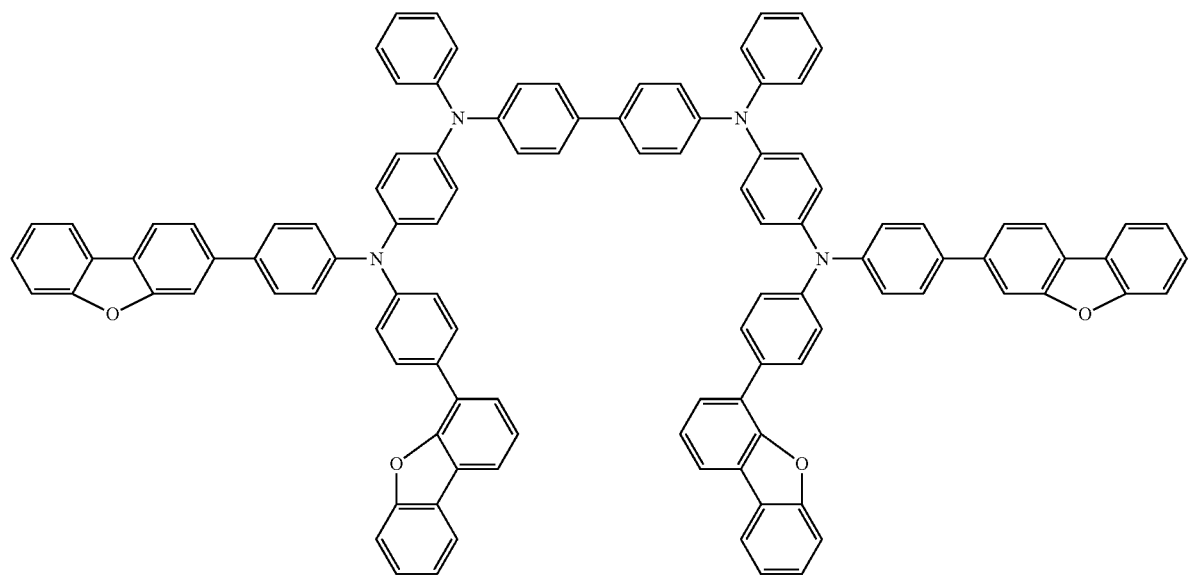

-continued
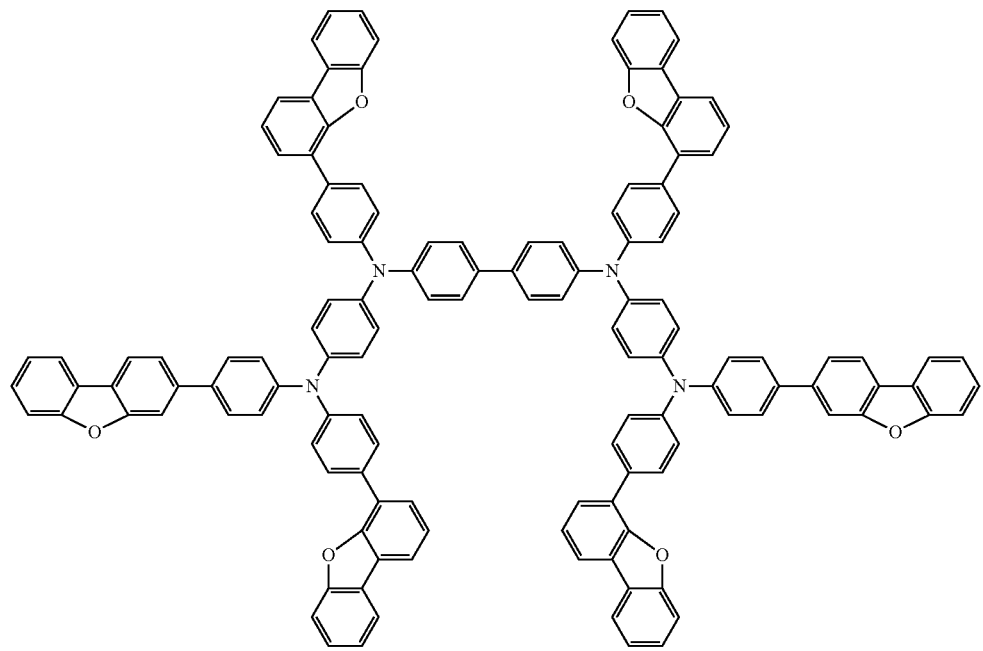
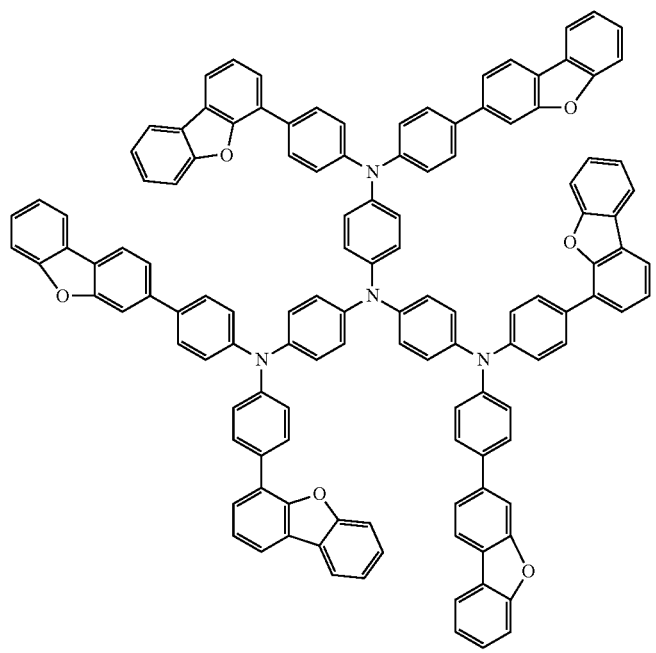

[Chem. 33]
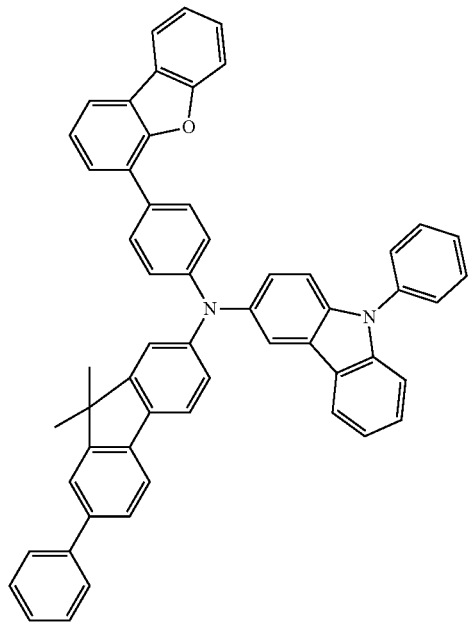 205
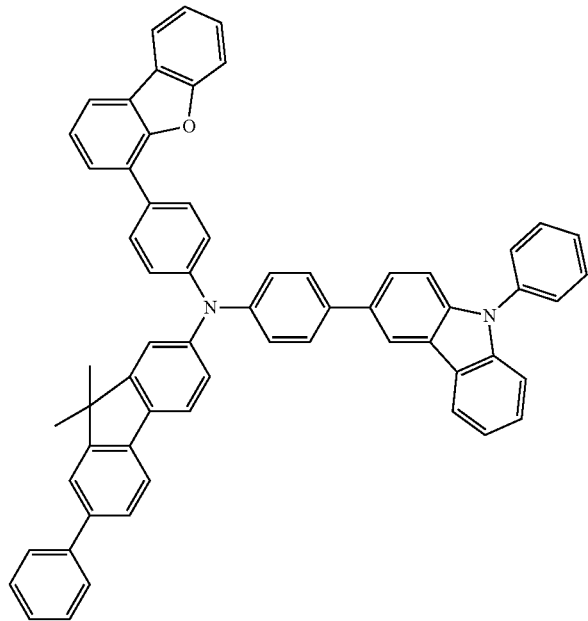 206
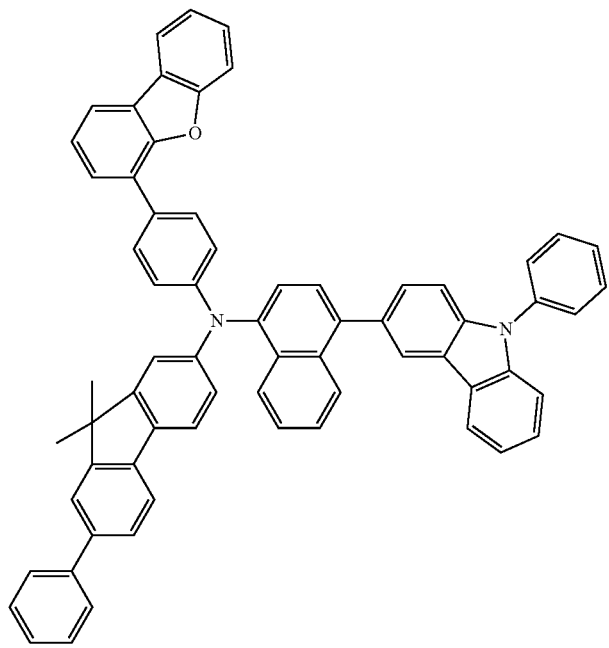
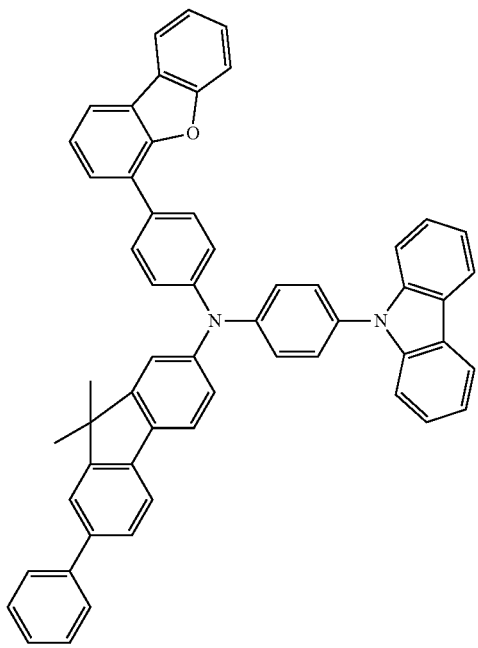

-continued
207
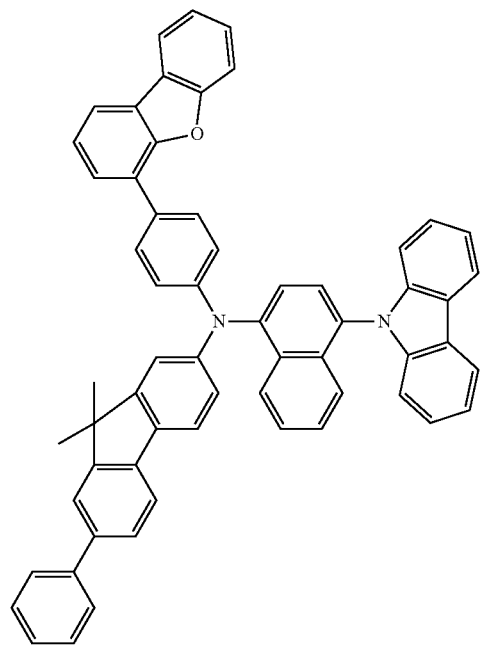
208
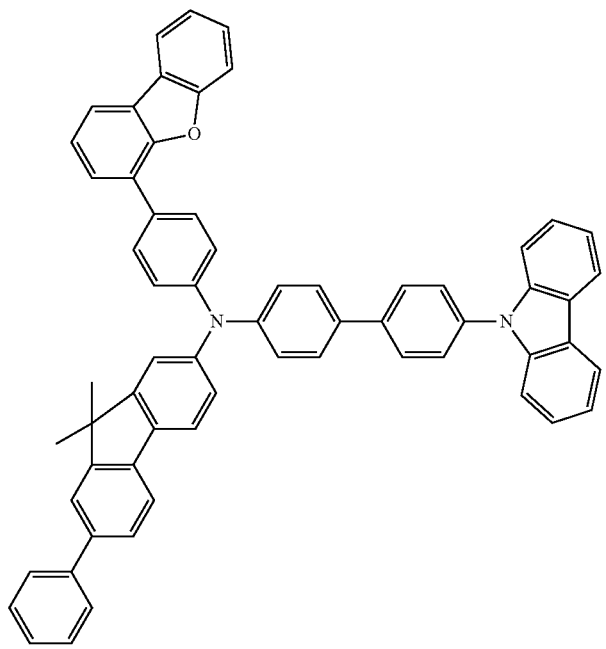
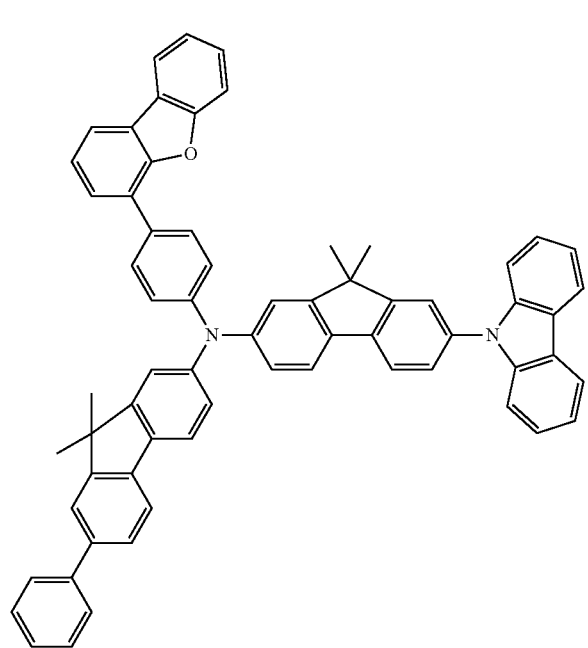
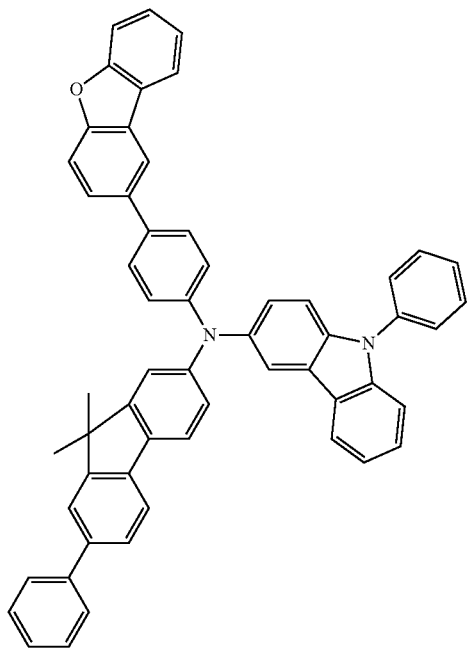

| 209 | 210 |
|---|---|
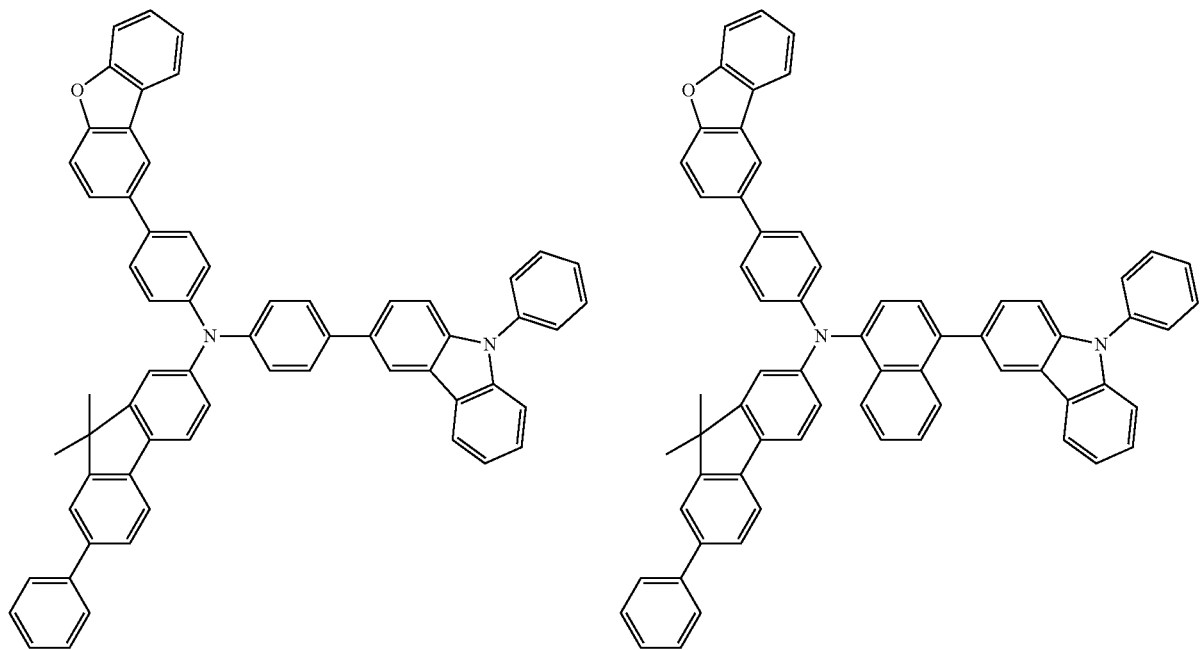
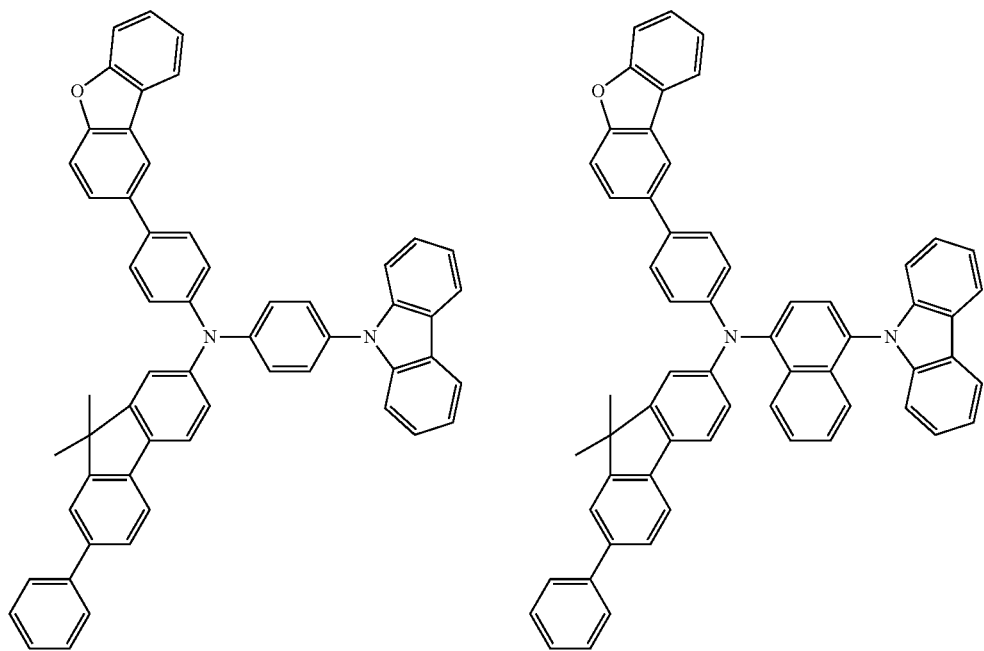

211 212
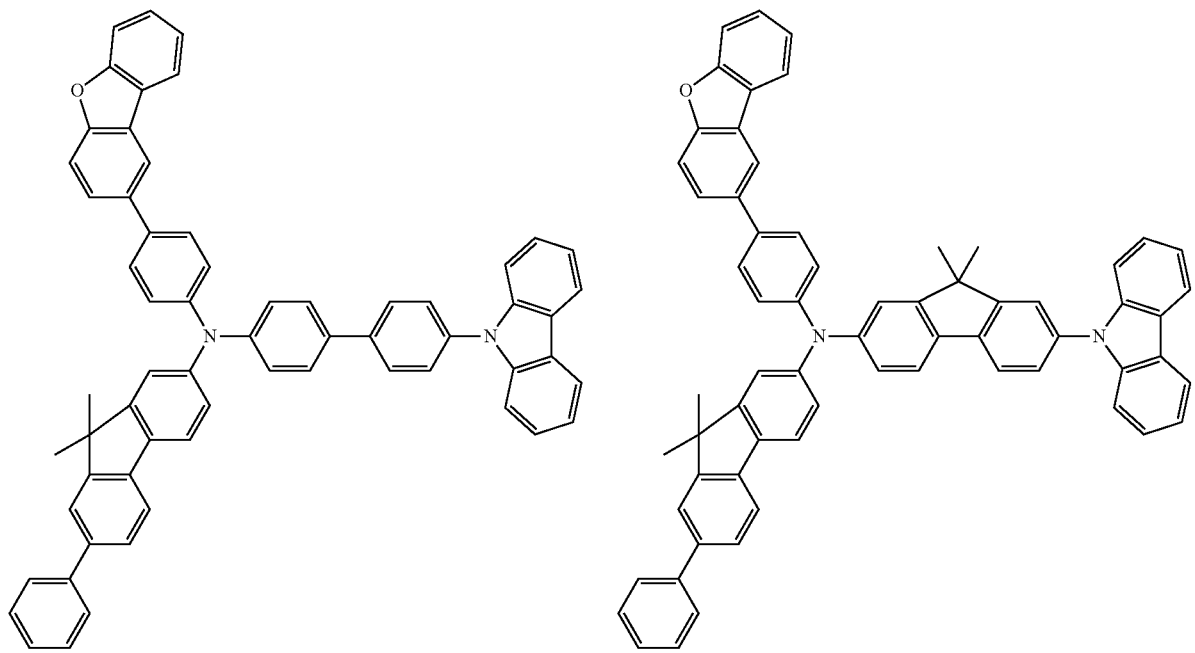
-continued
[Chem. 34]
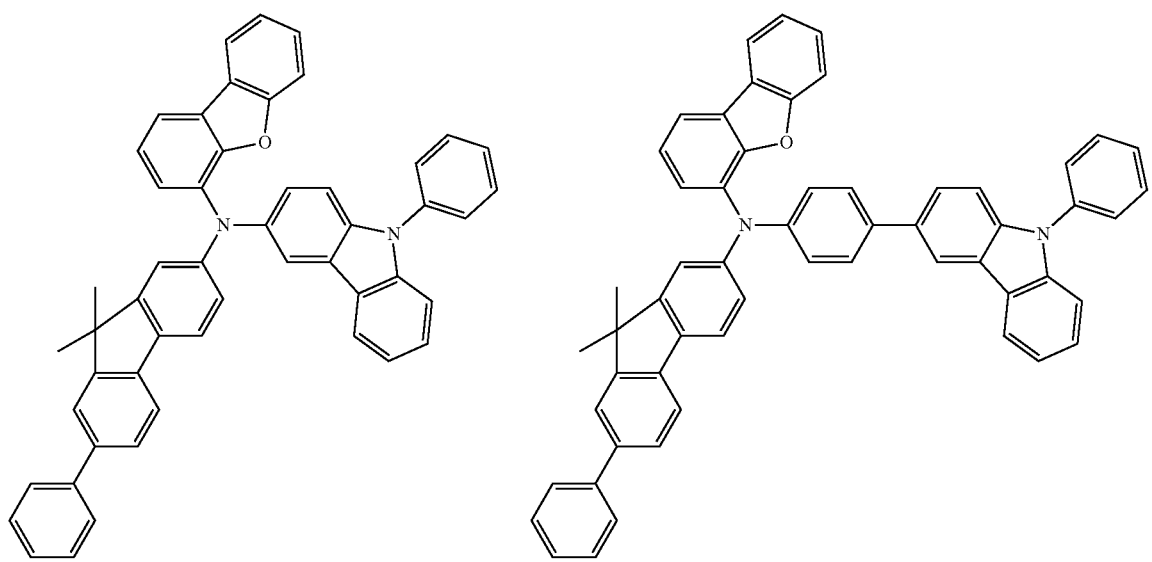

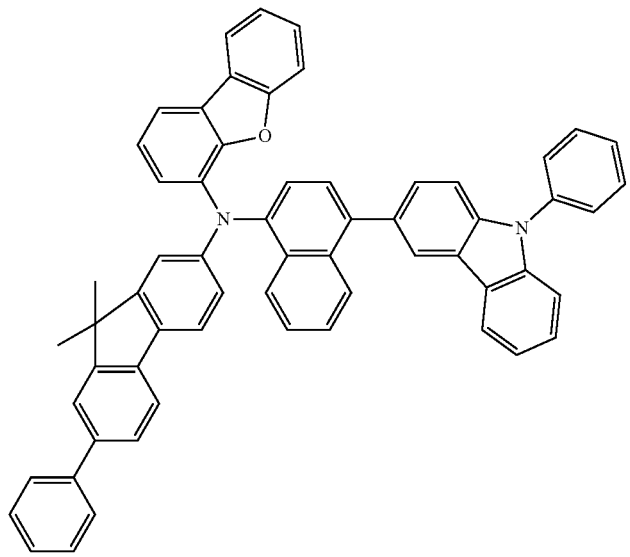
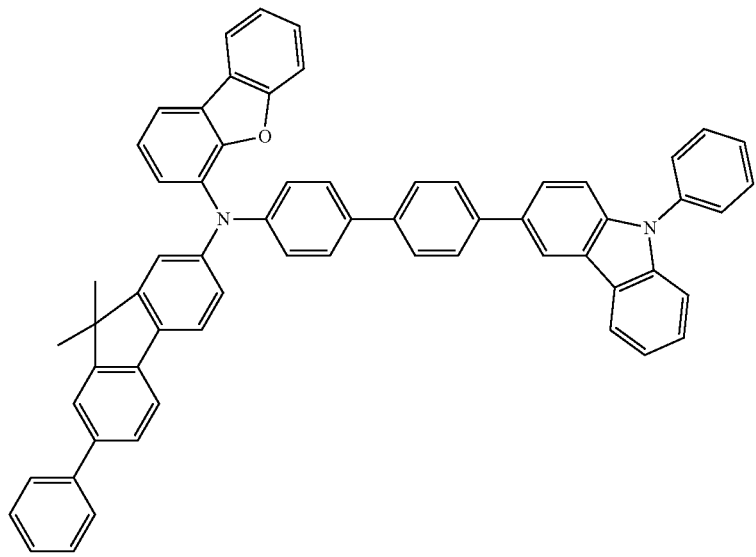
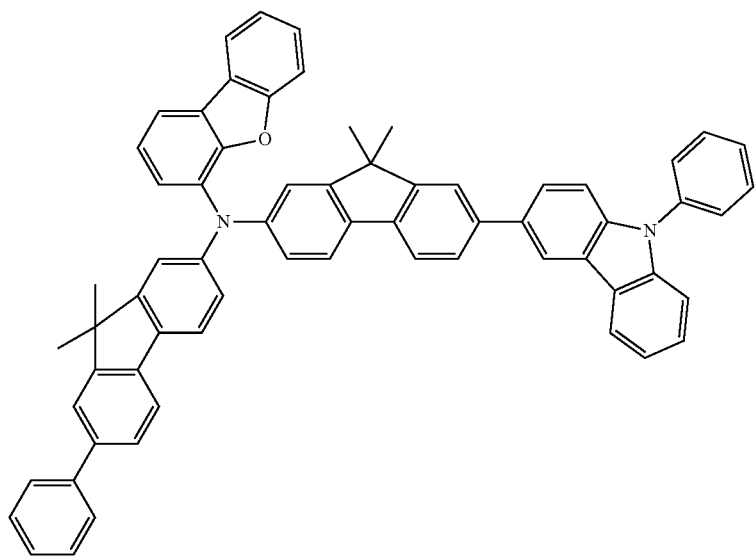

215
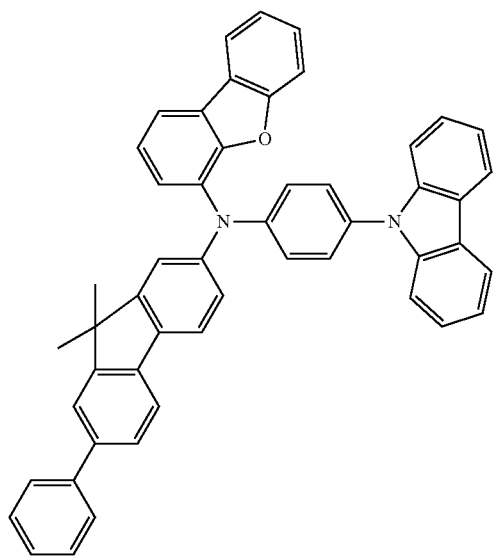
216
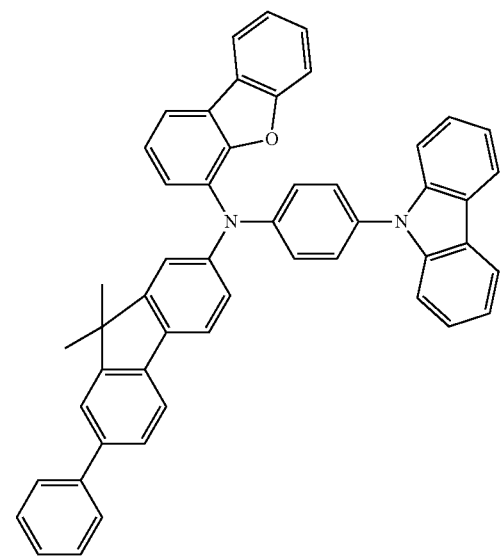
-continued
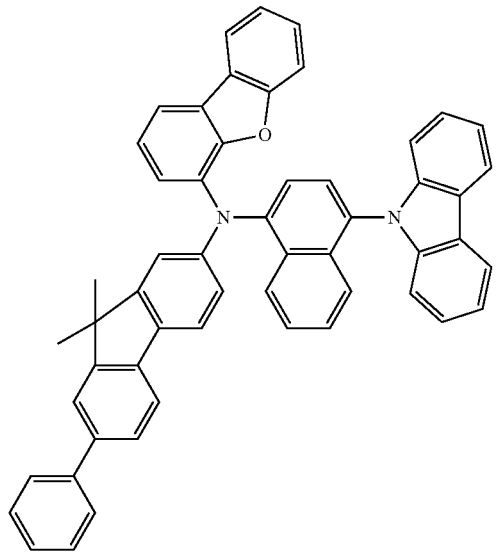
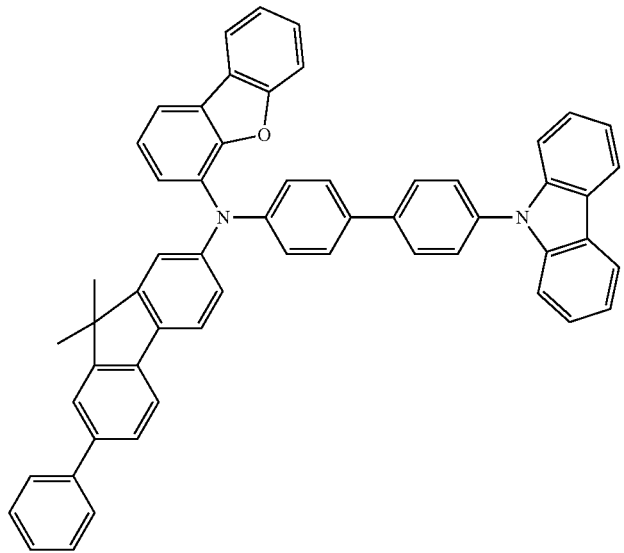
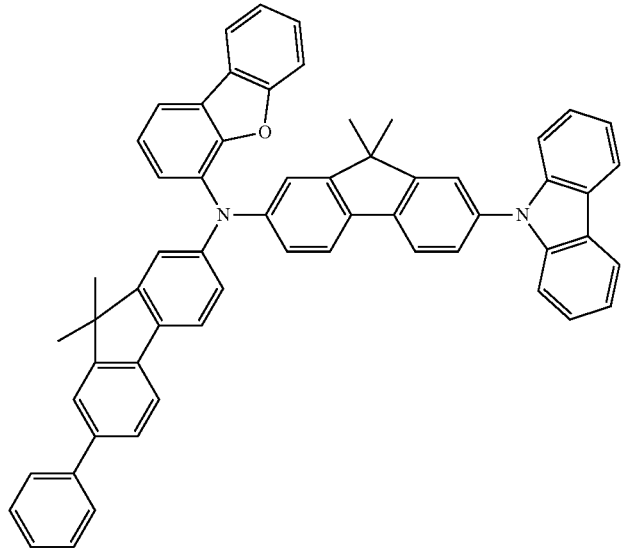

[Chem. 35]
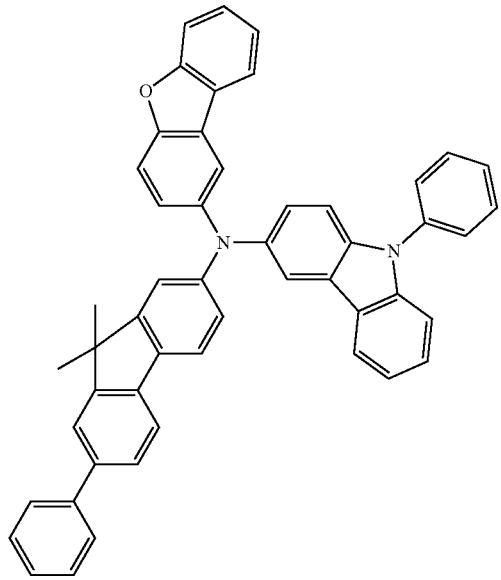
217
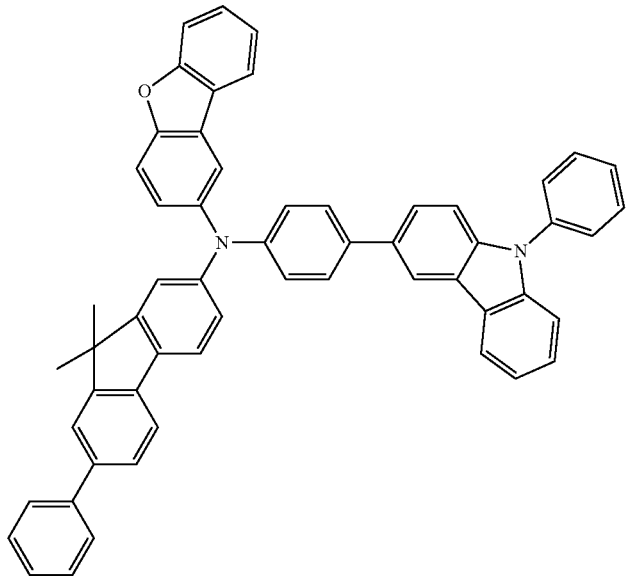
218
-continued
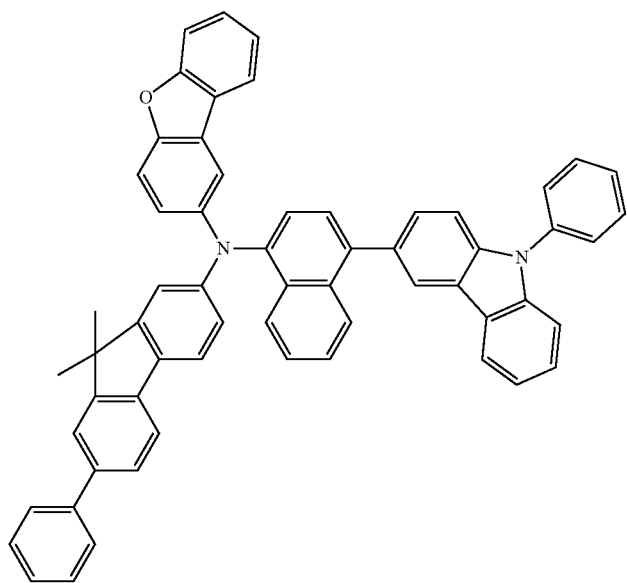

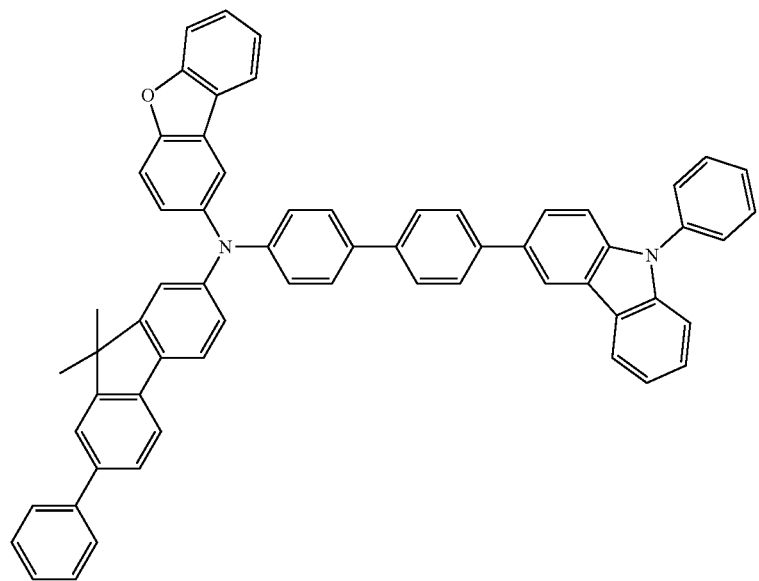
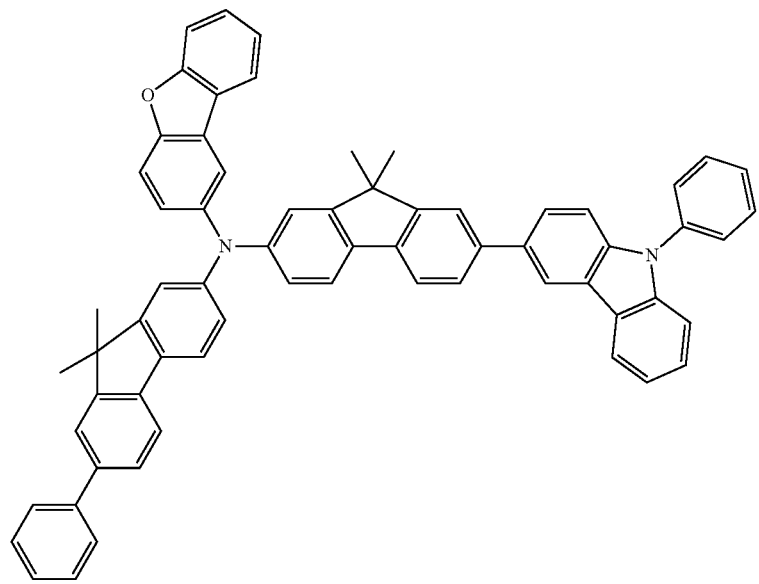

221
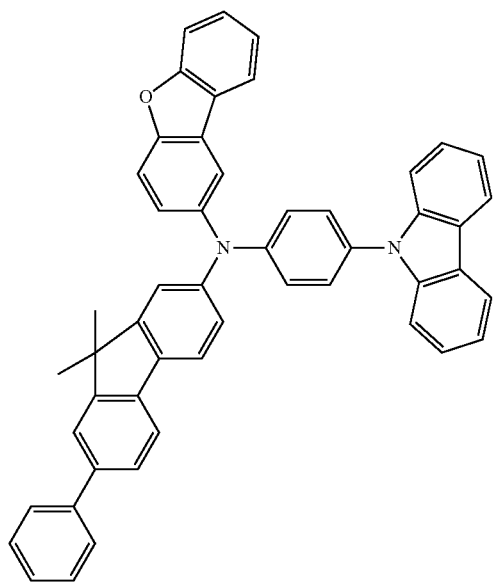
222
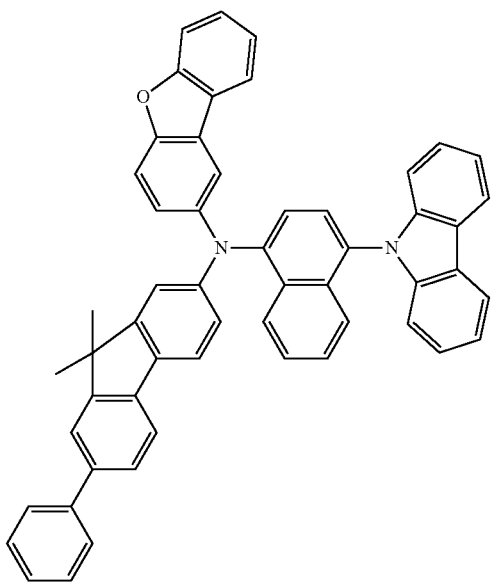
-continued
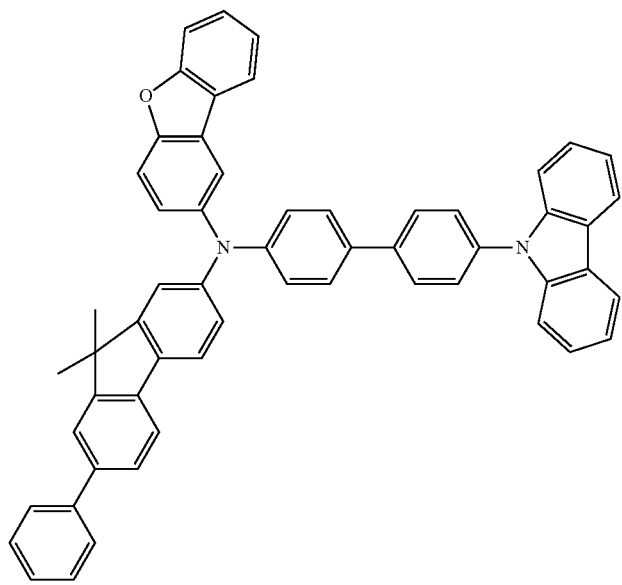

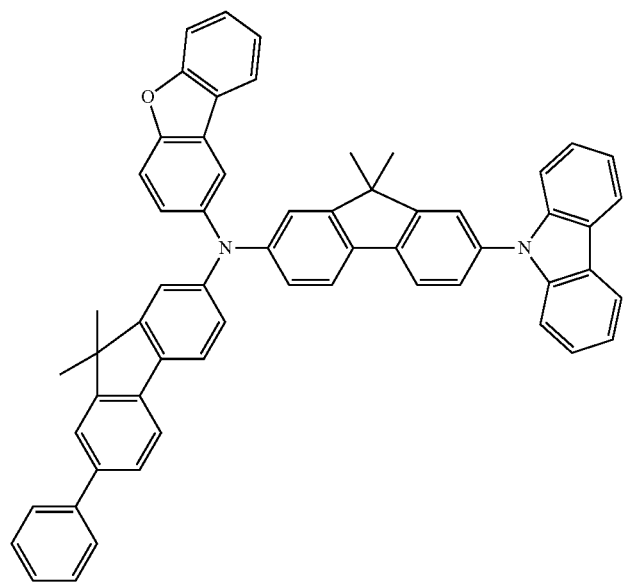
[Chem. 36]
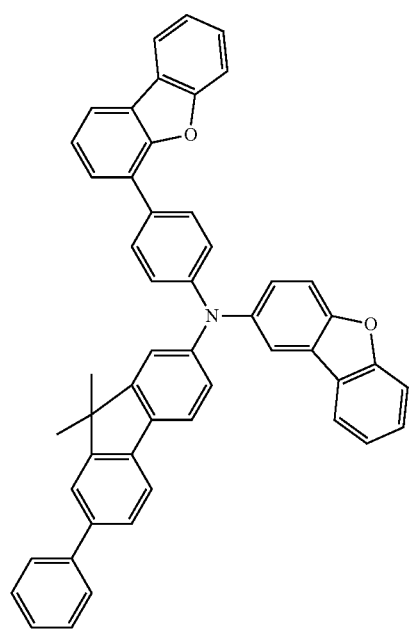
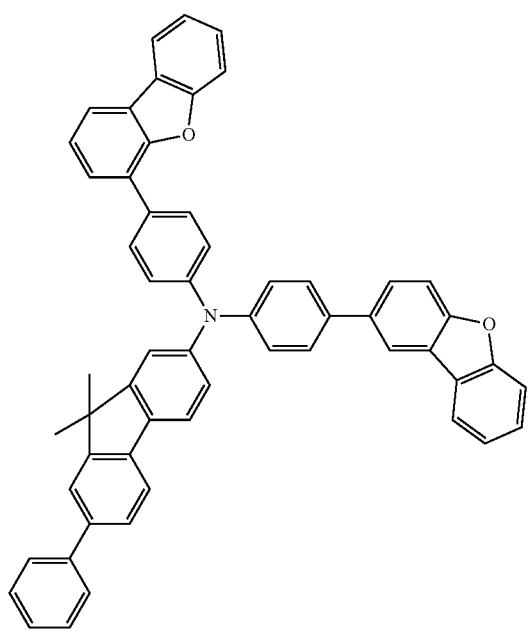

-continued
225
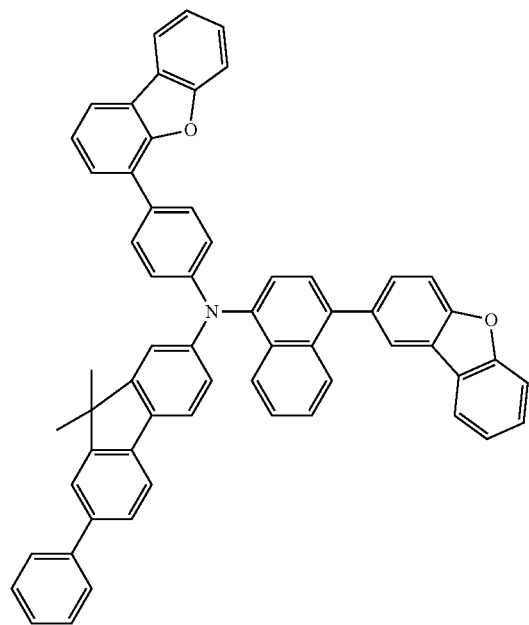
226
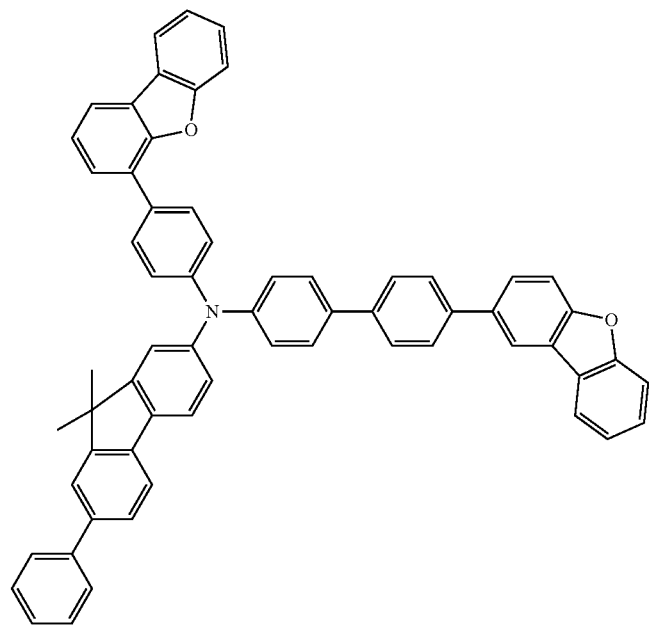
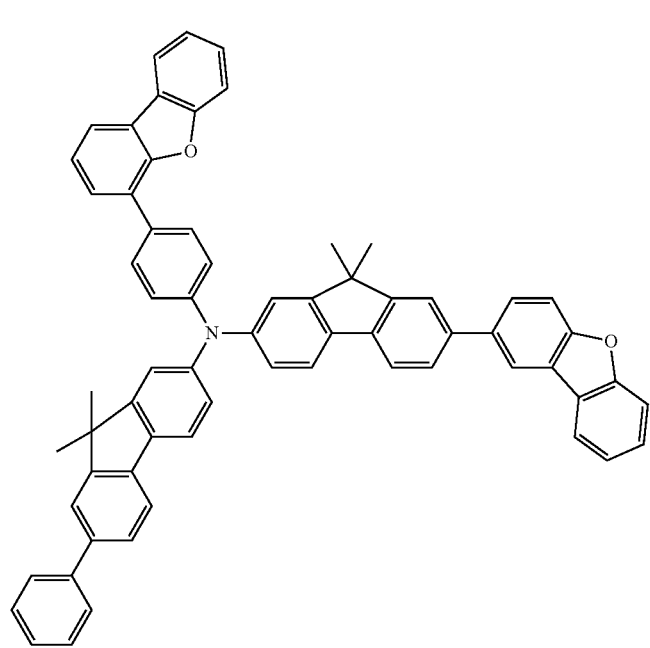
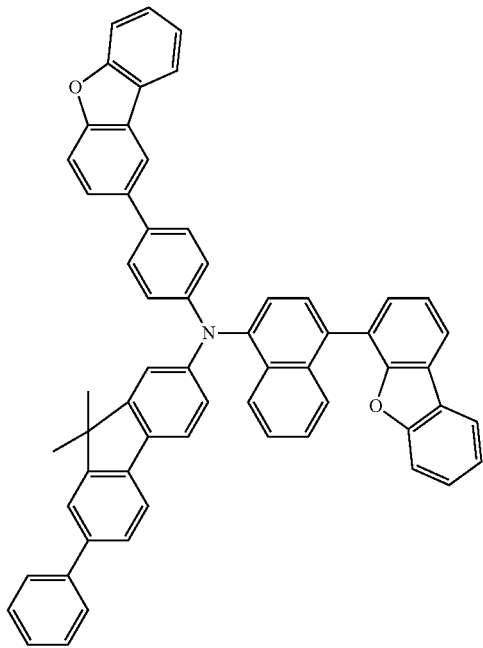

227
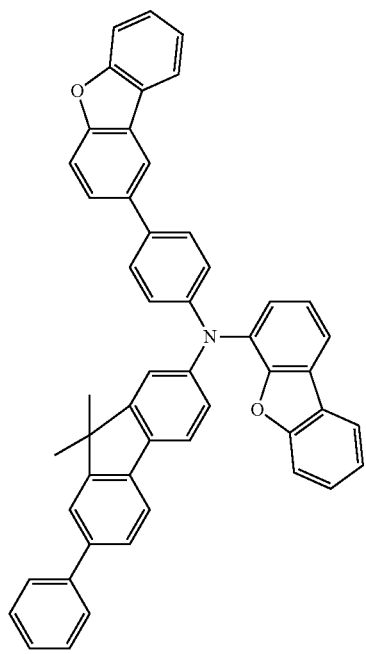
228
-continued
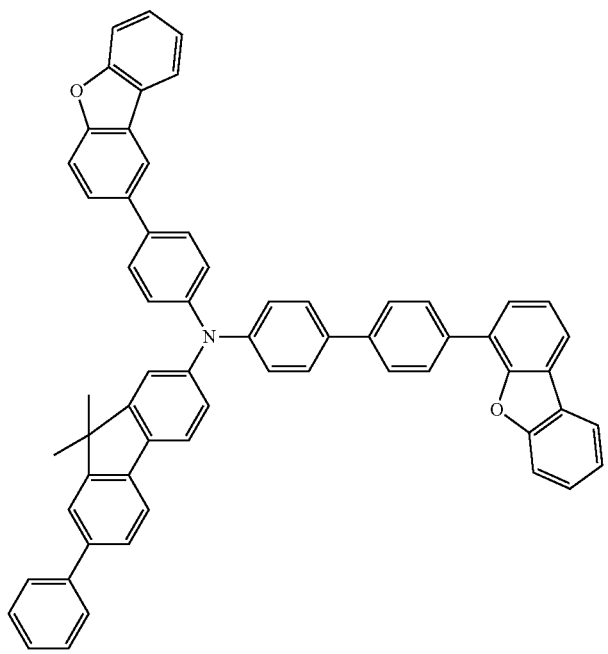
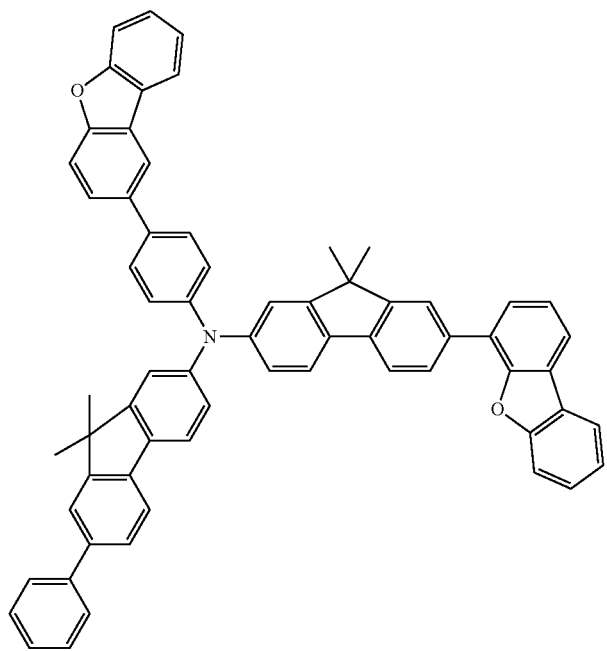

-continued
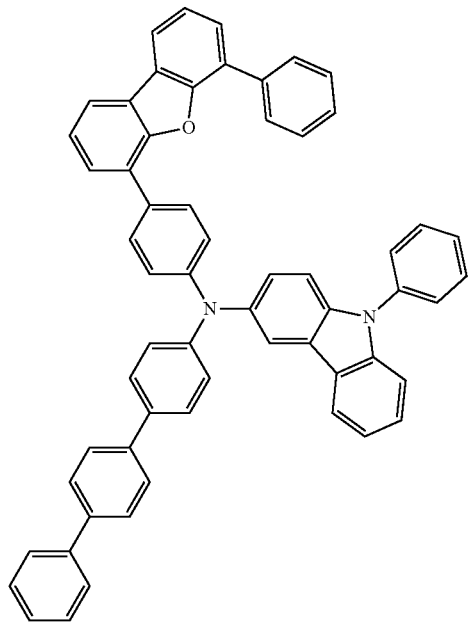 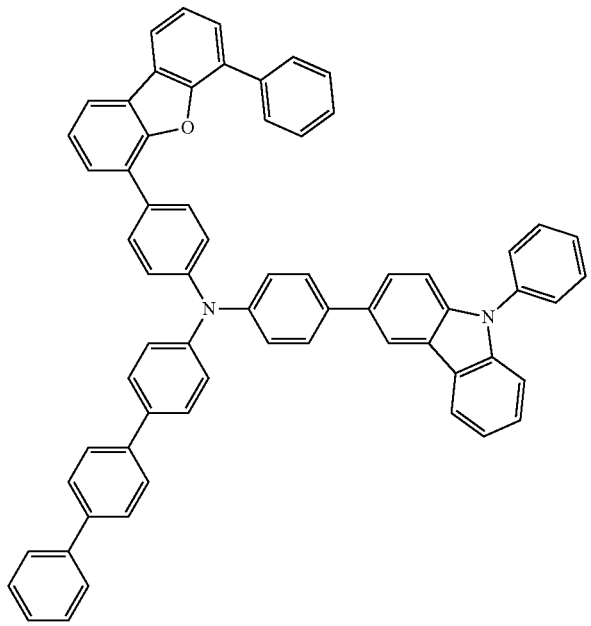
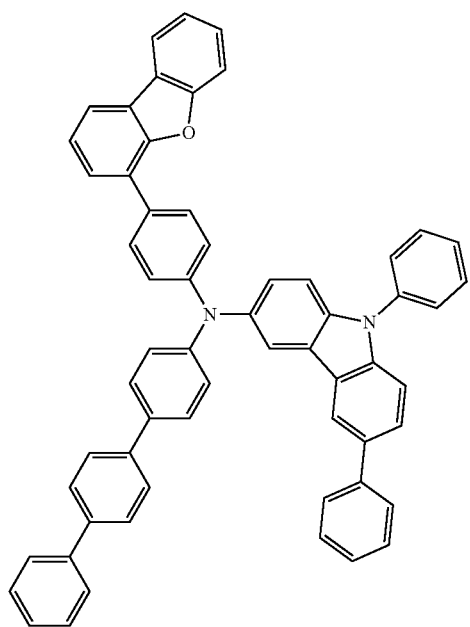 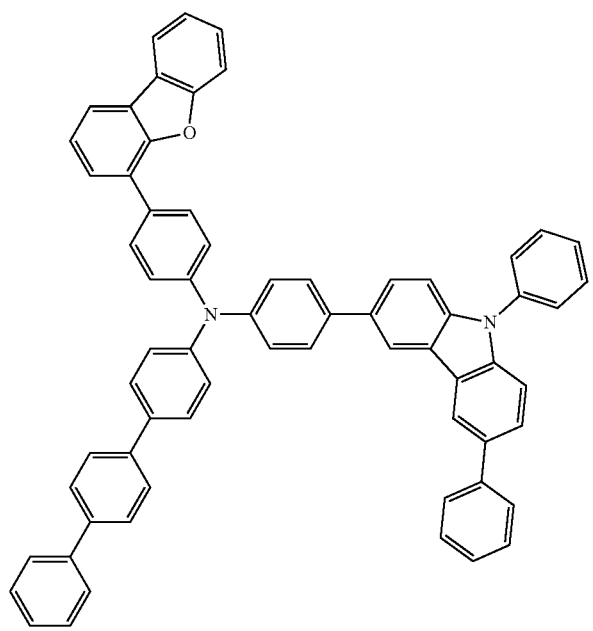

231
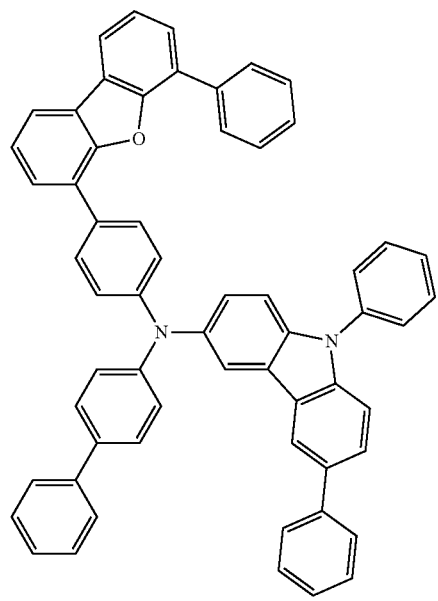
232
-continued
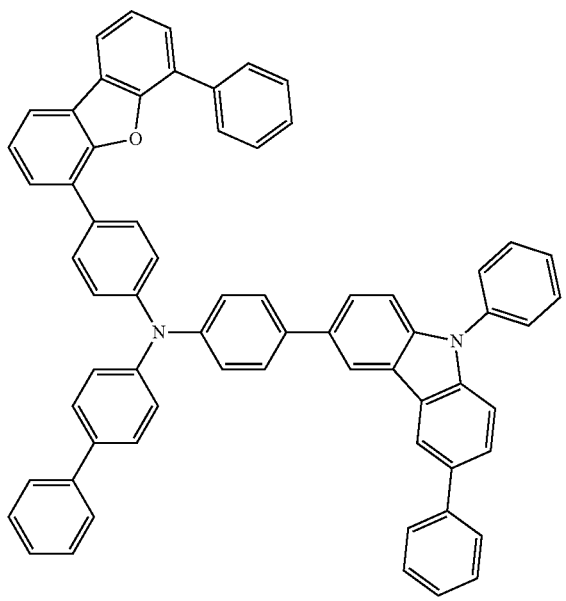
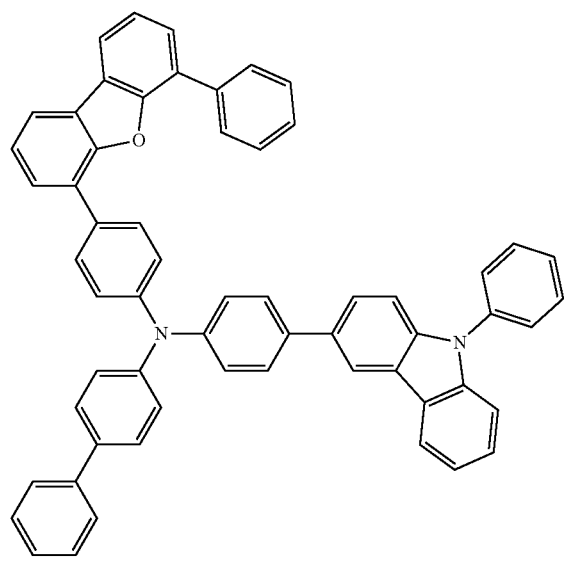
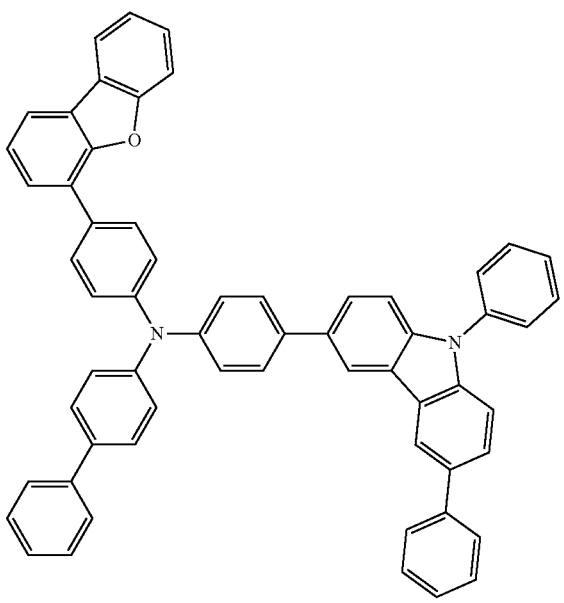

-continued
233
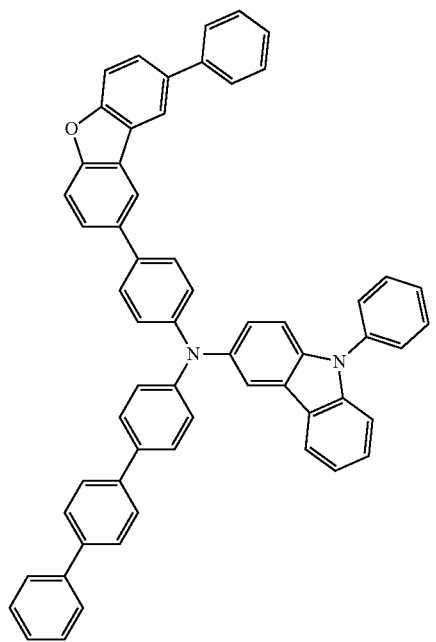
234
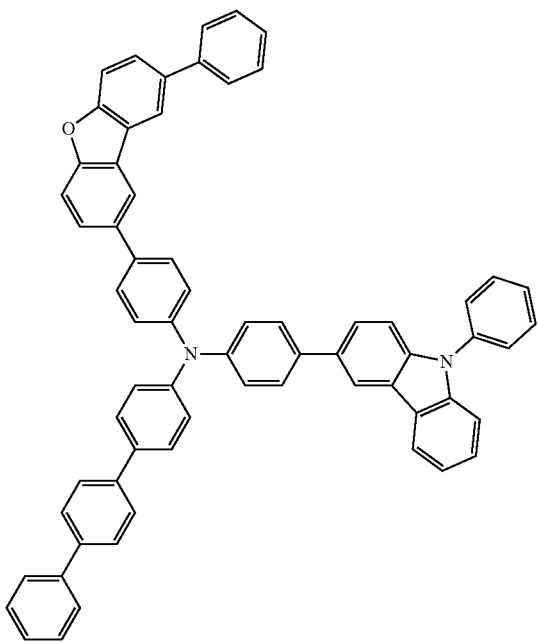
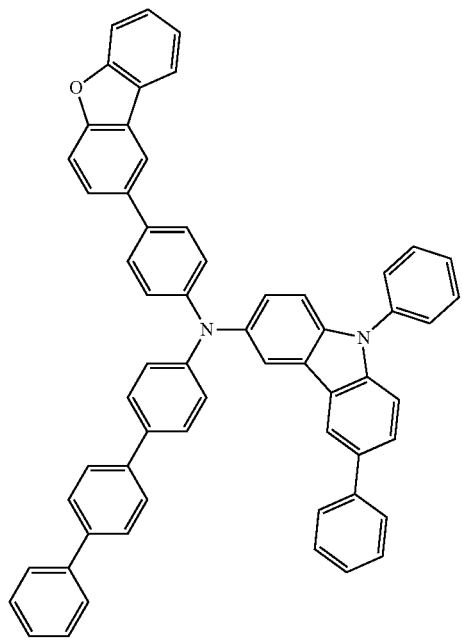
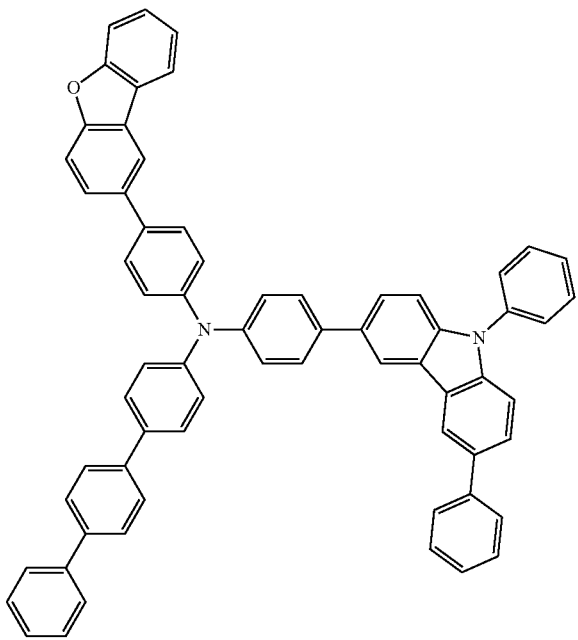

235
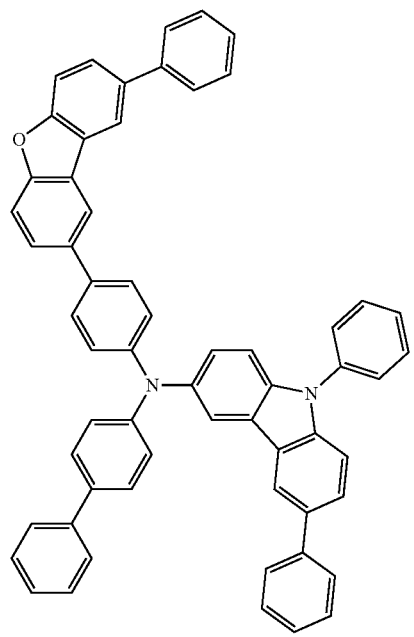
236
-continued
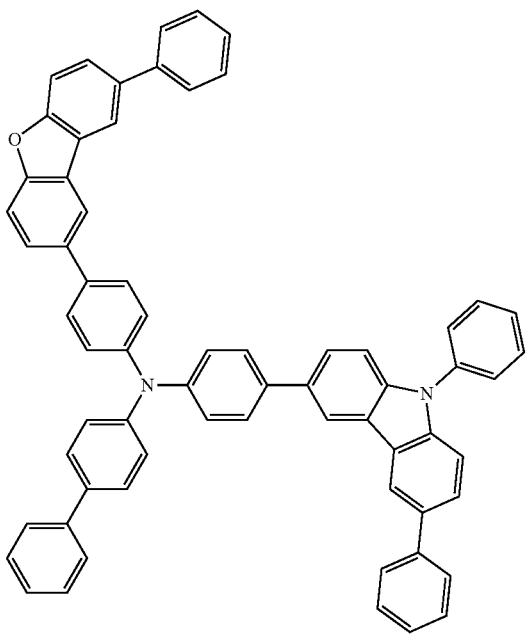
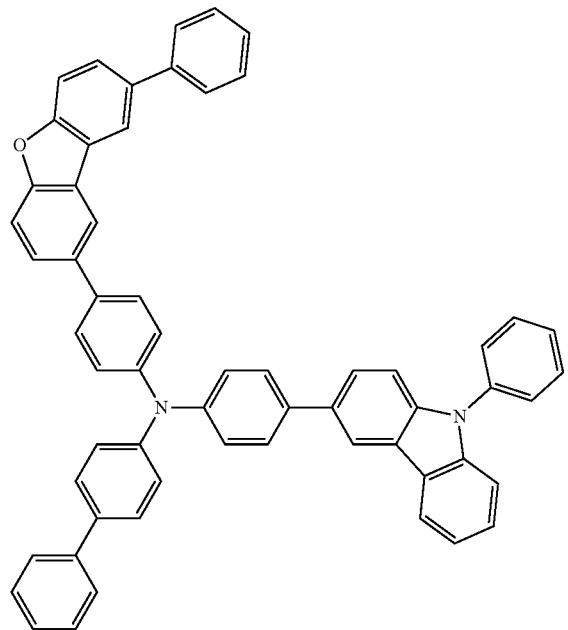
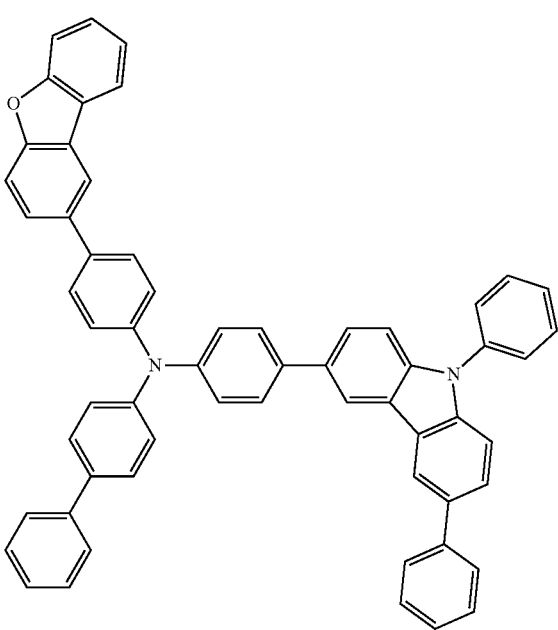

[Chem. 38]
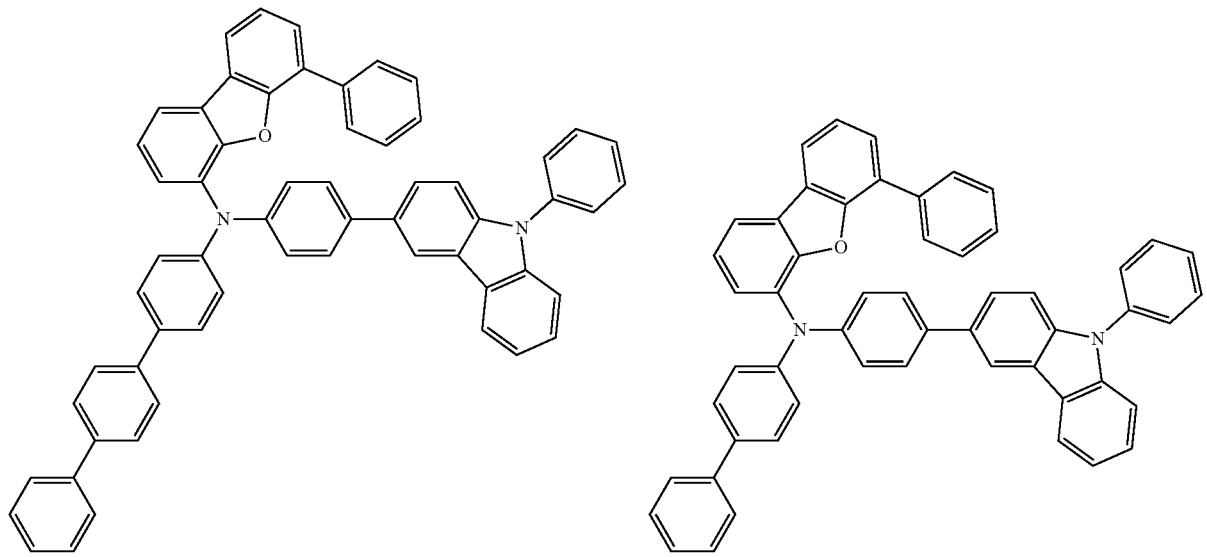
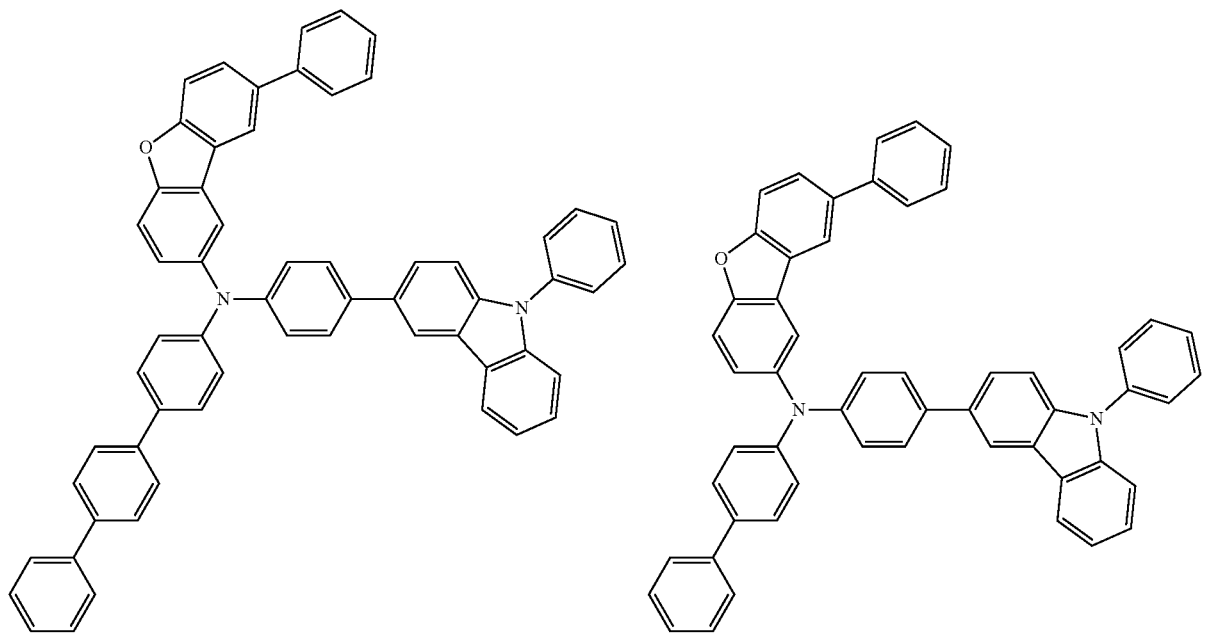

-continued
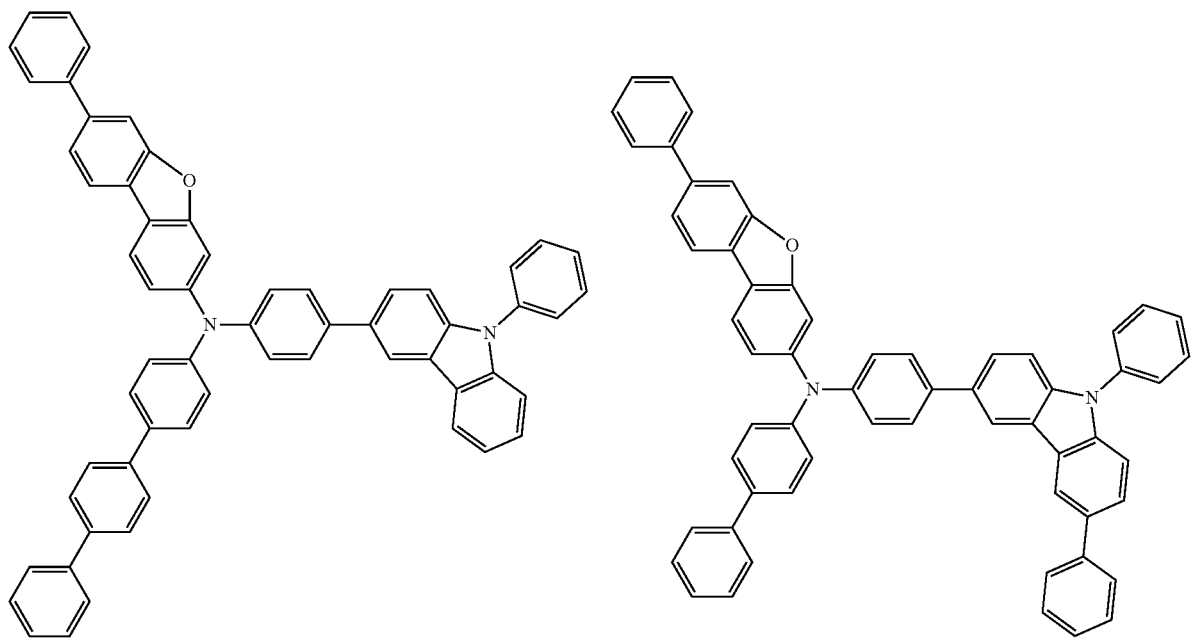
[Chem. 39]
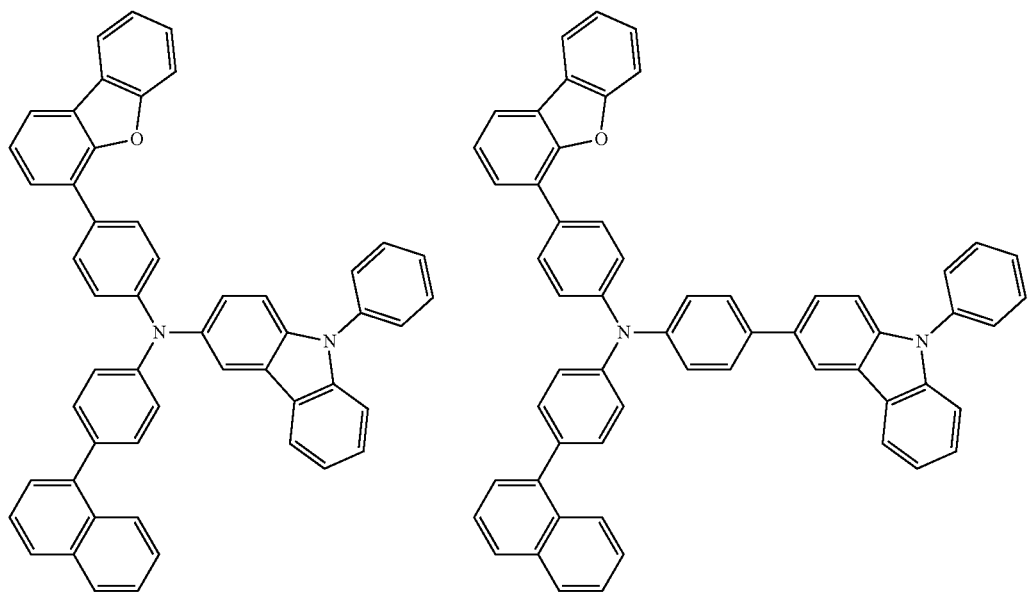

241
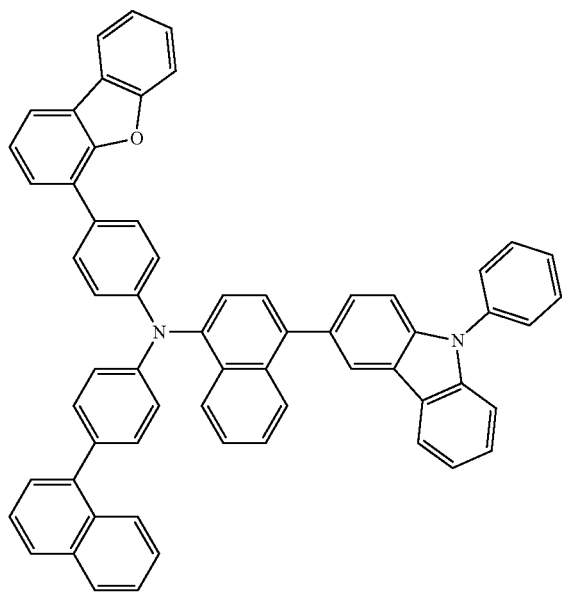
242
-continued
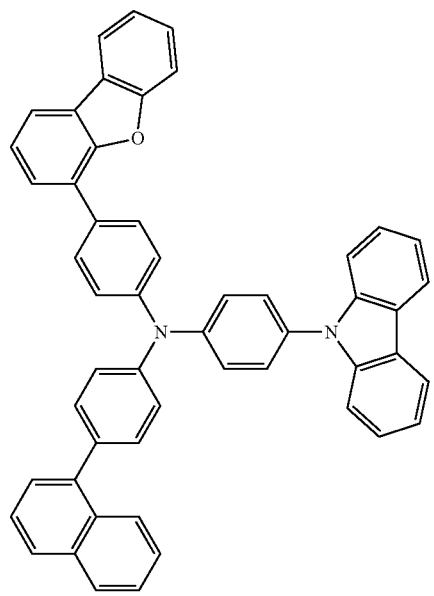
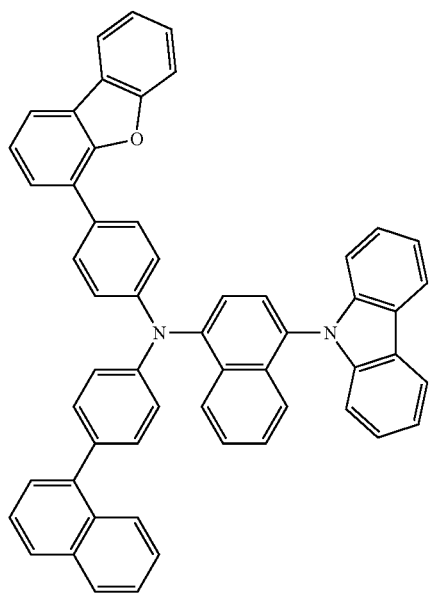
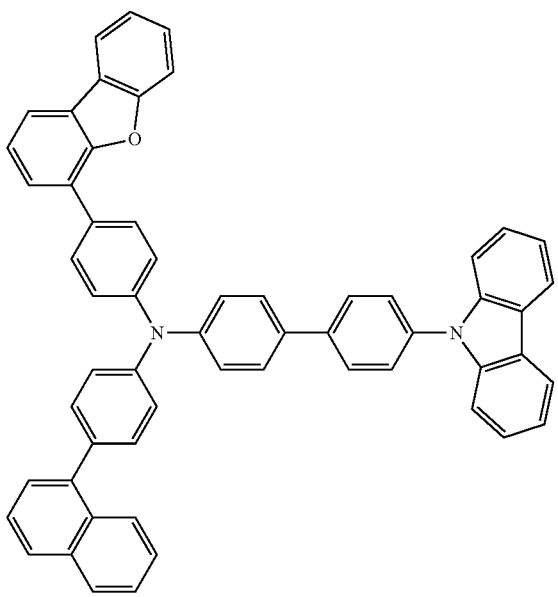

-continued
243
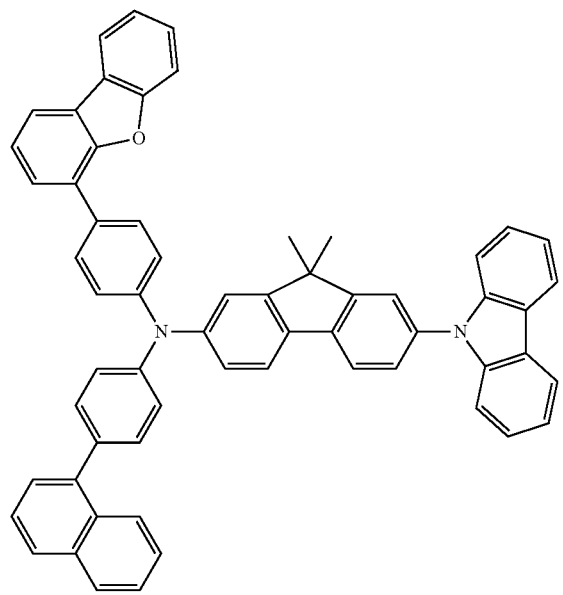
244
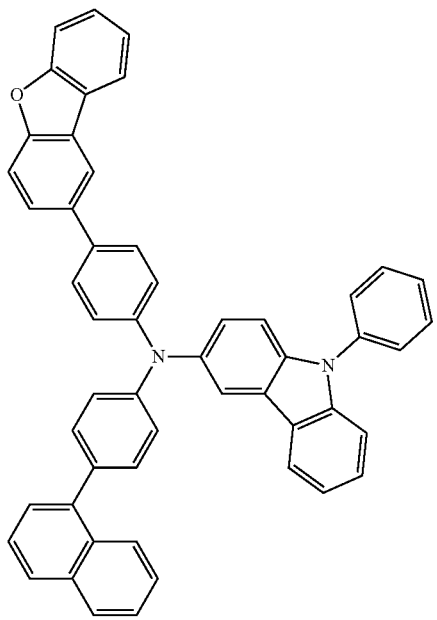
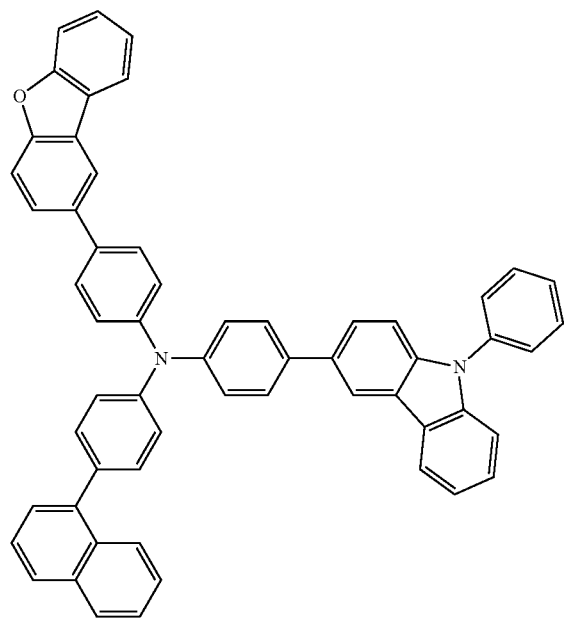
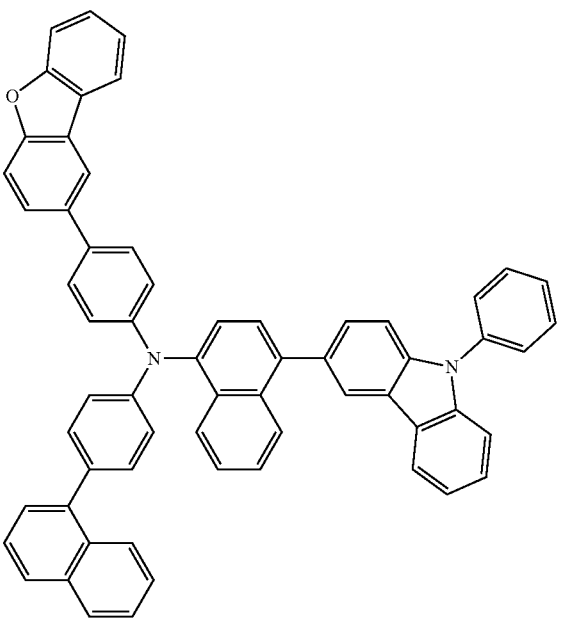

245
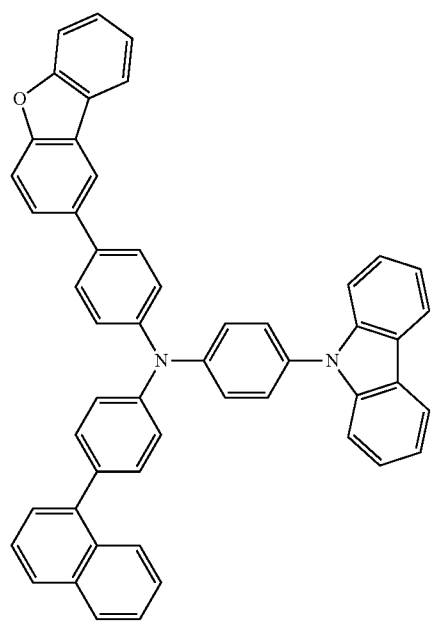
246
-continued
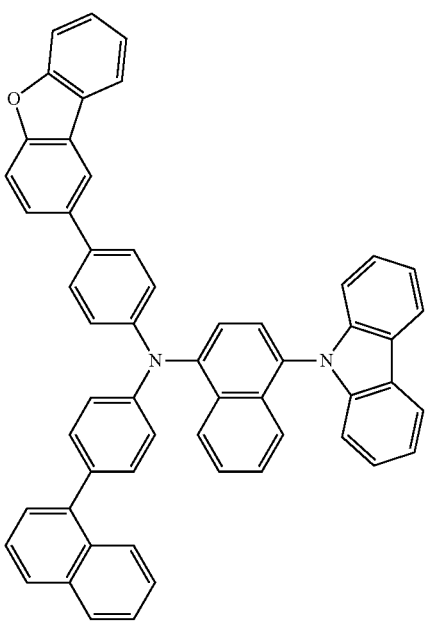
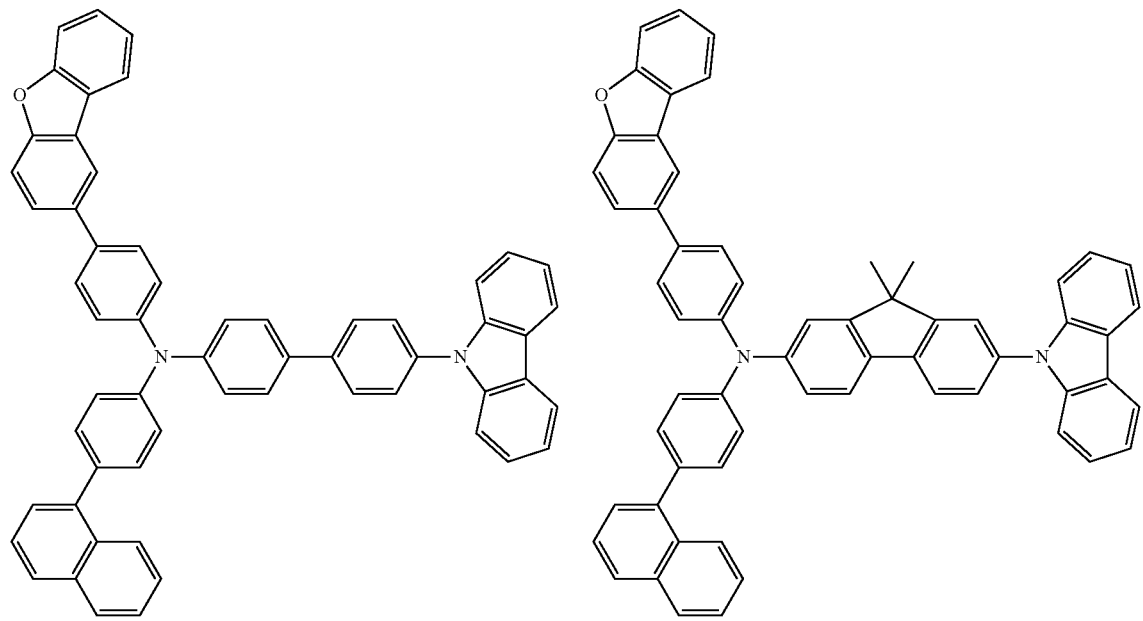

-continued
[Chem. 40]
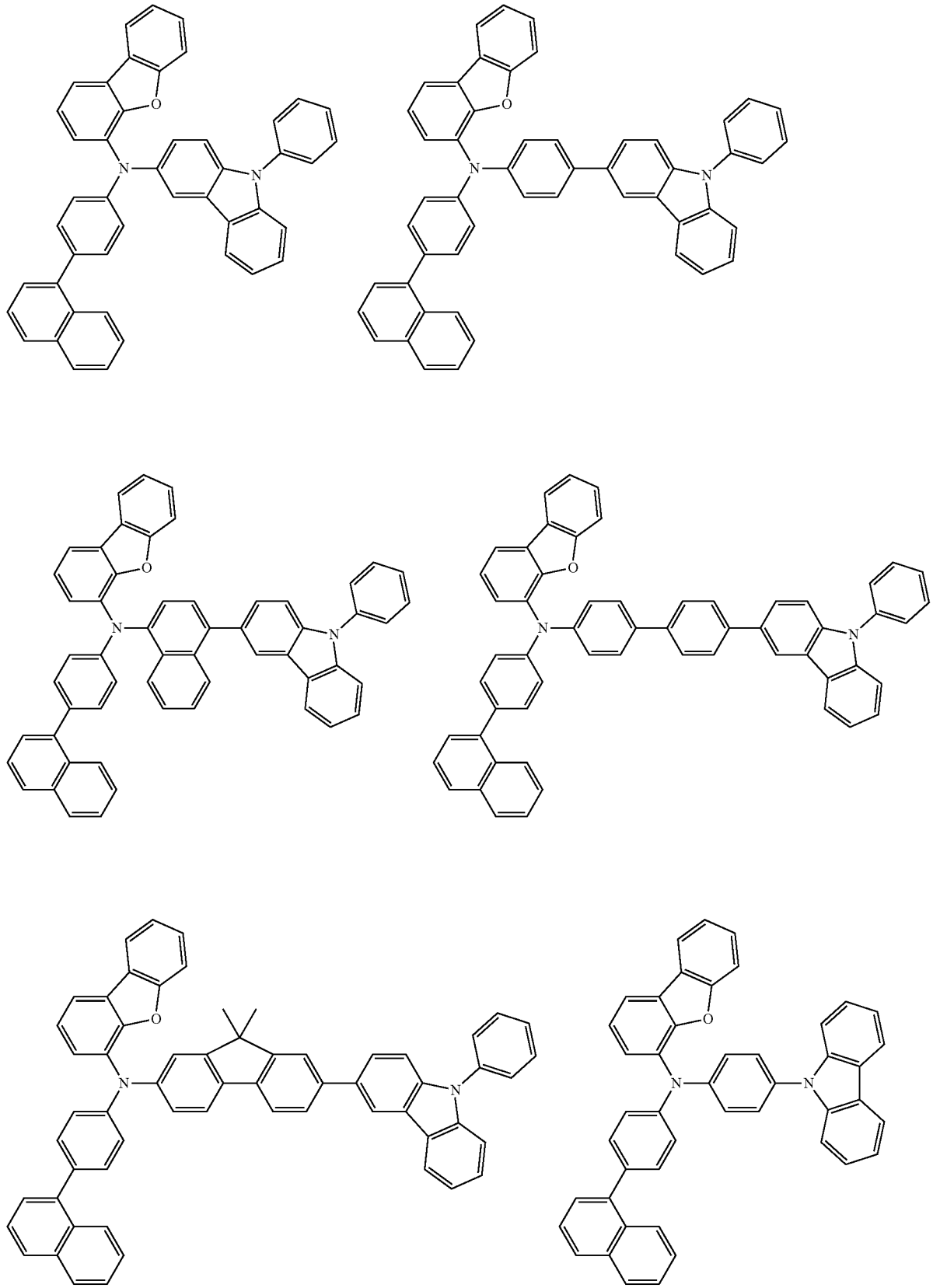

249
250
-continued
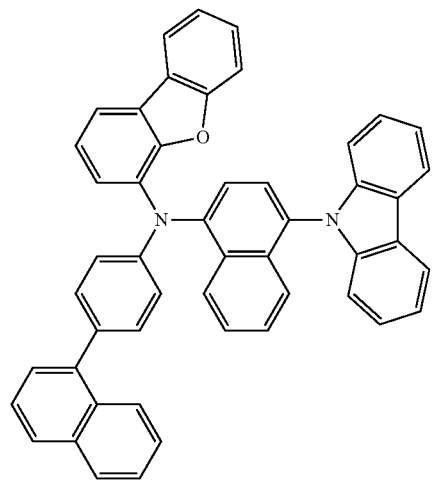
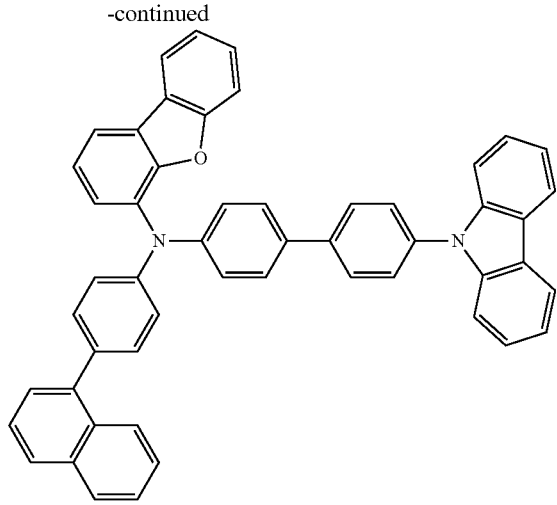
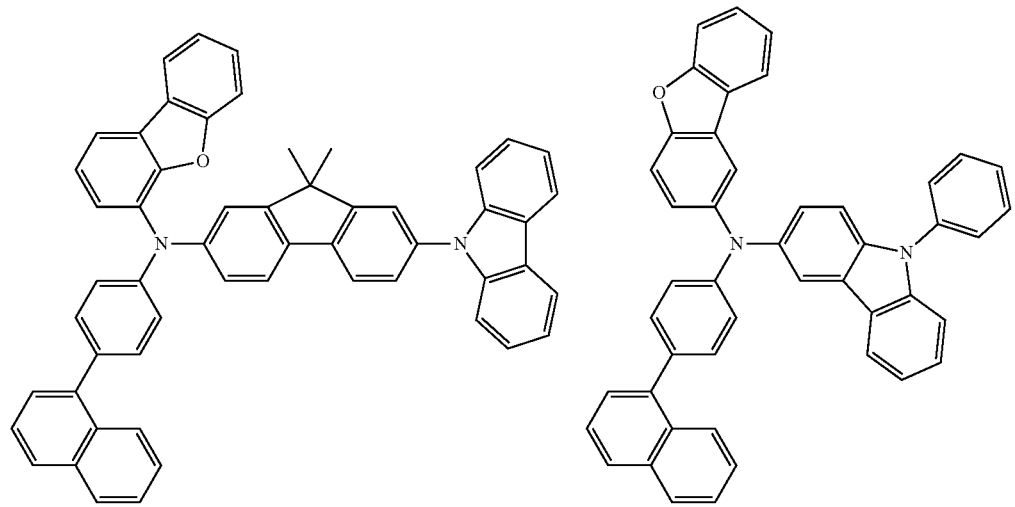
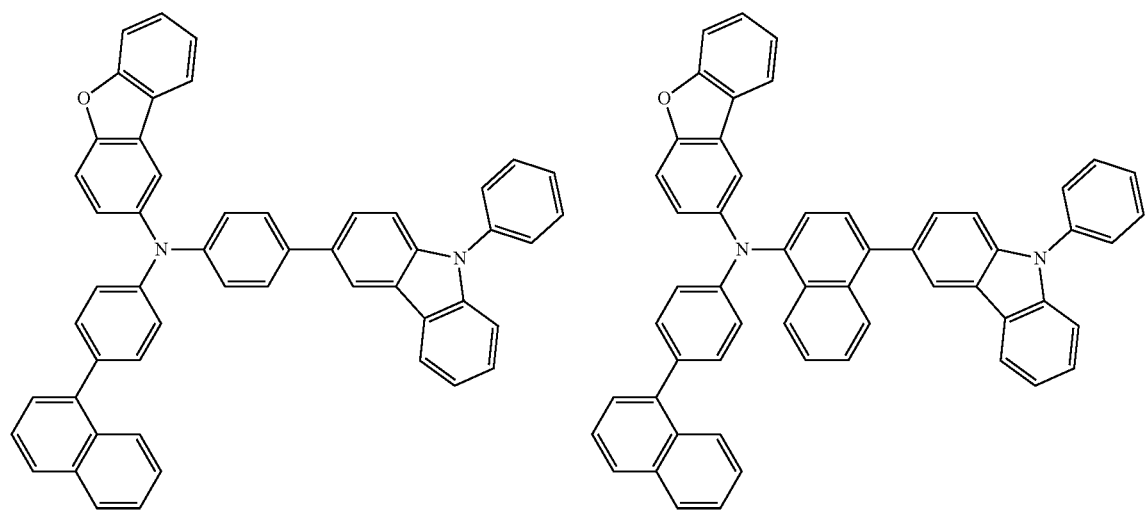

251
252
-continued
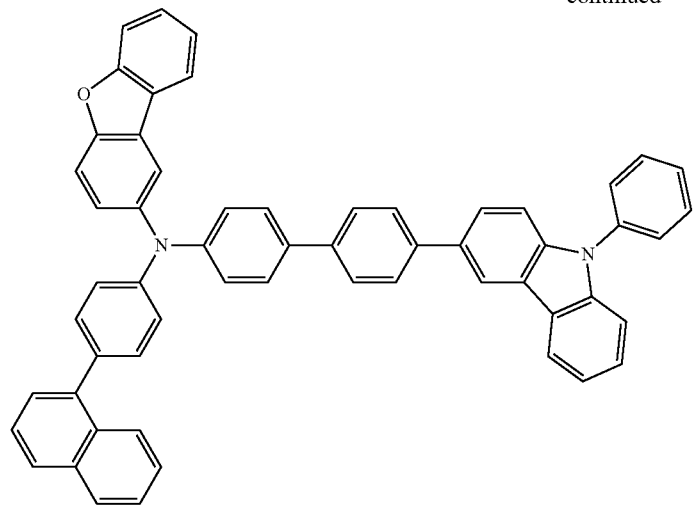
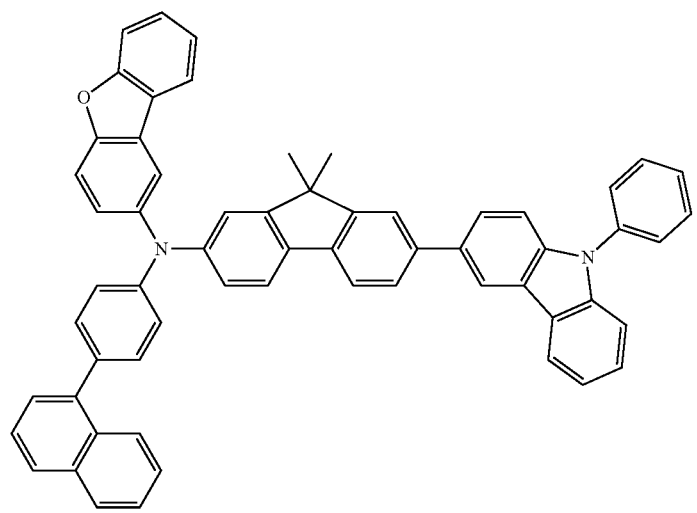
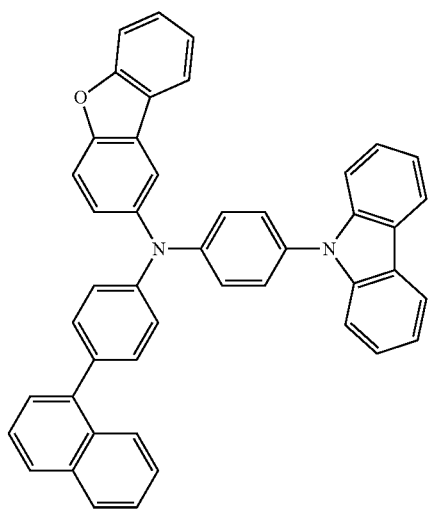
[Chem. 41]
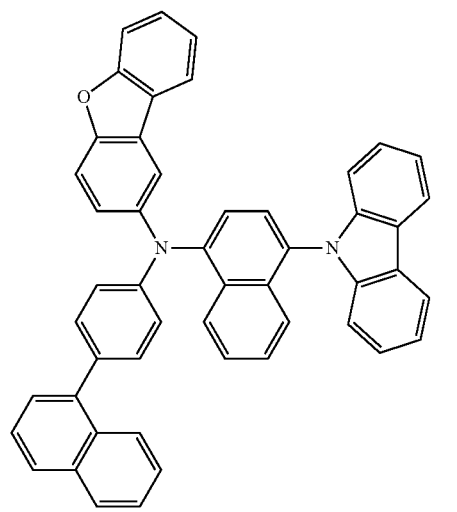
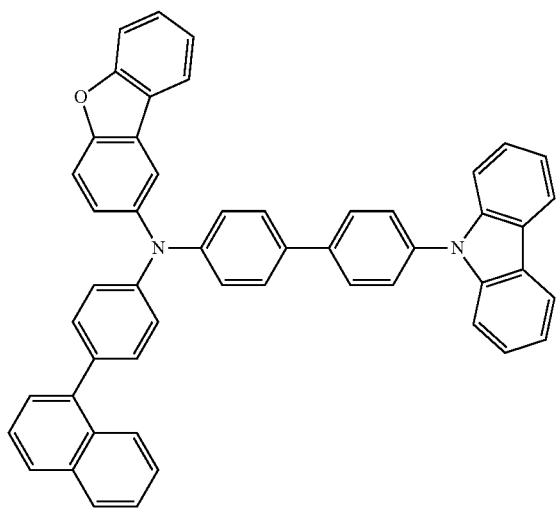

253
254
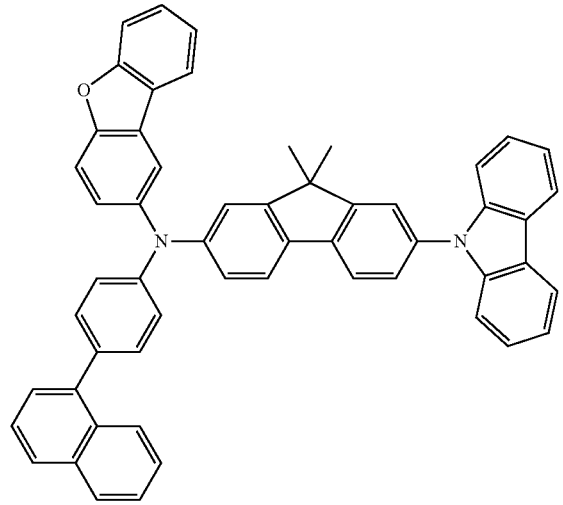
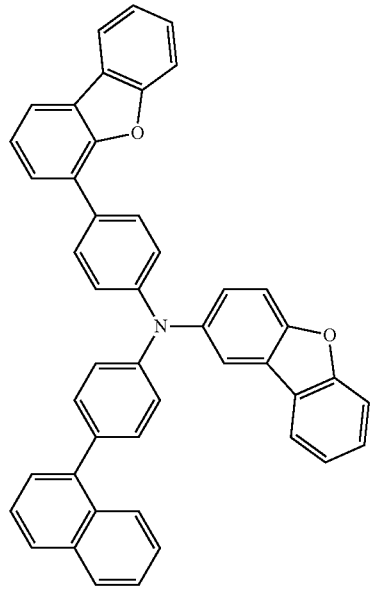
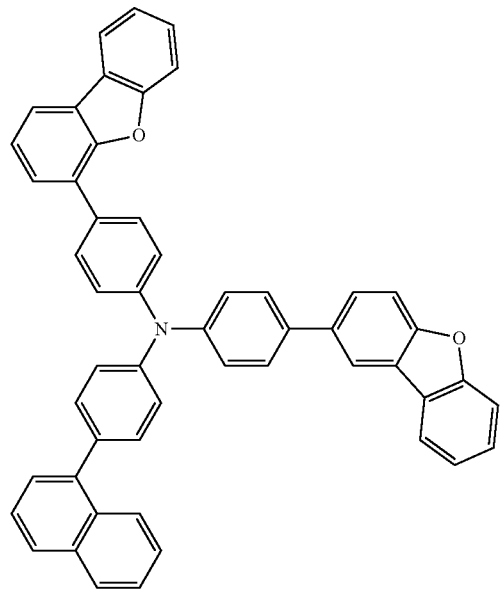
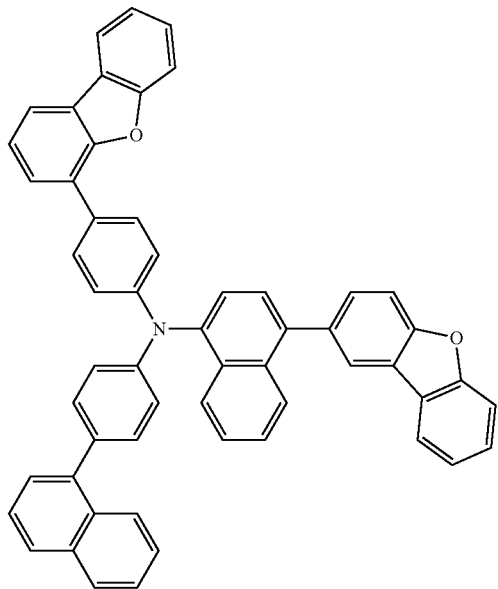

-continued
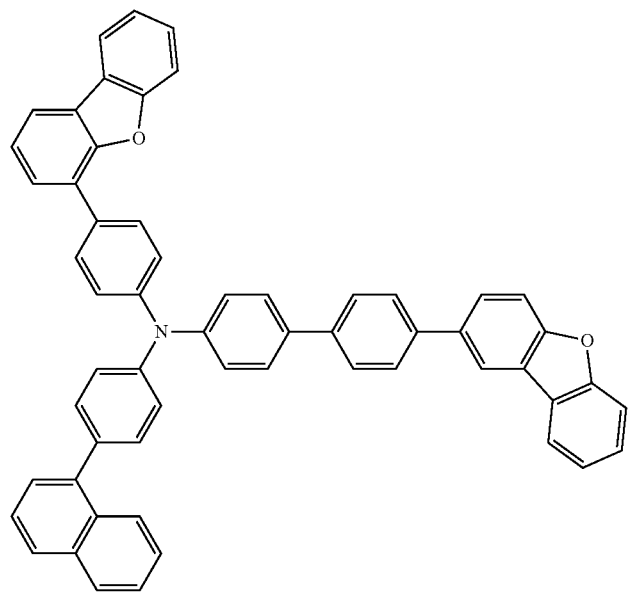
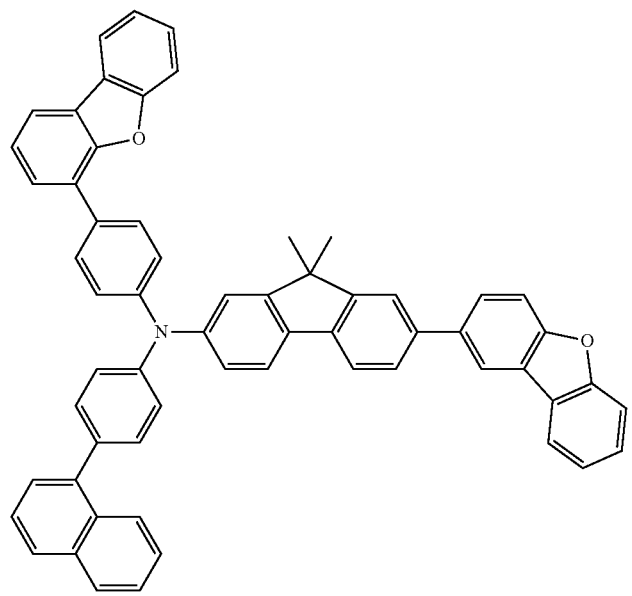

257 258
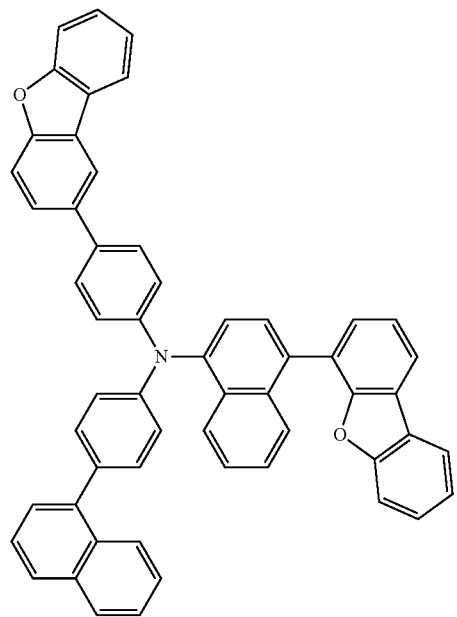
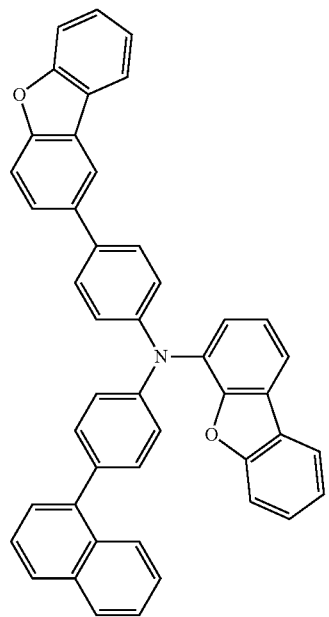
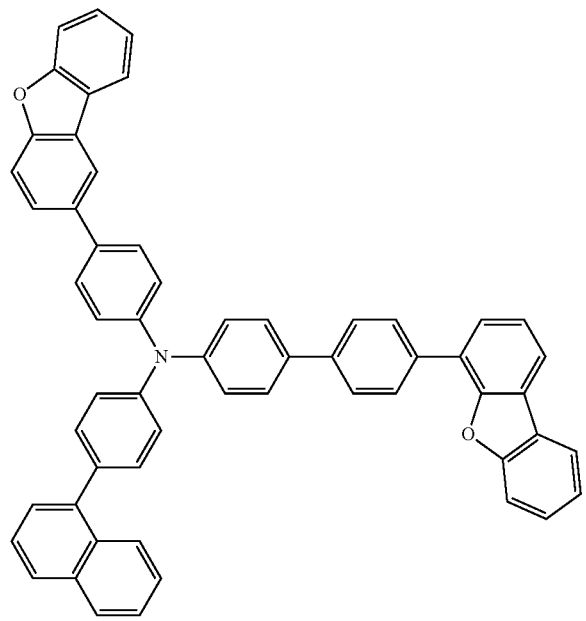
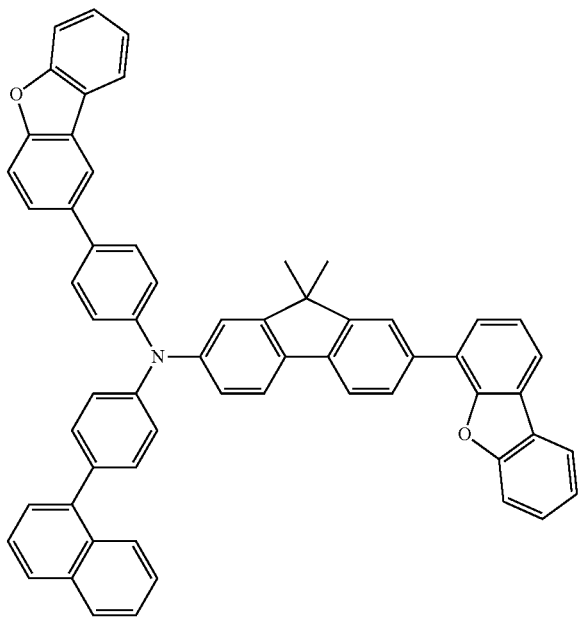

[Chem. 42]
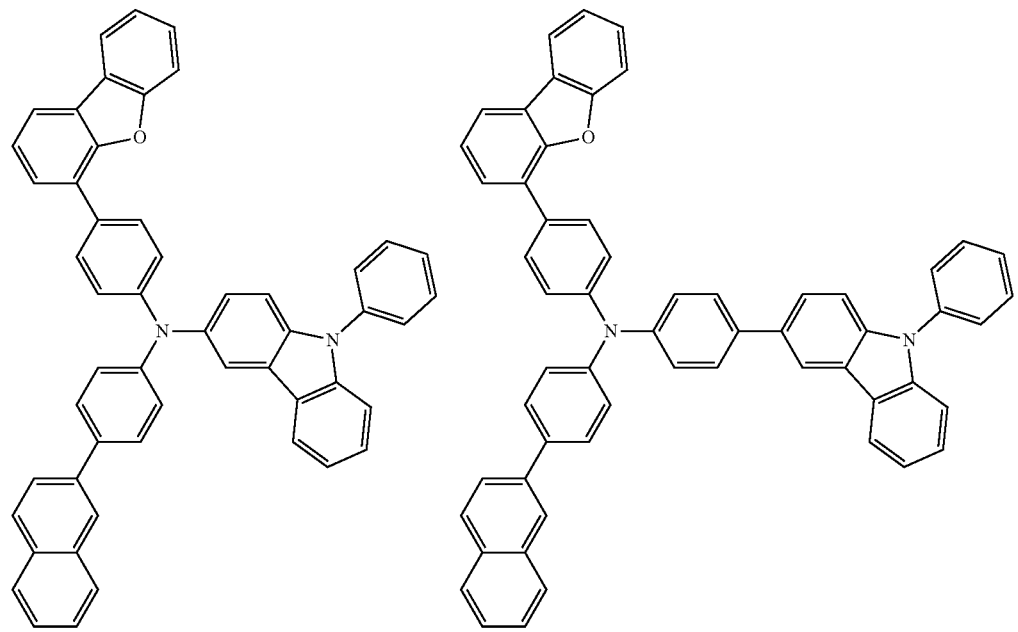
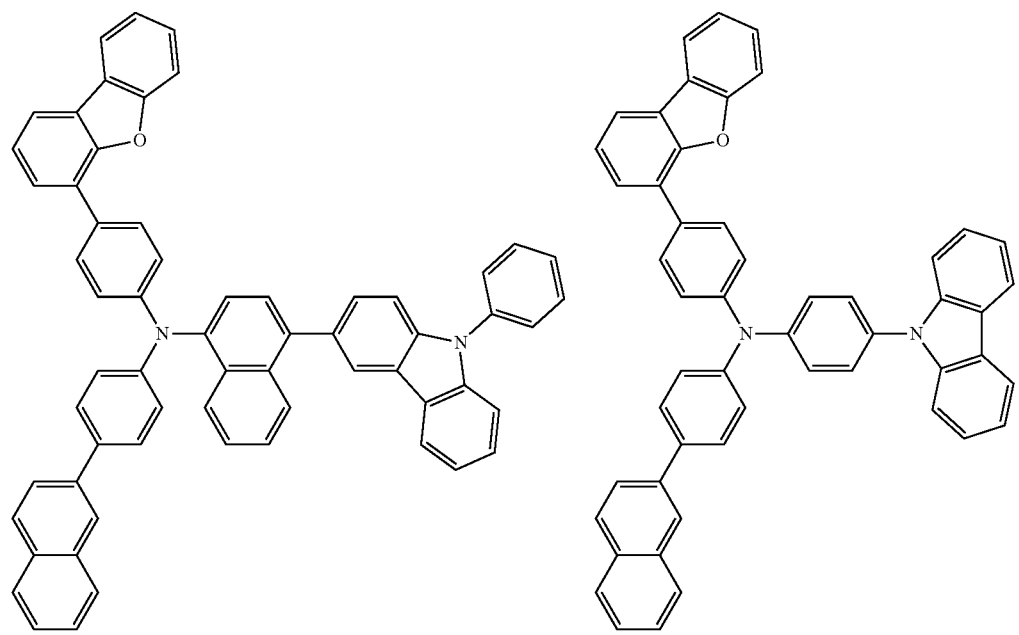

261
262
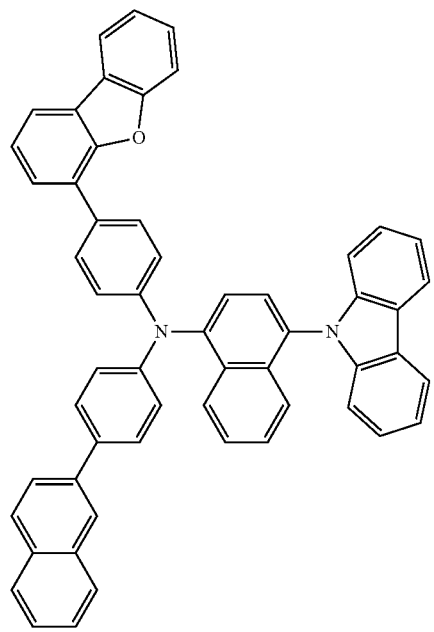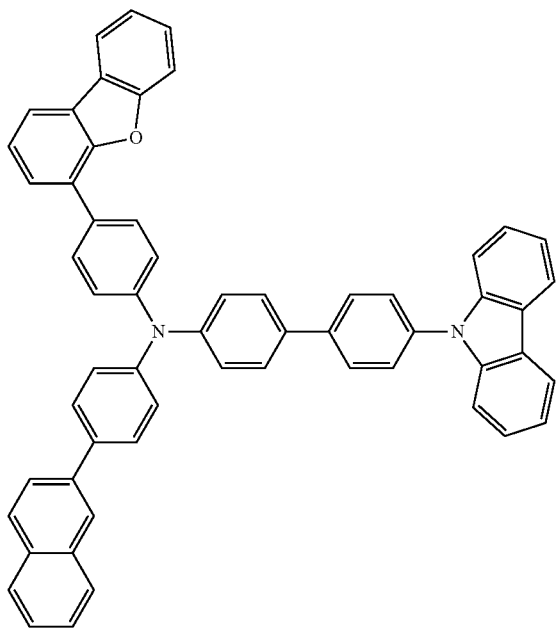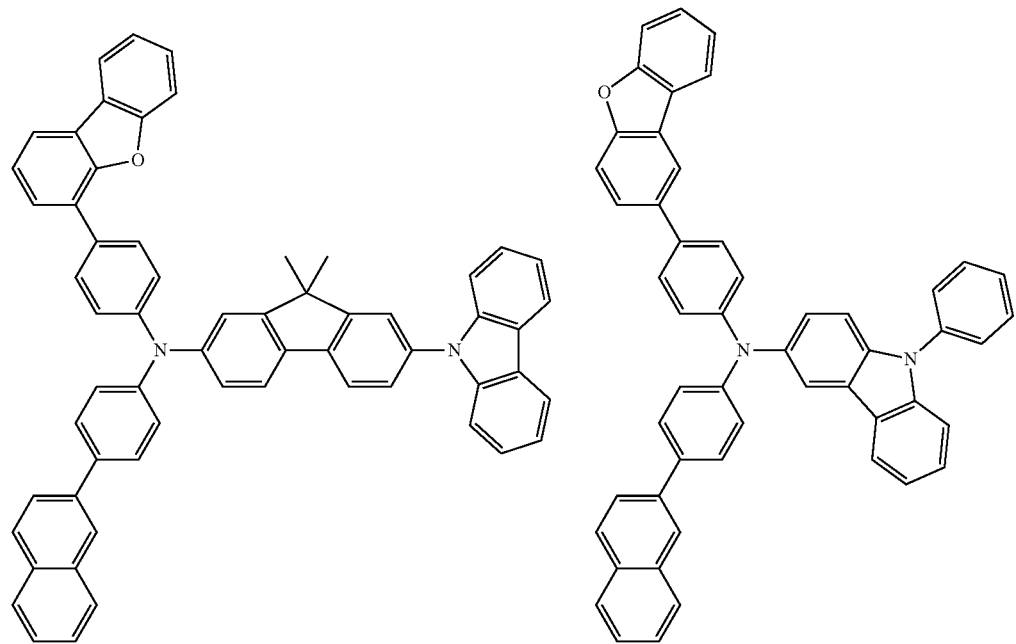

263
264
-continued
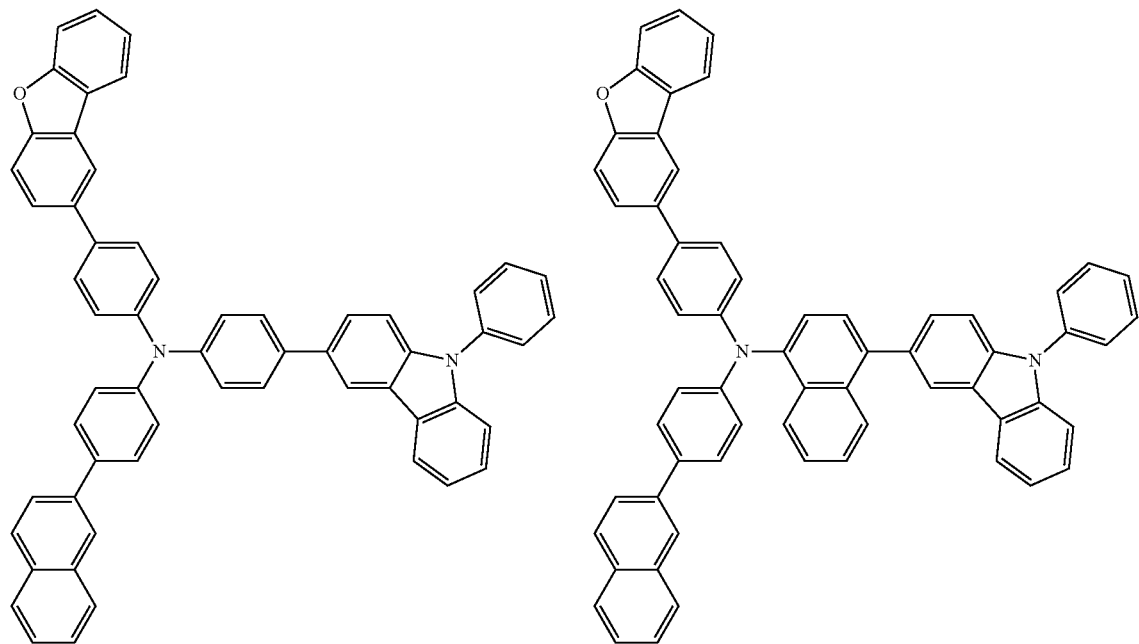
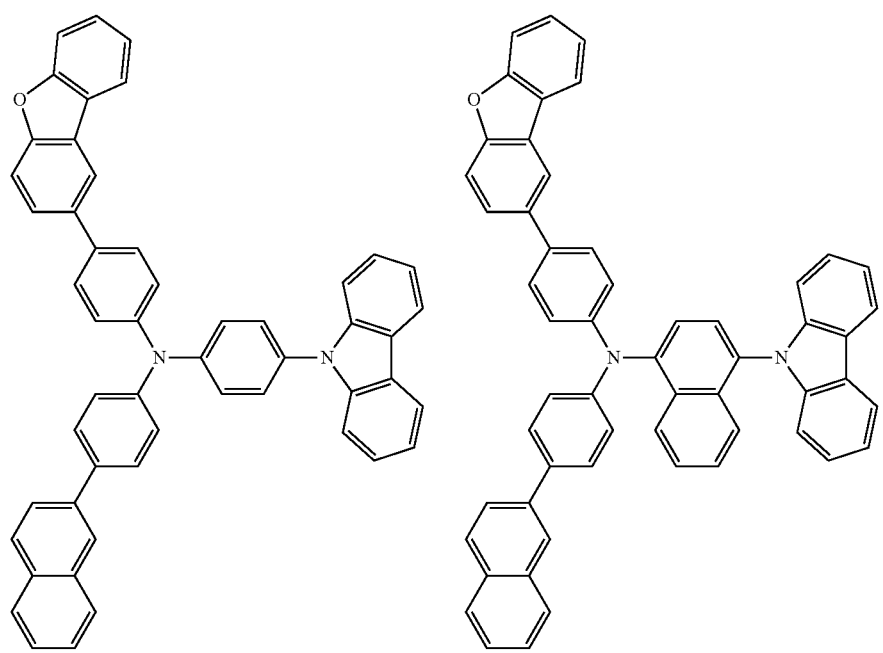

-continued
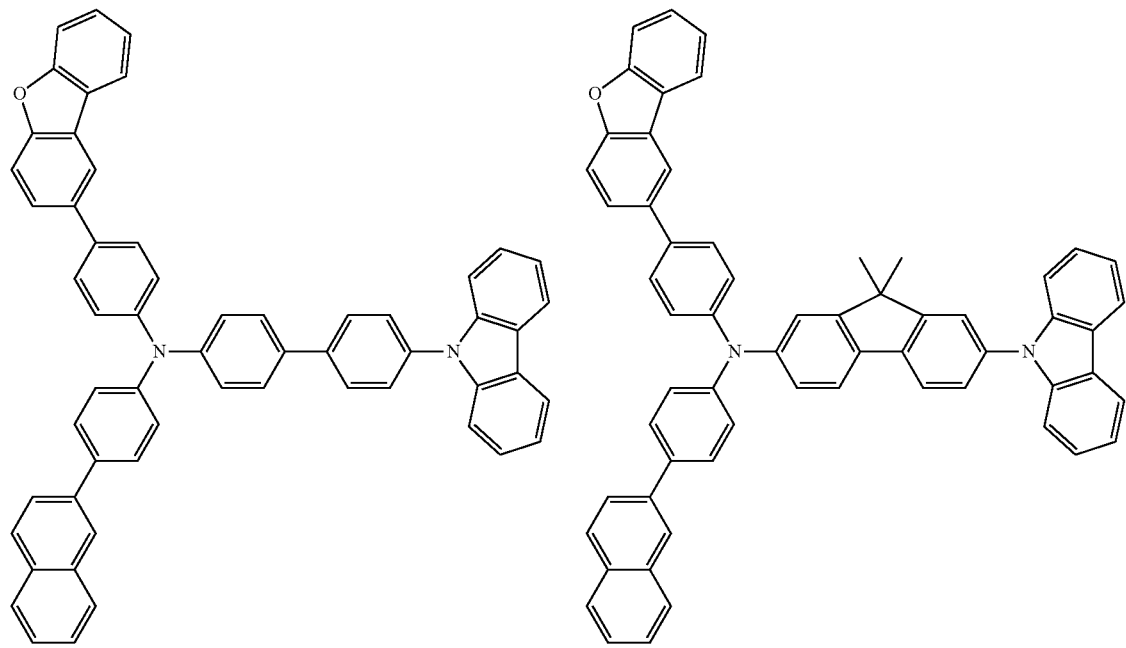
[Chem. 43]
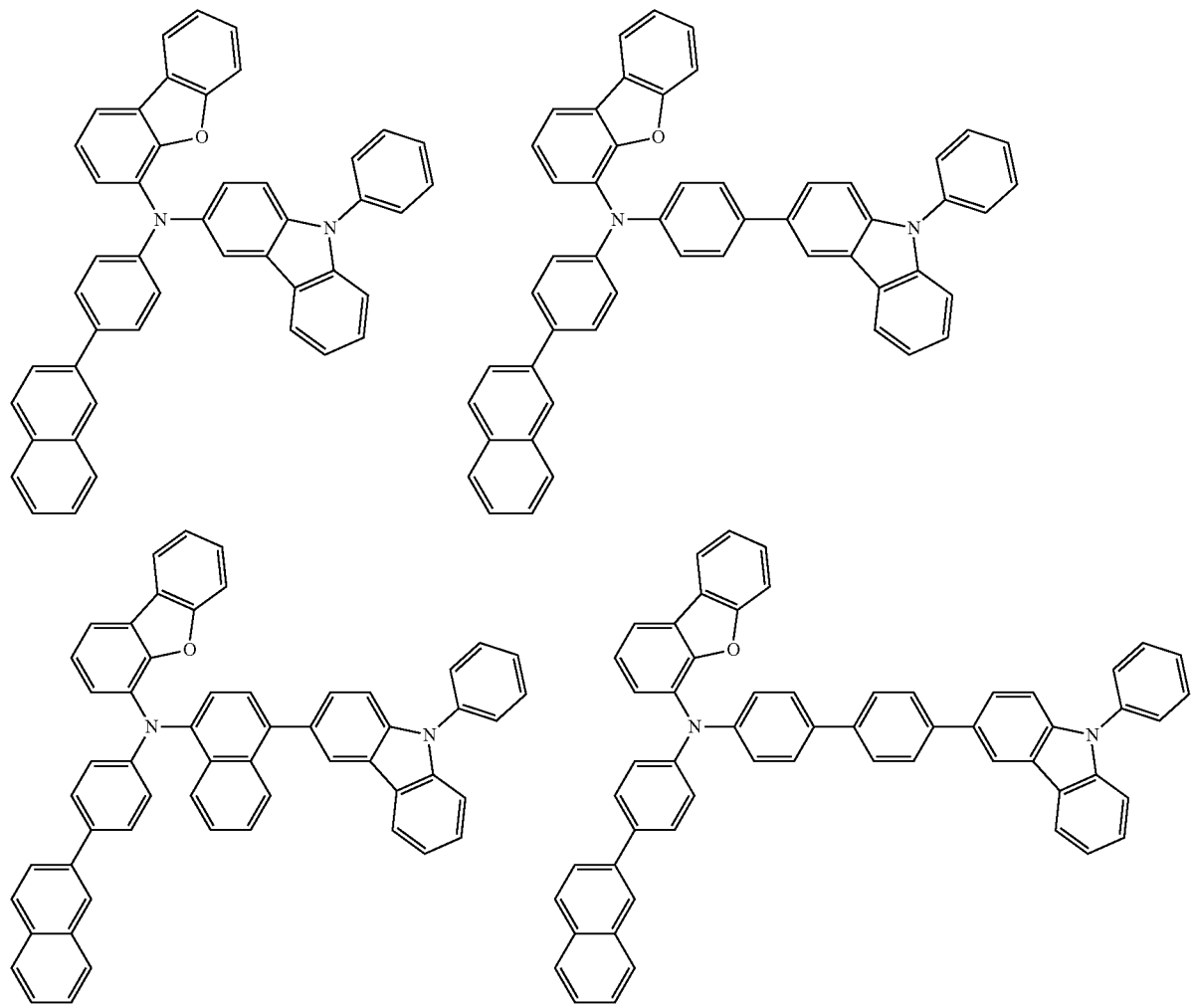

267 268
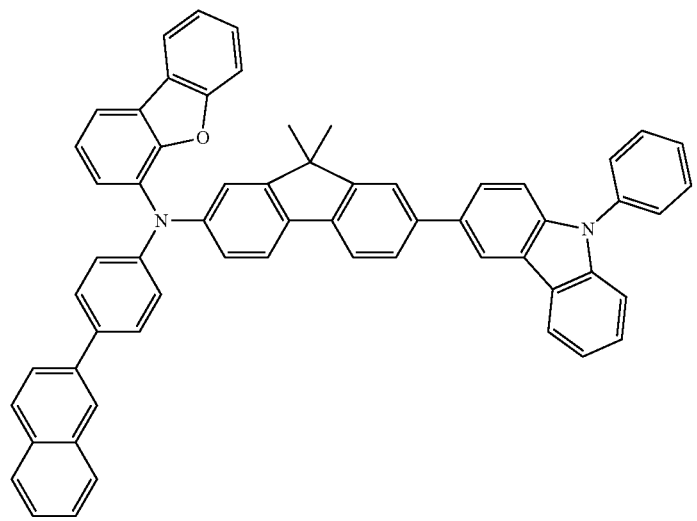
-continued 269 270
-continued
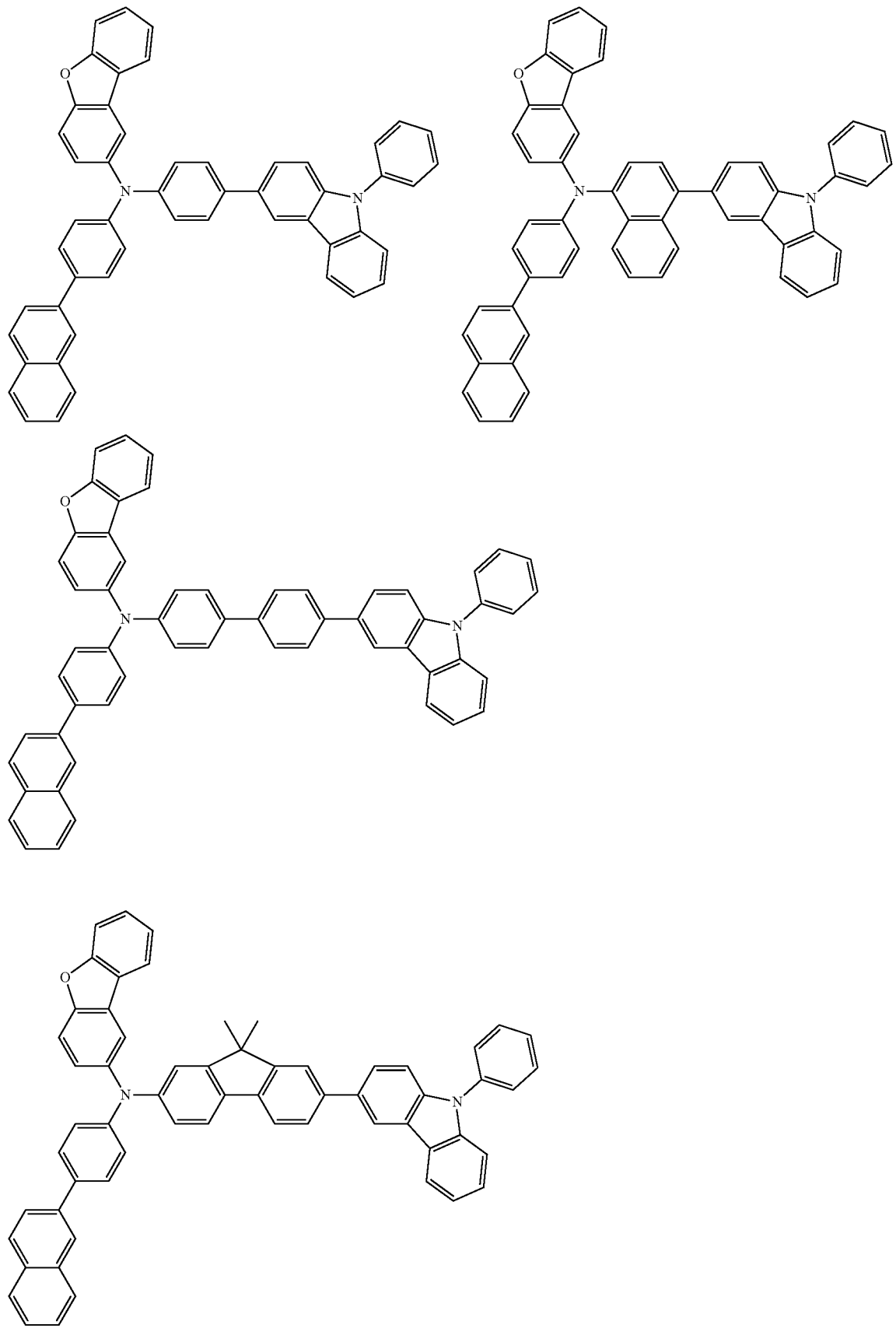 [SMILES: c1ccc(-n2c3ccccc3c3cc(-c4ccc(N(c5ccc(-c6ccc7ccccc7c6)cc5)c5ccc6oc7ccccc7c6c5)cc4)ccc32)cc1 ; c1ccc(-n2c3ccccc3c3cc(-c4ccc(N(c5ccc(-c6ccc7ccccc7c6)cc5)c5ccc6oc7ccccc7c6c5)c5ccccc45)ccc32)cc1 ; c1ccc(-n2c3ccccc3c3cc(-c4ccc(-c5ccc(N(c6ccc(-c7ccc8ccccc8c7)cc6)c6ccc7oc8ccccc8c7c6)cc5)cc4)ccc32)cc1 ; CC1(C)c2cc(-c3ccc4c(c3)c3ccccc3n4-c3ccccc3)ccc2-c2ccc(N(c3ccc(-c4ccc5ccccc5c4)cc3)c3ccc4oc5ccccc5c4c3)cc21]

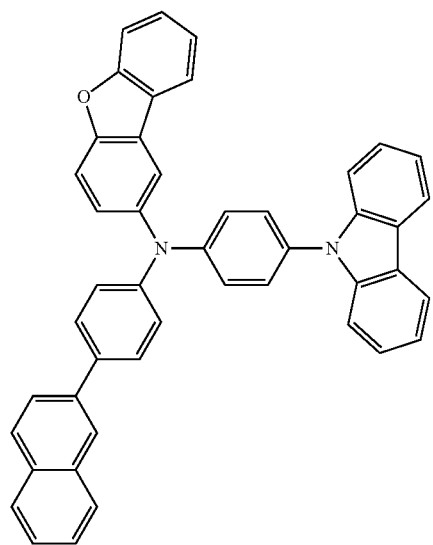 [SMILES: c1ccc2cc(-c3ccc(N(c4ccc(-n5c6ccccc6c6ccccc65)cc4)c4ccc5oc6ccccc6c5c4)cc3)ccc2c1]
[Chem. 44]
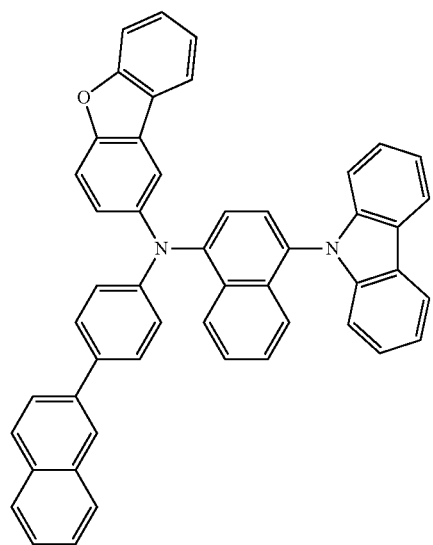 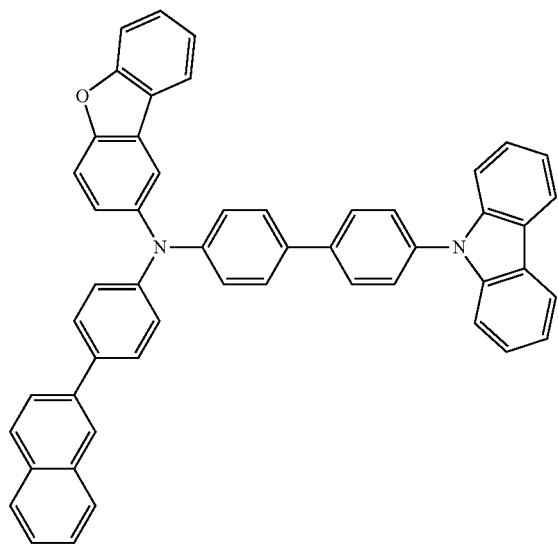

273
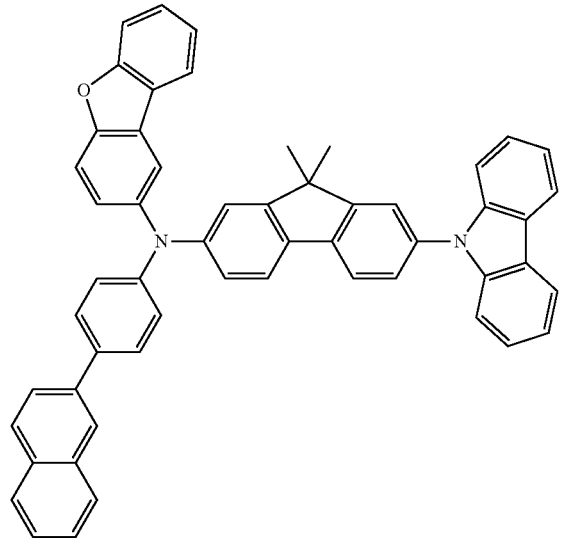
274
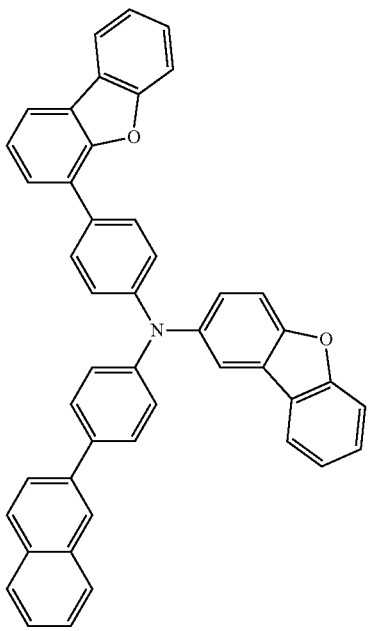
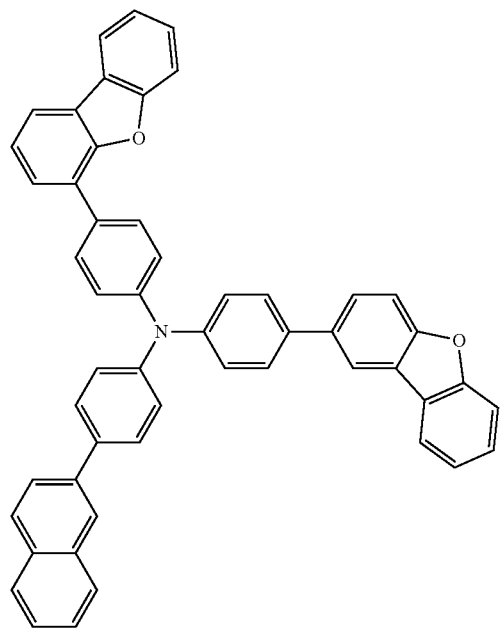
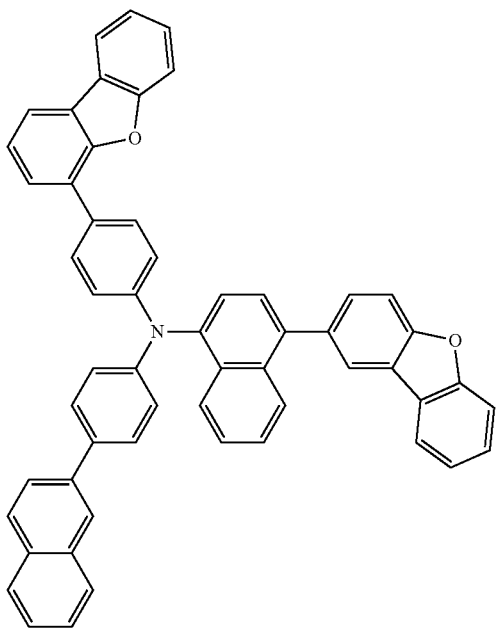

275
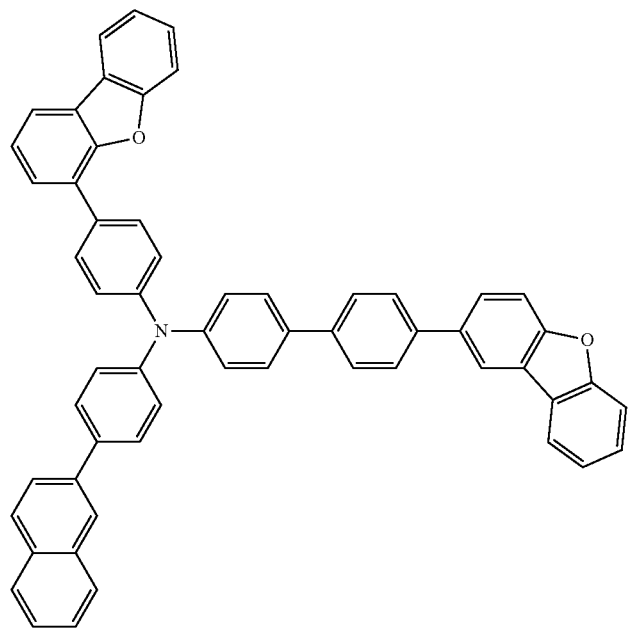
276
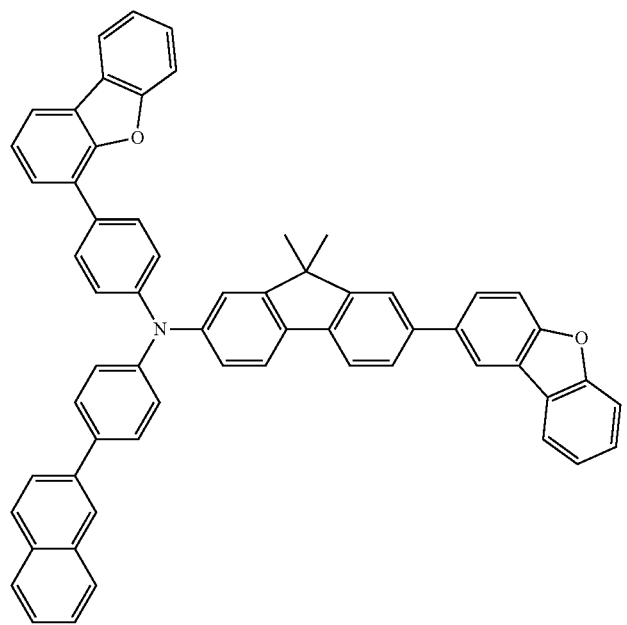
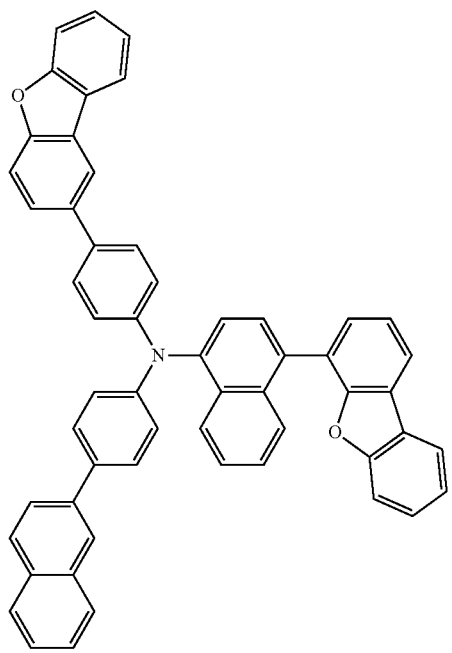

-continued

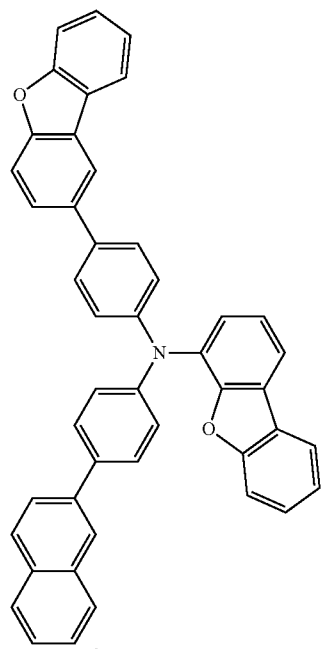
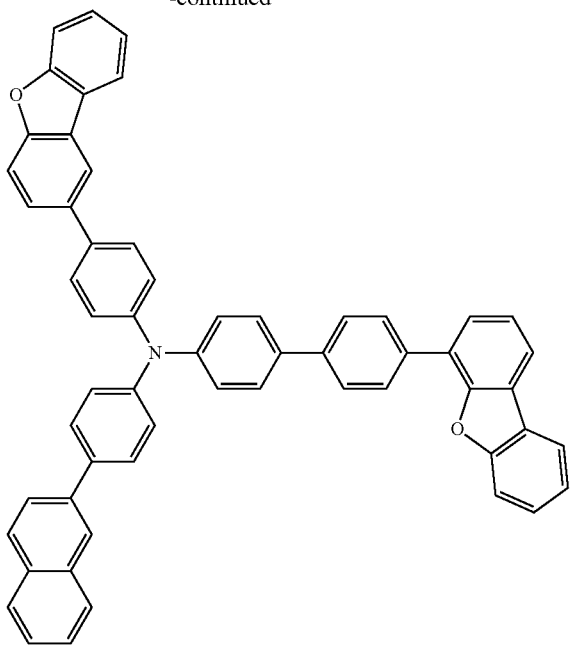
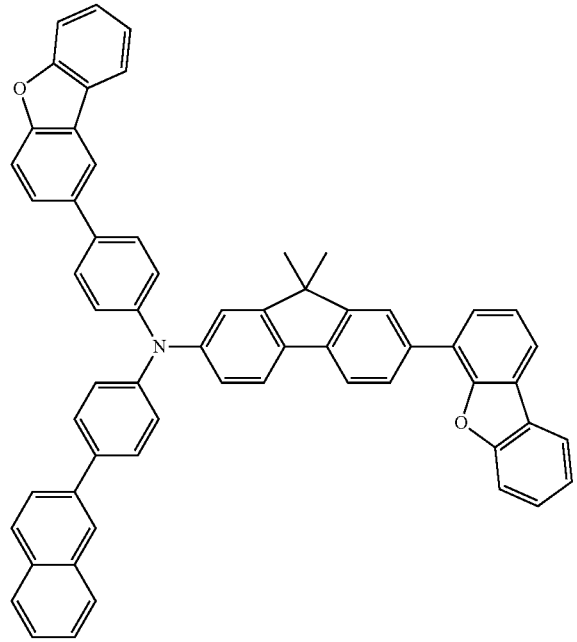

The aromatic amine derivative of the present invention hardly crystallizes, and is preferably used as a light emitting material for an organic EL device, in particular, as a hole transporting material for an organic EL device. An organic EL device using the aromatic amine derivative of the present invention not only provides high efficiency even at high temperatures but also has a long lifetime.

Next, a method of producing the aromatic amine derivative of the present invention is described.

The method of producing the aromatic amine derivative of the present invention is not particularly limited, and is, for example, as described below.

(Production Method 1)

The aromatic amine derivative of the present invention represented by the general formula (5) can be synthesized by, for example, any such reaction as described below.

(a) Synthesis of an Aromatic Amine Derivative in which all of $Ar^2$ to $Ar^4$ Each Represent the Substituent A or the Substituent B First, compounds that produce a structure represented by the general formula (1) [such as dibenzofuran-4-boronic acid and 4-iodobromobenzene] are caused to react with each other in the presence of a catalyst [such as tetrakis(triphenylphosphine)palladium(0)] in a solvent [such as toluene] and an aqueous solution of an alkaline compound [such as sodium carbonate] at 50 to 150° C. Thus, a halide is obtained. Further, the above-mentioned halide and a compound that produces an amino group [such as acetamide] are caused to react with each other in the presence of catalysts [a metal halide such as copper iodide and an amine such as N,N'-dimethylethylenediamine] and an alkaline substance [such as potassium carbonate] in a solvent [such as xylene] at 50 to 250° C. After that, the resultant is subjected to a reaction in the presence of an alkaline substance [such as potassium carbonate] and water in a solvent [such as xylene] at 50 to 250° C. Thus, an intermediate X is synthesized. The reactions are preferably performed under an atmosphere of an inert gas such as argon.

Separately, halides that produce a structure represented by the general formula (3) [such as carbazole and 4-iodobromobenzene] are caused to react with each other in the presence of catalysts [such as copper iodide (CuI) and an amine such as trans-1,2-cyclohexanediamine] in a solvent [such as 1,4-dioxane] and an alkaline compound [such as tripotassium phosphate] at 50 to 150° C. Thus, an intermediate Y is synthesized. The reaction is preferably performed under an atmosphere of an inert gas such as argon.

Next, the intermediate X and the intermediate Y are caused to react with each other in the presence of catalysts [such as t-butoxy sodium and tris(dibenzylideneacetone)dipalladium (0)] in a solvent [such as dry toluene] at 0 to 150° C. Thus, the aromatic amine derivative of the present invention can be synthesized. The reaction is preferably performed under an atmosphere of an inert gas such as argon.

After the completion of the reaction, the reaction product is cooled to room temperature, and then water is added to filtrate the product. The filtrate is extracted with a solvent such as toluene, and is then dried with a drying agent such as anhydrous magnesium sulfate. The dried product is desolvated under reduced pressure so as to be concentrated. The resultant coarse product is subjected to column purification, and is then recrystallized with a solvent such as toluene. The crystal is separated by filtration, and is then dried. Thus, the aromatic amine derivative of the present invention that has been purified is obtained.

In order that the general formula (1) and the general formula (2-1) may be introduced into the aromatic amine derivative represented by the general formula (5), upon synthesis of the above-mentioned intermediate Y, halides that produce a structure represented by the general formula (2-1) [such as 9-phenylcarbazole and iodine] are caused to react with each other in the presence of catalysts [such as periodic acid dihydrate, acetic acid, and sulfuric acid] in a solvent [such as water] at 50 to 100° C. so that the intermediate Y capable of introducing the general formula (2-1) may be synthesized. Next, the intermediate X and the intermediate Y are caused to reach with each other in the same manner as in the foregoing. Thus, the aromatic amine derivative of the present invention into which the general formula (1) and the general formula (2-1) have been introduced can be synthesized. The reactions are preferably performed under an atmosphere of an inert gas such as argon.

(b) Synthesis of an Aromatic Amine Derivative in which One of $Ar^2$ to $Ar^4$ has a Group Except the General Formula (1), (2-1), or (3)

In order that a substituted or unsubstituted aryl group having 6 to 50 ring carbon atoms except the general formula (1), (2-1), or (3) may be introduced into the aromatic amine derivative represented by the general formula (5), the introduction has only to be performed as described below. Upon synthesis of the intermediate X or at the time of the reaction between the intermediate X and the intermediate Y, a reacting weight ratio is controlled, and halides of substituted or unsubstituted aryl groups each having 6 to 50 ring carbon atoms except the general formula (1) and the general formula (3) [such as 4-bromo-p-terphenyl] are similarly subjected to reactions in sequence [for example, after acetamide and 4-(4-iodophenyl)-dibenzofuran have been caused to react with each other at 1:1, 1 equivalent of 4-bromo-p-terphenyl is loaded and caused to react with the reaction product, followed by the hydrolysis of the resultant, and as a result, the intermediate X into which the general formula (1-1) and the "aryl group except the general formulae (1-1), (1-2), and (2)" have been introduced is obtained].

A halide represented by the general formula (1), a halide represented by the general formula (3), and a halide of a substituted or unsubstituted aryl group having 6 to 50 ring carbon atoms except the general formula (1) and the general formula (3) can be arbitrarily introduced into the intermediate X. In addition, one or two aryl groups can be introduced, and further, an arbitrary combination of aryl groups can be introduced. A target product can be obtained by causing the amine compound (intermediate X) obtained as a result of the introduction and an arbitrary halide (intermediate Y) to react with each other. The order in which those halides are subjected to reactions and the manner in which the halides are combined can be determined in consideration of, for example, reactivity and the ease of purification.

Next, a method of producing the aromatic amine derivative represented by the general formula (6) is described.

(a) Synthesis of an Aromatic Amine Derivative in which all of $Ar^5$ to $Ar^8$ Each Have a Group Represented by the General Formula (1), (2-1), or (3)

An amine compound including the general formula (1) and the general formula (3) is synthesized as the intermediate X in the same manner as in the foregoing [for example, after acetamide and 4-(4-iodophenyl)-dibenzofuran have been caused to react with each other at 1:1, 1 equivalent of 9-(4-bromophenyl)carbazole is loaded and caused to react with the reaction product, followed by the hydrolysis of the resultant, and as a result, the intermediate X into which the general formula (1) and the general formula (3) have been introduced is obtained].

A dihalide [such as 4,4'-dibromobiphenyl] serving as a halide is used as the intermediate Y. The intermediate X and the intermediate Y are caused to react with each other at 0 to 150° C. in the same manner as in the foregoing. Thus, the aromatic amine derivative in which all of $Ar^5$ to $Ar^8$ in the general formula (6) are each represented by the general formula (1), (2-1), or (3) can be synthesized.

(b) Synthesis of an Aromatic Amine Derivative in which at Least One of $Ar^5$ to $Ar^8$ has a Group Except the General Formula (1), (2-1), or (3)

An amine compound including the general formula (1) and the general formula (3) is synthesized as the intermediate X in the same manner as in the foregoing [for example, after acetamide and 4-(4-iodophenyl)-dibenzofuran have been caused to react with each other at 1:1, 1 equivalent of 9-(4-bromophenyl)carbazole is loaded and caused to react with the reaction product, followed by the hydrolysis of the resultant, and as a result, the intermediate X into which the general formula (1) and the general formula (3) have been introduced is obtained].

An amino group-containing compound [such as 4-bromophenyl-diphenylamine] serving as a halide is used as the intermediate Y. The intermediate X and the intermediate Y are caused to react with each other at 0 to 150° C. in the same manner as in the foregoing. Thus, the aromatic amine derivative in which at least one of $Ar^5$ to $Ar^8$ in the general formula (6) is represented by a group except the general formula (1), (2-1), or (3) can be synthesized.

Next, a method of producing the aromatic amine derivative represented by the general formula (7) is described.

An amine compound including the general formula (1) is synthesized as the intermediate X in the same manner as in the foregoing [for example, after acetamide and 4-(4-iodophenyl)-dibenzofuran have been caused to react with each other at 1:1, the reaction product is hydrolyzed, and as a result, the intermediate X into which the general formula (1) has been introduced is obtained]. An amino group-containing compound serving as a halide is synthesized as the intermediate Y [for example, after aniline and carbazole have been caused to react with each other at 1:1, the reaction product and 4'-iodobromobiphenyl are further caused to react with each other at 1:1, and as a result, the intermediate Y into which the general formula (3) has been introduced is obtained]. The intermediate X and the intermediate Y are caused to react with each other at 0 to 150° C. in the same manner as in the foregoing. Thus, the aromatic amine derivative represented by the general formula (7) can be synthesized. The number and kinds of substituents of $Ar^{11}$ to $Ar^{15}$ can be changed by changing a starting material and a reaction intermediate. In addition, an aromatic amine derivative in which all of $Ar^{11}$ to $Ar^{15}$ each have a group represented by the general formula (1), (2-1), or (3) can be synthesized.

Next, a method of producing the aromatic amine derivative represented by the general formula (8) is described.

An amine compound including the general formula (1) is synthesized as the intermediate X in the same manner as in the foregoing [for example, after acetamide and 4-(4-iodophenyl)-dibenzofuran have been caused to react with each other at 1:1, the reaction product and 4,4'-diiodobiphenyl are caused to react with each other at 2:1, followed by the hydrolysis of the resultant, and as a result, the intermediate X as a diamine compound into which the general formula (1) has been introduced is obtained].

An amino group-containing compound serving as a halide is synthesized as the intermediate Y [for example, after aniline and carbazole have been caused to react with each other at 1:1, the reaction product and 4'-iodobromobenzene are further caused to react with each other at 1:1, and as a result, the intermediate Y into which the general formula (3) has been introduced is obtained]. The intermediate X and the intermediate Y are caused to react with each other at 0 to 150° C. in the same manner as in the foregoing. Thus, the aromatic amine derivative represented by the general formula (8) can be synthesized. The number and kinds of substituents of $Ar^{14}$ to $Ar^{19}$ can be changed by changing a starting material and a reaction intermediate. In addition, an aromatic amine derivative in which all of $Ar^{14}$ to $Ar^{19}$ each have a group represented by the general formula (1), (2-1), or (3) can be synthesized.

Next, a method of producing the aromatic amine derivative represented by the general formula (9) is described.

An amine compound including the general formula (1) is synthesized as the intermediate X in the same manner as in the foregoing [for example, after acetamide and 4-(4-iodophenyl)-dibenzofuran have been caused to react with each other at 1:1, 1 equivalent of 9-(4-bromo-phenyl)carbazole is loaded and caused to react with the reaction product, followed by the hydrolysis of the resultant, and as a result, the intermediate X into which the general formula (1) and the general formula (3) have been introduced is obtained].

An amino group-containing compound serving as a halide is used as the intermediate Y [such as commercially available tris(4-bromophenyl)amine]. The intermediate X and the intermediate Y are caused to react with each other at 0 to 150° C. in the same manner as in the foregoing. Thus, the aromatic amine derivative represented by the general formula (9) can be synthesized. The number and kinds of substituents of $Ar^{22}$ to $Ar^{27}$ can be changed by changing a starting material and a reaction intermediate. In addition, an aromatic amine derivative in which all of $Ar^{22}$ to $Ar^{27}$ each have a group represented by the general formula (1), (2-1), or (3) can be synthesized.

In addition, individual, similar synthesis methods described in known technologies (JP 2003-171366 A, WO 2006/114921 A1, WO 2006/073054 A1, WO 2007/125714 A1, and WO 2008/062636 A1) may each be employed for any such synthesis as described above.

(Production Method 2)

The aromatic amine derivative of the present invention represented by the general formula (5) can be synthesized by, for example, any such reaction as described below.

First, compounds that produce a structure represented by the general formula (1-2) [such as dibenzofuran-4-boronic acid and 4-iodobromobenzene] are caused to react with each other in the presence of a catalyst [such as tetrakis(triphenylphosphine)palladium(0)] in a solvent [such as toluene] and an aqueous solution of an alkaline compound [such as sodium carbonate] at 50 to 150° C. Thus, a halide is obtained. Further, the above-mentioned halide and a compound that produces an amino group [such as acetamide] are caused to react with each other in the presence of catalysts [a metal halide such as copper iodide and an amine such as N,N'-dimethylethylenediamine] and an alkaline substance [such as potassium carbonate] in a solvent [such as xylene] at 50 to 250° C. After that, the resultant is subjected to a reaction in the presence of an alkaline substance [such as potassium hydroxide] and water in a solvent [such as xylene] at 50 to 250° C. Thus, an intermediate X is synthesized. The reactions are preferably performed under an atmosphere of an inert gas such as argon.

Separately, halides that produce a structure represented by the general formula (1-1) [such as dibenzofuran-2-boronic acid and 4-iodobromobenzene] are caused to react with each other in the presence of a catalyst [such as tetrakis(triphenylphosphine)palladium(0)] in a solvent [such as toluene] and an aqueous solution of an alkaline compound [such as sodium carbonate] at 50 to 150° C. Thus, an intermediate Y is synthesized. The reaction is preferably performed under an atmosphere of an inert gas such as argon.

Next, the intermediate X and the intermediate Y are caused to react with each other in the presence of catalysts [such as t-butoxy sodium and tris(dibenzylideneacetone)dipalladium (0)] in a solvent [such as dry toluene] at 0 to 150° C. Thus, the aromatic amine derivative of the present invention can be synthesized. The reaction is preferably performed under an atmosphere of an inert gas such as argon.

After the completion of the reaction, the reaction product is cooled to room temperature, and then water is added to filtrate the product. The filtrate is extracted with a solvent such as toluene, and is then dried with a drying agent such as anhydrous magnesium sulfate. The dried product is desolvated under reduced pressure so as to be concentrated. The resultant coarse product is subjected to column purification, and is then recrystallized with a solvent such as toluene. The crystal is separated by filtration, and is then dried. Thus, the aromatic amine derivative of the present invention that has been purified is obtained.

Described above is a method of producing the aromatic amine derivative in which $Ar^2$ and $Ar^3$ are each represented by the general formula (1-2), and $Ar^4$ is represented by the general formula (1-1). It should be noted that an aromatic amine derivative in which $Ar^2$ is represented by the general formula (1-2), and $Ar^3$ and $Ar^4$ are each represented by the general formula (1-1) can be produced by a similar method. In this case, the derivative can be produced by synthesizing the intermediate X with the general formula (1-2), synthesizing the intermediate Y with the general formula (1-1), and causing the intermediate X and the intermediate Y to react with each other in the above-mentioned production.

In addition, similar synthesis can be performed even in the case where all of $Ar^2$ to $Ar^4$ represented by the general formula (1-2) and/or the general formula (1-1) are different from one another. In order that $Ar^2$ to $Ar^4$ that are different from one another may be introduced, the introduction has only to be performed as described below. Upon synthesis of the intermediate X or at the time of the reaction between the intermediate X and the intermediate Y, a reacting weight ratio is controlled, and a halide are similarly subjected to reactions in sequence [for example, after acetamide and 4-(4-bromophenyl)-dibenzofuran have been caused to react with each other at 1:1, 1 equivalent of 2-(4-bromophenyl)-dibenzofuran is loaded and caused to react with the reaction product, followed by the hydrolysis of the resultant, and as a result, the intermediate X into which the general formula (1-2) and the general formula (1-1) have been introduced is obtained]. After that, the intermediate X and the intermediate Y as a halide different from the substituents that have already been introduced [such as 4-(4-bromobiphenyl)-dibenzofuran] are caused to react with each other. Thus, the synthesis can be achieved.

A halide represented by the general formula (1-2) and a halide represented by the general formula (1-1) can be arbitrarily introduced into the intermediate X. A target product can be obtained by causing the amine compound (intermediate X) obtained as a result of the introduction and an arbitrary halide (intermediate Y) to react with each other. The order in which those halides are subjected to reactions and the manner in which the halides are combined can be determined in consideration of, for example, reactivity and the ease of purification.

Next, a method of producing the aromatic amine derivative represented by the general formula (6) is described.

An amine compound including the general formula (1-2) and the general formula (1-1) is synthesized as the intermediate X in the same manner as in the foregoing [for example, after acetamide and 4-(4-bromophenyl)-dibenzofuran have been caused to react with each other at 1:1, 1 equivalent of 2-(4-bromophenyl)-dibenzofuran is loaded and caused to react with the reaction product, followed by the hydrolysis of the resultant, and as a result, the intermediate X into which the general formula (1-2) and the general formula (1-1) have been introduced is obtained].

A dihalide [such as 4,4'-dibromobiphenyl] serving as a halide is used as the intermediate Y. The intermediate X and the intermediate Y are caused to react with each other at 0 to 150° C. in the same manner as in the foregoing. Thus, the aromatic amine derivative in which all of $Ar^7$ to $Ar^{10}$ in the general formula (6) are each represented by the general formula (1-2) or (1-1) can be synthesized.

Alternatively, an amino group-containing compound [such as 4-bromophenyl-diphenylamine] serving as a halide is used as the intermediate Y, and the intermediate X and the intermediate Y are caused to react with each other at 0 to 150° C. in the same manner as in the foregoing. Thus, the aromatic amine derivative in which at least one of $Ar^7$ to $Ar^{10}$ in the general formula (6) is represented by a group except the general formula (1-2) or (1-1) can be synthesized.

Next, a method of producing the aromatic amine derivative represented by the general formula (7) is described.

An amine compound (such as commercially available aniline) is used as the intermediate X.

In addition, a halogen compound containing an amine compound including the general formula (1-2) and the general formula (1-1) is synthesized as the intermediate Y in the same manner as in the foregoing [for example, after acetamide and 4-(4-bromophenyl)-dibenzofuran have been caused to react with each other at 1:1, 1 equivalent of 2-(4-bromophenyl)-dibenzofuran is loaded and caused to react with the reaction product, followed by the hydrolysis of the resultant, and as a result, the amine compound into which the general formula (1-2) and the general formula (1-1) have been introduced is obtained. Further, the amine compound and 4'-iodobromobiphenyl are caused to react with each other at 1:1, and as a result, the intermediate Y into which the general formula (1-2) and the general formula (1-1) have been introduced is obtained]. The intermediate X and the intermediate Y are caused to react with each other at 0 to 150° C. in the same manner as in the foregoing. Thus, the aromatic amine derivative represented by the general formula (7) can be synthesized. The number and kinds of substituents of $Ar^9$ to $Ar^{13}$ can be changed by changing a starting material and a reaction intermediate. In addition, an aromatic amine derivative in which all of $Ar^9$ to $Ar^{13}$ each have a group represented by the general formula (1-2) or (1-1) can be synthesized.

Next, a method of producing the aromatic amine derivative represented by the general formula (8) is described.

An amine compound (such as commercially available N,N'-diphenylbenzizine) is used as the intermediate X.

In addition, a halogen compound containing an amine compound including the general formula (1-2) and the general formula (1-1) is synthesized as the intermediate Y in the same manner as in the foregoing [for example, after acetamide and 4-(4-bromophenyl)-dibenzofuran have been caused to react with each other at 1:1, 1 equivalent of 2-(4-bromophenyl)-dibenzofuran is loaded and caused to react with the reaction product, followed by the hydrolysis of the resultant, and as a result, the amine compound into which the general formula (1-1-3) and the general formula (1-1-1) have been introduced is obtained. Further, the amine compound and 4'-iodobromobenzene are caused to react with each other at 1:1, and as a result, the intermediate Y into which the general formula (1-2) and the general formula (1-1) have been introduced is obtained]. The intermediate X and the intermediate Y are caused to react with each other at 0 to 150° C. in the same manner as in the foregoing. Thus, the aromatic amine derivative represented by the general formula (8) can be synthesized. The number and kinds of substituents of $Ar^{14}$ to $Ar^{19}$ can be changed by changing a starting material and a reaction intermediate. In addition, an aromatic amine derivative in which all of $Ar^{14}$ to $Ar^{19}$ each have a group represented by the general formula (1-2) or (1-1) can be synthesized.

Next, a method of producing the aromatic amine derivative represented by the general formula (9) is described.

An amine compound including the general formula (1-2) and the general formula (1-1) is synthesized as the intermediate X in the same manner as in the foregoing [for example, after acetamide and 4-(4-bromophenyl)-dibenzofuran have been caused to react with each other at 1:1, 1 equivalent of 2-(4-bromophenyl)-dibenzofuran is loaded and caused to react with the reaction product, followed by the hydrolysis of the resultant, and as a result, the intermediate X into which the general formula (1-2) and the general formula (1-1) have been introduced is obtained].

An amino group-containing compound serving as a halide is used as the intermediate Y [such as commercially available tris(4-bromophenyl)amine]. The intermediate X and the intermediate Y are caused to react with each other at 0 to 150° C. in the same manner as in the foregoing. Thus, the aromatic amine derivative represented by the general formula (9) can be synthesized. The number and kinds of substituents of $Ar^{20}$ to $Ar^{25}$ can be changed by changing a starting material and a reaction intermediate. In addition, an aromatic amine derivative in which all of $Ar^{20}$ to $Ar^{25}$ each have a group represented by the general formula (1-2) or (1-1) can be synthesized.

In addition, individual, similar synthesis methods described in known technologies (JP 2003-171366 A, WO 2006/114921 A1, WO 2006/073054 A1, WO 2007/125714 A1, and WO 2008/062636 A1) may each be employed for any such synthesis as described above.

Hereinafter, the structure of the organic EL device of the present invention is described.

Typical examples of the structure of the organic EL device of the present invention may include the following structures:

(1) anode/light emitting layer/cathode;
(2) anode/hole injecting layer/light emitting layer/cathode;
(3) anode/light emitting layer/electron injecting layer/cathode;
(4) anode/hole injecting layer/light emitting layer/electron injecting layer/cathode;
(5) anode/organic semiconductor layer/light emitting layer/cathode;
(6) anode/organic semiconductor layer/electron barrier layer/light emitting layer/cathode;
(7) anode/organic semiconductor layer/light emitting layer/adhesion improving layer/cathode;
(8) anode/hole injecting layer/hole transporting layer/light emitting layer/electron injecting layer/cathode;
(9) anode/insulating layer/light emitting layer/insulating layer/cathode;
(10) anode/inorganic semiconductor layer/insulating layer/light emitting layer/insulating layer/cathode;
(11) anode/organic semiconductor layer/insulating layer/light emitting layer/insulating layer/cathode;
(12) anode/insulating layer/hole injecting layer/hole transporting layer/light emitting layer/insulating layer/cathode; and
(13) anode/insulating layer/hole injecting layer/hole transporting layer/light emitting layer/electron injecting layer/cathode.

Of those, the structure (8) is preferably used in ordinary cases. However, the structure is not limited to the foregoing.

In addition, in the organic EL device of the present invention, the aromatic amine derivative represented by the general formula (1) of the present invention, which may be used in any layer of the above-mentioned organic thin film layer, is preferably incorporated into a hole injecting layer or a hole transporting layer. The content of the aromatic amine derivative represented by the general formula (1) is selected from 30 to 100 mol %.

The aromatic amine derivative of the present invention is preferably used as a material for a hole injecting layer or hole transporting layer.

The hole injecting layer and the hole transporting layer are layers which help injection of holes into the light emitting layer and transport the holes to the light emitting region. The layer exhibits a great mobility of holes and, in general, has an ionization energy as small as 5.5 eV or less.

For such hole injecting layers and hole transporting layers, a material which transports holes to the light emitting layer under an electric field of a smaller strength is preferred. Further, a material which exhibits, for example, a mobility of holes of at least $10^{-4}$ cm$^2$/V·s or more under application of an electric field of $10^4$ to $10^6$ V/cm is preferred.

The aromatic amine derivative of the present invention is preferred as a hole transporting material because the derivative has small ionization energy and a large hole mobility. In addition, the aromatic amine derivative of the present invention is preferred as a hole injecting material because of the following reasons. The derivative contains a polar group in any one of its molecules, and hence has good adhesiveness with the anode and is hardly affected by, for example, a condition under which the substrate is washed. The organic EL device using the aromatic amine derivative of the present invention is expected to have a lengthened lifetime by virtue of those factors.

The hole injecting layer or the hole transporting layer can be obtained by forming a thin film from the aromatic amine derivative of the present invention in accordance with a known process such as a vacuum vapor deposition process, a spin coating process, a casting process, and an LB process. The thickness of the hole injecting layer or the hole transporting layer is not particularly limited. In general, the thickness is 5 nm to 5 μm.

The hole injecting layer or the hole transporting layer may be formed of a single layer containing one or two or more kinds of the above-mentioned aromatic amine derivatives, or may be a laminate formed of hole injecting layers or hole transporting layers containing different kinds of compounds as long as the aromatic amine derivative of the present invention is incorporated in the hole transporting zone.

Further, an organic semiconductor layer is a layer for helping the injection of holes and electrons into the light emitting layer. As the organic semiconductor layer, a layer having a conductivity of $10^{-10}$ S/cm or more is preferred. As the material for the organic semiconductor layer, the following can be used: oligomers containing thiophene; conductive oligomers such as oligomers containing arylamine; conductive dendrimers such as dendrimers containing arylamine; and the like.

The organic EL device is generally prepared on a substrate having light-transmissive property (light-transmissive substrate). The light-transmissive substrate is the substrate which supports the organic EL device. It is preferred that the light-transmissive substrate have transmissive property which is a transmittance of light of 50% or more in the visible light region where the wavelength is 400 to 700 nm and still preferably be flat and smooth.

Preferred examples of the light-transmissive substrate include glass plates and synthetic resin plates. Examples of the glass plate include plates formed of soda-lime glass, glass containing barium and strontium, lead glass, aluminosilicate glass, borosilicate glass, barium borosilicate glass, and quartz. Further, examples of the synthetic resin plate include plates formed of a polycarbonate resin, an acrylic resin, a polyethylene terephthalate resin, a polyether sulfide resin, and a polysulfone resin.

The anode has the function of injecting holes to the hole transporting layer or the light emitting layer. It is effective that the anode has a work function of 4.5 eV or more. A material for the anode used in the present invention is specifically exemplified by indium tin oxide (ITO), a mixture of indium oxide and zinc oxide (IZO), a mixture of ITO and cerium oxide (ITCO), a mixture of IZO and cerium oxide (IZCO), a mixture of indium oxide and cerium oxide (ICO), a mixture of zinc oxide and aluminum oxide (AZO), tin oxide (NESA), gold, silver, platinum, and copper.

The anode may be obtained by forming a thin film with one of the materials for electrodes by, for example, a vapor deposition process or a sputtering process.

As described above, when the light emitted from the light emitting layer is obtained through the anode, it is preferred that the anode have a transmittance of more than 10% with respect to the emitted light. It is also preferred that the sheet resistance of the anode be several hundred Ω/cm or less. The thickness of the anode is, in general, selected in the range of 10 nm to 1 µm, preferably in the range of 10 to 200 nm although the preferred range may be different depending on the used material.

As the cathode, a material such as a metal, an alloy, an electroconductive compound, or a mixture of those materials, which have a small work function (4 eV or less) and are used as electrode materials, is used. Specific examples of the electrode material include sodium, sodium-potassium alloys, magnesium, lithium, cesium, magnesium-silver alloys, aluminum/aluminum oxide, $Al/Li_2O$, Al/LiO, Al/LiF, aluminum-lithium alloys, indium, and rare earth metals.

The cathode can be obtained by forming a thin film of the electrode material described above in accordance with a process such as the vapor deposition process or the sputtering process.

Here, when the light emitted from the light emitting layer is obtained through the cathode, it is preferred that the cathode have a transmittance of more than 10% with respect to the emitted light. It is also preferred that the sheet resistivity of the cathode be several hundred $\Omega/cm$ or less. The thickness of the cathode is generally 10 nm to 1 µm, preferably 50 to 200 nm.

In general, defects in pixels tend to be formed inorganic EL devices due to leak and short circuit because an electric field is applied to ultra-thin films. In order to prevent the formation of the defects, an insulating layer made of a thin film layer having insulating property may be inserted between the pair of electrodes. Examples of the material used for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. Mixtures of two or more kinds of the compounds and laminates formed of layers of two or more kinds of the compounds may also be used as the insulating layer.

In the organic EL device of the present invention, the light emitting layer has the following functions.

(i) The injecting function: the function of injecting holes from the anode or the hole injecting layer and injecting electrons from the cathode or the electron injecting layer when an electric field is applied.

(ii) The transporting function: the function of transporting injected charges (i.e., electrons and holes) by the force of the electric field.

(iii) The light emitting function: the function of providing the field for recombination of electrons and holes and leading the recombination to the emission of light.

Examples of the process of forming the light emitting layer include a known process such as a vapor deposition process, a spin coating process, and an LB process. The light emitting layer is particularly preferably a molecular deposit film. The term "molecular deposit film" as used here refers to a thin film formed by the deposition of a material compound in a vapor phase state, or a film formed by the solidification of a material compound in a solution state or a liquid phase state. The molecular deposit film can be typically distinguished from a thin film formed by the LB process (molecular accumulation film) on the basis of differences between the films in aggregation structure and higher order structure, and functional differences between the films caused by the foregoing differences.

In addition, the light emitting layer can also be formed by dissolving a binder such as a resin and a material compound into a solvent to thereby prepare a solution, and forming a thin film with the solution by the spin coating process or the like.

In the present invention, a light emitting material formed of a pyrene-based derivative and an amine compound, or any other known metal complex compound may be incorporated into the light emitting layer.

The metal complex compound is preferably a metal complex compound containing at least one metal selected from Ir, Ru, Pd, Pt, Os, and Re. The ligands of the complex preferably have at least one skeleton selected from a phenylpyridine skeleton, a bipyridyl skeleton, and a phenanthroline skeleton.

Specific examples of such metal complex compound include tris(2-phenylpyridine)iridium, tris(2-phenylpyridine)ruthenium, tris(2-phenylpyridine)palladium, bis(2-phenylpyridine)platinum, tris(2-phenylpyridine)osmium, tris(2-phenylpyridine)rhenium, octaethyl platinum porphyrin, octaphenyl platinum porphyrin, octaethyl palladium porphyrin, and octaphenyl palladium porphyrin. However, the metal complex compound is not limited thereto. An appropriate metal complex compound is selected in terms of a requested luminescent color, a device performance, and a relationship with a host compound.

In addition, a phosphorescent dopant or a fluorescent dopant may be used in the light emitting layer of the organic EL device of the present invention.

The phosphorescent dopant is a compound capable of emitting light from a triplet exciton. The dopant, which is not particularly limited as long as light is emitted from a triplet exciton, is preferably a metal complex containing at least one metal selected from the group consisting of Ir, Ru, Pd, Pt, Os, and Re, more preferably a porphyrin metal complex or an orthometalated metal complex. A porphyrin platinum complex is preferred as the porphyrin metal complex. One kind of phosphorescent dopant may be used alone, or two or more kinds of phosphorescent dopants may be used in combination.

There are various ligands which can be used for forming an orthometalated metal complex. Preferred examples of the ligands include 2-phenylpyridine derivatives, 7,8-benzoquinoline derivatives, 2-(2-thienyl)pyridine derivatives, 2-(1-naphthyl)pyridine derivatives, and 2-phenylquinoline derivatives. Each of those derivatives may have a substituent as required. A fluorinated compound or the above-mentioned derivative having a trifluoromethyl group is particularly preferred as a blue-based dopant. The metal complex may further include a ligand other than the above-mentioned ligands such as acetylacetonato or picric acid as an auxiliary ligand.

The content of the phosphorescent dopant in the light emitting layer is not particularly limited, and can be appropriately selected in accordance with the purpose. The content is, for example, 0.1 to 70 mass %, more preferably 1 to 30 mass %. When the content of the phosphorescent dopant is less than 0.1 mass %, the intensity of emitted light is weak, and an effect of the incorporation of the compound is not sufficiently exerted. When the content exceeds 70 mass %, a phenomenon called concentration quenching becomes remarkable, and device performance reduces. Further, the light emitting layer may contain a hole transporting material, an electron transporting material, and a polymer binder as required.

Further, the light emitting layer has a thickness of preferably 5 to 50 nm, more preferably 7 to 50 nm, most preferably 10 to 50 nm. When the thickness is less than 5 nm, the light emitting layer becomes difficult to form, and chromaticity may become difficult to adjust. When the thickness exceeds 50 nm, the voltage at which the device is driven may increase.

The fluorescent dopant is preferably a compound selected from, for example, an amine-based compound, an aromatic compound, a chelate complex such as a tris(8-quinolinolato) aluminum complex, a coumarin derivative, a tetraphenylbutadiene derivative, a bisstyrylarylene derivative, and an oxadiazole derivative in accordance with a requested luminescent color. An arylamine compound and an aryldiamine compound are particularly preferred examples of such compound; out of those compounds, a styrylamine compound, a styryldiamine compound, an aromatic amine compound, or an aromatic diamine compound is more preferred, and a fused polycyclic amine derivative is still more preferred. One kind of those fluorescent dopants may be used alone, or two or more kinds thereof may be used in combination.

The organic EL device of the present invention preferably contains at least one of a styrylamine compound and an arylamine as the fluorescent dopant. A compound represented by the following general formula (50) is preferably used as at least one of the styrylamine compound and the arylamine.

[Chem. 45]

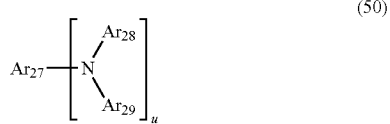

(50)

In the general formula (50), $Ar_{27}$ to $Ar_{29}$ each represent a substituted or unsubstituted aromatic group having 6 to 40 ring carbon atoms, and u represents an integer of 1 to 4, in particular, u preferably represents an integer of 1 or 2. One of $Ar_{27}$ to $Ar_{29}$ may represent a group containing a styryl group. When one of $Ar_{27}$ and $Ar_{28}$ has a styryl group, at least one of $Ar_{28}$ and $Ar_{29}$ is preferably substituted with a styryl group.

Here, examples of the aromatic group having 6 to 40 ring carbon atoms include a phenyl group, a naphthyl group, an anthranyl group, a phenanthryl group, a pyrenyl group, a coronyl group, a biphenyl group, a terphenyl group, a pyrrolyl group, a furanyl group, a thiophenyl group, a benzothiophenyl group, an oxadiazolyl group, a diphenylanthranyl group, an indolyl group, a carbazolyl group, a pyridyl group, a benzoquinolyl group, a fluoranthenyl group, an acenaphthofluoranthenyl group, a stilbene group, a perylenyl group, a chrysenyl group, a picenyl group, a triphenylenyl group, a rubicenyl group, a benzoanthracenyl group, a phenylanthracenyl group, a bisanthracenyl group, and arylene groups represented by the following general formulae (C) and (D). Of those, preferred are a naphthyl group, an anthranyl group, a chrysenyl group, a pyrenyl group, and an arylene group represented by the general formula (D).

[Chem. 46]

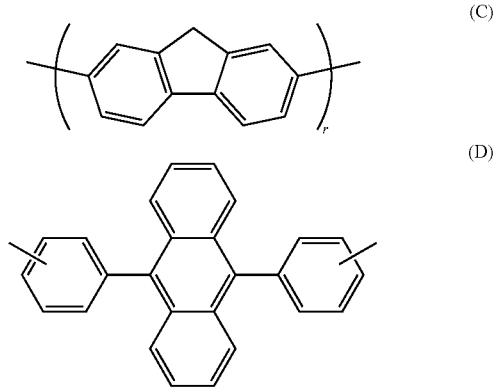

In the general formula (C), r represents an integer of 1 to 3.

It should be noted that preferred examples of the substituent which is substituted for the aryl group and arylene group include an alkyl group having 1 to 6 carbon atoms (such as an ethyl group, a methyl group, an i-propyl group, an n-propyl group, an s-butyl group, a t-butyl group, a pentyl group, a hexyl group, a cyclopentyl group, or a cyclohexyl group), an alkoxy group having 1 to 6 carbon atoms (such as an ethoxy group, a methoxy group, an i-propoxy group, an n-propoxy group, an s-butoxy group, a t-butoxy group, a pentoxy group, a hexyloxy group, a cyclopentoxy group, or a cyclohexyloxy group), an aryl group having 5 to 40 carbon atoms, an amino group substituted by an aryl group having 5 to 40 carbon atoms, an ester group containing an aryl group having 5 to 40 carbon atoms, an ester group containing an alkyl group having 1 to 6 carbon atoms, a cyano group, a nitro group, and a halogen atom.

The light emitting material contained in the light emitting layer is not particularly limited, and examples of the host materials include polycyclic aromatic compounds such as an anthracene compound, a phenanthrene compound, a fluoranthene compound, a tetracene compound, a triphenylene compound, a chrysene compound, a pyrene compound, a coronene compound, a perylene compound, a phthaloperylene compound, a naphthaloperylene compound, a naphthacene compound, and a pentacene compound, oxadiazole, bisbenzoxazoline, bisstyryl, cyclopentadiene, a quinoline metal complex, a tris(8-hydroxyquinolinato)aluminum complex, a tris(4-methyl-8-quinolinato)aluminum complex, a tris(5-phenyl-8-quinolinato)aluminum complex, an aminoquinoline metal complex, a benzoquinoline metal complex, tri-(p-terphenyl-4-yl)amine, a 1-aryl-2,5-di(2-thienyl)pyrrole derivative, pyran, quinacridone, rubrene, a distyrylbenzene derivative, a distyrylarylene derivative, a porphyrin derivative, a stilbene derivative, a pyrazoline derivative, a coumarin-based dye, a pyran-based dye, a phthalocyanine-based dye, a naphthalocyanine-based dye, a croconium-based dye, a squalium-based dye, an oxobenzanthracene-based dye, a fluorescein-based dye, a rhodamine-based dye, a pyrylium-based dye, a perylene-based dye, a stilbene-based dye, a polythiophene-based dye, a rare-earth complex-based fluorescent substance, a rare-earth-based phosphorescent complex (such as an Ir complex), and polymer materials such as conductive polymers including polyvinylcarbazole, polysilane, and polyethylenedioxidethiophene (PEDOT). Those compounds may be used alone, or a mixture of two or more kinds thereof may be used.

As the host material to be used in combination with the compounds of the present invention, compounds represented by the following formulae (11) to (17) are preferred.

An anthracene derivative represented by the following general formula (51).

[Chem. 47]

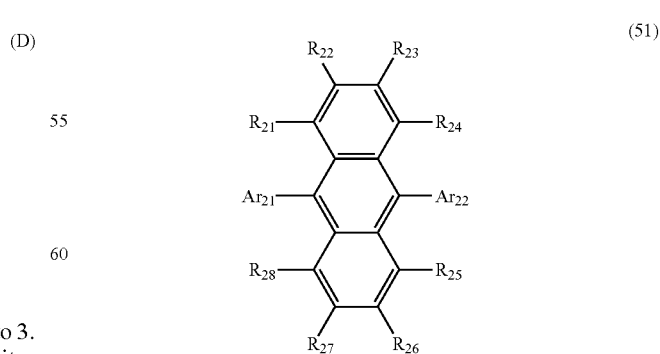

(51)

In the general formula (51), $A_{21}$ and $A_{22}$ each independently represent a substituted or unsubstituted aromatic cyclic group having 6 to 60 carbon atoms, and $R_{21}$ to $R_{28}$ each independently represent a hydrogen atom, a substituted or unsubstituted aromatic cyclic group having 6 to 50 carbon atoms, a substituted or unsubstituted aromatic heterocyclic group having 5 to 50 atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 atoms, a substituted or unsubstituted arylthio group having 5 to 50 atoms, a substituted or unsubstituted alkoxycarbonyl group having 1 to 50 carbon atoms, a substituted or unsubstituted silyl group, a carboxyl group, a halogen atom, a cyano group, a nitro group, or a hydroxy group.

A pyrene derivative represented by the following general formula (52).

[Chem. 48]

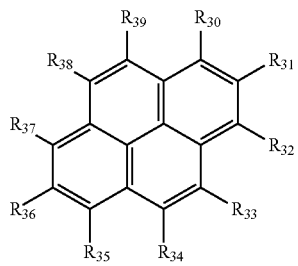

(52)

In the general formula (52), $R_{30}$ to $R_{39}$ each independently represent a hydrogen atom, a substituted or unsubstituted aromatic cyclic group having 6 to 50 carbon atoms, a substituted or unsubstituted aromatic heterocyclic group having 5 to 50 atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 atoms, a substituted or unsubstituted arylthio group having 5 to 50 atoms, a substituted or unsubstituted alkoxycarbonyl group having 1 to 50 carbon atoms, a substituted or unsubstituted silyl group, a carboxyl group, a halogen atom, a cyano group, a nitro group, or a hydroxy group.

An anthracene derivative represented by the following general formula (53).

[Chem. 49]

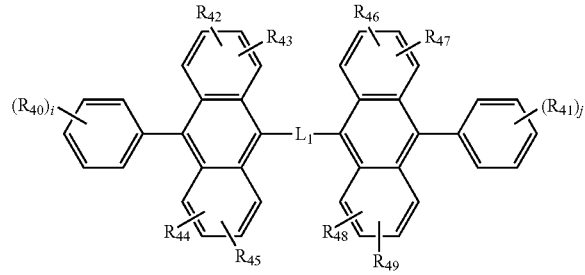

(53)

In the general formula (53), $R_{40}$ to $R_{49}$ each independently represent a hydrogen atom, an alkyl group, a cycloalkyl group, an aryl group which may be substituted, an alkoxyl group, an aryloxy group, an alkylamino group, an alkenyl group, an arylamino group, or a heterocyclic group which may be substituted.

i and j each represent an integer of 1 to 5, and, when i or j represents 2 or more, and $R_{40}$'s or $R_{41}$'s may be identical to or different from each other. Further, $R_{40}$'s or $R_{41}$'s may be bonded to each other to form a ring, and $R_{42}$ and $R_{43}$, $R_{44}$ and $R_{45}$, $R_{46}$ and $R_{47}$, or $R_{48}$ and $R_{49}$ may be bonded to each other to form a ring.

$L_1$ represents a single bond, —O—, —S—, —N(R)— (R represents an alkyl group or an aryl group which may be substituted), an alkylene group, or an arylene group.

An anthracene derivative represented by the following general formula (54).

[Chem. 50]

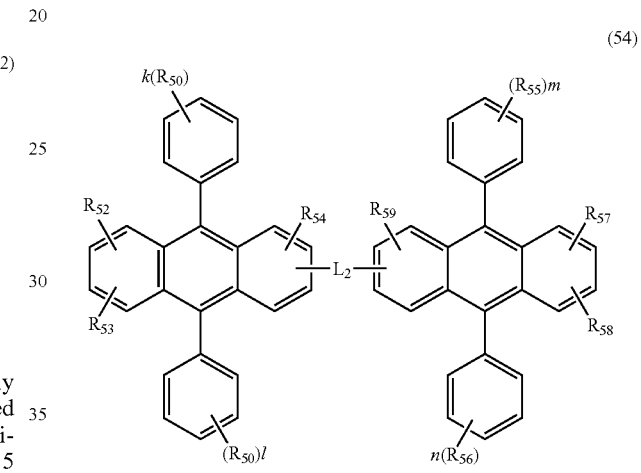

(54)

In the general formula (54), $R_{50}$ to $R_{59}$ each independently represent a hydrogen atom, an alkyl group, a cycloalkyl group, an aryl group, an alkoxyl group, an aryloxy group, an alkylamino group, an arylamino group, or a heterocyclic group which may be substituted.

k, l, m, and n each represent an integer of 1 to 5, and, when any one of k, l, m, and n represents 2 or more, $R_{50}$'s, $R_{51}$'s, $R_{55}$'s, or $R_{56}$'s may be identical to or different from each other. Further, $R_{52}$'s, $R_{53}$'s, $R_{54}$'s, or $R_{55}$'s may be bonded to each other to form a ring, and $R_{52}$ and $R_{53}$ or $R_{57}$ and $R_{58}$ may be bonded to each other to form a ring.

$L_2$ represents a single bond, —O—, —S—, —N(R)— (R represents an alkyl group or an aryl group which may be substituted), an alkylene group, or an arylene group.

A spirofluorene derivative represented by the following general formula (55).

[Chem. 51]

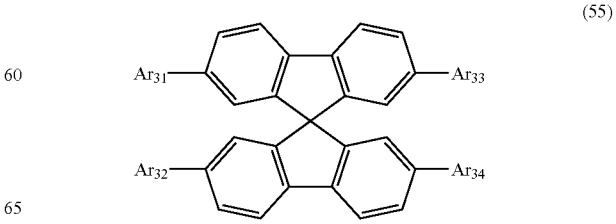

(55)

In the general formula (55), $A_{31}$ to $A_{34}$ each independently represent a substituted or unsubstituted biphenylyl group, or a substituted or unsubstituted naphthyl group.

A compound represented by the following general formula (56).

[Chem. 52]

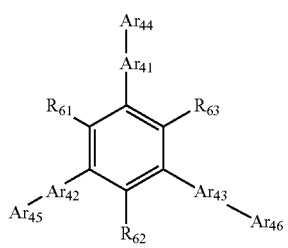

(56)

In the general formula (56), $Ar_{41}$ to $Ar_{43}$ each independently represent a substituted or unsubstituted arylene group having 6 to 60 carbon atoms, and $Ar_{44}$ to $Ar_{46}$ each independently represent a hydrogen atom, or a substituted or unsubstituted aryl group having 6 to 60 carbon atoms.

$R_{61}$ to $R_{63}$ each independently represent a hydrogen atom, an alkyl group having 1 to 6 carbon atoms, a cycloalkyl group having 3 to 6 carbon atoms, an alkoxyl group having 1 to 6 carbon atoms, an aryloxy group having 5 to 18 carbon atoms, an aralkyloxy group having 7 to 18 carbon atoms, an aryl amino group having 5 to 16 carbon atoms, a nitro group, a cyano group, an ester group having 1 to 6 carbon atoms, or a halogen atom.

A fluorene compound represented by the following general formula (57).

[Chem. 53]

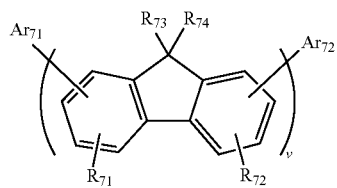

(57)

In the general formula (57), $R_{73}$ and $R_{74}$ each represent a hydrogen atom, a substituted or unsubstituted alkyl group, a substituted or unsubstituted aralkyl group, a substituted or unsubstituted aryl group, a substituted or unsubstituted heterocyclic group, a substituted amino group, a cyano group, or a halogen atom. $R_{71}$'s or $R_{72}$'s bonded to different fluorene groups may be identical to or different from each other, and $R_{71}$ and $R_{72}$ bonded to the same fluorene group may be identical to or different from each other.

$R_{93}$ and $R_{94}$ each represent a hydrogen atom, a substituted or unsubstituted alkyl group, a substituted or unsubstituted aralkyl group, a substituted or unsubstituted aryl group, or a substituted or unsubstituted heterocyclic group. $R_{73}$'s or $R_{74}$'s bonded to different fluorene groups may be identical to or different from each other, and $R_{73}$ and $R_{74}$ bonded to the same fluorene group may be identical to or different from each other.

$Ar_{71}$ and $Ar_{72}$ each represent a substituted or unsubstituted fused polycyclic aromatic group having three or more benzene rings in total, or a substituted or unsubstituted fused polycyclic heterocyclic group that has three or more rings each of which is a benzene ring or a heterocyclic ring in total and that is bonded to a fluorene group by carbon. $Ar_{71}$ and $Ar_{72}$ may be identical to or different from each other. v represents an integer of 1 to 10.

Of the above-mentioned host materials, an anthracene derivative is preferred, a monoanthracene derivative is more preferred, and an asymmetric anthracene is particularly preferred.

A host formed of a compound containing a carbazole ring and suitable for phosphorescence is a compound having a function of causing a phosphorescent compound to emit light as a result of the occurrence of energy transfer from the excited state of the host to the phosphorescent compound. A host compound is not particularly limited as long as it is a compound capable of transferring exciton energy to a phosphorescent compound, and can be appropriately selected in accordance with a purpose. The host compound may have, for example, an arbitrary heterocyclic ring in addition to a carbazole ring.

Specific examples of such host compound include a carbazole derivative, a triazole derivative, an oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic dimethylidene-based compound, a porphyrin-based compound, an anthraquinodimethane derivative, an anthrone derivative, a diphenylquinone derivative, a thiopyran dioxide derivative, a carbodiimide derivative, a fluorenylidenemethane derivative, a distyrylpyrazine derivative, a heterocyclic tetracarboxylic anhydride such as naphthaleneperylene, a phthalocyanine derivative, various metal complexes typified by a metal complex of an 8-quinolinol derivative and a metal complex having metal phthalocyanine, benzoxazole, or benzothiazole as a ligand, and high molecular weight compounds such as a polysilane-based compound, a poly(N-vinylcarbazole) derivative, an aniline-based copolymer, a conductive high molecular weight oligomer such as a thiophene oligomer or polythiophene, a polythiophene derivative, a polyphenylene derivative, a polyphenylene vinylene derivative, and a polyfluorene derivative. One kind of the host compounds may be used alone, or two or more kinds thereof may be used in combination.

Specific examples of the compounds include the following compounds.

[Chem. 54]

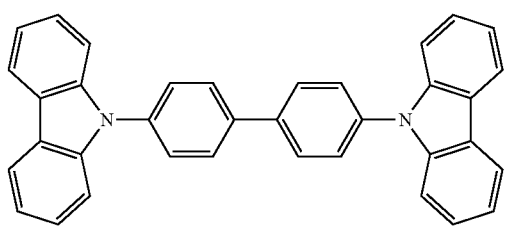

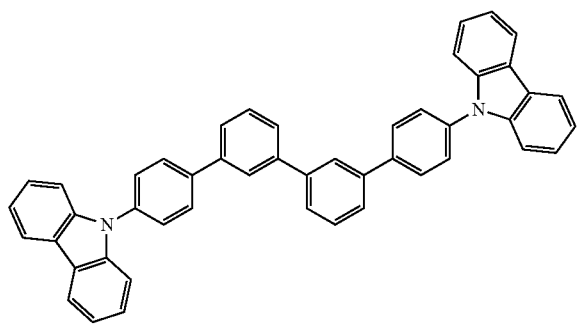

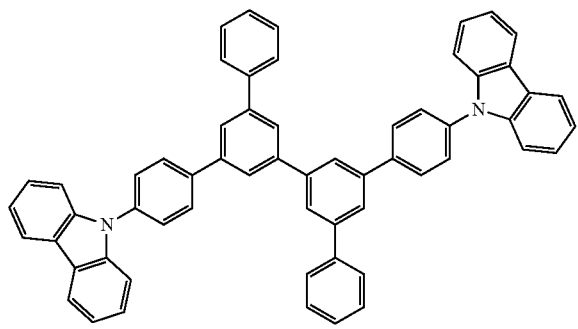

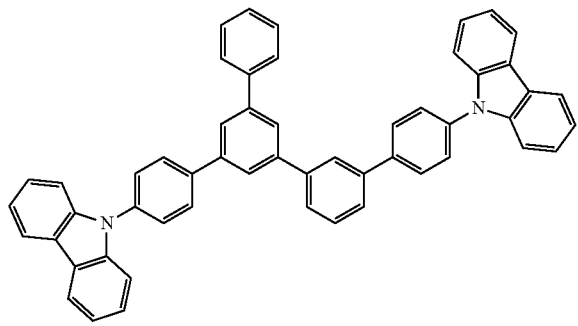

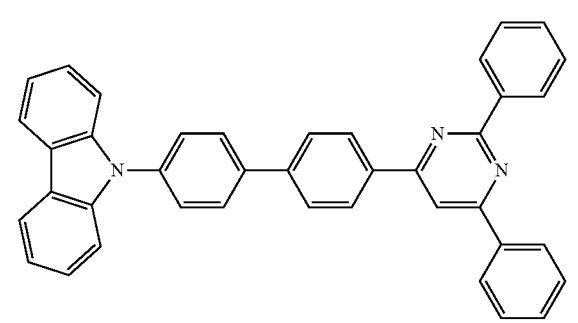

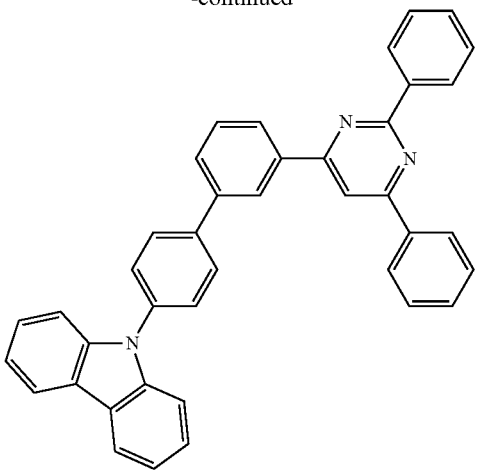

Next, each of the electron injecting layer and the electron transporting layer is a layer which helps injection of electrons into the light emitting layer, transports the electrons to the light emitting region, and exhibits a great mobility of electrons. Further, the adhesion improving layer is an electron injecting layer including a material exhibiting particularly improved adhesion with the cathode.

In addition, it is known that, in an organic EL device, emitted light is reflected by an electrode (cathode in this case), and hence emitted light directly extracted from an anode and emitted light extracted via the reflection by the electrode interfere with each other. The thickness of an electron transporting layer is appropriately selected from the range of several nanometers to several micrometers in order that the interference effect may be effectively utilized. In particular, when the thickness of the electron transporting layer is large, an electron mobility is preferably at least $10^{-6}$ cm²/V·s or more upon application of an electric field of $10^4$ to $10^6$ V/cm in order to avoid an increase in voltage.

A metal complex of 8-hydroxyquinoline or of a derivative of 8-hydroxyquinoline, or an oxadiazole derivative is suitable as a material to be used in an electron injecting layer. Specific examples of the above-mentioned metal complex of 8-hydroxyquinoline or of the derivative of 8-hydroxyquinoline that can be used as an electron injecting material include metal chelate oxynoid compounds each containing a chelate of oxine (generally 8-quinolinol or 8-hydroxyquinoline), such as tris(8-quinolinol)aluminum.

On the other hand, examples of the oxadiazole derivative include electron transfer compounds represented by the following general formulae.

[Chem. 55]

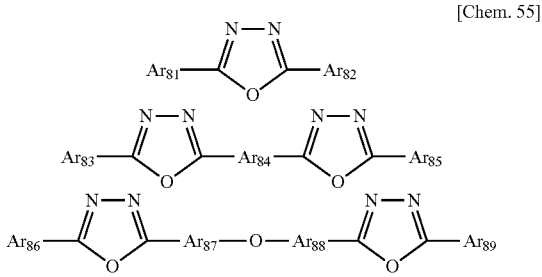

In the formulae: $Ar_{81}$, $Ar_{82}$, $Ar_{83}$, $Ar_{85}$, $Ar_{86}$, and $Ar_{89}$ each represent a substituted or unsubstituted aryl group and may be identical to or different from each other. Further, $Ar_{84}$, $Ar_{87}$, and $Ar_{88}$ each represent a substituted or unsubstituted arylene group and may be identical to or different from each other.

Examples of the aryl group include a phenyl group, a biphenylyl group, an anthryl group, a perylenyl group, and a pyrenyl group. Further, examples of the arylene group include a phenylene group, a naphthylene group, a biphenylylene group, an anthrylene group, a perylenylene group, and a pyrenylene group. In addition, examples of the substituent include an alkyl group having 1 to 10 carbon atoms, an alkoxyl group having 1 to 10 carbon atoms, and a cyano group. As the electron transfer compound, a compound which can form a thin film is preferred.

The hole injecting layer and the hole transporting layer are layers which help injection of holes into the light emitting layer and transports the holes to the light emitting region. The layers each exhibit a great mobility of holes and, in general, have an ionization energy as small as 5.5 eV or less.

As such hole injecting layer and hole transporting layer, a material which transports holes to the light emitting layer under an electric field of a smaller strength is preferred. A material which exhibits, for example, a mobility of holes of at least $10^{-4}$ cm$^2$/V·sec under application of an electric field of $10^4$ to $10^6$ V/cm is preferred.

When the aromatic amine derivative of the present invention is used in the hole transporting zone, the aromatic amine derivative of the present invention may be used alone or as a mixture with other materials for forming the hole injecting layer or the hole transporting layer.

The material which can be used as a mixture with the aromatic amine derivative of the present invention for forming the hole injecting layer and the hole transporting layer is not particularly limited as long as the material has the preferred property. The material can be arbitrarily selected from materials which are conventionally used as the charge transporting material of holes in photoconductive materials and known materials which are used for the hole injecting layer and the hole transporting layer in organic EL devices. In the present invention, a material which has a hole transporting ability and which can be used in a hole transporting zone is referred to as "hole transporting material".

Examples of the aromatic amine derivative to be used in each of the hole injecting layer and the hole transporting layer include compounds represented by the following formula.

[Chem.56]

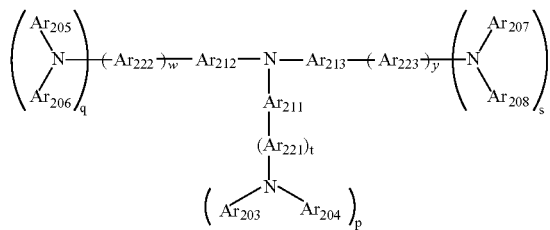

$Ar_{211}$ to $Ar_{213}$, $Ar_{221}$ to $Ar_{223}$, and $Ar_{203}$ to $Ar_{208}$ each represent a substituted or unsubstituted aromatic hydrocarbon group having 6 to 50 carbon atoms, or a substituted or unsubstituted aromatic heterocyclic group having 5 to 50 atoms, and p, q, s, t, w, and y each represent an integer of 0 to 3.

Specific examples of the substituted or unsubstituted aromatic hydrocarbon group having 6 to 50 carbon atoms include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, and a 4''-t-butyl-p-terphenyl-4-yl group.

Specific examples of the substituted or unsubstituted aromatic heterocyclic group having 5 to 50 atoms include a 1-pyrrolyl group, a 2-pyrrolyl group, a 3-pyrrolyl group, pyrazinyl group, a 2-pyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuryl group, a 3-benzofuryl group, a 4-benzofuryl group, a 5-benzofuryl group, a 6-benzofuryl group, a 7-benzofuryl group, a 1-isobenzofuryl group, a 3-isobenzofuryl group, a 4-isobenzofuryl group, a 5-isobenzofuryl group, a 6-isobenzofuryl group, a 7-isobenzofuryl group, a quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin- 4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 1-phenothiazinyl group, a 2-phenothiazinyl group, a 3-phenothiazinyl group, a 4-phenothiazinyl group, a 10-phenothiazinyl group, a 1-phenoxazinyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl1-indolyl group, a 4-t-butyl1-indolyl group, a 2-t-butyl3-indolyl group, and a 4-t-butyl3-indolyl group.

Further, a compound represented by the following formula can be used in each of the hole injecting layer and the hole transporting layer.

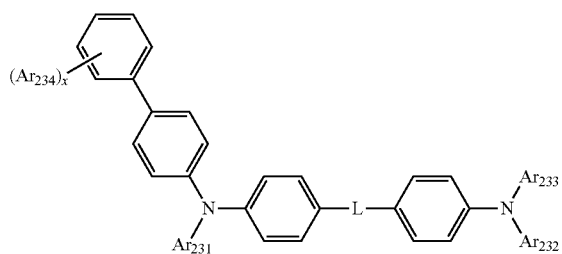

[Chem. 57]

$Ar_{231}$ to $Ar_{234}$ each represent a substituted or unsubstituted aromatic hydrocarbon group having 6 to 50 carbon atoms, or a substituted or unsubstituted aromatic heterocyclic group having 5 to 50 atoms.

L is a linking group and represents a single bond, a substituted or unsubstituted aromatic hydrocarbon group having 6 to 50 carbon atoms, or a substituted or unsubstituted aromatic heterocyclic group having 5 to 50 atoms, and x represents an integer of 0 to 5.

Here, specific examples of the substituted or unsubstituted aromatic hydrocarbon group having 6 to 50 carbon atoms, and the substituted or unsubstituted aromatic heterocyclic group having 5 to 50 atoms include the same examples as those described above.

Further, specific examples of the materials for the hole injecting layer and the hole transporting layer include a triazole derivative, an oxadiazole derivative, an imidazole derivative, a polyarylalkane derivative, a pyrazoline derivative, and a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, a polysilane-based copolymer, an aniline-based copolymer, and a conductive high molecular weight oligomer (in particular, a thiophene oligomer).

The above-mentioned materials may be used as the materials for the hole injecting layer and the hole transporting layer, and it is preferred to use a porphyrin compound, an aromatic tertiary amine compound, and a styrylamine compound. It is particularly preferred to use an aromatic tertiary amine compound.

Further, there may be given a compound having two fused aromatic rings in any one of its molecules such as 4,4'-bis(N-(1-naphthyl)-N-phenylamino)biphenyl (hereinafter abbreviated as "NPD"), 4,4',4"-tris(N-(3-methylphenyl)-N-phenylamino)triphenylamine (hereinafter abbreviated as "MTDATA") in which three triphenylamine units are linked to each other in a starburst pattern, and the like.

In addition to the foregoing, a nitrogen-containing heterocyclic derivative represented by the following formula can be used.

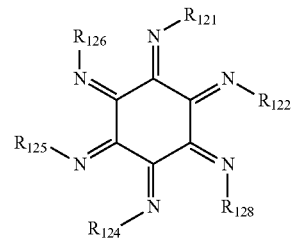

[Chem. 58]

In the above-mentioned formula, $R_{121}$ to $R_{126}$ each represent any one of a substituted or unsubstituted alkyl group, a substituted or unsubstituted aryl group, a substituted or unsubstituted aralkyl group, and a substituted or unsubstituted heterocyclic group, provided that $R_{121}$ to $R_{126}$ may be identical to or different from one another, and $R_{121}$ and $R_{122}$, $R_{123}$ and $R_{124}$, $R_{125}$ and $R_{126}$, $R_{121}$ and $R_{126}$, $R_{122}$ and $R_{123}$, or $R_{124}$ and $R_{125}$ may form a fused ring.

Further, a compound represented by the following formula can be used.

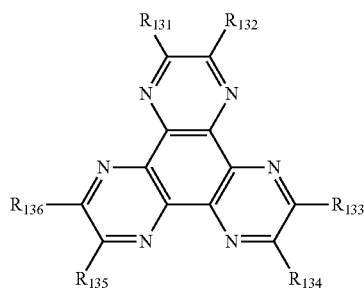

[Chem. 59]

In the above-mentioned formula, $R_{131}$ to $R_{136}$ each represent a substituent, preferably an electron-withdrawing group such as a cyano group, a nitro group, a sulfonyl group, a carbonyl group, a trifluoromethyl group, or a halogen.

As typified by those materials, acceptor materials can each also be used as the hole injecting material. Specific examples of the materials are as described above.

Further, in addition to the aromatic dimethylidyne-based compounds described above as the material for the light emitting layer, inorganic compounds such as Si of the p-type and SiC of the p-type can also be used as the material for the hole injecting layer and the hole transporting layer.

The hole injecting layer and the hole transporting layer can be obtained by forming a thin film from the aromatic amine derivative of the present invention in accordance with a known process such as the vacuum vapor deposition process, the spin coating process, the casting process, and the LB process.

The thickness of each of the hole injecting layer and the hole transporting layer is not particularly limited. In general, the thickness is 5 nm to 5 µm. The hole injecting layer and the hole transporting layer may be formed of a single layer containing one kind or two or more kinds of materials described above or may be a laminate formed of a hole injecting layer and a hole transporting layer containing different kinds of compounds as long as the aromatic amine derivative of the present invention is incorporated in the hole transporting zone.

Further, an organic semiconductor layer may be formed as a layer for helping the injection of holes into the light emitting layer. A layer having a conductivity of $10^{-10}$ S/cm or more is preferred. As a material for the organic semiconductor layer, there may be used as conductive oligomers such as oligomers containing thiophene and oligomers containing arylamine, conductive dendrimers such as dendrimers containing arylamine, and the like.

As for a method of producing the organic EL device of the present invention, the anode, light emitting layer, hole injecting layer, and electron injecting layer may be formed in accordance with the above-mentioned process using the materials, and the cathode may be formed in the last step. Further, the organic EL device may also be produced by forming the above-mentioned layers in the order reverse to the order described above, i.e., the cathode being formed in the first step and the anode in the last step.

Hereinafter, an example of producing an organic EL device having a configuration in which an anode, a hole injecting layer, a light emitting layer, an electron injecting layer, and a cathode are formed successively on a light-transmissive substrate is described.

First, on a suitable light-transmissive substrate, a thin film made of a material for the anode is formed in accordance with the vapor deposition process or the sputtering process so that the thickness of the formed thin film is 1 µm or less, preferably in the range of 10 to 200 nm. The formed thin film is used as the anode.

Then, a hole injecting layer is formed on the anode. The hole injecting layer can be formed in accordance with the vacuum vapor deposition process, the spin coating process, the casting process, the LB process, or the like, as described above. The vacuum vapor deposition process is preferred because a uniform film can be easily obtained and the possibility of formation of pin holes is small.

When the hole injecting layer is formed in accordance with the vacuum vapor deposition process, in general, it is preferred that the conditions be suitably selected from the following ranges: the temperature of the source of the deposition: 50 to 450° C.; the degree of vacuum: $10^{-7}$ to $10^{-3}$ Torr; the rate of deposition: 0.01 to 50 nm/s; the temperature of the substrate: −50 to 300° C.; and the thickness of the film: 5 nm to 5 µm, although the conditions of the vacuum vapor deposition are different depending on the compound to be used (material for the hole injecting layer) and the crystal structure and the recombination structure of the target hole injecting layer.

Then, the light emitting layer is formed on the hole injecting layer. The formation of the light emitting layer can be achieved by forming a thin film of the light emitting material using the light emitting material according to the present invention in accordance with a process such as the vacuum vapor deposition process, the sputtering process, the spin coating process, or the casting process. The vacuum vapor deposition process is preferred because a uniform film can be easily obtained and the possibility of formation of pin holes is small.

When the light emitting layer is formed in accordance with the vacuum vapor deposition process, in general, the conditions of the vapor deposition process can be selected from the same condition ranges as those for the formation of the hole injecting layer, although the conditions are different depending on the compound to be used. The thickness is preferably within the range of 10 to 40 nm.

Next, an electron injecting layer is formed on the light emitting layer. In this case, similarly to the hole injecting layer and the light emitting layer, it is preferred that the electron injecting layer be formed in accordance with the vacuum vapor deposition process because a uniform film is requested to be obtained. The conditions of the vapor deposition can be selected from the same condition ranges as those for the hole injecting layer and the light emitting layer.

After that, a cathode is laminated, and an organic EL device can be obtained. The cathode is formed of a metal and can be formed in accordance with the vapor deposition process, the sputtering process, or the like. It is preferred that the vacuum vapor deposition process be used in view of preventing damages of the lower organic thin film layers during the formation of the film.

In the production of the organic EL device as describe above, it is preferred that the layers from the anode to the cathode be formed successively by vacuuming once.

The method of forming the respective layers in the organic EL device of the present invention is not particularly limited. A conventionally known process such as the vacuum vapor deposition process or the spin coating process can be used. The organic thin film layer which is used in the organic EL device of the present invention and includes the compound represented by the general formula (1) can be formed in accordance with a known process such as the vacuum vapor deposition process, the molecular beam epitaxy process (MBE process), or a coating process such as the dipping process, the spin coating process, the casting process, the bar coating process, or the roll coating process using a solution prepared by dissolving the compounds into a solvent.

The thickness of each organic thin film layer in the organic EL device of the present invention is not particularly limited. However, a thickness in the range of several nanometers to 1 µm is preferred in order to prevent defects such as pin holes and to improve efficiency.

It should be noted that, in a case of applying a direct voltage to the organic EL device, emitted light can be observed, when a direct voltage of 5 to 40 V is applied in the condition that the polarity of the anode is plus (+) and the polarity of the cathode is minus (−). In addition, when the polarities are reversed and an electric voltage is applied, no electric current flows and no light is emitted at all. Further, when an alternating voltage is applied, a uniform emitted light can be observed only in the condition that the polarity of the anode is plus (+) and the polarity of the cathode is minus (−). When an alternating voltage is applied, any type of wave shape can be used.

The organic EL device of the present invention can find use in: flat luminous bodies for the flat panel displays of wall-hung televisions and the like; light sources for the backlights, measuring gauges, and the like of copying machines, printers, and liquid crystal displays; display boards; and marker lamps. In addition, the material of the present invention can be used not only in an organic EL device but also in the fields of, for example, an electrophotographic photosensitive member, a photoelectric converter, a solar cell, and an image sensor.

EXAMPLES

Synthesis Example 1-1

Synthesis of Intermediate 1-1

In a stream of argon, to a 1,000-mL three-necked flask, 47 g of 4-bromobiphenyl, 23 g of iodine, 9.4 g of periodic acid dihydrate, 42 mL of water, 360 mL of acetic acid, and 11 mL of sulfuric acid were charged, and the mixture was stirred at 65° C. for 30 minutes and was then subjected to a reaction at 90° C. for 6 hours. The reactant was poured into ice water, followed by filtering. The resultant was washed with water, and then washed with methanol, whereby 67 g of a white powder were obtained. Main peaks having ratios m/z of 358 and 360 were obtained with respect to $C_{12}H_8BrI=359$ by a field desorption mass spectrometry (hereinafter, FD-MS) analysis, so the powder was identified as Intermediate 1-1.

Synthesis Example 1-2

Synthesis of Intermediate 1-2

A reaction was performed in the same manner as in Synthesis Example 1-1 except that 2-bromo-9,9-dimethylfluorene was used instead of 4-bromobiphenyl. As a result, 61 g of a white powder were obtained. The powder was identified as Intermediate 1-2 by FD-MS analysis because main peaks having ratios m/z of 398 and 400 were obtained with respect to $C_{15}H_{12}BrI=399$.

Synthesis Example 1-3

Synthesis of Intermediate 1-3

150 grams (892 mmol) of dibenzofuran and 1 L of acetic acid were loaded into a flask. The air in the flask was replaced with nitrogen, and then the contents were dissolved under heat. 188 grams (1.18 mol) of bromine were dropped to the solution while the flask was sometimes cooled with water. After that, the mixture was stirred for 20 hours under air cooling. The precipitated crystal was separated by filtration, and was then sequentially washed with acetic acid and water. The washed crystal was dried under reduced pressure. The resultant crystal was purified by distillation under reduced pressure, and was then repeatedly recrystallized with methanol several times. Thus, 66.8 g of 2-bromodibenzofuran were obtained (in 31% yield). The resultant was identified as Intermediate 1-3 by FD-MS analysis.

Synthesis Example 1-4

Synthesis of Intermediate 1-4

Under an argon atmosphere, 400 mL of anhydrous THF were added to 24.7 g (100 mmol) of 2-bromodibenzofuran (Intermediate 1-3), and then 63 mL (100 mmol) of a solution of n-butyllithium in hexane having a concentration of 1.6 M were added to the mixture during the stirring of the mixture at −40° C. The reaction solution was stirred for 1 hour while being heated to 0° C. The reaction solution was cooled to −78° C. again, and then a solution of 26.0 g (250 mmol) of trimethyl borate in 50 mL of dry THF was dropped to the solution. The reaction solution was stirred at room temperature for 5 hours. 200 milliliters of 1N hydrochloric acid were added to the solution, and then the mixture was stirred for 1 hour. After that, the aqueous layer was removed. The organic layer was dried with magnesium sulfate, and then the solvent was removed by distillation under reduced pressure. The resultant solid was washed with toluene. Thus, 15.2 g of dibenzofuran-2-boronic acid were obtained (in 72% yield). The resultant was identified as Intermediate 1-4 by FD-MS analysis because a main peak having a ratio m/z of 212 was obtained with respect to $C_{12}H_9BO_3=212$.

Synthesis Example 1-5

Synthesis of Intermediate 1-5

Under an argon atmosphere, 300 mL of toluene and 150 mL of an aqueous solution of sodium carbonate having a concentration of 2 M were added to 28.3 g (100 mmol) of 4-iodobromobenzene, 22.3 g (105 mmol) of dibenzofuran-2-boronic acid (Intermediate 1-4), and 2.31 g (2.00 mmol) of tetrakis(triphenylphosphine) palladium(0), and then the mixture was heated while being refluxed for 10 hours.

Immediately after the completion of the reaction, the resultant was filtrated, and then the aqueous layer was removed. The organic layer was dried with sodium sulfate, and was then concentrated. The residue was purified by silica gel column chromatography. Thus, 26.2 g of a white crystal of 4-(4-bromophenyl)dibenzofuran were obtained (in 81% yield). The crystal was identified as Intermediate 1-5 by FD-MS analysis.

Synthesis Example 1-6

Synthesis of Intermediate 1-6

A reaction was performed in the same manner as in Synthesis Example 1-5 except that 22.3 g of dibenzofuran-4-boronic acid were used instead of dibenzofuran-2-boronic acid. As a result, 23.1 g of a white powder were obtained. The powder was identified as Intermediate 1-6 by FD-MS analysis.

Synthesis Example 1-7

Synthesis of Intermediate 1-7

A reaction was performed in the same manner as in Synthesis Example 1-6 except that 36 g of Intermediate 1-1 were used instead of 4-iodobromobenzene. As a result, 28.1 g of a white powder were obtained. The powder was identified as Intermediate 1-6 by FD-MS analysis.

Synthesis Example 1-8

Synthesis of Intermediate 1-8

A reaction was performed in the same manner as in Synthesis Example 1-6 except that 40 g of Intermediate 1-2 were used instead of 4-iodobromobenzene. As a result, 30.2 g of a white powder were obtained. The powder was identified as Intermediate 1-8 by FD-MS analysis.

Synthesis Example 1-9

Synthesis of Intermediate 1-9

Under an argon atmosphere, 2 mL of trans-1,2-cyclohexanediamine and 300 mL of 1,4-dioxane were added to 28.3 g (100 mmol) of 4-iodobromobenzene, 16.7 g (100 mmol) of carbazole, 0.2 g (1.00 mmol) of copper iodide (CuI), and 42.4 g (210 mmol) of tripotassium phosphate, and then the mixture was stirred at 100° C. for 20 hours.

After the completion of the reaction, 300 mL of water were added to the resultant. After that, the mixture was subjected to liquid separation, and then the aqueous layer was removed. The organic layer was dried with sodium sulfate, and was then concentrated. The residue was purified by silica gel column chromatography. Thus, 18.3 g of a white crystal were obtained (in 57% yield). The resultant was identified as Intermediate 1-9 by FD-MS analysis.

Synthesis Example 1-10

Synthesis of Intermediate 1-10

A reaction was performed in the same manner as in Synthesis Example 1-9 except that 36 g of Intermediate 1-1 were used instead of 4-iodobromobenzene. As a result, 23.1 g of a white powder were obtained. The powder was identified as Intermediate 1-10 by FD-MS analysis.

Synthesis Example 1-11

Synthesis of Intermediate 1-11

In a stream of argon, 670 g of carbazole, 850 kg of iodobenzene, 20 L of xylene, 460 g of t-BuONa, and palladium acetate (Pd(OAc)$_2$) were loaded, and then the mixture was refluxed for 8 hours. Impurities were filtrated, and then the filtrate was concentrated under reduced pressure and washed with hexane. After that, the washed product was dried. As a result, 820 g of phenylcarbazole were obtained as a white powder. A reaction was performed in the same manner as in the synthesis of Intermediate 1-1 except that phenylcarbazole was used instead of 4-bromobiphenyl. As a result, 650 g of a white powder were obtained. The powder was identified as Intermediate 1-11 by FD-MS analysis.

Synthesis Example 1-12

Synthesis of Intermediate 1-12

A reaction was performed in the same manner as in Synthesis Examples 1-4 and 1-5 except that Intermediate 1-11 was used instead of Intermediate 1-3. As a result, 250 g of a white powder were obtained. The powder was identified as Intermediate 1-12 by FD-MS analysis.

Synthesis Example 1-13

Synthesis of Intermediate 1-13

In a stream of argon, 16.8 g of diphenylamine, 36.0 g of Intermediate 1-1, 10 g of t-butoxy sodium (manufactured by Hiroshima Wako Ltd.), 1.6 g of bis(triphenylphosphine) palladium (II) chloride (manufactured by TOKYO CHEMICAL INDUSTRY CO., LTD.), and 500 mL of xylene were loaded and subjected to a reaction at 130° C. for 24 hours.

After the resultant had been cooled, 1,000 mL of water were added to the resultant, and then the mixture was filtrated with celite. The filtrate was extracted with toluene, and was then dried with anhydrous magnesium sulfate. The dried product was concentrated under reduced pressure. The resultant coarse product was subjected to column purification, and was then recrystallized with toluene. The crystal was taken by filtration, and was then dried. As a result, 12.4 g of a pale yellow powder were obtained. The powder was identified as Intermediate 1-13 by FD-MS analysis.

Synthesis Example 1-14

Synthesis of Intermediate 1-14

A reaction was performed in the same manner as in Synthesis Example 1-13 except that 4-iodobromobenzene was used instead of Intermediate 1-1. As a result, 9.3 g of a white powder were obtained. The powder was identified as Intermediate 1-14 by FD-MS analysis.

Synthesis Example 1-15

Synthesis of Intermediate 1-15

In a stream of argon, 185 g of 1-acetamide (manufactured by TOKYO CHEMICAL INDUSTRY CO., LTD.), 323 g of Intermediate 1-6 (manufactured by Wako Pure Chemical Industries, Ltd.), 544 g of potassium carbonate (manufactured by Wako Pure Chemical Industries, Ltd.), 12.5 g of a copper powder (manufactured by Wako Pure Chemical Industries, Ltd.), and 2 L of decalin were loaded and subjected to a reaction at 190° C. for 4 days. After the reaction, the resultant was cooled, and then 2 L of toluene were added to the resultant. The insoluble portion was taken by filtration. The product taken by filtration was dissolved in 4.5 L of chloroform, and then the insoluble portion was removed. After that, the remainder was subjected to an activated carbon treatment and concentrated. 3 liters of acetone were added to the resultant, and then 181 g of the precipitated crystal were taken by filtration. The crystal was identified as Intermediate 1-15 by FD-MS analysis.

Synthesis Example 1-16

Synthesis of Intermediate 1-16

In a stream of argon, Intermediate 1-15 was suspended in 5 L of ethylene glycol (manufactured by Wako Pure Chemical Industries, Ltd.) and 50 mL of water, and then 210 g of an 85% aqueous solution of potassium hydroxide were added to the suspension. After that, the mixture was subjected to a reaction at 120° C. for 8 hours. After the reaction, the reaction liquid was injected into 10 L of water, and then the precipitated crystal was taken by filtration. The crystal was washed with water and methanol. The resultant crystal was dissolved in 3 L of tetrahydrofuran under heat. The solution was subjected to an activated carbon treatment, and was then concentrated. Acetone was added to the resultant to precipitate a crystal. The crystal was taken by filtration. Thus, 151 g of a white powder were obtained. The powder was identified as Intermediate 1-16 by FD-MS analysis.

Synthesis Example 1-17

Synthesis of Intermediate 1-17

A reaction was performed in the same manner as in Synthesis Examples 1-15 and 1-16 except that Intermediate 1-7 was used instead of Intermediate 1-6. As a result, 172 g of a white powder were obtained. The powder was identified as Intermediate 1-17 by FD-MS analysis.

Synthesis Example 1-18

Synthesis of Intermediate 1-18

A reaction was performed in the same manner as in Synthesis Examples 1-15 and 1-16 except that Intermediate 1-8 was used instead of Intermediate 1-6. As a result, 168 g of a white powder were obtained. The powder was identified as Intermediate 1-18 by FD-MS analysis.

Synthesis Example 1-19

Synthesis of Intermediate 1-19

A reaction was performed in the same manner as in Synthesis Examples 1-15 and 1-16 except that Intermediate 1-5 was used instead of Intermediate 1-6. As a result, 153 g of a white powder were obtained. The powder was identified as Intermediate 1-19 by FD-MS analysis.

Synthesis Example 1-20

Synthesis of Intermediate 1-20

A reaction was performed in the same manner as in Synthesis Examples 1-15 and 1-16 except that the usage of Intermediate 1-6 was changed from 323 g to 678 g. As a result, 280 g of a white powder were obtained. The powder was identified as Intermediate 1-20 by FD-MS analysis.

Synthesis Example 1-21

Synthesis of Intermediate 1-21

A reaction was performed in the same manner as in Synthesis Examples 1-15 and 1-16 except that: Intermediate 1-15 was used instead of 1-acetamide; and 4-bromo-p-terphenyl was used instead of Intermediate 1-6. As a result, 280 g of a white powder were obtained. The powder was identified as Intermediate 1-21 by FD-MS analysis.

Synthesis Example 1-22

Synthesis of Intermediate 1-22

A reaction was performed in the same manner as in Synthesis Examples 1-15 and 1-16 except that Intermediate 1-5 was used instead of Intermediate 1-6. As a result, 245 g of a white powder were obtained. The powder was identified as Intermediate 1-22 by FD-MS analysis.

Synthesis Example 1-23

Synthesis of Intermediate 1-23

A reaction was performed in the same manner as in Synthesis Examples 1-15 and 1-16 except that: Intermediate 1-15 was used instead of 1-acetamide; and Intermediate 1-9 was used instead of Intermediate 1-6. As a result, 255 g of a white powder were obtained. The powder was identified as Intermediate 1-23 by FD-MS analysis.

Synthesis Example 1-24

Synthesis of Intermediate 1-24

In a stream of argon, 11.0 g of aniline, 32.3 g of Intermediate 1-9, 13.6 g of t-butoxy sodium (manufactured by Hiroshima Wako Ltd.), 0.92 g of tris(dibenzylideneacetone)dipalladium(0) (manufactured by Sigma Aldrich Co.), and 600 mL of dry toluene were loaded and subjected to a reaction at 80° C. for 8 hours.

After the resultant had been cooled, 500 mL of water were added to the resultant, and then the mixture was filtrated with celite. The filtrate was extracted with toluene, and was then dried with anhydrous magnesium sulfate. The dried product was concentrated under reduced pressure. The resultant coarse product was subjected to column purification, and was then recrystallized with toluene. The crystal was taken by filtration, and was then dried. As a result, 23.8 g of an amine derivative (pale yellow powder) were obtained. Further, a reaction was performed in the same manner as in Synthesis Example 1-13 except that the amine derivative (pale yellow powder) obtained in the foregoing was used instead of diphenylamine. As a result, 28.4 g of a white powder were obtained. The powder was identified as Intermediate 1-24 by FD-MS analysis.

Synthesis Example 1-25

Synthesis of Intermediate 1-25

A reaction was performed in the same manner as in Synthesis Example 1-24 except that 4-iodobromobenzene was used instead of Intermediate 1-1 in the reaction on the second stage. As a result, 22.5 g of an amine intermediate (white powder) were obtained. Further, a reaction was performed in the same manner as in Synthesis Example 1-13 except that the amine intermediate (white powder) obtained in the foregoing was used instead of diphenylamine. As a result, 23.4 g of a white powder were obtained. The powder was identified as Intermediate 1-25 by FD-MS analysis.

Synthesis Example 1-26

Synthesis of Intermediate 1-26

In a stream of argon, 185 g of 1-acetamide (manufactured by TOKYO CHEMICAL INDUSTRY CO., LTD.), 323 g of Intermediate 1-6 (manufactured by Wako Pure Chemical Industries, Ltd.), 544 g of potassium carbonate (manufactured by Wako Pure Chemical Industries, Ltd.), 12.5 g of a copper powder (manufactured by Wako Pure Chemical Industries, Ltd.), and 2 L of decalin were loaded and subjected to a reaction at 190° C. for 4 days. After the reaction, the resultant was cooled, and then 2 L of toluene were added to the resultant. The insoluble portion was taken by filtration. The product taken by filtration was dissolved in 4.5 L of chloroform, and then the insoluble portion was removed. After that, the remainder was subjected to an activated carbon treatment and concentrated. 3 liters of acetone were added to the resultant, and then 175 g of the precipitated crystal were taken by filtration.

To the resultant, 120 g of 4,4'-diiodobiphenyl (manufactured by Wako Pure Chemical Industries, Ltd.), 163 g of potassium carbonate (manufactured by Wako Pure Chemical Industries, Ltd.), 3.8 g of a copper powder (manufactured by Wako Pure Chemical Industries, Ltd.), and 600 mL of decalin were loaded and subjected to a reaction at 190° C. for 4 days.

After the reaction, the resultant was cooled, and then 600 mL of toluene were added to the resultant. The insoluble portion was taken by filtration. The product taken by filtration was dissolved in 1.4 L of chloroform, and then the insoluble portion was removed. After that, the remainder was subjected to an activated carbon treatment and concentrated. 1 liter of acetone were added to the resultant, and then 391 g of the precipitated crystal were taken by filtration.

The resultant was suspended in 1.5 L of ethylene glycol (manufactured by Wako Pure Chemical Industries, Ltd.) and 15 mL of water, and then 44 g of an 85% aqueous solution of potassium hydroxide were added to the suspension. After that, the mixture was subjected to a reaction at 120° C. for 8 hours. After the reaction, the reaction liquid was injected into 10 L of water, and then the precipitated crystal was taken by filtration. The crystal was washed with water and methanol. The resultant crystal was dissolved in 1 L of tetrahydrofuran under heat. The solution was subjected to an activated carbon treatment, and was then concentrated. Acetone was added to the resultant to precipitate a crystal. The crystal was taken by filtration. Thus, 140 g of a white powder were obtained. The powder was identified as Intermediate 1-26 by FD-MS analysis.

Synthesis Example 1-27

Synthesis of Intermediate 1-27

A reaction was performed in the same manner as in Synthesis Examples 1-15 and 1-16 except that Intermediate 1-9 was used instead of Intermediate 1-6. As a result, 221 g of a white powder were obtained. The powder was identified as Intermediate 1-27 by FD-MS analysis.

Synthesis Example 1-28

Synthesis of Intermediate 1-28

A reaction was performed in the same manner as in Synthesis Examples 1-15 and 1-16 except the following. After 323 g of Intermediate 1-6 had been subjected to a reaction, 323 g of Intermediate 1-5 were added to the reaction liquid, and then the mixture was continuously subjected to a reaction. As a result, 232 g of a white powder were obtained. The powder was identified as Intermediate 1-28 by FD-MS analysis.

Synthesis Example 1-29

Synthesis of Intermediate 1-29

A reaction was performed in the same manner as in Synthesis Example 1-9 except that 40 g of Intermediate 1-2 were used instead of 4-iodobromobenzene. As a result, 25.4 g of a white powder were obtained. The powder was identified as Intermediate 1-29 by FD-MS analysis.

Synthesis Example 1-30

Synthesis of Intermediate 1-30

A reaction was performed in the same manner as in Synthesis Examples 1-15 and 1-16 except that: acetanilide was used instead of 1-acetamide; and Intermediate 1-29 was used instead of Intermediate 1-6. As a result, 20.5 g of a white powder were obtained. The powder was identified as Intermediate 1-30 by FD-MS analysis.

Synthesis Example 1-31

Synthesis of Intermediate 1-31

A reaction was performed in the same manner as in Synthesis Examples 1-4 and 1-5 except that: Intermediate 1-11 was used instead of Intermediate 1-3; and Intermediate 1-2 was used instead of 4-iodobromobenzene. As a result, 26 g of a white powder were obtained. The powder was identified as Intermediate 1-31 by FD-MS analysis.

Synthesis Example 1-32

Synthesis of Intermediate 1-32

A reaction was performed in the same manner as in Synthesis Examples 1-15 and 1-16 except that: acetanilide was used instead of 1-acetamide; and Intermediate 1-31 was used instead of Intermediate 1-6. As a result, 19.5 g of a white powder were obtained. The powder was identified as Intermediate 1-32 by FD-MS analysis.

Synthesis Example 1-33

Synthesis of Intermediate 1-33

A reaction was performed in the same manner as in Synthesis Examples 1-15 and 1-16 except that: acetanilide was used instead of 1-acetamide; and Intermediate 1-8 was used instead of Intermediate 1-6. As a result, 19.8 g of a white powder were obtained. The powder was identified as Intermediate 1-33 by FD-MS analysis.

Synthesis Example 1-34

Synthesis of Intermediate 1-34

A reaction was performed in the same manner as in Synthesis Examples 1-4 and 1-5 except that Intermediate 1-2 was used instead of 4-iodobromobenzene. As a result, 30 g of a white powder were obtained. The powder was identified as Intermediate 1-34 by FD-MS analysis.

Synthesis Example 1-35

Synthesis of Intermediate 1-35

A reaction was performed in the same manner as in Synthesis Examples 1-15 and 1-16 except that: acetanilide was used instead of 1-acetamide; and Intermediate 1-34 was used instead of Intermediate 1-6. As a result, 23.2 g of a white powder were obtained. The powder was identified as Intermediate 1-35 by FD-MS analysis.

Synthesis Example 1-36

Synthesis of Intermediate 1-36

Under an argon atmosphere, 600 mL of dry tetrahydrofuran were added to 78.0 g of dibenzofuran, and then the mixture was cooled to −30° C. 300 milliliters of a solution of n-butyllithium in hexane (1.65 M) were dropped to the mixture, and then the temperature of the whole was increased to room temperature over 1 hour while the whole was stirred. After having been stirred at room temperature for 5 hours, the resultant was cooled to −60° C., and then 60 mL of 1,2-dibromoethane were dropped to the resultant over 1 hour.

After having been stirred at room temperature for 15 hours, the mixture was poured into 1,000 mL of ice water, and then the organic layer was extracted with dichloromethane. The organic layer was washed with a saturated salt solution, and was then dried with anhydrous magnesium sulfate. The dried product was separated by filtration, and was then concentrated. The resultant solid was purified by silica gel chromatography (toluene), washed with tetrahydrofuran and methanol, and dried under reduced pressure. As a result, 70 g of a solid were obtained. The solid was identified as Intermediate 1-36 by FD-MS analysis.

Synthesis Example 1-37

Synthesis of Intermediate 1-37

Under an argon atmosphere, 1,000 mL of toluene and 500 mL of an aqueous solution of sodium carbonate having a concentration of 2 M were added to 120.0 g (399 mmol) of 1-bromo-3-fluoro-4-iodobenzene, 72.7 g (479 mmol) of 2-methoxyphenyl boronic acid, and 9.2 g (7.96 mmol) of tetrakis(triphenylphosphine)palladium(0), and then the mixture was heated while being refluxed for 10 hours.

Immediately after the completion of the reaction, the resultant was filtered, and then the aqueous layer was removed. The organic layer was dried with sodium sulfate, and was then concentrated. The residue was purified by silica gel column chromatography. Thus, 89.6 g of a white crystal of 4-bromo-2-fluoro-2'-methoxybiphenyl were obtained (in 80% yield).

Under an argon atmosphere, 900 mL of dichloromethane were added to 89.6 g (319 mmol) of 4-bromo-2-fluoro-2'-methoxybiphenyl, and then the mixture was stirred under ice cooling. 95.9 grams (382 mmol) of boron tribromide were added dropwise to the mixture, and then the whole was stirred at room temperature for 12 hours. After the completion of the reaction, 200 mL of water were added to the resultant, and then the mixture was stirred for 1 hour. After that, the aqueous layer was removed. The organic layer was dried with magnesium sulfate, and was then concentrated. The residue was purified by silica gel column chromatography. Thus, 68.1 g of a white crystal of 4-bromo-2-fluoro-2'-hydroxybiphenyl were obtained (in 70% yield).

1,500 milliliters of N-methylpyrrolidone were added to 68.1 g (255 mmol) of 4-bromo-2-fluoro-2'-hydroxybiphenyl and 70.4 g (510 mmol) of potassium carbonate, and then the mixture was stirred at 180° C. for 3 hours. After the completion of the reaction, water was added to the resultant, and then extraction with toluene was performed. The organic layer was dried with sodium sulfate, and was then concentrated. The residue was recrystallized from toluene so as to be purified. Thus, 44.2 g of a white crystal of 3-bromodibenzofuran were obtained (in 60% yield). The crystal was identified as Intermediate 1-37 by FD-MS analysis.

Synthesis Embodiment 1-1

Synthesis of Compound 1-H1

In a stream of argon, 5.0 g of Intermediate 1-20, 3.2 g of Intermediate 1-9, 1.3 g of t-butoxy sodium (manufactured by Hiroshima Wako Ltd.), 46 mg of tris(dibenzylideneacetone)dipalladium(0) (manufactured by Sigma Aldrich Co.), 21 mg of tri-t-butylphosphine, and 50 mL of dry toluene were loaded and subjected to a reaction at 80° C. for 8 hours.

After the resultant had been cooled, 500 mL of water were added to the resultant, and then the mixture was filtered with celite. The filtrate was extracted with toluene, and was then dried with anhydrous magnesium sulfate. The dried product was concentrated under reduced pressure. The resultant coarse product was subjected to column purification, and was then recrystallized with toluene. The crystal was taken by filtration, and was then dried. As a result, 4.4 g of a pale yellow powder were obtained. The powder was identified as Compound 1-H1 (Exemplified Compound AD-2 shown above) by FD-MS analysis.

Synthesis Embodiment 1-2

Synthesis of Compound 1-H2

A reaction was performed in the same manner as in Synthesis Embodiment 1-1 except that 4.0 g of Intermediate 1-10 were used instead of Intermediate 1-9. As a result, 5.6 g of a pale yellow powder were obtained. The powder was identified as Compound 1-H2 (Exemplified Compound AD-14 shown above) by FD-MS analysis.

Synthesis Embodiment 1-3

Synthesis of Compound 1-H3

A reaction was performed in the same manner as in Synthesis Embodiment 1-1 except that 4.9 g of Intermediate 1-21 were used instead of Intermediate 1-20. As a result, 4.4 g of a pale yellow powder were obtained. The powder was identified as Compound 1-H3 (Exemplified Compound AD-4 shown above) by FD-MS analysis.

Synthesis Embodiment 1-4

Synthesis of Compound 1-H4

A reaction was performed in the same manner as in Synthesis Embodiment 1-2 except that 4.9 g of Intermediate 1-21 were used instead of Intermediate 1-20. As a result, 4.8 g of a pale yellow powder were obtained. The powder was identified as Compound 1-H4 (Exemplified Compound AD-16 shown above) by FD-MS analysis.

Synthesis Embodiment 1-5

Synthesis of Compound 1-H5

A reaction was performed in the same manner as in Synthesis Embodiment 1-1 except that 5.0 g of Intermediate 1-22 were used instead of Intermediate 1-20. As a result, 5.2 g of a pale yellow powder were obtained. The powder was identified as Compound 1-H5 (Exemplified Compound AD-34 shown above) by FD-MS analysis.

Synthesis Embodiment 1-6

Synthesis of Compound 1-H6

A reaction was performed in the same manner as in Synthesis Embodiment 1-2 except that 5.0 g of Intermediate 1-22 were used instead of Intermediate 1-20. As a result, 5.6 g of a pale yellow powder were obtained. The powder was identified as Compound 1-H6 (Exemplified Compound AD-46 shown above) by FD-MS analysis.

A synthesis method has been changed in association with the change of the compound in the example (Intermediate 22→28)

Synthesis Embodiment 1-7

Synthesis of Compound 1-H7

A reaction was performed in the same manner as in Synthesis Embodiment 1-1 except that: 5.0 g of Intermediate 1-28 were used instead of Intermediate 1-20; and 4.0 g of Intermediate 1-12 were used instead of Intermediate 1-9. As a result, 5.2 g of a pale yellow powder were obtained. The powder was identified as Compound 1-H7 by FD-MS analysis.

Synthesis Embodiment 1-8

Synthesis of Compound 1-H8

A reaction was performed in the same manner as in Synthesis Embodiment 1-1 except that: 1.3 g of Intermediate 1-16 were used instead of Intermediate 1-20; and 6.4 g of Intermediate 1-9 were used. As a result, 2.2 g of a pale yellow powder were obtained. The powder was identified as Compound 1-H8 (Exemplified Compound AD-190 shown above) by FD-MS analysis.

Synthesis Embodiment 1-9

Synthesis of Compound 1-H9

A reaction was performed in the same manner as in Synthesis Embodiment 1-1 except that: 1.7 g of Intermediate 1-17 were used instead of Intermediate 1-20; and 6.4 g of Intermediate 1-9 were used. As a result, 2.3 g of a pale yellow powder were obtained. The powder was identified as Compound 1-H9 (Exemplified Compound AD-192 shown above) by FD-MS analysis.

Synthesis Embodiment 1-10

Synthesis of Compound 1-H10

A reaction was performed in the same manner as in Synthesis Embodiment 1-1 except that: 1.9 g of Intermediate 1-18 were used instead of Intermediate 1-20; and 6.4 g of Intermediate 1-9 were used. As a result, 2.4 g of a pale yellow powder were obtained. The powder was identified as Compound 1-H10 (Exemplified Compound AD-194 shown above) by FD-MS analysis.

Synthesis Embodiment 1-11

Synthesis of Compound 1-H11

A reaction was performed in the same manner as in Synthesis Embodiment 1-1 except that: 1.3 g of Intermediate 1-19 were used instead of Intermediate 1-20; and 6.4 g of Intermediate 1-9 were used. As a result, 1.9 g of a pale yellow powder were obtained. The powder was identified as Compound 1-H11 (Exemplified Compound AD-196 shown above) by FD-MS analysis.

Synthesis Embodiment 1-12

Synthesis of Compound 1-H12

A reaction was performed in the same manner as in Synthesis Embodiment 1-1 except that 3.7 g of Intermediate 1-11 were used instead of Intermediate 1-9. As a result, 4.6 g of a pale yellow powder were obtained. The powder was identified as Compound 1-H12 (Exemplified Compound AD-1 shown above) by FD-MS analysis.

Synthesis Embodiment 1-13

Synthesis of Compound 1-H13

A reaction was performed in the same manner as in Synthesis Embodiment 1-1 except that: 5.0 g of Intermediate 1-22 were used instead of Intermediate 1-20; and 3.7 g of Intermediate 1-11 were used instead of Intermediate 1-9. As a result, 4.3 g of a pale yellow powder were obtained. The powder was identified as Compound 1-H13 (Exemplified Compound AD-33 shown above) by FD-MS analysis.

Synthesis Embodiment 1-14

Synthesis of Compound 1-H14

A reaction was performed in the same manner as in Synthesis Embodiment 1-1 except that: 5.0 g of Intermediate 1-27 were used instead of Intermediate 1-20; and 2.5 g of Intermediate 1-3 were used instead of Intermediate 1-9. As a result, 3.8 g of a pale yellow powder were obtained. The powder was identified as Compound 1-H14 (Exemplified Compound AD-191 shown above) by FD-MS analysis.

Synthesis Embodiment 1-15

Synthesis of Compound 1-H15

A reaction was performed in the same manner as in Synthesis Embodiment 1-1 except that: 1.3 g of Intermediate 1-16 were used instead of Intermediate 1-20; and 7.4 g of Intermediate 1-11 were used instead of Intermediate 1-9. As a result, 2.6 g of a pale yellow powder were obtained. The powder was identified as Compound 1-H15 (Exemplified Compound AD-193 shown above) by FD-MS analysis.

Synthesis Embodiment 1-16

Synthesis of Compound 1-H16

A reaction was performed in the same manner as in Synthesis Embodiment 1-1 except that: 1.3 g of Intermediate 1-19 were used instead of Intermediate 1-20; and 7.4 g of Intermediate 1-11 were used instead of Intermediate 1-9. As a result, 2.4 g of a pale yellow powder were obtained. The powder was identified as Compound 1-H16 (Exemplified Compound AD-24 shown above) by FD-MS analysis.

Synthesis Embodiment 1-17

Synthesis of Compound 1-H17

A reaction was performed in the same manner as in Synthesis Embodiment 1-1 except that: 5.0 g of Intermediate 1-23 were used instead of Intermediate 1-20; and 2.5 g of Intermediate 1-3 were used instead of Intermediate 1-9. As a result, 4.3 g of a pale yellow powder were obtained. The powder was identified as Compound 1-H17 (Exemplified Compound AD-195 shown above) by FD-MS analysis.

Synthesis Embodiment 1-18

Synthesis of Compound 1-H18

A reaction was performed in the same manner as in Synthesis Embodiment 1-1 except that: 5.0 g of Intermediate 1-23 were used instead of Intermediate 1-20; and 4.0 g of Intermediate 1-13 were used instead of Intermediate 1-9. As a result, 5.3 g of a pale yellow powder were obtained. The powder was identified as Compound 1-H18 (Exemplified Compound AD-120 shown above) by FD-MS analysis.

Synthesis Embodiment 1-19

Synthesis of Compound 1-H19

A reaction was performed in the same manner as in Synthesis Embodiment 1-1 except that: 5.0 g of Intermediate 1-23 were used instead of Intermediate 1-20; and 3.2 g of Intermediate 1-14 were used instead of Intermediate 1-9. As a result, 4.9 g of a pale yellow powder were obtained. The powder was identified as Compound 1-H19 (Exemplified Compound AD-197 shown above) by FD-MS analysis.

Synthesis Embodiment 1-20

Synthesis of Compound 1-H20

A reaction was performed in the same manner as in Synthesis Embodiment 1-1 except that 3.3 g of Intermediate 1-26 were used instead of Intermediate 1-20. As a result, 3.9 g of a pale yellow powder were obtained. The powder was identified as Compound 1-H20 (Exemplified Compound AD-129 shown above) by FD-MS analysis.

Synthesis Embodiment 1-21

Synthesis of Compound 1-H21

A reaction was performed in the same manner as in Synthesis Embodiment 1-1 except that: 1.3 g of Intermediate 1-16 were used instead of Intermediate 1-20; and 13.2 g of Intermediate 1-24 were used instead of Intermediate 1-9. As a result, 4.3 g of a pale yellow powder were obtained. The powder was identified as Compound 1-H21 (Exemplified Compound AD-151 shown above) by FD-MS analysis.

Synthesis Embodiment 1-22

Synthesis of Compound 1-H22

A reaction was performed in the same manner as in Synthesis Embodiment 1-1 except that: 3.3 g of Intermediate 1-26 were used instead of Intermediate 1-20; and 9.8 g of Intermediate 1-25 were used instead of Intermediate 1-9. As a result, 5.6 g of a pale yellow powder were obtained. The powder was identified as Compound 1-H22 (Exemplified Compound AD-171 shown above) by FD-MS analysis.

Synthesis Embodiment 1-23

Synthesis of Compound 1-H23

A reaction was performed in the same manner as in Synthesis Embodiment 1-1 except that: 5.0 g of Intermediate 1-23 were used instead of Intermediate 1-20; and 9.8 g of tris(4-bromophenyl)amine were used instead of Intermediate 1-9. As a result, 3.8 g of a pale yellow powder were obtained. The powder was identified as Compound 1-H23 (Exemplified Compound AD-187 shown above) by FD-MS analysis.

Synthesis Embodiment 1-24

Synthesis of Compound 1-H24

A reaction was performed in the same manner as in Synthesis Embodiment 1-1 except that 4.0 g of Intermediate 1-12 were used instead of Intermediate 1-9. As a result, 5.4 g of a pale yellow powder were obtained. The powder was identified as Compound 1-H24 by FD-MS analysis.

Synthesis Embodiment 1-25

Synthesis of Compound 1-H25

A reaction was performed in the same manner as in Synthesis Embodiment 1-1 except that: 4.5 g of Intermediate 1-30 were used instead of Intermediate 1-20; and 2.5 g of Intermediate 1-36 were used instead of Intermediate 1-9. As a result, 3.3 g of a pale yellow powder were obtained. The powder was identified as Compound 1-H25 by FD-MS analysis.

Synthesis Embodiment 1-26

Synthesis of Compound 1-H26

A reaction was performed in the same manner as in Synthesis Embodiment 1-1 except that: 4.5 g of Intermediate 1-30 were used instead of Intermediate 1-20; and 2.5 g of Intermediate 1-3 were used instead of Intermediate 1-9. As a result, 3.5 g of a pale yellow powder were obtained. The powder was identified as Compound 1-H26 by FD-MS analysis.

Synthesis Embodiment 1-27

Synthesis of Compound 1-H27

A reaction was performed in the same manner as in Synthesis Embodiment 1-1 except that: 4.5 g of Intermediate 1-30 were used instead of Intermediate 1-20; and 2.5 g of Intermediate 1-37 were used instead of Intermediate 1-9. As a result, 3.9 g of a pale yellow powder were obtained. The powder was identified as Compound 1-H27 by FD-MS analysis.

Synthesis Embodiment 1-28

Synthesis of Compound 1-H28

A reaction was performed in the same manner as in Synthesis Embodiment 1-1 except that: 5.3 g of Intermediate 1-32 were used instead of Intermediate 1-20; and 2.5 g of Intermediate 1-37 were used instead of Intermediate 1-9. As a result, 4.0 g of a pale yellow powder were obtained. The powder was identified as Compound 1-H28 by FD-MS analysis.

Synthesis Embodiment 1-29

Synthesis of Compound 1-H29

A reaction was performed in the same manner as in Synthesis Embodiment 1-1 except that: 5.3 g of Intermediate 1-32 were used instead of Intermediate 1-20; and 2.5 g of Intermediate 1-3 were used instead of Intermediate 1-9. As a result, 3.8 g of a pale yellow powder were obtained. The powder was identified as Compound 1-H29 by FD-MS analysis.

Synthesis Embodiment 1-30

Synthesis of Compound 1-H30

A reaction was performed in the same manner as in Synthesis Embodiment 1-1 except that: 5.3 g of Intermediate 1-32 were used instead of Intermediate 1-20; and 2.5 g of Intermediate 1-37 were used instead of Intermediate 1-9. As a result, 4.3 g of a pale yellow powder were obtained. The powder was identified as Compound 1-H30 by FD-MS analysis.

Synthesis Embodiment 1-31

Synthesis of Compound 1-H31

A reaction was performed in the same manner as in Synthesis Embodiment 1-1 except that: 4.5 g of Intermediate 1-33 were used instead of Intermediate 1-20; and 3.7 g of Intermediate 1-11 were used instead of Intermediate 1-9. As a result, 4.2 g of a pale yellow powder were obtained. The powder was identified as Compound 1-H31 by FD-MS analysis.

Synthesis Embodiment 1-32

Synthesis of Compound 1-H32

A reaction was performed in the same manner as in Synthesis Embodiment 1-1 except that: 4.5 g of Intermediate 1-35 were used instead of Intermediate 1-20; and 3.7 g of Intermediate 1-11 were used instead of Intermediate 1-9. As a result, 4.3 g of a pale yellow powder were obtained. The powder was identified as Compound 1-H32 by FD-MS analysis.

The structural formulae of Intermediates 1-1 to 1-37 synthesized in Synthesis Examples 1-1 to 1-37 described above, Compounds 1-H1 to 1-H32 synthesized in Synthesis Embodiments 1-1 to 1-32 each serving as the aromatic amine derivative of the present invention, and Comparative Compounds 1-1 to 1-6 are as shown below.

[Chem. 60]

Intermediate 1-1

Intermediate 1-2
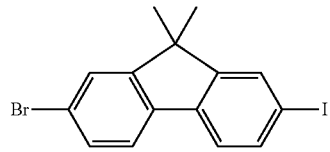

Intermediate 1-3
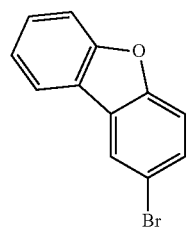

Intermediate 1-4
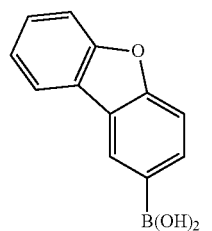

Intermediate 1-5
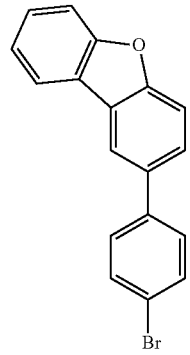

Intermediate 1-6
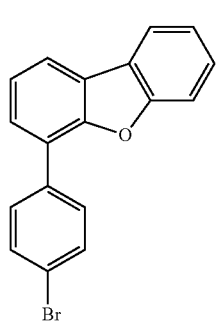

Intermediate 1-7
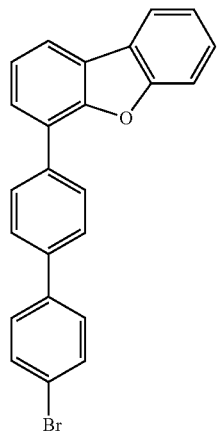

Intermediate 1-8
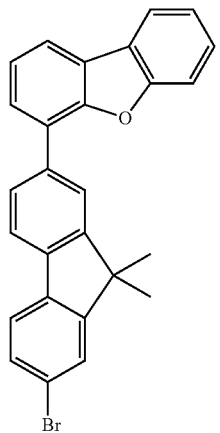

-continued
Intermediate 1-9
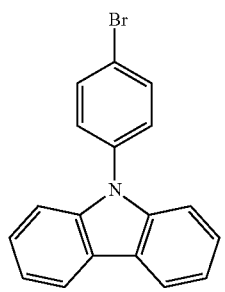
Intermediate 1-10
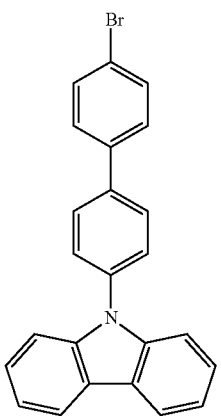
Intermediate 1-11
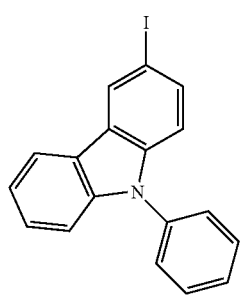
Intermediate 1-12
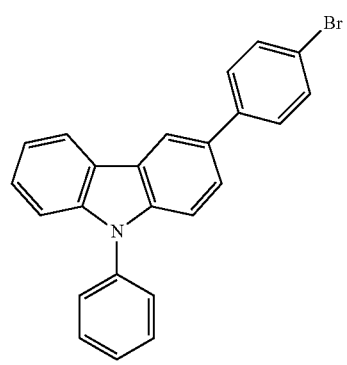
Intermediate 1-13
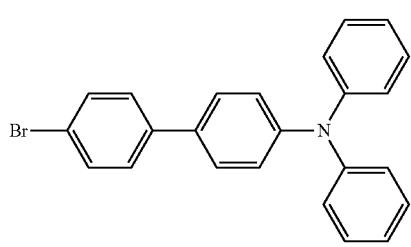
Intermediate 1-14
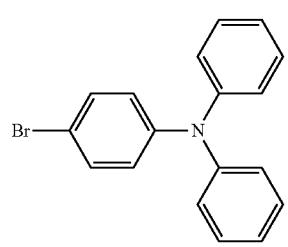
Intermediate 1-15
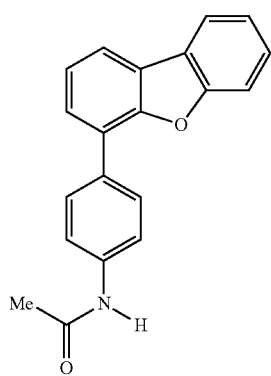

[Chem. 61]
Intermediate 1-16
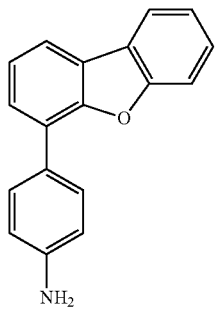
Intermediate 1-17
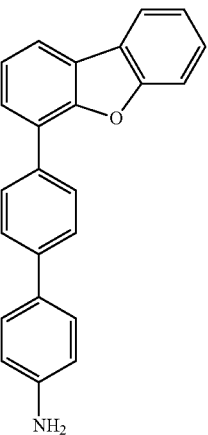
Intermediate 1-18
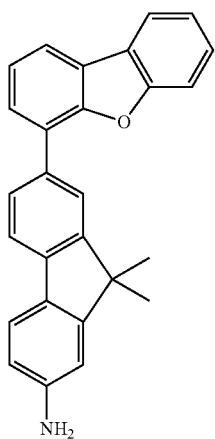
Intermediate 1-19
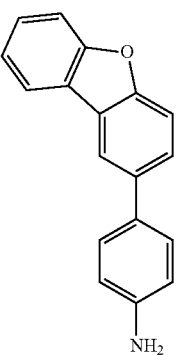
Intermediate 1-20
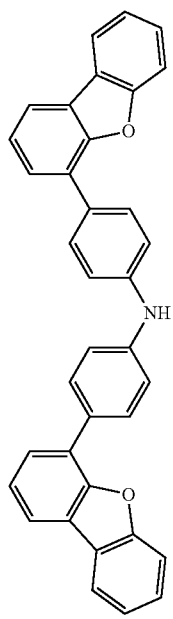
Intermediate 1-21
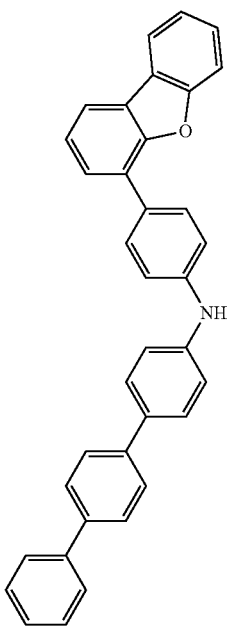

-continued
Intermediate 1-22
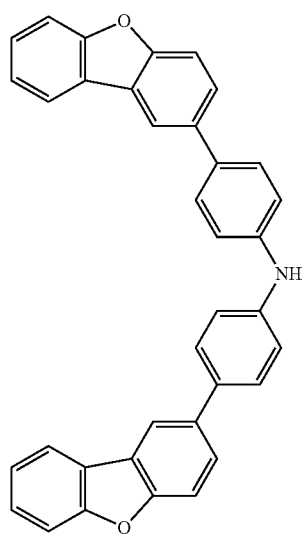
Intermediate 1-23
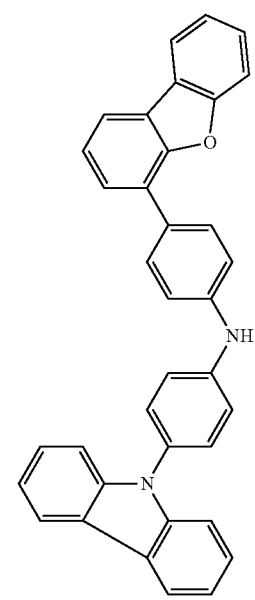
Intermediate 1-24
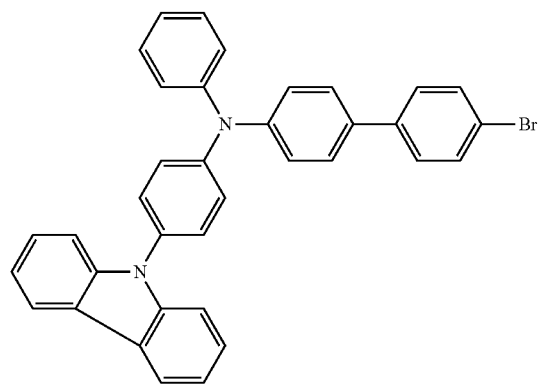
Intermediate 1-25
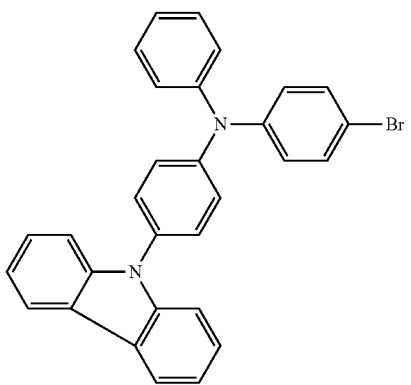
Intermediate 1-26
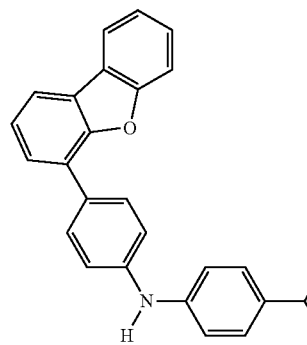
Intermediate 1-27
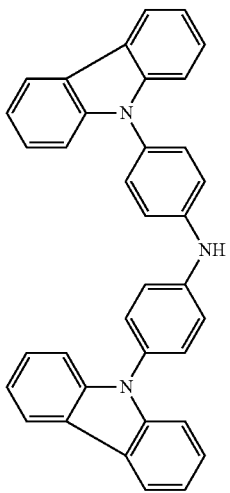

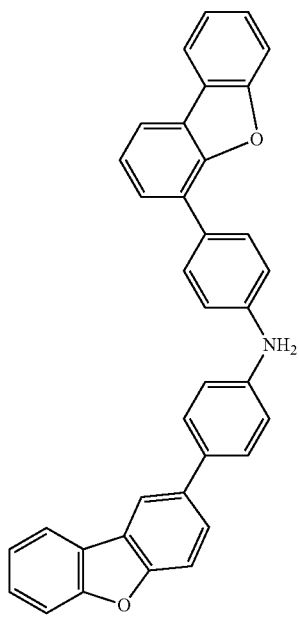
[Chem. 62]
Intermediate 1-28
Intermediate 1-29
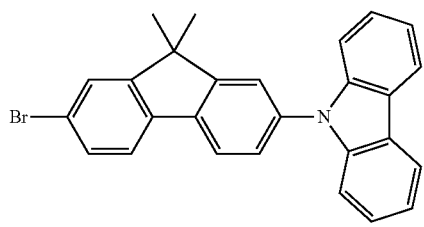
Intermediate 1-30
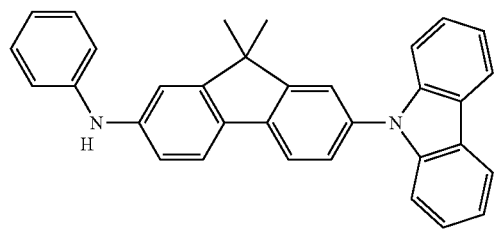
Intermediate 1-31
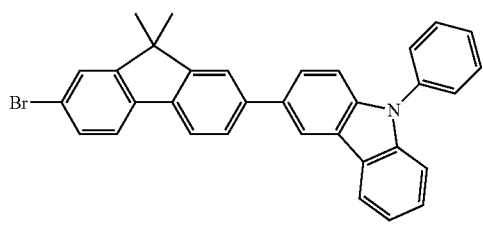
Intermediate 1-32
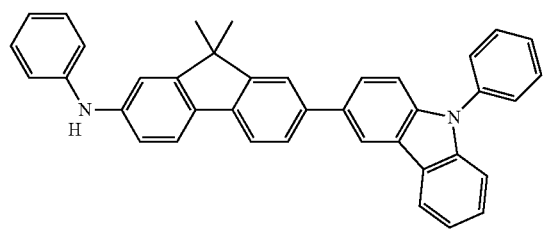
Intermediate 1-33
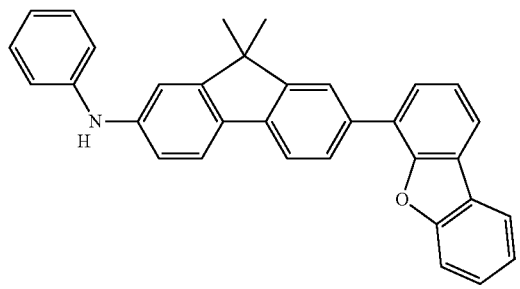
Intermediate 1-34
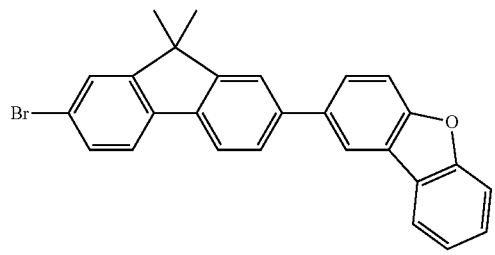

-continued
Intermediate 1-35
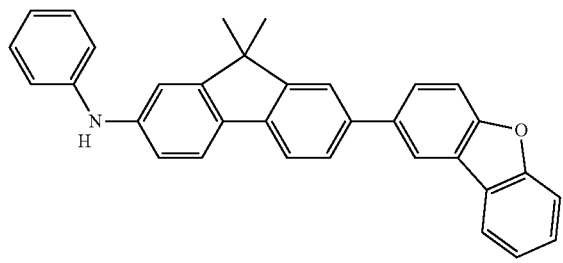
Intermediate 1-36
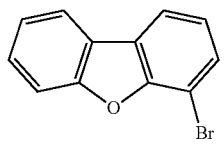
Intermediate 1-37
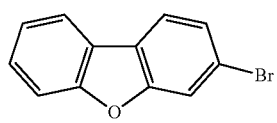
[Chem. 63]
1-H1
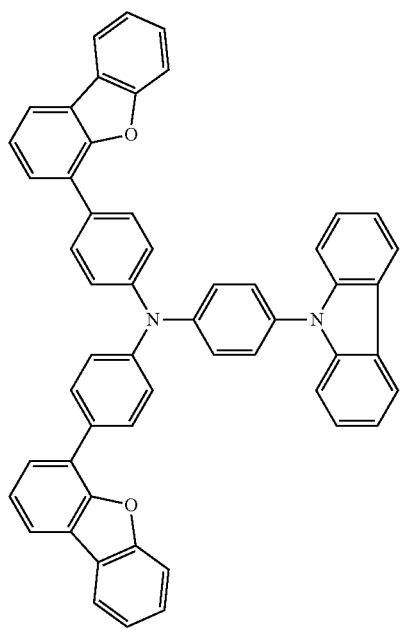
1-H2
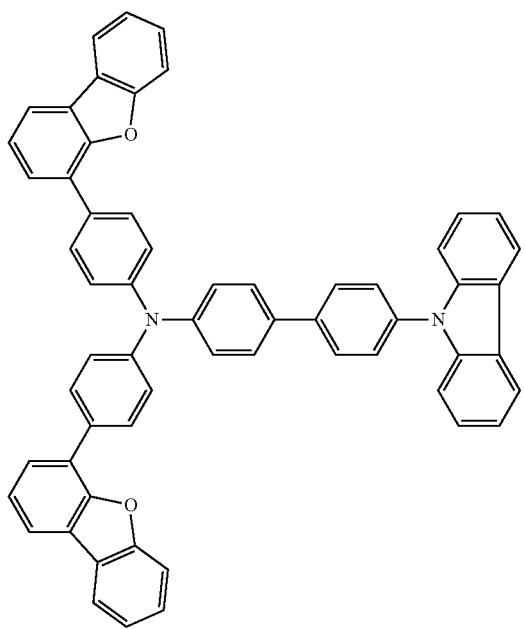

-continued
1-H3
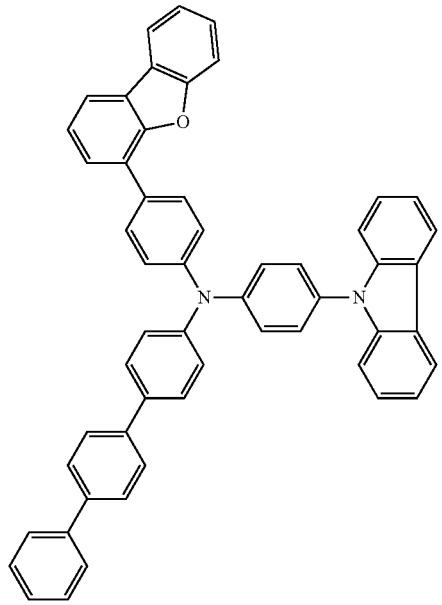
1-H4
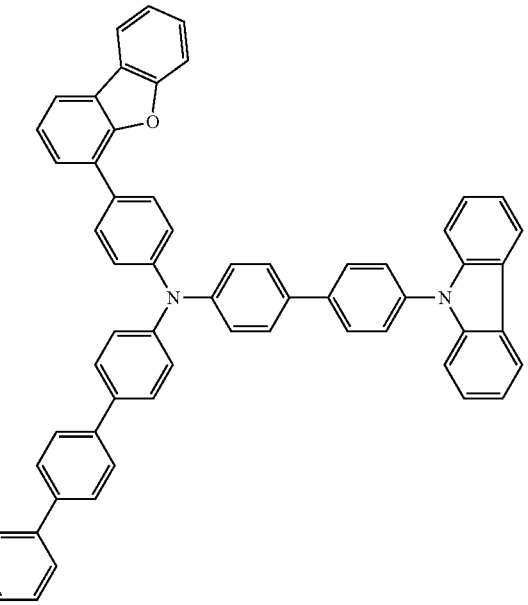
1-H5
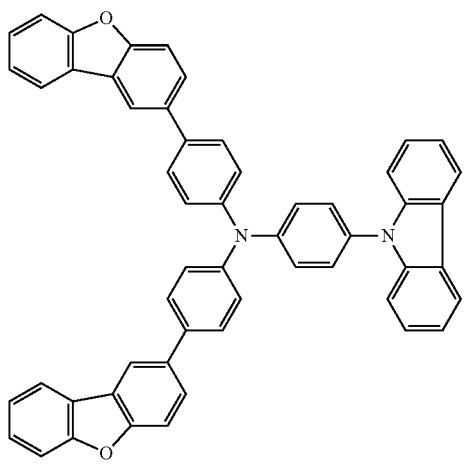
1-H6
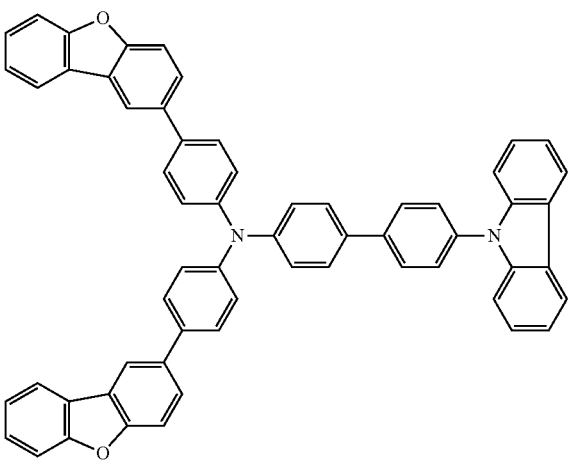
1-H7
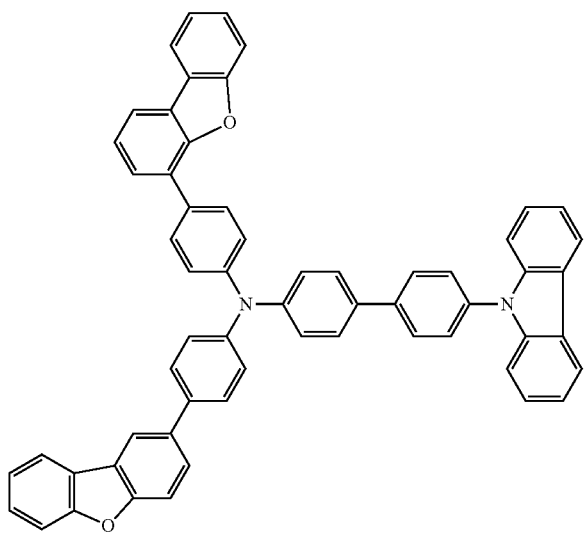
1-H8
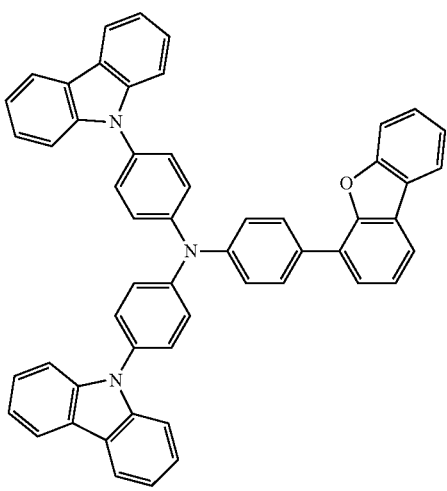

-continued
1-H9
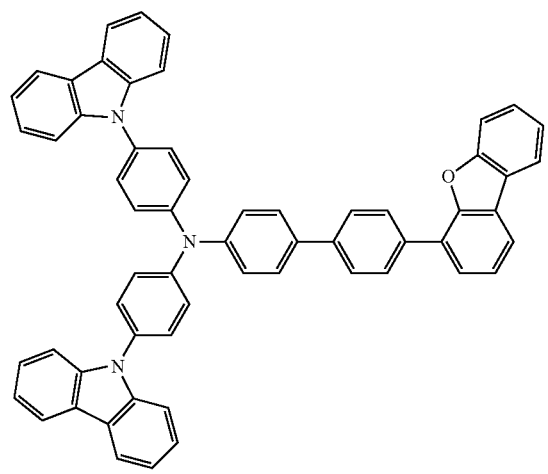
1-H10
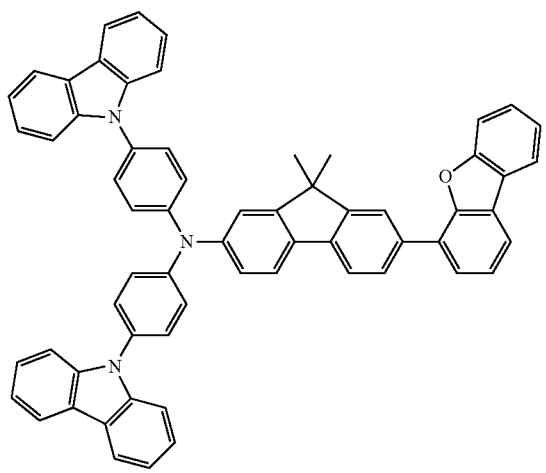
1-H11
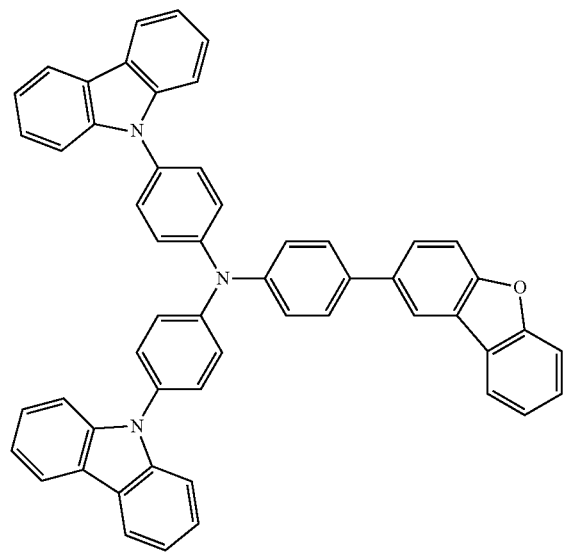
1-H12
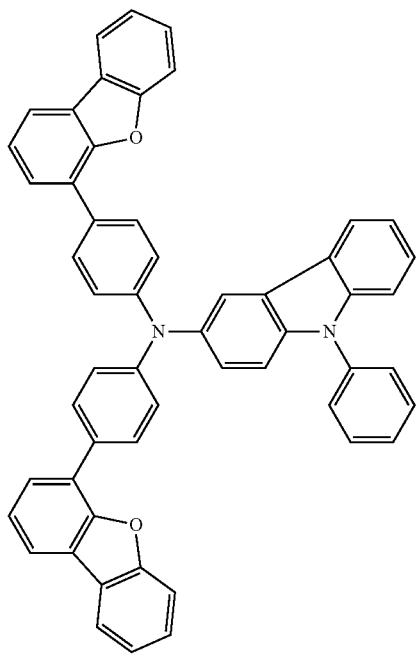

-continued
1-H13
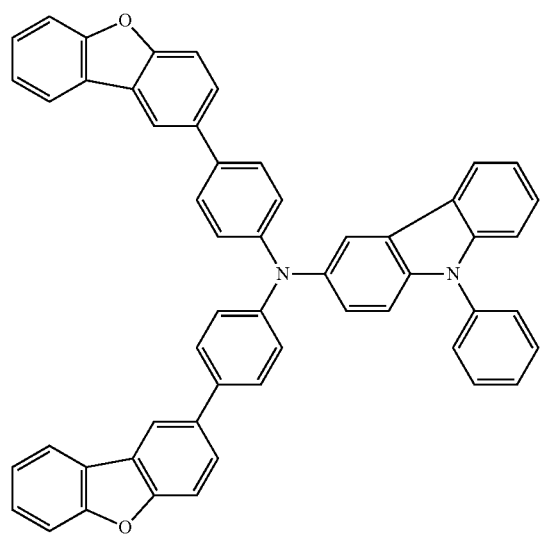
1-H14
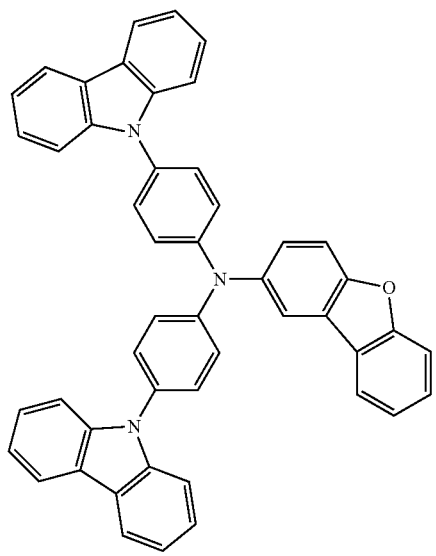
1-H15
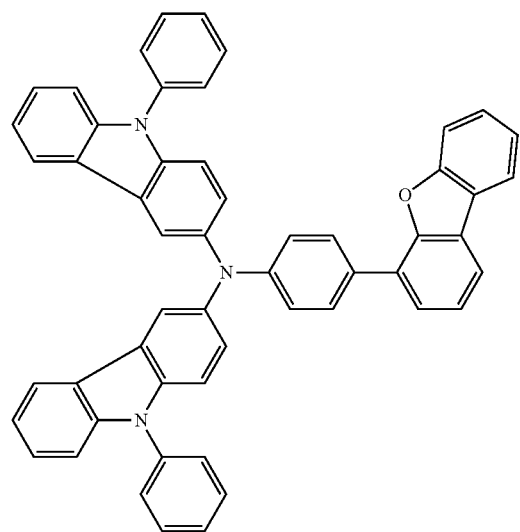

-continued
1-H16
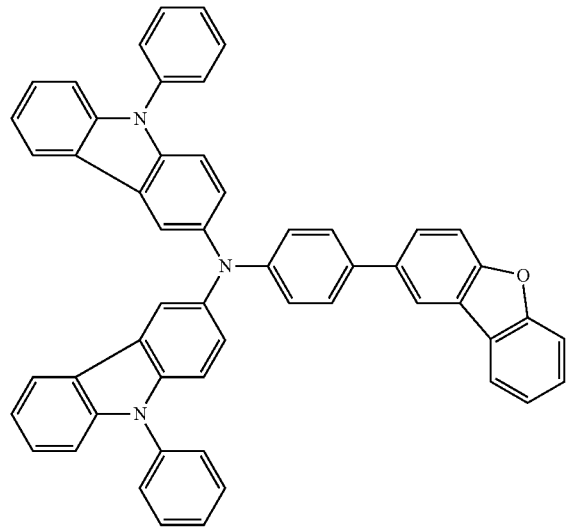
1-H17
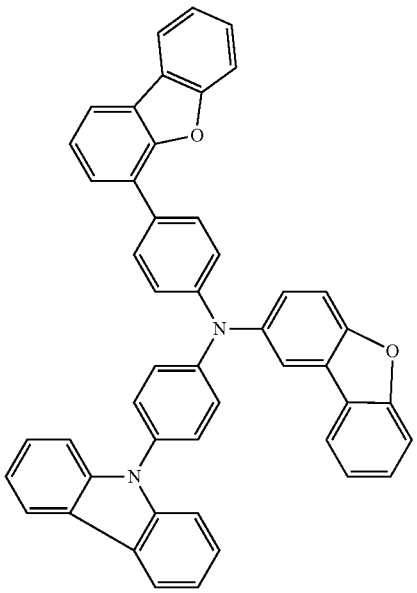
1-H18
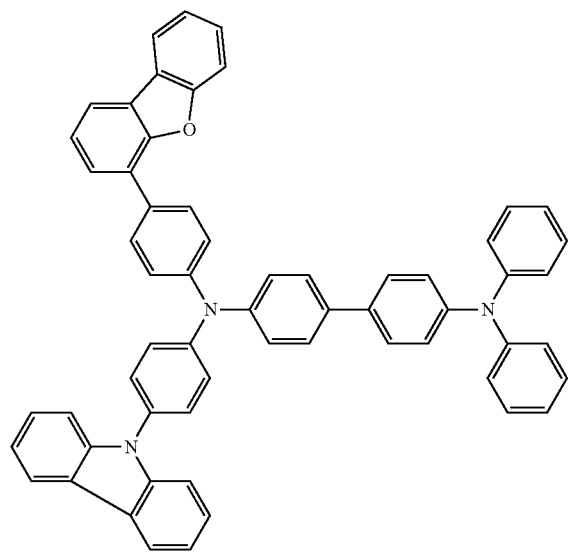
1-H19
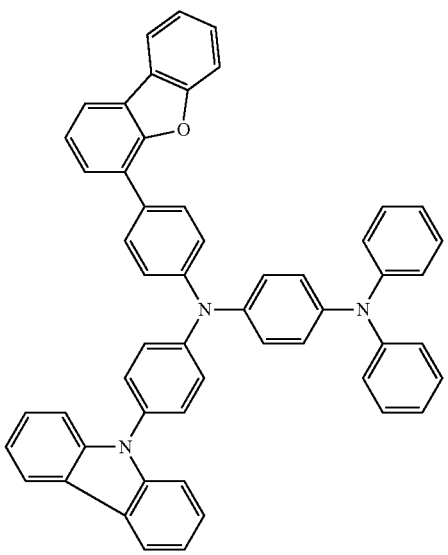

-continued
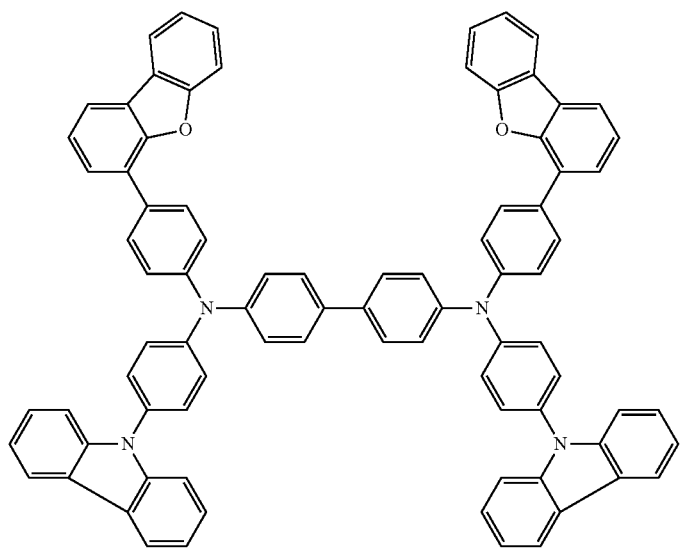
1-H20
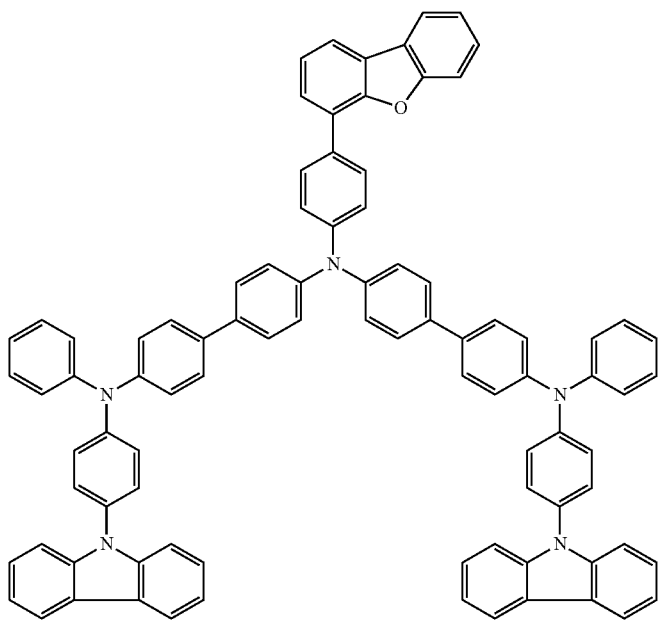
1-H21

-continued
1-H22
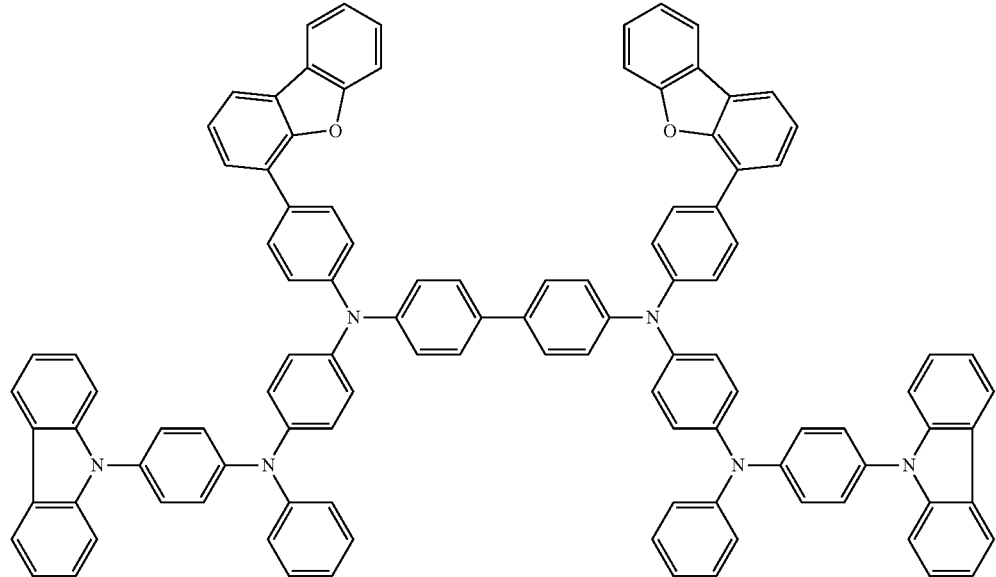
1-H23
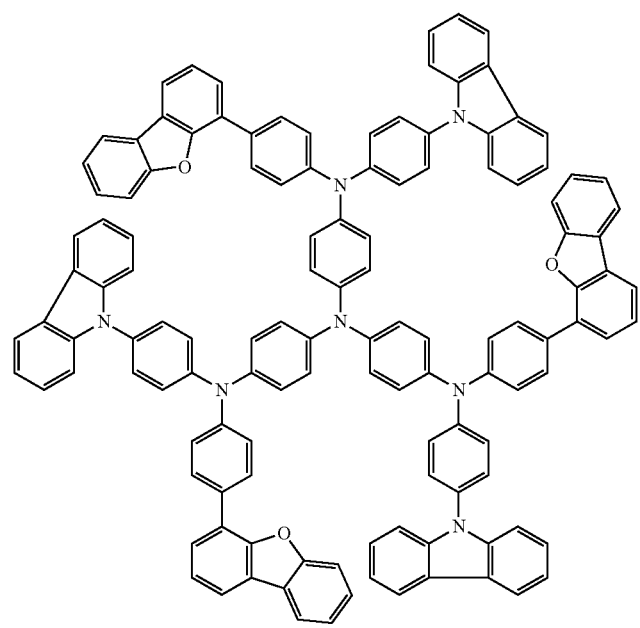

-continued
1-H24
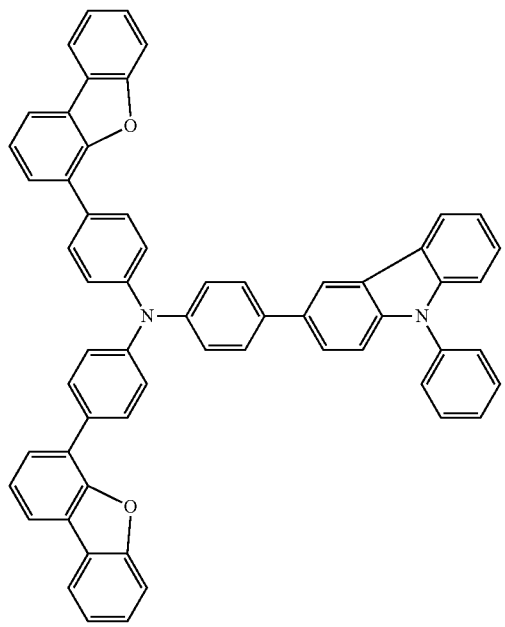
1-H25
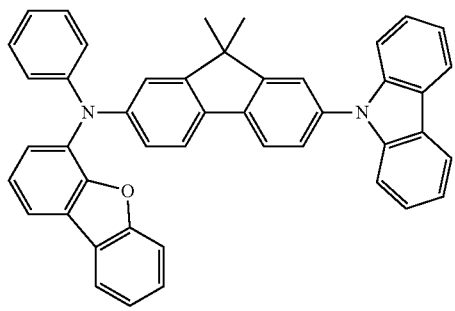
1-H26
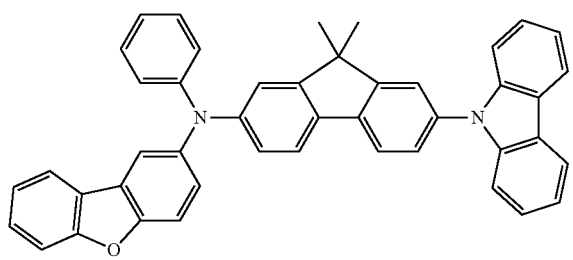
1-H27
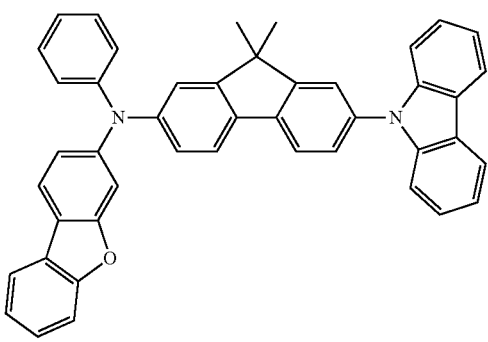
1-H28
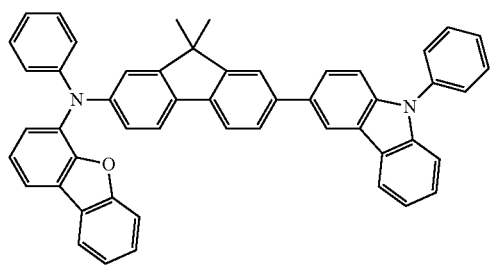
[Chem. 65]
1-H29
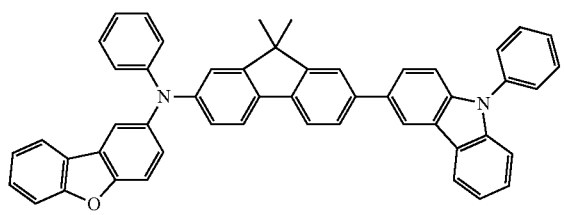
1-H30
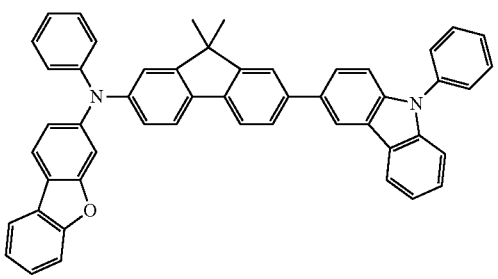

-continued
1-H31
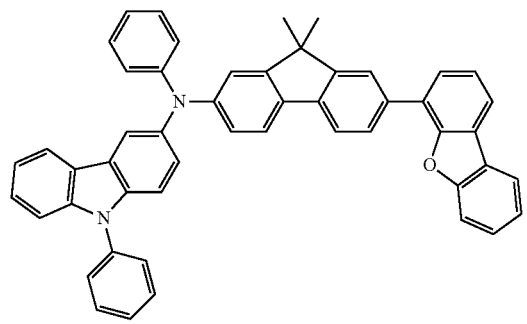
1-H32
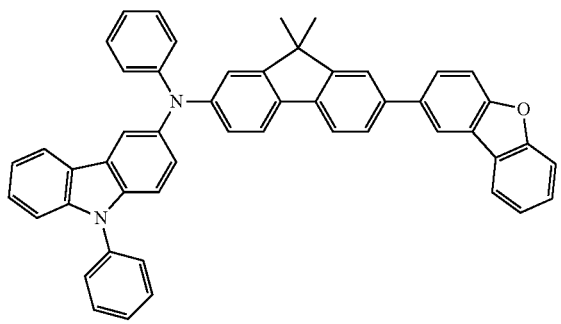
[Chem. 66]
Comparative compound 1-1
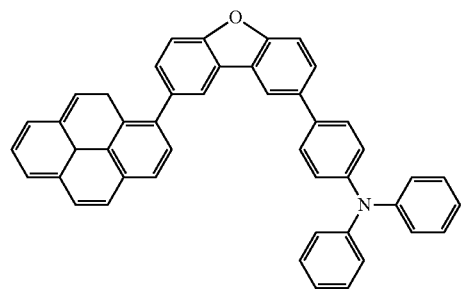
Comparative compound 1-2
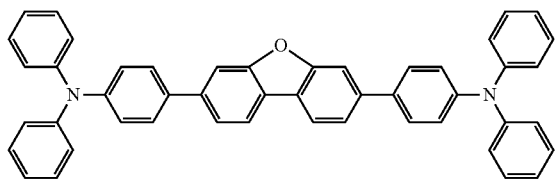
Comparative compound 1-3
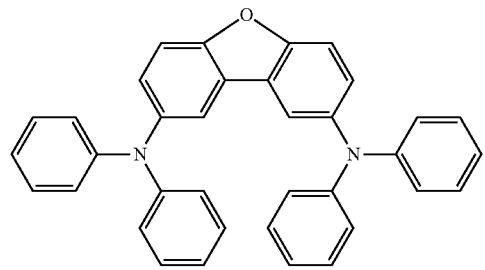
Comparative compound 1-4-
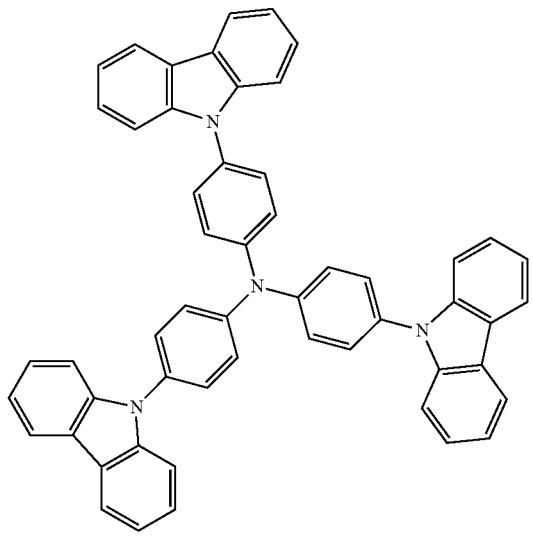

-continued

Comparative compound 1-5

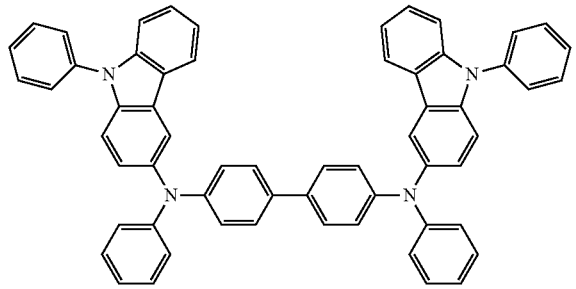

Comparative compound 1-6

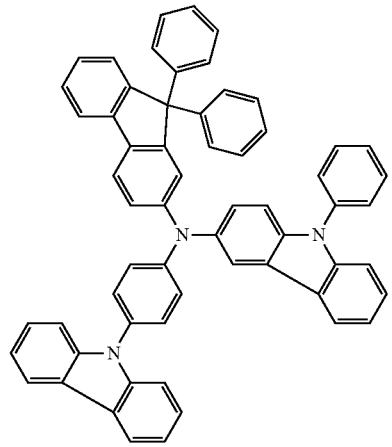

Example 1-1

Production of Organic EL Device

A glass substrate with an ITO transparent electrode measuring 25 mm wide by 75 mm long by 1.1 mm thick (manufactured by GEOMATEC Co., Ltd.) was subjected to ultrasonic cleaning in isopropyl alcohol for 5 minutes. After that, the substrate was subjected to UV ozone cleaning for 30 minutes.

The glass substrate with the transparent electrode line after the cleaning was mounted on a substrate holder of a vacuum vapor deposition device. First, the following compound H232 was deposited from vapor on the surface on the side where the transparent electrode line was formed so as to cover the transparent electrode. Then, the H232 film having a thickness of 60 nm was formed as the hole injecting layer. The above-mentioned compound 1-H1 was deposited from vapor and formed into a hole transporting layer having a thickness of 20 nm on the H232 film. Further, the following compound EM1 was deposited from vapor and formed into a light emitting layer having a thickness of 40 nm. Simultaneously with this formation, the following amine compound D1 having a styryl group, as a light emitting molecule, was deposited from vapor in such a manner that a weight ratio between the compound EM1 and the amine compound D1 was 40:2.

The following Alq was formed into a film having a thickness of 10 nm on the resultant film. The film functions as an electron injecting layer. After that, Li serving as a reducing dopant (Li source: manufactured by SAES Getters) and Alq were subjected to co-vapor deposition. Thus, an Alq:Li film (having a thickness of 10 nm) was formed as an electron injecting layer (cathode). Metal Al was deposited from vapor onto the Alq:Li film to form a metal cathode. Thus, an organic EL device was formed.

Next, after the resultant organic EL device had been stored at 105° C. for 8 hours, the luminous efficiency of the organic EL device was measured, and the luminescent color of the device was observed. A luminous efficiency at 10 mA/cm² was calculated by measuring a luminance by using a CS1000 manufactured by Minolta. Further, the half lifetime of emitted light in DC constant current driving at an initial luminance of 5,000 cd/m² and room temperature was measured. Table 1 shows the results.

[Chem. 67]

H232

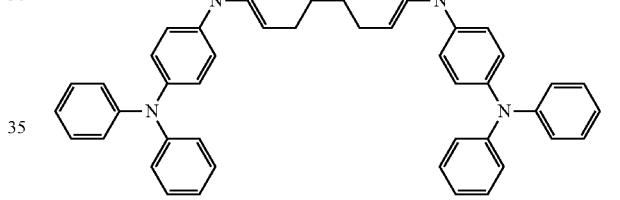

EM1

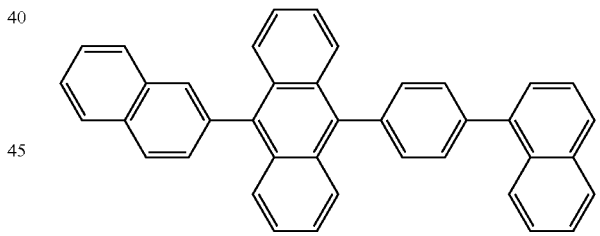

D1

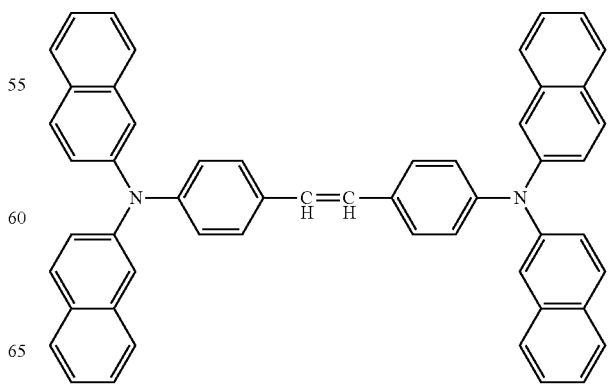

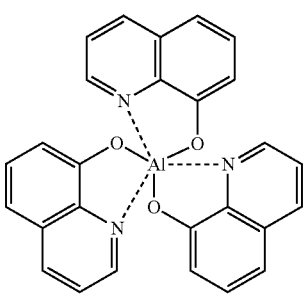

Alq

[Chem. 68]

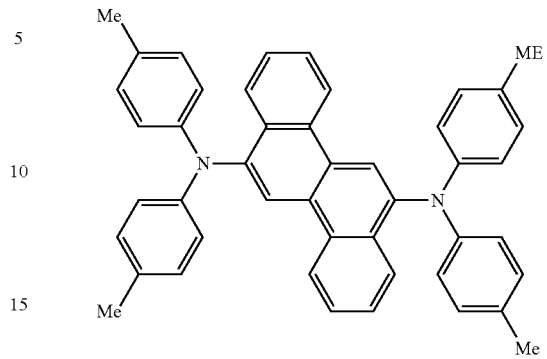

D2

Examples 1-2 to 1-11

Production of Organic EL Device

Each organic EL device was produced in the same manner as in Example 1-1 except that the respective compounds shown in Table 1 were used as hole transporting materials instead of the compound 1-H1.

The luminous efficiency of the resultant organic EL device was measured, and the luminescent color of the device was observed in the same manner as in Example 1-1. Further, the half lifetime of emitted light in DC constant current driving at an initial luminance of 5,000 cd/m$^2$ and room temperature was measured. Table 1 shows the results.

Comparative Examples 1-1 to 1-6

Each organic EL device was produced in the same manner as in Example 1-1 except that the respective comparative compounds 1-1 to 1-6 were used as hole transporting materials instead of the compound 1-H1.

Further, in the same manner as in Example 1-1, the luminous efficiency of the resultant organic EL device was measured, the luminescent color of the device was observed, and the half lifetime of emitted light in DC constant current driving at an initial luminance of 5,000 cd/m$^2$ and room temperature was measured. Table 1 shows the results.

Example 1-12

Production of Organic EL Device

An organic EL device was produced in the same manner as in Example 1-1 except that the following arylamine compound 1D2 was used instead of the amine compound D1 having a styryl group. Me represents a methyl group.

Further, in the same manner as in Example 1-1, the luminous efficiency of the resultant organic EL device was measured, the luminescent color of the device was observed, and the half lifetime of emitted light in DC constant current driving at an initial luminance of 5,000 cd/m$^2$ and room temperature was measured. Table 1 shows the results.

Comparative Example 1-7

An organic EL device was produced in the same manner as in Example 1-12 except that the above-mentioned comparative compound 1-4 was used as a hole transporting material instead of the compound 1-H1.

Further, in the same manner as in Example 1-1, the luminous efficiency of the resultant organic EL device was measured, the luminescent color of the device was observed, and the half lifetime of emitted light in DC constant current driving at an initial luminance of 5,000 cd/m$^2$ and room temperature was measured. Table 1 shows the results.

TABLE 1

| Example | Hole transporting material | Luminous efficiency (cd/A) | Luminescent color | Half lifetime (h) |
|---|---|---|---|---|
| 1-1 | 1-H1 | 6.2 | Blue | 380 |
| 1-2 | 1-H2 | 6.0 | Blue | 420 |
| 1-3 | 1-H3 | 6.1 | Blue | 390 |
| 1-4 | 1-H4 | 5.9 | Blue | 430 |
| 1-5 | 1-H5 | 6.4 | Blue | 360 |
| 1-6 | 1-H6 | 6.3 | Blue | 410 |
| 1-7 | 1-H7 | 5.7 | Blue | 430 |
| 1-8 | 1-H19 | 5.6 | Blue | 330 |
| 1-9 | 1-H25 | 6.4 | Blue | 370 |
| 1-10 | 1-H26 | 6.4 | Blue | 370 |
| 1-11 | 1-H27 | 6.4 | Blue | 370 |
| 1-12 | 1-H1 | 6.1 | Blue | 390 |
| Comparative Example 1-1 | Comparative Compound 1-1 | 3.1 | Blue | 100 |
| Comparative Example 1-2 | Comparative Compound 1-2 | 1.5 | Blue | 120 |
| Comparative Example 1-3 | Comparative Compound 1-3 | 1.2 | Blue | 60 |
| Comparative Example 1-4 | Comparative Compound 1-4 | 3.9 | Blue | 160 |
| Comparative Example 1-5 | Comparative Compound 1-5 | 5.2 | Blue | 150 |
| Comparative Example 1-6 | Comparative Compound 1-6 | 4.9 | Blue | 230 |
| Comparative Example 1-7 | Compound 1-4 | 4.1 | Blue | 130 |

As is apparent from the results of Table 1, an organic EL device using the aromatic amine derivative of the present invention provides high luminous efficiency even at high temperatures and has a long half lifetime as compared with an organic EL device using an aromatic amine derivative for comparison.

Synthesis Example 2-1

Synthesis of Intermediate 2-1

Under an argon stream, to a 1,000-mL three-necked flask, 47 g of 4-bromobiphenyl, 23 g of iodine, 9.4 g of periodic acid dihydrate, 42 mL of water, 360 mL of acetic acid, and 11 mL of sulfuric acid were charged, and the mixture was stirred at 65° C. for 30 minutes and was then subjected to a reaction at 90° C. for 6 hours. The reactant was poured into ice water, followed by filtering. The resultant was washed with water, and then washed with methanol, whereby 67 g of a white powder were obtained. Main peaks having ratios m/z of 358 and 360 with respect to $C_{12}H_8BrI=359$ were obtained by a field desorption mass spectrometry (hereinafter, FD-MS) analysis, so the white powder was identified as Intermediate 2-1.

Synthesis Example 2-2

Synthesis of Intermediate 2-2

A reaction was performed in the same manner as in Synthesis Example 2-1 except that 2-bromo-9,9-dimethylfluorene was used instead of 4-bromobiphenyl. As a result, 61 g of a white powder were obtained. The powder was identified as Intermediate 2-2 by FD-MS analysis because main peaks having ratios m/z of 398 and 400 were obtained with respect to $C_{15}H_{12}BrI=399$.

Synthesis Example 2-3

Synthesis of Intermediate 2-3

150 grams (892 mmol) of dibenzofuran and 1 L of acetic acid were loaded into a flask. The air in the flask was replaced with nitrogen, and then the contents were dissolved under heat. 188 grams (1.18 mol) of bromine were dropped to the solution while the flask was sometimes cooled with water. After that, the mixture was stirred for 20 hours under air cooling. The precipitated crystal was separated by filtration, and was then sequentially washed with acetic acid and water. The washed crystal was dried under reduced pressure. The resultant crystal was purified by distillation under reduced pressure, and was then repeatedly recrystallized with methanol several times. Thus, 66.8 g of 2-bromodibenzofuran were obtained (in 31% yield). The resultant was identified as Intermediate 2-3 by FD-MS analysis.

Synthesis Example 2-4

Synthesis of Intermediate 2-4

Under an argon atmosphere, 400 mL of anhydrous THF were added to 24.7 g (100 mmol) of 2-bromodibenzofuran, and then 63 mL (100 mmol) of a solution of n-butyllithium in hexane having a concentration of 1.6 M were added to the mixture during the stirring of the mixture at −40° C. The reaction solution was stirred for 1 hour while being heated to 0° C. The reaction solution was cooled to −78° C. again, and then a solution of 26.0 g (250 mmol) of trimethyl borate in 50 mL of dry THF was dropped to the solution. The reaction solution was stirred at room temperature for 5 hours. 200 milliliters of 1N hydrochloric acid were added to the solution, and then the mixture was stirred for 1 hour. After that, the aqueous layer was removed. The organic layer was dried with magnesium sulfate, and then the solvent was removed by distillation under reduced pressure. The resultant solid was washed with toluene. Thus, 15.2 g of dibenzofuran-2-boronic acid were obtained (in 72% yield). The resultant was identified as Intermediate 2-4 by FD-MS analysis because a main peak having a ratio m/z of 212 was obtained with respect to $C_{12}H_9BO_3=212$.

Synthesis Example 2-5

Synthesis of Intermediate 2-5

Under an argon atmosphere, 300 mL of toluene and 150 mL of an aqueous solution of sodium carbonate having a concentration of 2 M were added to 28.3 g (100 mmol) of 4-iodobromobenzene, 22.3 g (105 mmol) of dibenzofuran-2-boronic acid (Intermediate 2-4), and 2.31 g (2.00 mmol) of tetrakis(triphenylphosphine)palladium(0), and then the mixture was heated while being refluxed for 10 hours. Immediately after the completion of the reaction, the resultant was filtrated, and then the aqueous layer was removed. The organic layer was dried with sodium sulfate, and was then concentrated. The residue was purified by silica gel column chromatography. Thus, 26.2 g of a white crystal of 4-(4-bromophenyl)dibenzofuran were obtained (in 81% yield). The crystal was identified as Intermediate 2-5 by FD-MS analysis.

Synthesis Example 2-6

Synthesis of Intermediate 2-6

A reaction was performed in the same manner as in Synthesis Example 2-5 except that 35.9 g of Intermediate 2-1 were used instead of 4-iodobromobenzene. As a result, 28.1 g, of a white powder were obtained. The powder was identified as Intermediate 2-6 by FD-MS analysis.

Synthesis Example 2-7

Synthesis of Intermediate 2-7

A reaction was performed in the same manner as in Synthesis Example 2-5 except that 39.9 g of Intermediate 2-2 were used instead of 4-iodobromobenzene. As a result, 27.5 g of a white powder were obtained. The powder was identified as Intermediate 2-7 by FD-MS analysis.

Synthesis Example 2-8

Synthesis of Intermediate 2-8

A reaction was performed in the same manner as in Synthesis Example 2-5 except that 22.3 g of dibenzofuran-4-boronic acid were used instead of dibenzofuran-2-boronic acid. As a result, 23.1 g of a white powder were obtained. The powder was identified as Intermediate 2-8 by FD-MS analysis.

Synthesis Example 2-9

Synthesis of Intermediate 2-9

A reaction was performed in the same manner as in Synthesis Example 2-8 except that 36 g of Intermediate 2-1 were used instead of 4-iodobromobenzene. As a result, 28.1 g of a white powder were obtained. The powder was identified as Intermediate 2-9 by FD-MS analysis.

Synthesis Example 2-10

Synthesis of Intermediate 2-10

A reaction was performed in the same manner as in Synthesis Example 2-8 except that 40 g of Intermediate 2-2 were used instead of 4-iodobromobenzene. As a result, 30.2 g of a white powder were obtained. The powder was identified as Intermediate 2-10 by FD-MS analysis.

Synthesis Example 2-11

Synthesis of Intermediate 2-11

In a stream of argon, 16.8 g of diphenylamine, 36.0 g of Intermediate 2-1, 10 g of t-butoxy sodium (manufactured by Hiroshima Wako Ltd.), 1.6 g of bis(triphenylphosphine)palladium(II) chloride (manufactured by TOKYO CHEMICAL INDUSTRY CO., LTD.), and 500 mL of xylene were loaded and subjected to a reaction at 130° C. for 24 hours.

After the resultant had been cooled, 1,000 mL of water were added to the resultant, and then the mixture was filtrated with celite. The filtrate was extracted with toluene, and was then dried with anhydrous magnesium sulfate. The dried product was concentrated under reduced pressure. The resultant coarse product was subjected to column purification, and was then recrystallized with toluene. The crystal was taken by filtration, and was then dried. As a result, 12.4 g of a pale yellow powder were obtained. The powder was identified as Intermediate 2-11 by FD-MS analysis.

Synthesis Example 2-12

Synthesis of Intermediate 2-12

A reaction was performed in the same manner as in Synthesis Example 2-11 except that 4-iodobromobenzene was used instead of Intermediate 2-1. As a result, 9.3 g of a white powder were obtained. The powder was identified as Intermediate 2-12 by FD-MS analysis.

Synthesis Example 2-13

Synthesis of Intermediate 2-13

In a stream of argon, 185 g of 1-acetamide (manufactured by TOKYO CHEMICAL INDUSTRY CO., LTD.), 323 g of Intermediate 2-8 (manufactured by Wako Pure Chemical Industries, Ltd.), 544 g of potassium carbonate (manufactured by Wako Pure Chemical Industries, Ltd.), 12.5 g of a copper powder (manufactured by Wako Pure Chemical Industries, Ltd.), and 2 L of decalin were loaded and subjected to a reaction at 190° C. for 4 days. After the reaction, the resultant was cooled, and then 2 L of toluene were added to the resultant. The insoluble portion was taken by filtration. The product taken by filtration was dissolved in 4.5 L of chloroform, and then the insoluble portion was removed. After that, the remainder was subjected to an activated carbon treatment and concentrated. 3 liters of acetone were added to the resultant, and then 181 g of the precipitated crystal were taken by filtration. The crystal was identified as Intermediate 2-13 by FD-MS analysis.

Synthesis Example 2-14

Synthesis of Intermediate 2-14

A reaction was performed in the same manner as in Synthesis Example 2-13 except that the usage of Intermediate 2-8 was changed from 323 g to 678 g. As a result, 330 g of a white powder were obtained. Further, in a stream of argon, the resultant white powder was suspended in 5 L of ethylene glycol (manufactured by Wako Pure Chemical Industries, Ltd.) and 50 mL of water, and then 210 g of an 85% aqueous solution of potassium hydroxide were added to the suspension. After that, the mixture was subjected to a reaction at 120° C. for 8 hours. After the reaction, the reaction liquid was injected into 10 L of water, and then the precipitated crystal was taken by filtration. The crystal was washed with water and methanol. The resultant crystal was dissolved in 3 L of tetrahydrofuran under heat. The solution was subjected to an activated carbon treatment, and was then concentrated. Acetone was added to the resultant to precipitate a crystal. The crystal was taken by filtration. Thus, 198 g of a white powder were obtained. The powder was identified as Intermediate 2-14 by FD-MS analysis.

Synthesis Example 2-15

Synthesis of Intermediate 2-15

A reaction was performed in the same manner as in Synthesis Example 2-14 except that Intermediate 2-5 was used instead of Intermediate 2-8. As a result, 221 g of a white powder were obtained. The powder was identified as Intermediate 2-15 by FD-MS analysis.

Synthesis Example 2-16

Synthesis of Intermediate 2-16

A reaction was performed in the same manner as in Synthesis Example 2-13 except that: Intermediate 2-13 was used instead of 1-acetamide; and Intermediate 2-5 was used instead of Intermediate 2-8. As a result, 190 g of a white powder were obtained. The powder was identified as Intermediate 2-16 by FD-MS analysis.

Synthesis Example 2-17

Synthesis of Intermediate 2-17

A reaction was performed in the same manner as in Synthesis Example 2-11 except that: Intermediate 2-16 was used instead of diphenylamine; and 4-iodobromobenzene was used instead of Intermediate 2-1. As a result, 45 g of a white powder were obtained. The powder was identified as Intermediate 2-17 by FD-MS analysis.

Synthesis Example 2-18

Synthesis of Intermediate 2-18

A reaction was performed in the same manner as in Synthesis Example 2-11 except that Intermediate 2-16 was used instead of diphenylamine. As a result, 56 g of a white powder were obtained. The powder was identified as Intermediate 2-18 by FD-MS analysis.

Synthesis Example 2-19

Synthesis of Intermediate 2-19

Under an argon atmosphere, 600 mL of dry tetrahydrofuran were added to 78.0 g of dibenzofuran, and then the mixture was cooled to −30° C. 300 milliliters of a solution of n-butyllithium in hexane (1.65 M) were dropped to the mixture, and then the temperature of the whole was increased to room temperature over 1 hour while the whole was stirred. After having been stirred at room temperature for 5 hours, the resultant was cooled to −60° C., and then 60 mL of 1,2-dibromoethane were dropped to the resultant over 1 hour.

After having been stirred at room temperature for 15 hours, the mixture was poured into 1,000 mL of ice water, and then the organic layer was extracted with dichloromethane. The organic layer was washed with a saturated salt solution, and was then dried with anhydrous magnesium sulfate. The dried product was separated by filtration, and was then concentrated. The resultant solid was purified by silica gel chromatography (toluene), washed with tetrahydrofuran and methanol, and dried under reduced pressure. As a result, 70 g of a solid were obtained. The solid was identified as Intermediate 2-19 by FD-MS analysis.

Synthesis Example 2-20

Synthesis of Intermediate 2-20

Under an argon atmosphere, 1,000 mL of toluene and 500 mL of an aqueous solution of sodium carbonate having a concentration of 2M were added to 120.0 g (399 mmol) of 1-bromo-3-fluoro-4-iodobenzene, 72.7 g (479 mmol) of 2-methoxyphenyl boronic acid, and 9.2 g (7.96 mmol) of tetrakis(triphenylphosphine)palladium(0), and then the mixture was heated while being refluxed for 10 hours.

Immediately after the completion of the reaction, the resultant was filtrated, and then the aqueous layer was removed. The organic layer was dried with sodium sulfate, and was then concentrated. The residue was purified by silica gel column chromatography. Thus, 89.6 g of a white crystal of 4-bromo-2-fluoro-2'-methoxybiphenyl were obtained (in 80% yield).

Under an argon atmosphere, 900 mL of dichloromethane were added to 89.6 g (319 mmol) of 4-bromo-2-fluoro-2'-methoxybiphenyl, and then the mixture was stirred under ice cooling. 95.9 g (382 mmol) of boron tribromide were added dropwise to the mixture, and then the whole was stirred at room temperature for 12 hours. After the completion of the reaction, 200 mL of water were added to the resultant, and then the mixture was stirred for 1 hour. After that, the aqueous layer was removed. The organic layer was dried with magnesium sulfate, and was then concentrated. The residue was purified by silica gel column chromatography. Thus, 68.1 g of a white crystal of 4-bromo-2-fluoro-2'-hydroxybiphenyl were obtained (in 70% yield).

1,500 milliliters of N-methylpyrrolidone were added to 68.1 g (255 mmol) of 4-bromo-2-fluoro-2'-hydroxybiphenyl and 70.4 g (510 mmol) of potassium carbonate, and then the mixture was stirred at 180° C. for 3 hours. After the completion of the reaction, water was added to the resultant, and then extract ion with toluene was performed. The organic layer was dried with sodium sulfate, and was then concentrated. The residue was recrystallized from toluene so as to be purified. Thus, 44.2 g of a white crystal were obtained (in 60% yield). The crystal was identified as Intermediate 2-20 by FD-MS analysis.

Synthesis Example 2-21

Synthesis of Intermediate 2-21

Under an argon atmosphere, 350 mL of toluene and 170 mL of an aqueous solution of sodium carbonate having a concentration of 2 M were added to 34.2 g (138 mmol) of Intermediate 2-20, 26.0 g (166 mmol) of 4-chlorophenyl boronic acid, and 3.2 g (2.77 mmol) of tetrakis(triphenylphosphine)palladium(0), and then the mixture was heated while being refluxed for 12 hours.

Immediately after the completion of the reaction, the resultant was filtrated, and then the aqueous layer was removed. The organic layer was dried with sodium sulfate, and was then concentrated. The residue was purified by silica gel column chromatography. Thus, 23.1 g of a white crystal were obtained (in 60% yield). The crystal was identified as Intermediate 2-21 by FD-MS analysis.

Synthesis Example 2-22

Synthesis of Intermediate 2-22

A reaction was performed in the same manner as in Synthesis Example 2-14 except that Intermediate 2-21 was used instead of Intermediate 2-8. As a result, 35 g of a white powder were obtained. The powder was identified as Intermediate 2-22 by FD-MS analysis.

Synthesis Embodiment 2-1

Synthesis of Compound 2-H1

In a stream of argon, 5.0 g of Intermediate 2-14, 3.2 g of Intermediate 2-5, 1.3 g of t-butoxy sodium (manufactured by Hiroshima Wako Ltd.), 46 mg of tris(dibenzylideneacetone)dipalladium(0) (manufactured by Sigma Aldrich Co.), 21 mg of tri-t-butylphosphine, and 50 mL of dry toluene were loaded and subjected to a reaction at 80° C. for 8 hours.

After the resultant had been cooled, 500 mL of water were added to the resultant, and then the mixture was filtrated with celite. The filtrate was extracted with toluene, and was then dried with anhydrous magnesium sulfate. The dried product was concentrated under reduced pressure. The resultant coarse product was subjected to column purification, and was then recrystallized with toluene. The crystal was taken by filtration, and was then dried. As a result, 4.3 g of a pale yellow powder were obtained. The powder was identified as Intermediate 2-H1 by FD-MS analysis.

Synthesis Embodiment 2-2

Synthesis of Compound 2-H2

A reaction was performed in the same manner as in Synthesis Embodiment 2-1 except that 4.0 g of Intermediate 2-6 were used instead of Intermediate 2-5. As a result, 5.3 g of a pale yellow powder were obtained. The powder was identified as Compound 2-H2 by FD-MS analysis.

Synthesis Embodiment 2-3

Synthesis of Compound 2-H3

A reaction was performed in the same manner as in Synthesis Embodiment 2-1 except that 4.9 g of Intermediate 2-7 were used instead of Intermediate 2-5. As a result, 4.4 g of a pale yellow powder were obtained. The powder was identified as Compound 2-H3 by FD-MS analysis.

Synthesis Embodiment 2-4

Synthesis of Compound 2-H4

A reaction was performed in the same manner as in Synthesis Embodiment 2-1 except that: 5.0 g of Intermediate 2-15 were used instead of Intermediate 2-14; and 3.2 g of Intermediate 2-8 were used instead of Intermediate 2-5. As a result, 3.8 g of a pale yellow powder were obtained. The powder was identified as Compound 2-H4 by FD-MS analysis.

Synthesis Embodiment 2-5

Synthesis of Compound 2-H5

Synthesis Embodiment 2-5

Synthesis of Compound 2-H5

A reaction was performed in the same manner as in Synthesis Embodiment 2-4 except that 4.0 g of Intermediate 2-9 were used instead of Intermediate 2-8. As a result, 4.2 g of a pale yellow powder were obtained. The powder was identified as Compound 2-H5 by FD-MS analysis.

Synthesis Embodiment 2-6

Synthesis of Compound 2-H6

A reaction was performed in the same manner as in Synthesis Embodiment 2-4 except that 4.4 g of Intermediate 2-10 were used instead of Intermediate 2-8. As a result, 5.1 g of a pale yellow powder were obtained. The powder was identified as Compound 2-H6 by FD-MS analysis.

Synthesis Embodiment 2-7

Synthesis of Compound 2-H7

A reaction was performed in the same manner as in Synthesis Embodiment 2-1 except that 4.0 g of Intermediate 2-9 were used instead of Intermediate 2-5. As a result, 4.5 g of a pale yellow powder were obtained. The powder was identified as Compound 2-H7 by FD-MS analysis.

Synthesis Embodiment 2-8

Synthesis of Compound 2-H8

A reaction was performed in the same manner as in Synthesis Embodiment 2-4 except that 4.0 g of Intermediate 2-6 were used instead of Intermediate 2-8. As a result, 4.2 g of a pale yellow powder were obtained. The powder was identified as Compound 2-H8 by FD-MS analysis.

Synthesis Embodiment 2-9

Synthesis of Compound 2-H9

A reaction was performed in the same manner as in Synthesis Embodiment 2-1 except that: 5.0 g of Intermediate 2-16 were used instead of Intermediate 2-14; and 3.2 g of Intermediate 2-12 were used instead of Intermediate 2-5. As a result, 3.8 g of a pale yellow powder were obtained. The powder was identified as Compound 2-H9 by FD-MS analysis.

Synthesis Embodiment 2-10

Synthesis of Compound 2-H10

A reaction was performed in the same manner as in Synthesis Embodiment 2-1 except that: 1.9 g of Intermediate 2-16 were used instead of Intermediate 2-14; and 4.0 g of Intermediate 2-11 were used instead of Intermediate 2-5. As a result, 4.5 g of a pale yellow powder were obtained. The powder was identified as Compound 2-H10 by FD-MS analysis.

Synthesis Embodiment 2-11

Synthesis of Compound 2-H11

A reaction was performed in the same manner as in Synthesis Embodiment 2-1 except that: 5.0 g of Intermediate 2-16 were used instead of Intermediate 2-14; and 1.6 g of 4,4'-dibromobiphenyl were used instead of Intermediate 2-5. As a result, 2.8 g of a pale yellow powder were obtained. The powder was identified as Compound 2-H11 by FD-MS analysis.

Synthesis Embodiment 2-12

Synthesis of Compound 2-H12

A reaction was performed in the same manner as in Synthesis Embodiment 2-1 except that: 0.4 g of aniline was used instead of Intermediate 2-14; and 7.3 g of Intermediate 2-18 were used instead of Intermediate 2-5. As a result, 2.1 g of a pale yellow powder were obtained. The powder was identified as Compound 2-H12 by FD-MS analysis.

Synthesis Embodiment 2-13

Synthesis of Compound 2-H13

A reaction was performed in the same manner as in Synthesis Embodiment 2-1 except that: 0.9 g of N,N'-diphenylbenzidine was used instead of Intermediate 2-14; and 6.6 g of Intermediate 2-17 were used instead of Intermediate 2-5. As a result, 2.4 g of a pale yellow powder were obtained. The powder was identified as Compound 2-H13 by FD-MS analysis.

Synthesis Embodiment 2-14

Synthesis of Compound 2-H14

A reaction was performed in the same manner as in Synthesis Embodiment 2-1 except that: 5.0 g of Intermediate 2-16 were used instead of Intermediate 2-14; and 1.6 g of tris(4-bromophenyl)amine were used instead of Intermediate 2-5. As a result, 1.8 g of a pale yellow powder were obtained. The powder was identified as Compound 2-H14 by FD-MS analysis.

Synthesis Embodiment 2-15

Synthesis of Compound 2-H15

A reaction was performed in the same manner as in Synthesis Embodiment 2-1 except that: 5.0 g of Intermediate 2-16 were used instead of Intermediate 2-14; and 3.0 g of 4-bromo-p-terphenyl were used instead of Intermediate 2-5. As a result, 3.5 g of a pale yellow powder were obtained. The powder was identified as Compound 2-H15 by FD-MS analysis.

Synthesis Embodiment 2-16

Synthesis of Compound 2-H16

A reaction was performed in the same manner as in Synthesis Embodiment 2-1 except that 2.5 g of Intermediate 2-3 were used instead of Intermediate 2-5. As a result, 4.1 g of a pale yellow powder were obtained. The powder was identified as Compound 2-H16 by FD-MS analysis.

Synthesis Embodiment 2-17

Synthesis of Compound 2-H17

A reaction was performed in the same manner as in Synthesis Embodiment 2-1 except that 2.5 g of Intermediate 2-20 were used instead of Intermediate 2-5. As a result, 3.9 g of a pale yellow powder were obtained. The powder was identified as Compound 2-H17 by FD-MS analysis.

Synthesis Embodiment 2-18

Synthesis of Compound 2-H18

A reaction was performed in the same manner as in Synthesis Embodiment 2-1 except that: 5.0 g of Intermediate 2-15 were used instead of Intermediate 2-14; and 2.5 g of Intermediate 2-19 were used instead of Intermediate 2-5. As a result, 3.8 g of a pale yellow powder were obtained. The powder was identified as Compound 2-H18 by FD-MS analysis.

Synthesis Embodiment 2-19

Synthesis of Compound 2-H19

A reaction was performed in the same manner as in Synthesis Embodiment 2-1 except that: 5.0 g of Intermediate 2-15 were used instead of Intermediate 2-14; and 2.5 g of Intermediate 2-20 were used instead of Intermediate 2-5. As a result, 3.6 g of a pale yellow powder were obtained. The powder was identified as Compound 2-H19 by FD-MS analysis.

Synthesis Embodiment 2-20

Synthesis of Compound 2-H20

A reaction was performed in the same manner as in Synthesis Embodiment 2-1 except that: 5.0 g of Intermediate 2-22 were used instead of Intermediate 2-14; and 2.5 g of Intermediate 2-19 were used instead of Intermediate 2-5. As a result, 4.0 g of a pale yellow powder were obtained. The powder was identified as Compound 2-H20 by FD-MS analysis.

Synthesis Embodiment 2-21

Synthesis of Compound 2-H21

A reaction was performed in the same manner as in Synthesis Embodiment 2-1 except that: 5.0 g of Intermediate 2-22 were used instead of Intermediate 2-14; and 2.5 g of Intermediate 2-3 were used instead of Intermediate 2-5. As a result, 4.1 g of a pale yellow powder were obtained. The powder was identified as Compound 2-H21 by FD-MS analysis.

The structural formulae of Intermediates 2-1 to 2-22 synthesized in Synthesis Examples 2-1 to 2-22 described above, Compounds 2-H1 to 2-H21 synthesized in Synthesis Embodiments 2-1 to 2-21 each serving as the aromatic amine derivative of the present invention, and Comparative Compounds 2-1 to 2-7 are as shown below.

[Chem. 69]

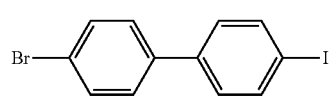

Intermediate 2-1

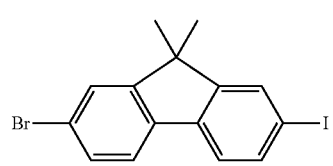

Intermediate 2-2

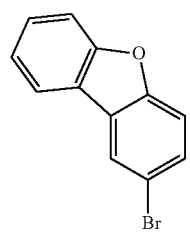

Intermediate 2-3

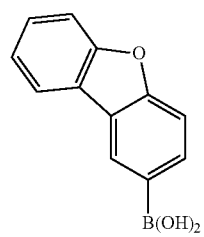

Intermediate 2-4

-continued
Intermediate 2-5
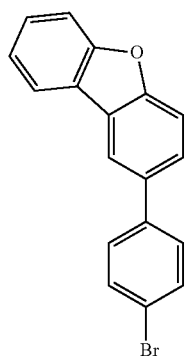
Intermediate 2-6
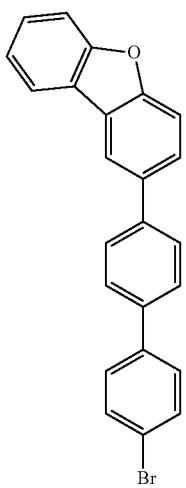
Intermediate 2-7
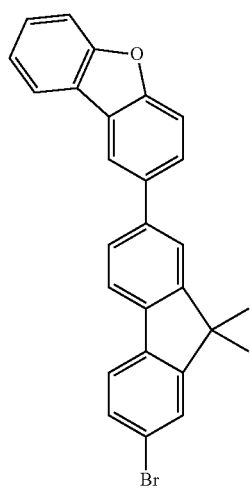
Intermediate 2-8
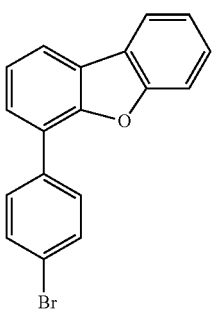
Intermediate 2-9
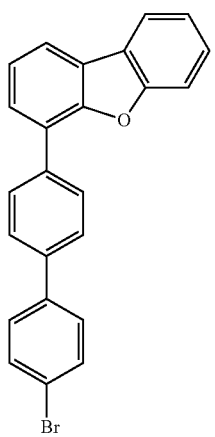
Intermediate 2-10
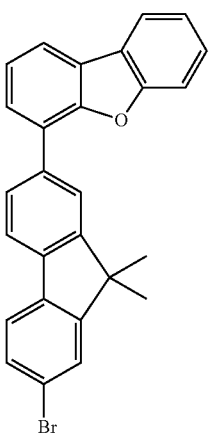
Intermediate 2-11
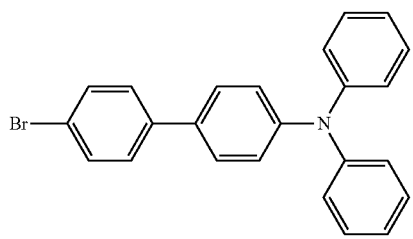
Intermediate 2-12
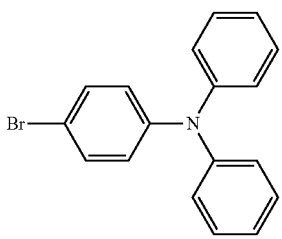

-continued
Intermediate 2-13
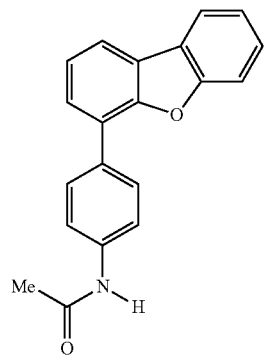
Intermediate 2-14
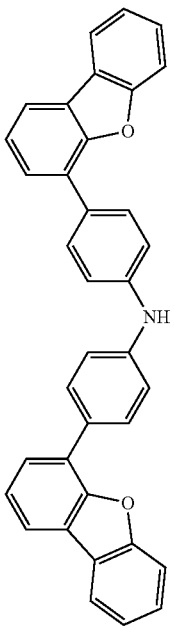
Intermediate 2-15
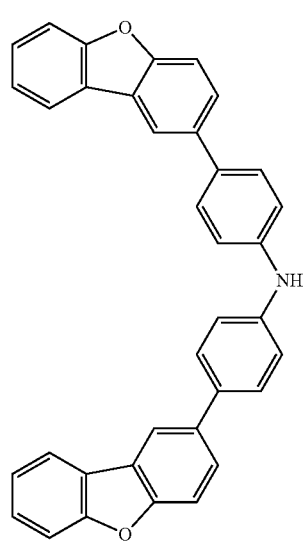

[Chem. 70]
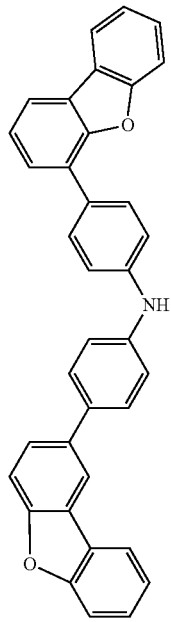
Intermediate 2-16
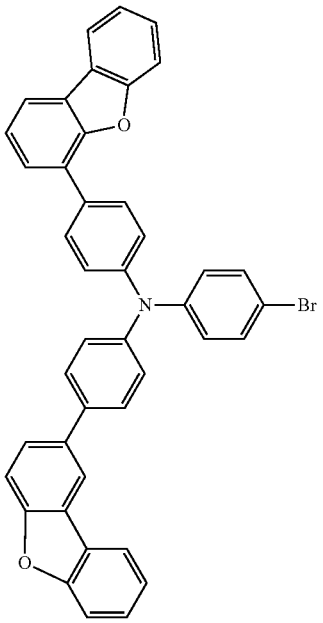
Intermediate 2-17
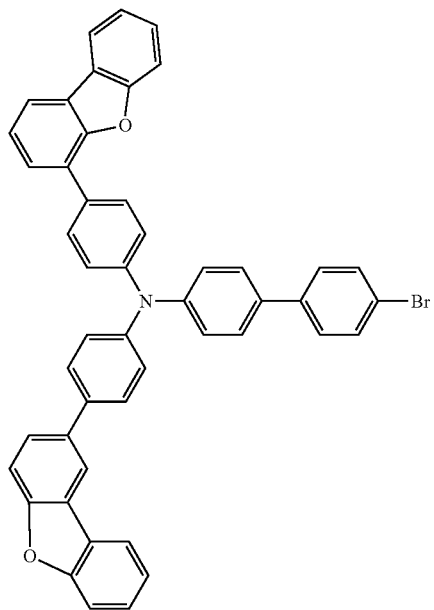
Intermediate 2-18
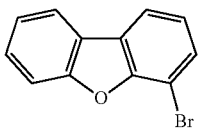
Intermediate 2-19
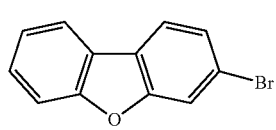
Intermediate 2-20
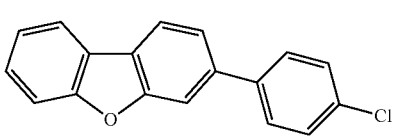
Intermediate 2-21

-continued
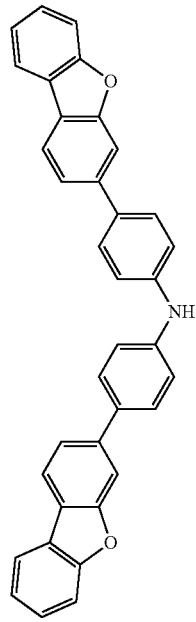
Intermediate 2-22
[Chem. 71]
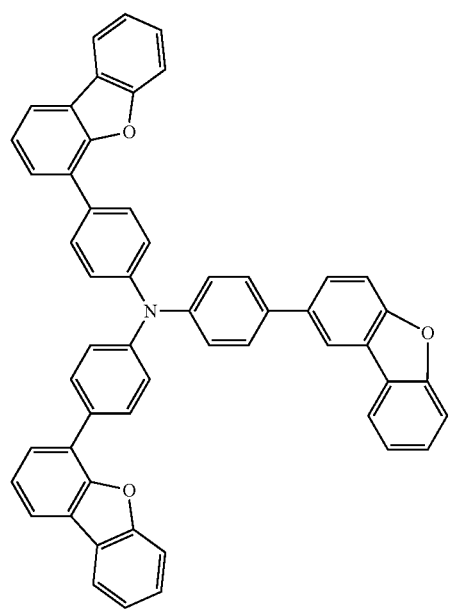
2-H1
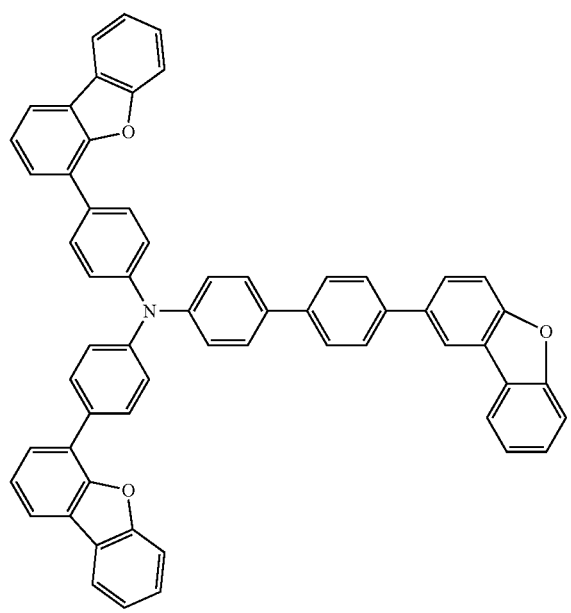
2-H2

367
368
-continued
2-H3
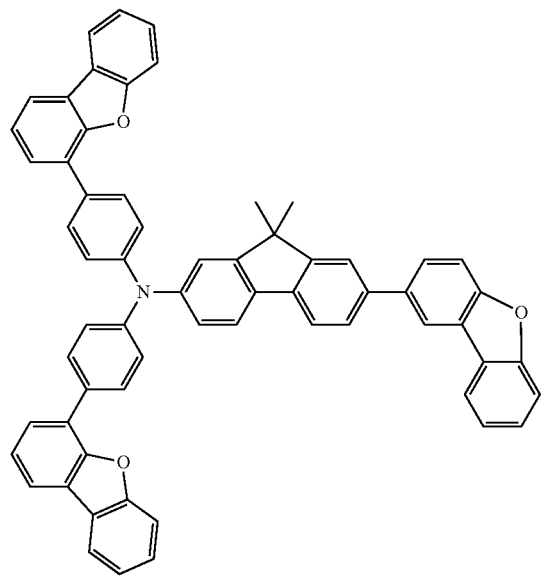
2-H4
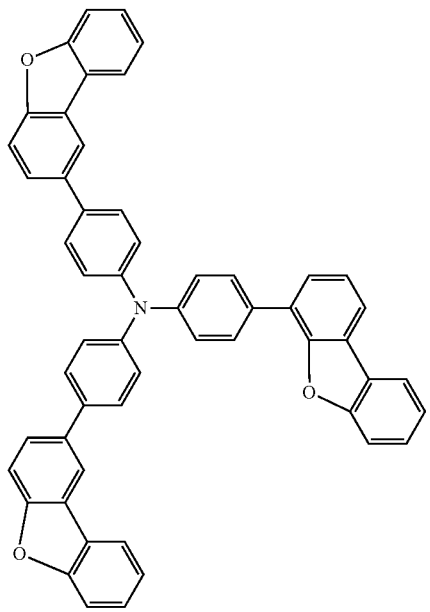
2-H5
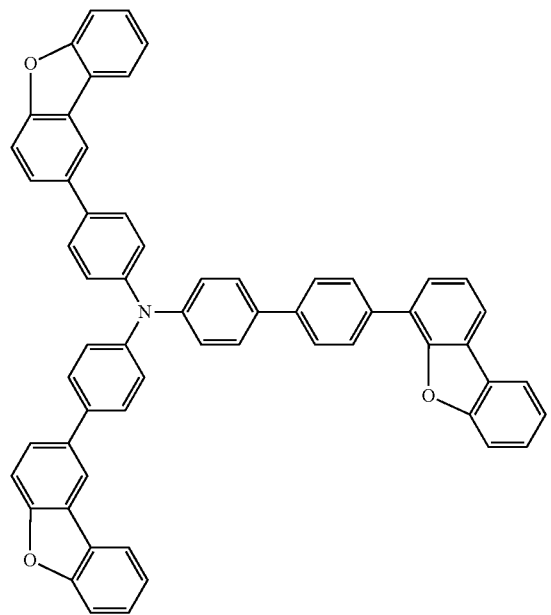
2-H6
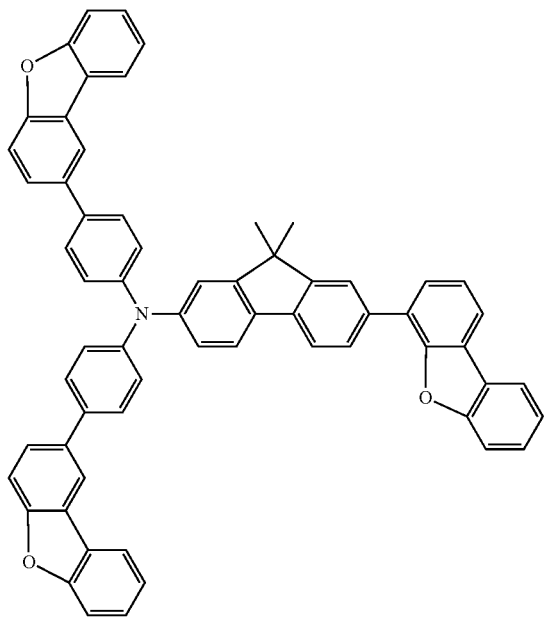

-continued
2-H7
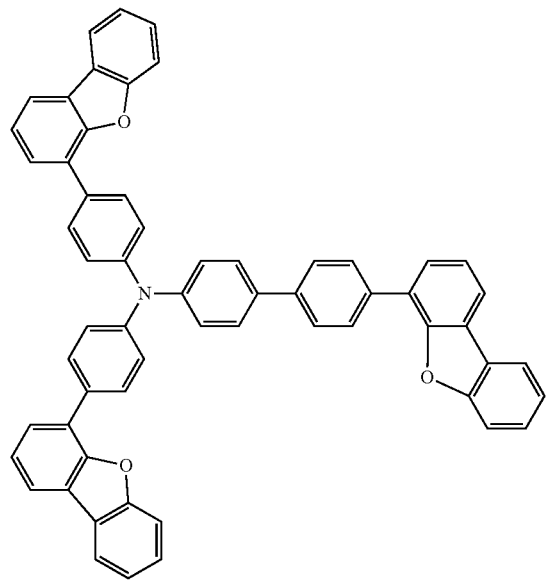
2-H8
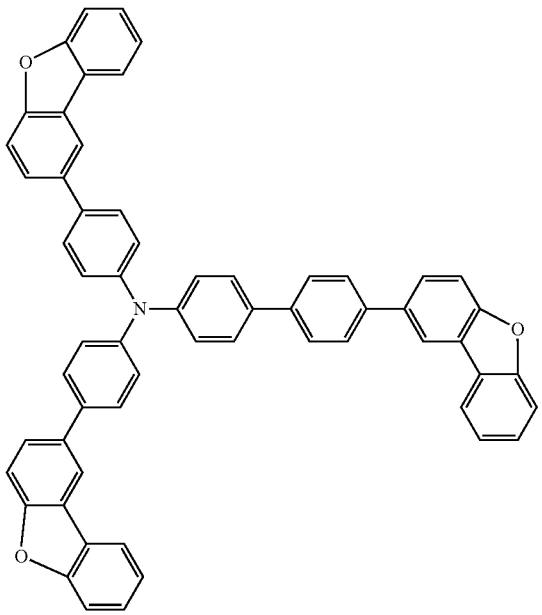
2-H9
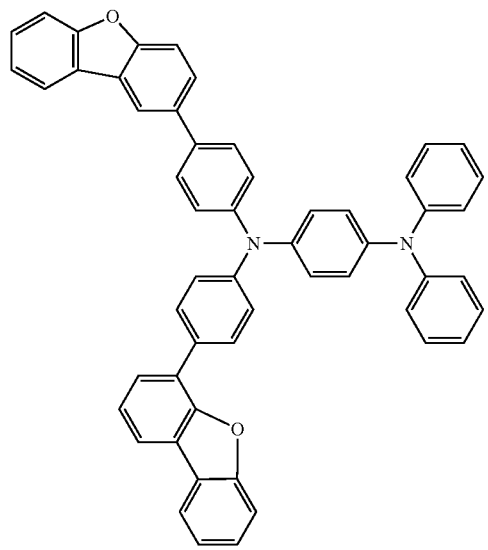
2-H10
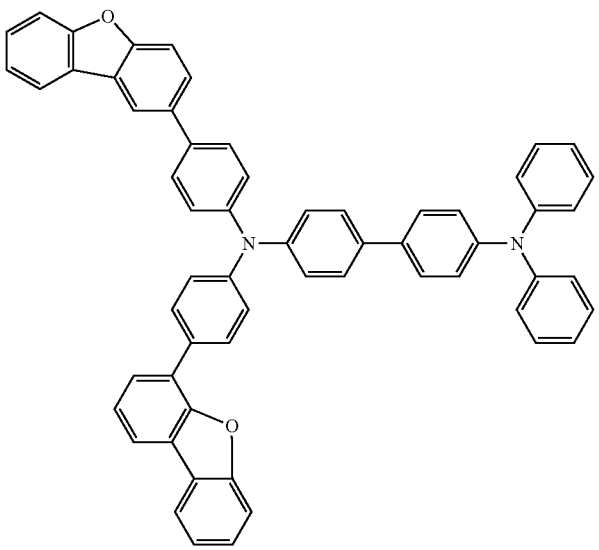

2-H11
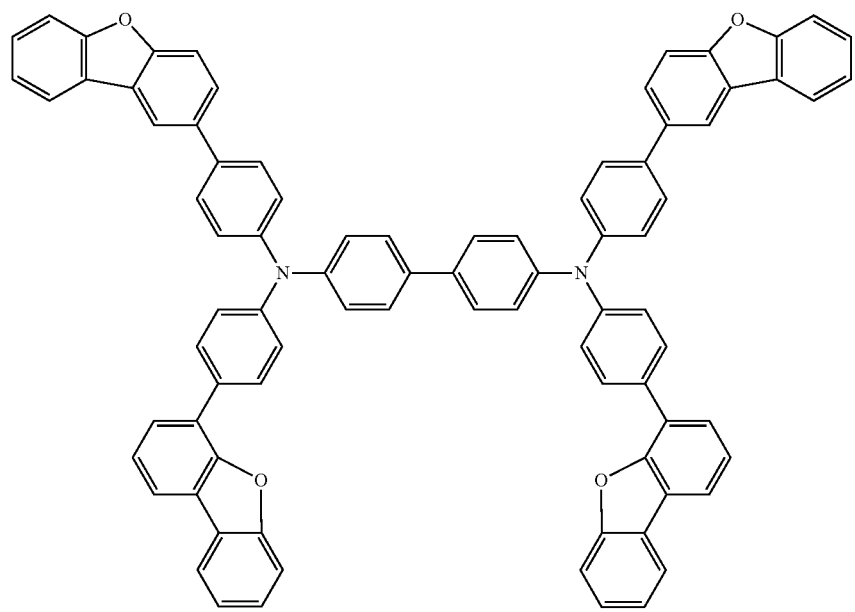
[Chem. 72]
2-H12
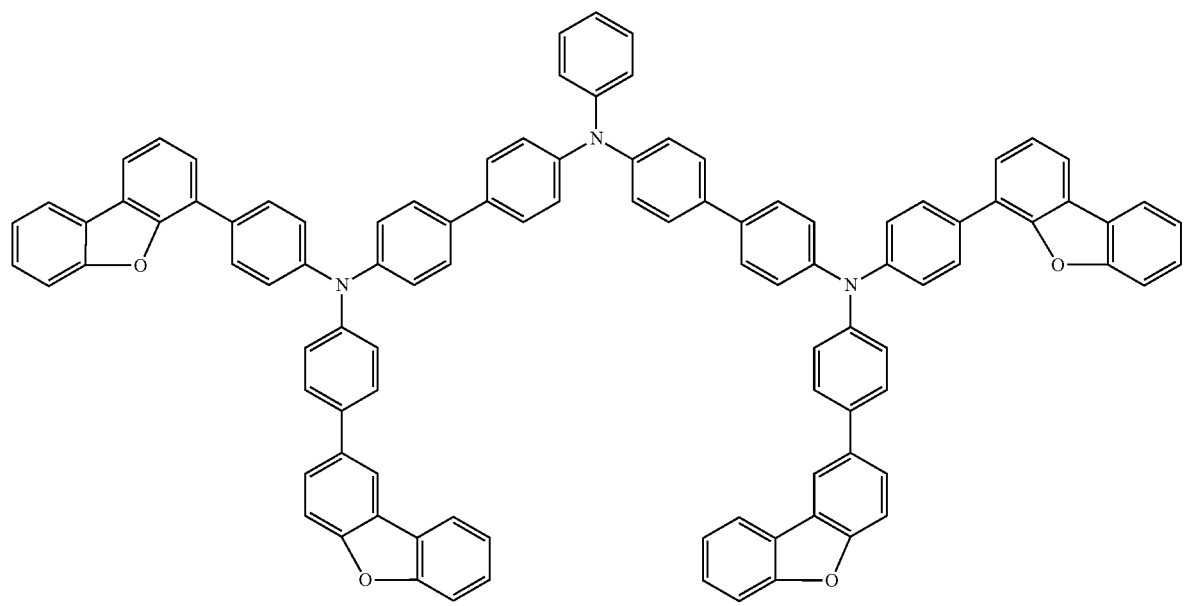

-continued
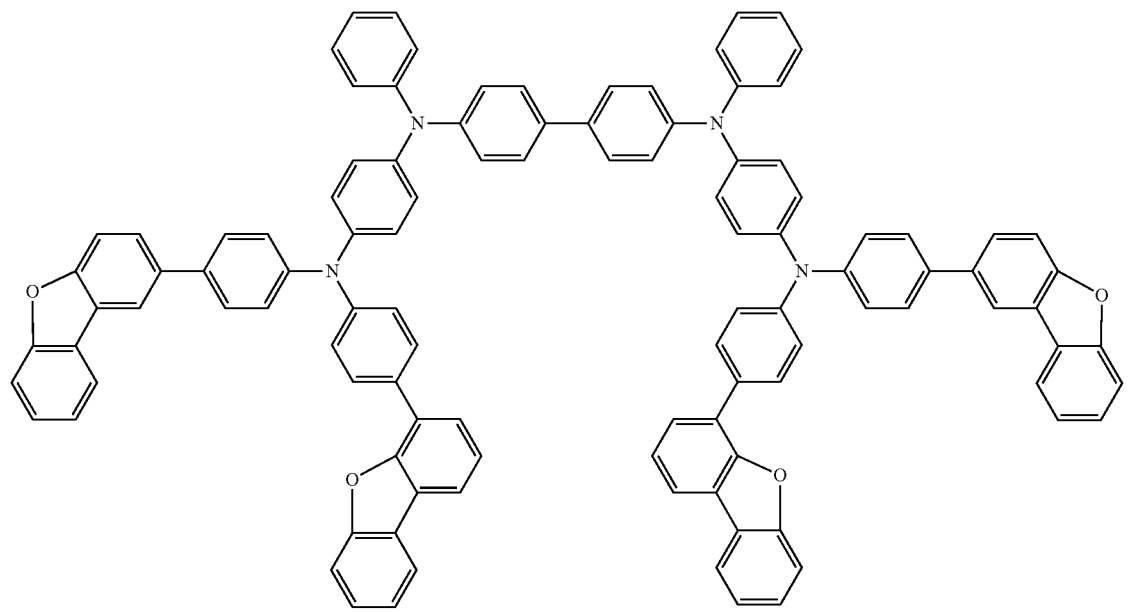
2-H13
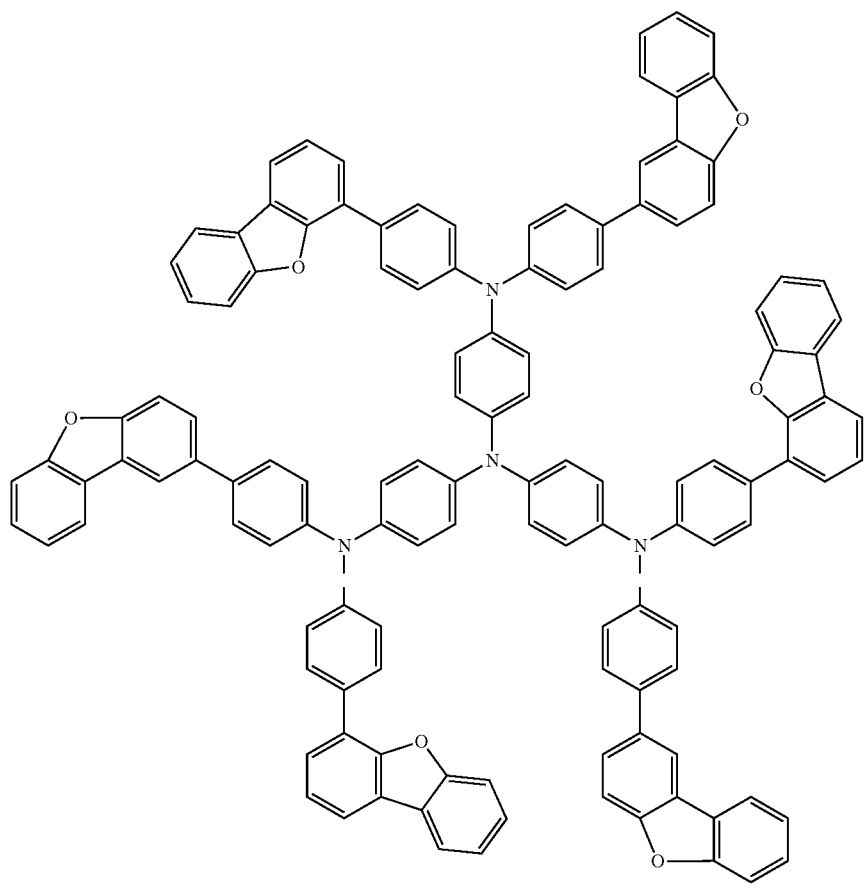
2-H14

2-H15
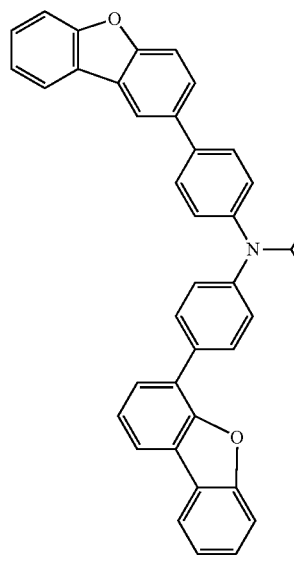
2-H16
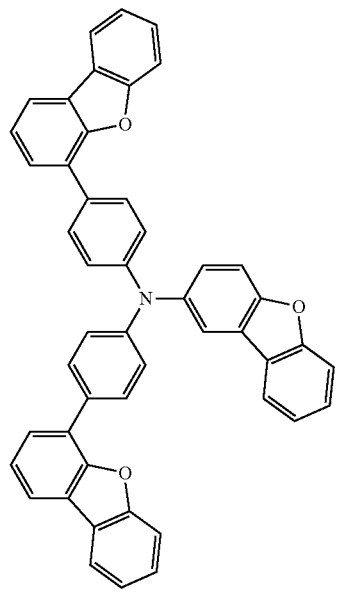
2-H17
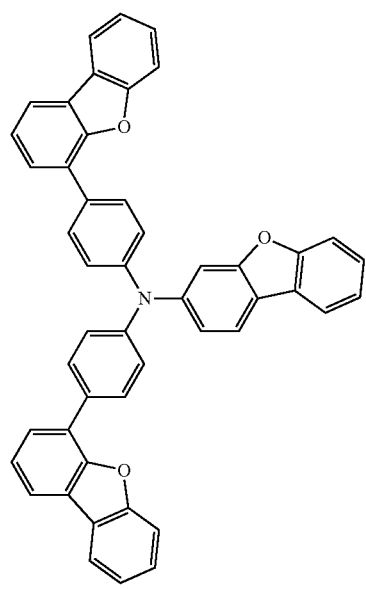
2-H18
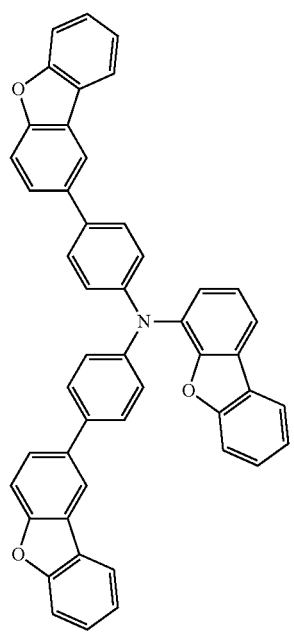

-continued
2-H19
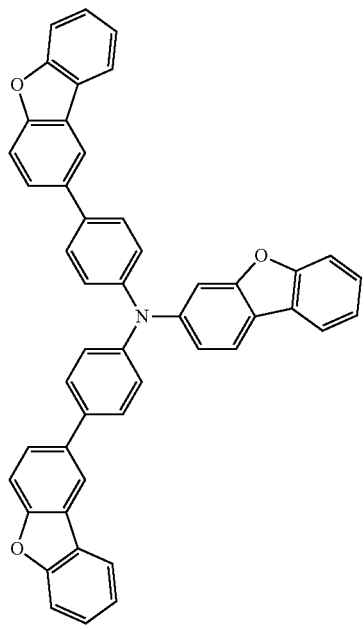
2-H20
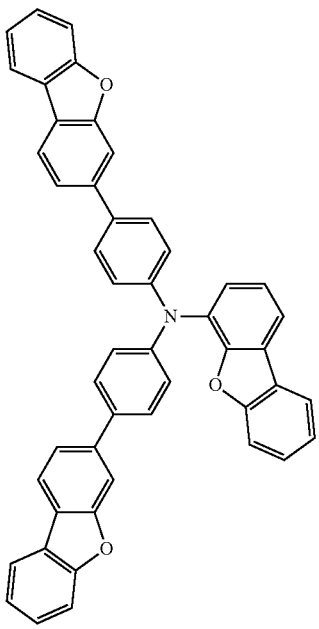
2-H21
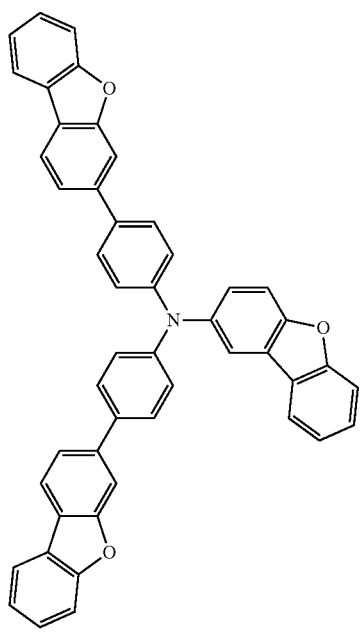
[Chem. 73]
Comparative compound 2-1
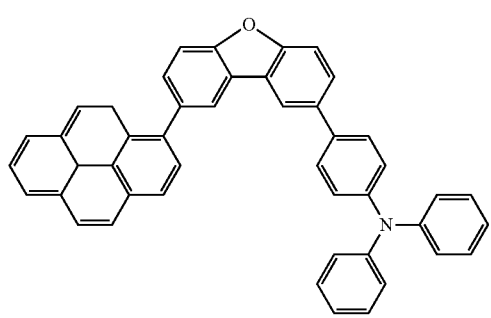
Comparative compound 2-2
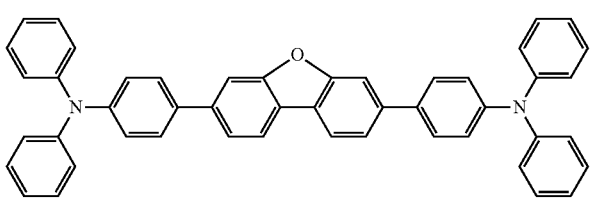

Comparative compound 2-3
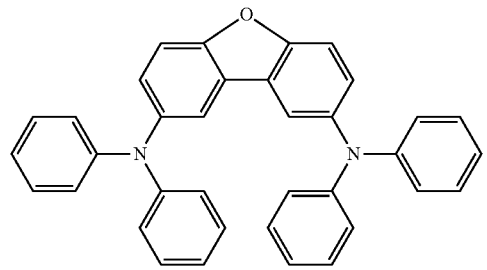
Comparative compound 2-4
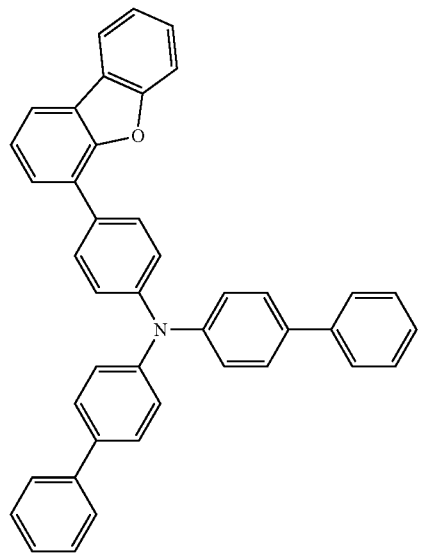
Comparative compound 2-5
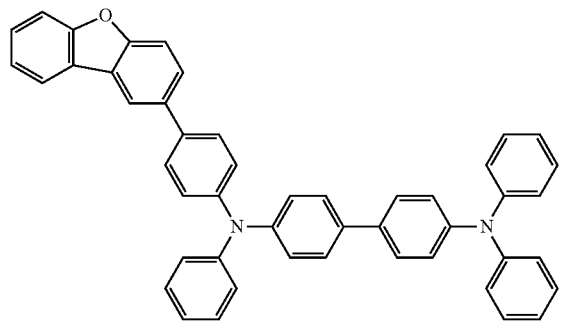
Comparative compound 2-6
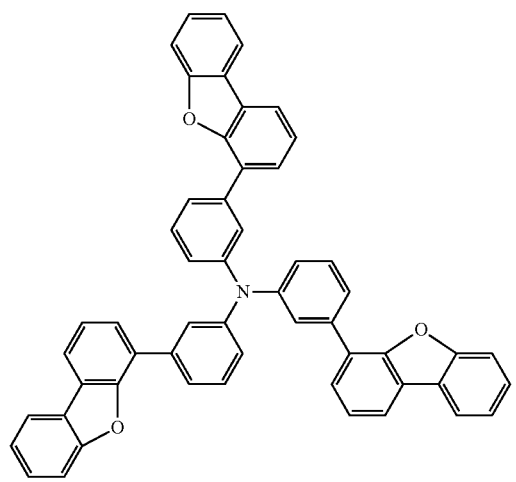

Comparative compound 2-7

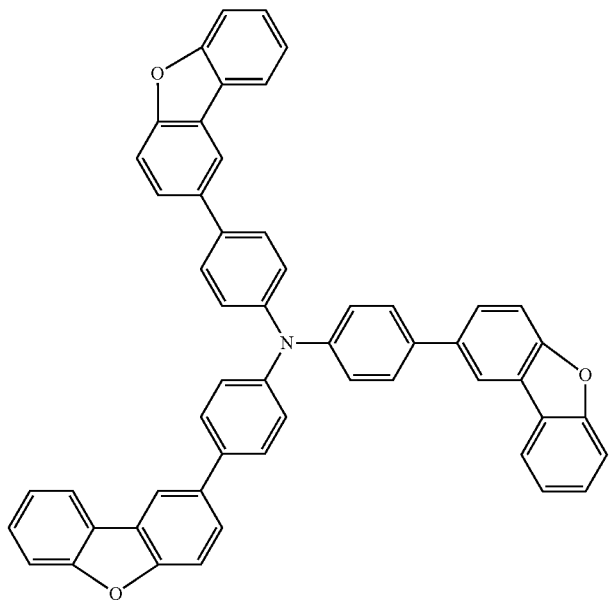

Example 2-1

Production of Organic EL Device

A glass substrate with an ITO transparent electrode measuring 25 mm wide by 75 mm long by 1.1 mm thick (manufactured by GEOMATEC Co., Ltd.) was subjected to ultrasonic cleaning in isopropyl alcohol for 5 minutes. After that, the substrate was subjected to UV ozone cleaning for 30 minutes.

The glass substrate with the transparent electrode line after the cleaning was mounted on a substrate holder of a vacuum vapor deposition device. First, the following compound H232 was deposited from vapor on the surface on the side where the transparent electrode line was formed so as to cover the transparent electrode. Then, the H232 film having a thickness of 60 nm was formed as the hole injecting layer. The above-mentioned compound 2-H1 was deposited from vapor and formed into a hole transporting layer having a thickness of 20 nm on the H232 film. Further, the following compound EM1 was deposited from vapor and formed into a light emitting layer having a thickness of 40 nm. Simultaneously with this formation, the following amine compound D1 having a styryl group, as a light emitting molecule, was deposited from vapor in such a manner that a weight ratio between the compound EM1 and the amine compound D1 was 40:2.

The following Alq was formed into a film having a thickness of 10 nm on the resultant film. The film functions as an electron injecting layer. After that, Li serving as a reducing dopant (Li source: manufactured by SAES Getters) and Alq were subjected to co-vapor deposition. Thus, an Alq:Li film (having a thickness of 10 nm) was formed as an electron injecting layer (cathode). Metal Al was deposited from vapor onto the Alq:Li film to form a metal cathode. Thus, an organic EL device was formed.

Next, after the resultant organic EL device had been stored at 105° C. for 8 hours, the luminous efficiency of the organic EL device was measured, and the luminescent color of the device was observed. A luminous efficiency at 10 mA/cm² was calculated by measuring a luminance by using a CS1000 manufactured by Minolta. Further, the half lifetime of emitted light in DC constant current driving at an initial luminance of 5,000 cd/m² and room temperature was measured. Table 2-1 shows the results.

[Chem. 74]

H232

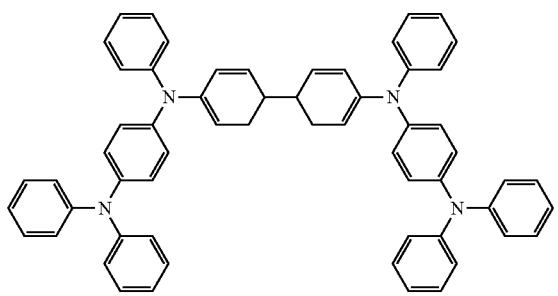

EM1

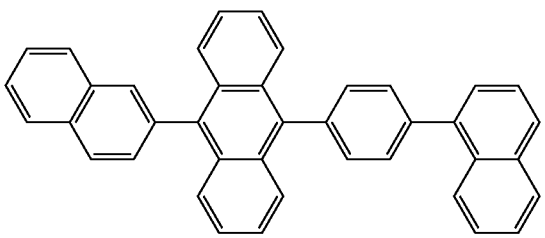

-continued

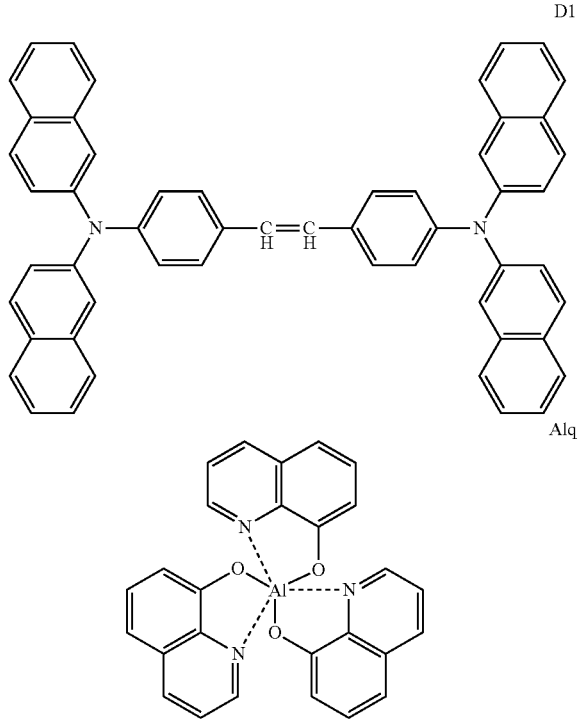

Examples 2-2 to 2-8

Production of Organic EL Device

Each organic EL device was produced in the same manner as in Example 2-1 except that the respective compounds shown in Table 2 were used as hole transporting materials instead of the compound 2-H1.

In the same manner as in Example 2-1, the luminous efficiency of the resultant organic EL device was measured, the luminescent color of the device was observed, and the half lifetime of emitted light in DC constant current driving at an initial luminance of 5,000 cd/m$^2$ and room temperature was measured. Table 2 shows the results.

Comparative Examples 2-1 to 2-7

Each organic EL device was produced in the same manner as in Example 2-1 except that the respective comparative compounds 2-1 to 2-7 were used as hole transporting materials instead of the compound 2-H1.

Further, in the same manner as in Example 2-1, the luminous efficiency of the resultant organic EL device was measured, the luminescent color of the device was observed, and the half lifetime of emitted light in DC constant current driving at an initial luminance of 5,000 cd/m$^2$ and room temperature was measured. Table 2 shows the results.

Example 2-9

Production of Organic EL Device

An organic EL device was produced in the same manner as in Example 2-1 except that the following arylamine compound D2 was used instead of the amine compound D1 having a styryl group. Me represents a methyl group.

In addition, in the same manner as in Example 2-1, the luminous efficiency of the resultant organic EL device was measured, the luminescent color of the device was observed, and the half lifetime of emitted light in DC constant current driving at an initial luminance of 5,000 cd/m$^2$ and room temperature was measured. Table 2 shows the results.

[Chem. 75]

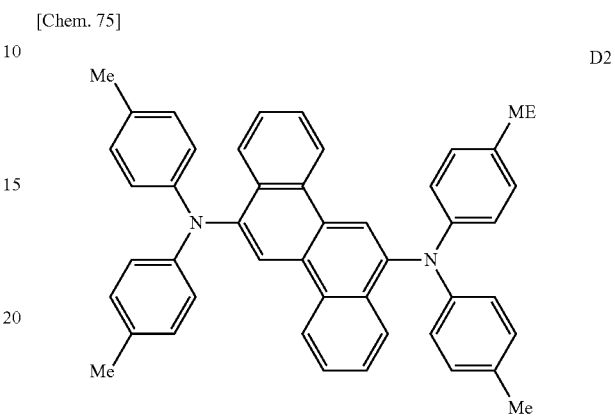

Comparative Example 2-8

An organic EL device was produced in the same manner as in Example 2-9 except that the above-mentioned comparative compound 2-1 was used as a hole transporting material instead of the compound 2-H1.

Further, in the same manner as in Example 2-1, the luminous efficiency of the resultant organic EL device was measured, the luminescent color of the device was observed, and the half lifetime of emitted light in DC constant current driving at an initial luminance of 5,000 cd/m$^2$ and room temperature was measured. Table 2-1 shows the results.

TABLE 2

| Example | Hole transporting material | Luminous efficiency (cd/A) | Luminescent color | Half lifetime (h) |
|---|---|---|---|---|
| 2-1 | 2-H1 | 6.0 | Blue | 430 |
| 2-2 | 2-H2 | 5.9 | Blue | 420 |
| 2-3 | 2-H4 | 6.3 | Blue | 390 |
| 2-4 | 2-H5 | 6.2 | Blue | 370 |
| 2-5 | 2-H7 | 6.1 | Blue | 350 |
| 2-6 | 2-H8 | 6.2 | Blue | 320 |
| 2-7 | 2-H10 | 5.8 | Blue | 310 |
| 2-8 | 2-H15 | 6.1 | Blue | 410 |
| 2-9 | 2-H1 | 6.0 | Blue | 420 |
| Comparative Example 2-1 | Comparative Compound 2-1 | 3.1 | Blue | 100 |
| Comparative Example 2-2 | Comparative Compound 2-2 | 1.5 | Blue | 120 |
| Comparative Example 2-3 | Comparative Compound 2-3 | 1.2 | Blue | 60 |
| Comparative Example 2-4 | Comparative Compound 2-4 | 4.2 | Blue | 140 |
| Comparative Example 2-5 | Comparative Compound 2-5 | 4.6 | Blue | 150 |
| Comparative Example 2-6 | Comparative Compound 2-6 | 5.1 | Blue | 210 |
| Comparative Example 2-7 | Comparative Compound 2-7 | 5.6 | Blue | 250 |
| Comparative Example 2-8 | Comparative Compound 2-1 | 3.2 | Blue | 120 |

As is apparent from the results of Table 2, an organic EL device using the aromatic amine derivative of the present invention provides high luminous efficiency even at high temperatures and has a long half lifetime as compared with an organic EL device using an aromatic amine derivative for comparison.

INDUSTRIAL APPLICABILITY

As described above in detail, the molecules of the aromatic amine derivative of the present invention hardly crystallize, and the incorporation of the derivative into an organic thin film layer improves a yield upon production of an organic EL device and can realize an organic EL device having high efficiency and a long lifetime. Accordingly, the derivative is extremely useful as a material for an organic EL device having high practicality.

The invention claimed is:
1. An aromatic amine compound represented by any one of the following formulae (5) to (9):

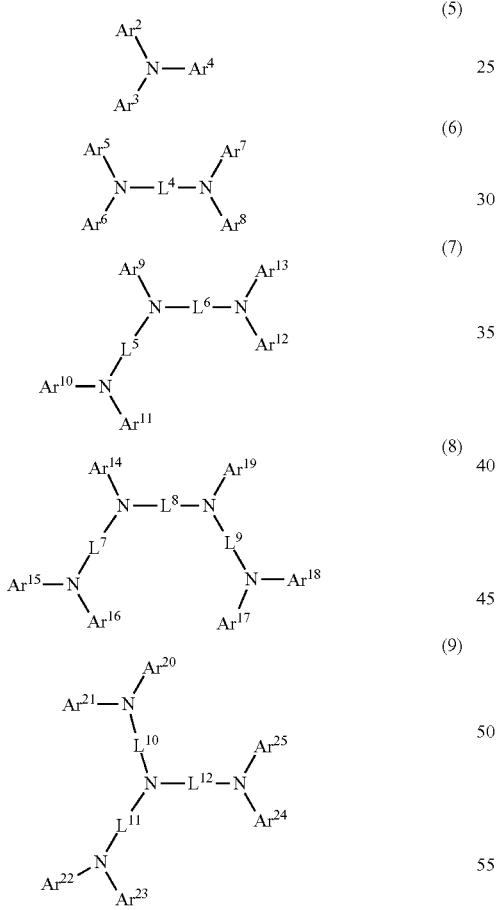

wherein:
one of $Ar^2$ to $Ar^4$ represents a substituent A, one of $Ar^2$ to $Ar^4$ represents a substituent B, and one of $Ar^2$ to $Ar^4$ represents a group selected from a substituent A, a substituent B and a substituted or unsubstituted aryl group having 6 to 50 ring carbon atoms;
one of $Ar^5$ to $Ar^8$ represents a substituent A, one of $Ar^5$ to $Ar^8$ represents a substituent B, and the rest of $Ar^5$ to $Ar^8$ represent a group selected from the group consisting of a substituent A, a substituent B and a substituted or unsubstituted aryl group having 6 to 50 ring carbon atoms;
one of $Ar^9$ to $Ar^{13}$ represents a substituent A, one of $Ar^9$ to $Ar^{13}$ represents a substituent B, and the rest of $Ar^9$ to $Ar^{13}$ represent a group selected from the group consisting of a substituent A, a substituent B and a substituted or unsubstituted aryl group having 6 to 50 ring carbon atoms;
one of $Ar^{14}$ to $Ar^{19}$ represents a substituent A, one of $Ar^{14}$ to $Ar^{19}$ represents a substituent B, and the rest of $Ar^{14}$ to $Ar^{19}$ represent a group selected from the group consisting of a substituent A, a substituent B and a substituted or unsubstituted aryl group having 6 to 50 ring carbon atoms;
one of $Ar^{20}$ to $Ar^{25}$ represents a substituent A, one of $Ar^{20}$ to $Ar^{25}$ represents a substituent B, and the rest of $Ar^{20}$ to $Ar^{25}$ represent a group selected from the group consisting of a substituent A, a substituent B and a substituted or unsubstituted aryl group having 6 to 50 ring carbon atoms;
the substituent A and the substituent B are different from each other;
the substituent A and the substituent B are each independently represented by formula (1):

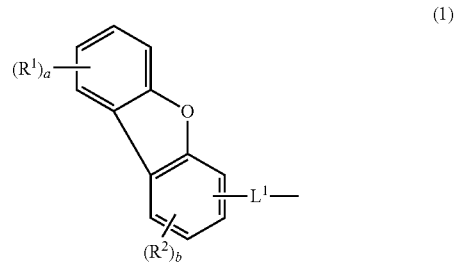

wherein:
L¹ represents a substituted or unsubstituted divalent arylene group having 6 to 50 ring carbon atoms, wherein the optional substituent of L¹ is selected from the group consisting of a linear or branched alkyl group having 1 to 10 carbon atoms, a cycloalkyl group having 3 to 10 ring carbon atoms, a trialkylsilyl group having 3 to 10 carbon atoms, a triarylsilyl group having 18 to 30 ring carbon atoms, an alkylarylsilyl group having 8 to 15 carbon atoms whose aryl portion has 6 to 14 ring carbon atoms, an aryl group having 6 to 14 ring carbon atoms, a halogen atom, and a cyano group, and wherein a plurality of such substituents adjacent to each other may be bonded to each other to form a saturated or unsaturated ring;
a represents an integer of 0 to 4;
b represents an integer of 0 to 3;
R¹ and R² each independently represent a linear or branched alkyl group having 1 to 10 carbon atoms, a cycloalkyl group having 3 to 10 ring carbon atoms, a trialkylsilyl group having 3 to 10 carbon atoms, a triarylsilyl group having 18 to 30 ring carbon atoms, an alkylarylsilyl group having 8 to 15 carbon atoms whose aryl portion has 6 to 14 ring carbon atoms, an aryl group having 6 to 14 ring carbon atoms, a halogen atom, or a cyano group, and a plurality of R¹'s and R²'s adjacent to each other may be bonded to each other to form a saturated or unsaturated, divalent group that forms a ring, and
wherein the optional substituents on the substituted or unsubstituted aryl group are selected from the group consisting of a linear or branched alkyl group having 1 to 10 carbon atoms, a cycloalkyl group having 3 to 10 ring carbon atoms, a trialkylsilyl group having 3 to 10 carbon atoms, a triarylsilyl group having 18 to 30 ring carbon atoms, an alkylarylsilyl group having 8 to 15 carbon atoms whose aryl portion has 6 to 14 ring carbon atoms, an aryl group having 6 to 14 ring carbon atoms, a halogen atom, or a cyano group, and the adjacent optional substituents may be bonded to each other to form a saturated or unsaturated, divalent group that forms a ring;

$L^4$ to $L^{12}$ each independently represent a substituted or unsubstituted divalent arylene group having 6 to 50 ring carbon atoms; and the substituents which $L^4$ to $L^{12}$ may have are each independently selected from the group consisting of a linear or branched alkyl group having 1 to 10 carbon atoms, a cycloalkyl group having 3 to 10 ring carbon atoms, a trialkylsilyl group having 3 to 10 carbon atoms, a triarylsilyl group having 18 to 30 ring carbon atoms, an alkylarylsilyl group having 8 to 15 carbon atoms whose aryl portion has 6 to 14 ring carbon atoms, an aryl group having 6 to 14 ring carbon atoms, a halogen atom, and a cyano group, and wherein a plurality of such substituents adjacent to each other may be bonded to each other to form a saturated or unsaturated ring.

2. The aromatic amine compound according to claim 1, wherein the substituent A and the substituent B are each independently represented by any one of the following formulae (1-1) to (1-3):

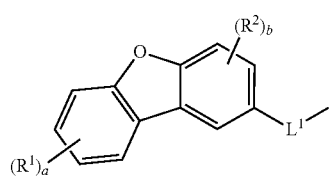

(1-1)

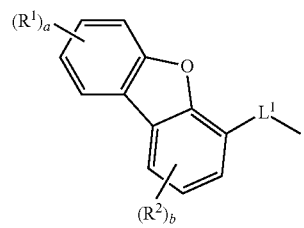

(1-2)

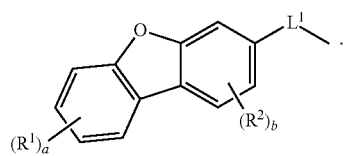

(1-3)

3. The aromatic amine compound according to claim 2, wherein the substituent A is represented by the formula (1-1) and the substituent B is represented by the formula (1-2).

4. The aromatic amine compound according to claim 2, wherein the substituent A is represented by the following formula (1-1) or (1-2):

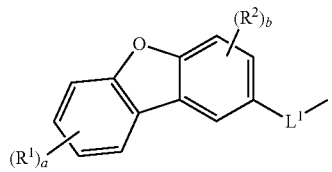

(1-1)

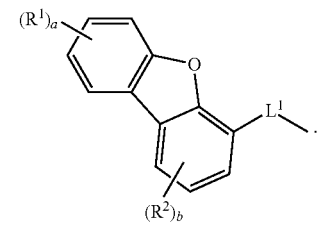

(1-2)

5. The aromatic amine compound according to claim 2, wherein the aromatic amine compound is represented by the formula (5) in which the $Ar^2$ to $Ar^4$ are each represented by the formula (1-2).

6. The aromatic amine compound according to claim 2, wherein the aromatic amine compound is represented by the formula (5) in which the $Ar^2$ to $Ar^4$ are each represented by the formula (1-1).

7. The aromatic amine compound according to claim 2, wherein the aromatic amine compound is represented by the formula (5) in which
two of the $Ar^2$ to $Ar^4$ are each represented by the formula (1-2), and
one of the $Ar^2$ to $Ar^4$ represents a substituted or unsubstituted aryl group having 6 to 16 ring carbon atoms.

8. The aromatic amine compound according to claim 2, wherein the aromatic amine compound is represented by the formula (5) in which
two of the $Ar^2$ to $Ar^4$ are each represented by the formula (1-1), and
one of the $Ar^2$ to $Ar^4$ represents a substituted or unsubstituted aryl group having 6 to 16 ring carbon atoms.

9. The aromatic amine compound according to claim 2, wherein the aromatic amine compound is represented by the formula (5) in which
at least one of the $Ar^2$ to $Ar^4$ is represented by the formula (1-2), and
at least one of the $Ar^2$ to $Ar^4$ is represented by the formula (1-1).

10. The aromatic amine compound according to claim 2, wherein the aromatic amine compound is represented by the formula (5) in which
the $Ar^2$ is represented by the formula (1-2), and
the $Ar^3$ and the $Ar^4$ are each independently represented by the formula (1-1).

11. The aromatic amine compound according to claim 2, wherein the aromatic amine compound is represented by the formula (5) in which
the $Ar^2$ and the $Ar^3$ are each represented by the formula (1-3), and
the $Ar^4$ is represented by the general formula (1-1).

12. The aromatic amine compound according to claim 1, wherein the compound has a substituted or unsubstituted aryl group having 6 to 50 ring carbon atoms which is a terphenyl group.

13. The aromatic amine compound according to claim 1, wherein the aromatic amine compound is represented by the formula (5).

14. A material for an organic electroluminescence device comprising the aromatic amine compound according to claim 1.

15. A hole transporting material for an organic electroluminescence device comprising the aromatic amine compound according to claim 1.

16. An organic electroluminescence device, comprising an organic thin film layer formed of one or more layers including at least a light emitting layer, the organic thin film layer being interposed between a cathode and an anode, wherein at least one layer of the organic thin film layer comprises the aromatic amine compound according to claim 1.

17. The organic electroluminescence device according to claim 16, wherein:
the organic thin film layer has a hole transporting layer and/or a hole injecting layer; and
the aromatic amine compound is incorporated into the hole transporting layer and/or the hole injecting layer.

18. The organic electroluminescence device according to claim 16, wherein:
the organic thin film layer has a hole transporting zone including at least a hole transporting layer and a hole injecting layer; and
the aromatic amine compound is incorporated into a layer out of direct contact with the light emitting layer in the hole transporting zone.

19. The organic electroluminescence device according to claim 16, wherein the light emitting layer comprises a styrylamine compound and/or an arylamine compound.

20. The organic electroluminescence device according to claim 16, wherein a layer in contact with the anode, which is a layer for forming a hole injecting layer and/or a hole transporting layer, comprises a layer containing an acceptor material.

21. The organic electroluminescence device according to claim 16, wherein the organic electroluminescence device emits blue light.

22. The aromatic amine compound according to claim 1, wherein $L^1$ and $L^4$ to $L^{12}$ each independently represent a phenylene group, a naphthylene group, a biphenylene group, a terphenylene group, a fluorenylene group or a 9,9-dimethylfluorenylene group.

23. The aromatic amine compound according claim 1, wherein the $L^1$ and $L^4$ to $L^{12}$ are each independently represented by any one of the following formulae (4), (10), and (11):

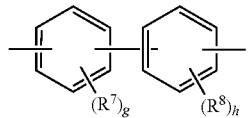
(4)

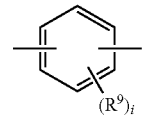
(10)

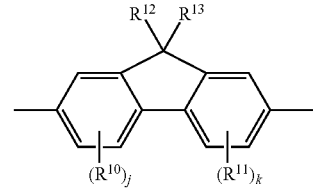
(11)

where:
$R^7$ to $R^{11}$ each independently represent a linear or branched alkyl group having 1 to 10 carbon atoms, a cycloalkyl group having 3 to 10 ring carbon atoms, a trialkylsilyl group having 3 to 10 carbon atoms, a triarylsilyl group having 18 to 30 ring carbon atoms, an alkylarylsilyl group having 8 to 15 carbon atoms whose aryl portion has 6 to 14 ring carbon atoms, an aryl group having 6 to 14 ring carbon atoms, a halogen atom, or a cyano group, and a plurality of $R^7$'s to $R^{11}$'s adjacent to each other may be bonded to each other to form a saturated or unsaturated ring;

$R^{12}$ and $R^{13}$ each independently represent a linear or branched alkyl group having 1 to 10 carbon atoms, or a cycloalkyl group having 3 to 10 ring carbon atoms;

g, h, and i each independently represent an integer of 0 to 4; and j and k each independently represent an integer of 0 to 3.

24. The aromatic amine compound according to claim 1, wherein the aryl group having 6 to 50 ring carbon atoms represents a phenyl group, a naphthyl group, a biphenyl group, a terphenyl group or a fluorenyl group.

* * * * *